United States Patent [19]

Inaba et al.

[11] Patent Number: 6,017,919

[45] Date of Patent: Jan. 25, 2000

[54] COMPOUNDS AND PHARMACEUTICAL USE THEREOF

[75] Inventors: Takashi Inaba; Tetsudo Kaya; Hiroyuki Iwamura, all of Takatsuki, Japan

[73] Assignee: Japan Tobacco Inc., Tokyo, Japan

[21] Appl. No.: 09/117,879

[22] PCT Filed: Feb. 6, 1997

[86] PCT No.: PCT/JP97/00291

§ 371 Date: Aug. 6, 1998

§ 102(e) Date: Aug. 6, 1998

[87] PCT Pub. No.: WO97/29079

PCT Pub. Date: Aug. 14, 1997

[30] Foreign Application Priority Data

Feb. 6, 1996 [JP] Japan .................................. 8-020083
Apr. 17, 1996 [JP] Japan .................................. 8-094989

[51] Int. Cl.[7] .................... A61K 31/525; C07D 401/00; C07D 403/00; C07D 417/00
[52] U.S. Cl. ............................ 514/251; 544/284
[58] Field of Search .............................. 544/284; 514/259

[56] References Cited

U.S. PATENT DOCUMENTS 5,264,438  11/1993  Shimazaki et al. ..................... 514/259

*Primary Examiner*—Alan L. Rotman
*Assistant Examiner*—Rita Desai
*Attorney, Agent, or Firm*—Foley & Lardner

[57] ABSTRACT

The compounds of the formula (I)

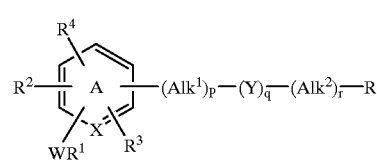

(I)

wherein each symbol is as defined in the specification, pharmaceutically acceptable salts thereof and pharmaceutical use thereof. The Compound (I) and pharmaceutically acceptable salts thereof of the present invention selectively act on cannabinoid receptors, particularly peripheral receptors, cause less side effects on the central system, and have superior immunoregulating action, antiinflammatory action, antiallergic action and therapeutic effect on nephritis. Therefore, they are useful as cannabinoid receptor, particularly peripheral cannabinoid receptor activators and antagonists, immunoregulators, therapeutic agents for autoimmune diseases, antiinflammatory agents, antiallergic agents and therapeutic agents for nephritis.

10 Claims, No Drawings

COMPOUNDS AND PHARMACEUTICAL USE THEREOF

CROSS REFERENCE

This application is a 371 of PCT/JP97/00291 filed Feb. 6, 1997.

TECHNICAL FIELD

The present invention relates to a novel compound which selectively acts on a cannabinoid receptor, particularly a peripheral receptor, and pharmaceutical use thereof. More particularly, the present invention relates to a novel compound that causes less central side effects and which exhibits immunoregulating action, antiinflammatory action, antiallergic action and nephritis therapy effect, and to pharmaceutical use thereof.

BACKGROUND ART

There have been heretofore known, as an indian hemp ingredient, a series of compounds called cannabinoid, consisting of C, H and O. Of these, tetrahydrocannabinol (THC) is considered to be the hallucinogen, and the main ingredient contained in hemp is known to be Δ9-THC. The Δ9-THC has been observed to cause pharmacological actions such as ataxia, increase in irritability, suppression of emesis, analgetic action, body temperature fall, suppression of respiration, induction of catalepsy, vasodilation, immunosuppressive action and the like.

The mechanism of these pharmacological actions is considered to mainly concern central nervous system (Devane et al., Mol Pharmacol. 1988,34,605–613; Hollister et al., Pharmacol. Rev., 1986,38, 1–20; Renv et al., Prog. Drug. Exp. Ther., 1991, 36, 71–114) and peripheral cells (Nye et al., J. Pharmacol. Exp. Ther., 1985, 234, 784–791; Flynn et al., Mol Pharmacol. 1992, 42, 736–742), and part of the action through the central nervous system has been reported to be applicable to the medical care.

In particular, the development of an agonist of peripheral cell receptor such as one having antiinflammatory action, antiallergic action and nephritis therapy effect in addition to its immunoregulating action by regulating immunoreaction has been expected based on the finding of a receptor on macrophage (Munnro et al., Nature, 1993, 365, 61–65).

As the agonist of the cannabinoid receptor, pyrazole derivatives (Japanese Patent Unexamined Publication No. 73014/1994, EP 656354, EP 658546), THC derivatives (Japanese Patent Unexamined Publication No. 209377/1991), benzoxazine derivatives (U.S. Pat. No. 5,112,820), indole derivatives (U.S. Pat. No. 5,081,122) and fatty acid derivatives (WO94/12466) are known.

There have been documented various reports on amide derivatives. For example, Japanese Patent Unexamined Publication No. 54/1986 discloses 5-lipoxygenase inhibitors such as benzoylamino acid amide; Japanese Patent Examined Publication No. 49686/1994 discloses an intermediate compound, allyl-ethylbenzamide; Japanese Patent Unexamined Publication No. 85137/1977 discloses 2-butoxyphenyl-ethylbenzamide as a hypoglycemic; Japanese Patent Unexamined Publication No. 131846/1976 discloses 2-butoxyphenyl-ethylbenzamide bezoic acid as a hypoglycemic benzoic acid derivative; Japanese Patent Unexamined Publication No. 213877/1993 discloses N-acetyl-3,4-bis(heptyloxy)-N-(2-pyridinylmethyl)benzamide as a platelet activator inhibitor, Japanese Patent Examined Publication No. 31852/1971 discloses 1-(N)-methyl-2-(4'-butoxy-2',6'-dimethylbenzoylamino)-methyl-piperidine as a local anesthetic; Japanese Patent Unexamined Publication No. 137972/1975 discloses 4-butoxy-N-(3-pyridyl)-benzamide as an antitubercular agent; U.S. Pat. No. 4,743,610 discloses amino-alkoxy-pyridinyl-alkyl-benzamide as a thromboxane synthesis inhibitor, and Japanese Patent Unexamined Publication No. 85963/1989 discloses alkoxy-naphthalenyl-pyridinyl-amide as a platelet activator inhibitor. However, these publications do not teach pharmacological actions based on the action mechanism via cannabinoid receptors.

It is therefore an object of the present invention to provide a novel compound which selectively acts on a cannabinoid receptor, particularly a peripheral receptor, and which is free of the above-mentioned problems, and pharmaceutical use thereof.

More particularly, an object of the present invention is to provide a novel compound which selectively acts on a cannabinoid receptor, particularly, peripheral cells, which has immunoregulating action, antiinflammatory action, antiallergic action and nephritis therapy effect, and which is associated with less effects on the central nervous system (e.g., side effects such as excitation, hallucination, ataxia, increase in irritability, body temperature fall, suppression of respiration, induction of catalepsy, blood pressure elevation and the like), and pharmaceutical use thereof.

DISCLOSURE OF THE INVENTION

The present inventors have made intensive studies in an attempt to achieve the above-mentioned objects and found that the novel compound of the present invention has selective affinity for a cannabinoid receptor, particularly for a peripheral cell receptor, and exhibits pharmaceutical effects in the medical conditions known to be related to a cannabinoid receptor, particularly the medical conditions (e.g., immune diseases, various inflammations, allergic diseases, nephritis and the like) known to be related to peripheral cell tissues.

Accordingly, the present invention provides the following.

(1) A cannabinoid receptor activator or antagonist comprising, as an active ingredient, a compound of the formula (I)

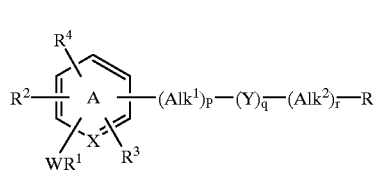

(I)

wherein
X is CH or N;
W is —O—, —S(O)$_t$—, —CR$^5$R$^6$—, —NR$^7$—, —NR$^7$CO—, —CONR$^7$—, —COO— or —OCO—
   wherein
   R$^5$ and R$^6$ are the same or different and each is hydrogen atom or alkyl, R$^7$ is hydrogen atom or alkyl, and t is 0, 1 or 2;
R$^1$ is an alkyl, an alkenyl, an alkynyl, an aryl, an arylalkyl, a heteroaryl, a heteroarylalkyl, a cycloalkyl or a cycloalkylalkyl
   wherein
   each group at R$^1$ is optionally substituted by alkyl, alkylamino, amino, hydroxy, alkoxy, alkoxycarbonyl, acyl, acyloxy, acylthio, mercapto, allylthio, alkylsulfinyl or alkylsulfonyl;

$R^2$ is a hydrogen atom, an alkyl, —$OR^{15}$ wherein $R^{15}$ is hydrogen atom, alkyl, alkenyl, alkynyl, aryl, arylalkyl, heteroaryl, heteroarylalkyl, cycloalkyl or cycloalkylalkyl, —$NR^8R^9$ wherein $R^8$ and $R^9$ are the same or different and each is hydrogen atom, amyl, alkenyl, alkynyl, acyl, aryl, arylalkyl, heteroaryl, heteroarylalkyl, cycloalkyl or cycloalkylalkyl, or $R^8$ and $R^9$ optionally form heteroaryl together with the adjacent nitrogen atom, or —$(CH_2)_u,S(O)_{u'}R^{12}$ wherein $R^{12}$ is hydrogen atom, alkyl, alkenyl or alkynyl, u is 0, 1 or 2 and u' is 0, 1 or 2
wherein
each group at said $R^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
$R^3$ is a hydrogen atom, an alkoxy, an alkyl, a carboxyl, an alkoxycarbonyl, a halogen atom or nitro, said alkyl being optionally substituted by alkoxy or hydroxy;
$R^4$ is a hydrogen atom, or $R^4$ and $R^2$ form, together with A ring, a condensed ring of the formula (II)

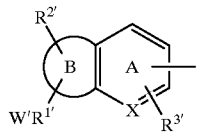

(II)

wherein W'$R^{1'}$, $R^{2'}$ and $R^{3'}$ are substituted at an optional position of A ring or B ring, W'$R^{1'}$, $R^{2'}$ and $R^{3'}$ are each as defined above for $WR^1$, $R^2$ and $R^3$, respectively, and B ring is a benzene ring, pyridine ring or furan ring;
$Alk^1$ is —CH=CH—, —$CH_2CH_2$— or —C≡C—;
Y is —$CONR^{10}$—, —$NR^{11}CO$—, —COO—, —$CH_2NR^{10}$— or —NHCONH—
wherein,
$R^{10}$ and $R^{11}$ are the same or different and each is hydrogen atom, alkyl, alkenyl or amino-protecting group, said alkyl being optionally substituted by heteroaryl, arylsulfinyl or alkoxycarbonyl, and said alkenyl being optionally substituted by phenylthio;
$Alk^2$ is an alkenylene, an alkenylene, —$COCH_2$— or —$CONH(CH_2)_v$— wherein v is 0, 1 or 2
wherein
alkylene and alkenylene at said $Alk^2$ are each optionally substituted hydroxy, carboxyl, alkoxycarbonyl, alkyl optionally substituted by hydroxy, alkoxy or alkylthio, or —$CONR^{13}R^{14}$ wherein $R^{13}$ and $R^{14}$ are the same or different and each is hydrogen atom or alkyl, or $R^{13}$ and $R^{14}$ optionally form heteroaryl together with the adjacent nitrogen atom;
R is an aryl, a heteroaryl, a cycloalkyl or a benzene-condensed cycloalkyl
wherein
said aryl and heteroaryl are each optionally substituted by alkyl optionally substituted by hydroxy, hydroxy, alkoxy, alkenyloxy, acyl, acyloxy, halogen atom, nitro, amino, sulfonamide, alkylamino, aralkyloxy, pyridyl, piperidino, carboxyl, alkoxycarbonyl, acylamino, aminocarbonyl or cyano, said cycloalkyl is optionally substituted by hydroxy, alkoxy or =O, and said benzene-condensed cycloalkyl is optionally substituted by hydroxy or alkoxy; and
p, q and r are each independently 0 or 1,
provided that
when p=1 and q=1, $Alk^1$ is —CH=CH—, Y is —$CONR^{10}$—, and $R^3$ and $R^{10}$ in combination optionally show —NHCO— to form a condensed ring with A ring, when p=0 and q=1, Y is —$CONR^{10}$— or —$CH_2NR^{10}$—, and $R^3$ and $R^{10}$ in combination optionally show —CH=CH—, —$CH_2CHR^{27}$—, —$CH_2$—, —S—, —CHOH—, —CO—, —$CH_2CO$—, —$NHCR^{28}(CH_2)_{v'}$—, —$NHCR^{29}R^{30}$— or —N=$CR^{31}$— to form a condensed ring with A ring
wherein
$R^{27}$ is hydrogen atom or hydroxy, $R^{28}$ is oxygen atom or sulfur atom, $R^{29}$ and $R^{30}$ are the same or different and each is alkyl, $R^{31}$ is allyl or hydrogen atom and v' is 0 or 1,
when r=0 and q=1, Y is —$CONR^{10}$— or —$CH_2NR^{10}$—, and R and $R^{10}$ optionally form heteroaryl together with the adjacent nitrogen atom, and
when p=q=r=0, R is a group of the formula (i)

(i)

wherein said group is optionally substituted by alkyl optionally substituted by hydroxy, hydroxy, alkoxy, alkenyloxy, acyl, acyloxy, halogen atom, nitro, amino, sulfonamide, alkylamino, aralkyloxy or pyridyl;
[hereinafter also referred to as Compound (I)], and a pharmaceutically acceptable salt thereof.
(2) A cannabinoid receptor activator or antagonist of (1) above, comprising, as an active ingredient, a compound of the formula (I)

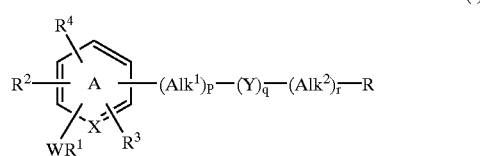

(I)

wherein
X is CH or N;
W is —O—, —$S(O)_t$—, —$CR^5R^6$—, —$NR^7$—, —$NR^7CO$— or —$CONR^7$—
wherein
$R^5$ and $R^6$ are the same or different and each is hydrogen atom or alkyl, $R^7$ is hydrogen atom or alkyl, and t is 0, 1 or 2;
$R^1$ is an alkyl, an alkenyl, an alkynyl, an arylalkyl or a cycloalkylalkyl
wherein
each group at $R^1$ is optionally substituted by alkyl, alkylamino or hydroxy;
$R^2$ is a hydrogen atom, an alkyl, —$OR^{15}$ wherein $R^{15}$ is hydrogen atom, alkyl, alkenyl, alkynyl, arylalkyl or cycloalkylalkyl, —$NR^8R^9$ wherein $R^8$ and $R^9$ are the same or different and each is hydrogen atom, alkyl or acyl, or —$(CH_2)_u,S(O)_uR^{12}$ wherein $R^{12}$ is alkyl, u is 0, 1 or 2 and u' is 0, 1 or 2
wherein
each group at said $R^2$ except hydrogen atom is optionally substituted by alkyl, alkylamino or hydroxy;
$R^3$ is a hydrogen atom, an alkoxy, an alkyl, an alkoxycarbonyl, a halogen atom or nitro, said alkyl being optionally substituted by hydroxy,
$R^4$ is a hydrogen atom, or $R^4$ and $R^2$ form, together with A ring, a condensed ring of the formula (II)

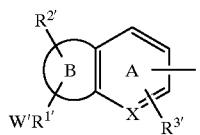

(II)

wherein W'R$^{1'}$, R$^{2'}$ and R$^{3'}$ are substituted at an optional position of A ring or B ring, W'R$^{1'}$, R$^{2'}$ and R$^{3'}$ are each as defined above for WR$^1$, R$^2$ and R$^3$, respectively, and B ring is a benzene ring or furan ring;

Alk$^1$ is —CH=CH— or —CH$_2$CH$_2$—;

Y is —CONR$^{10}$—, —NR$^{11}$CO—, —COO—, —CH$_2$NR$^{10}$— or —NHCONH— wherein

R$^{10}$ and R$^{11}$ are the same or different and each is hydrogen atom, alkyl, alkenyl or amino-protecting group, said alkyl being optionally substituted by heteroaryl, arylsulfinyl or alkoxycarbonyl, and said alkenyl being optionally substituted by phenylthio;

Alk$^2$ is an alkylene, an alkenylene, —COCH$_2$— or —CONH(CH$_2$)$_v$— wherein v is 0, 1 or 2 wherein alkylene and alkenylene at said Alk$^2$ are each optionally substituted hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl;

R is an aryl, a heteroaryl, a cycloalkyl or a benzene-condensed cycloalkyl wherein said aryl and heteroaryl are each optionally substituted by alkyl, hydroxy, alkoxy, alkenyloxy, acyloxy, halogen atom, nitro, amino, sulfonamide, alkylamino, aralkyloxy, piperidino, carboxyl, acylamino, aminocarbonyl or cyano, said cycloalkyl is optionally substituted by hydroxy or =O, and said benzene-condensed cycloalkyl is optionally substituted by hydroxy, and p, q and r are each independently 0 or 1, provided that when p=0 and q=1, Y is —CONR$^{10}$— or —CH$_2$NR$^{10}$—, and R$^3$ and R$^{10}$ in combination optionally show —CH=CH—, —CH$_2$CHR$^{27}$—, —CH$_2$—, —S—, —CHOH—, —CO—, —CH$_2$CO—, —NHCR$^{28}$(CH$_2$)$_{v'}$—, —NHCR$^{29}$R$^{30}$— or —N=CW$^{31}$— to form a condensed ring with A ring wherein R$^{27}$ is hydrogen atom or hydroxy, R$^{28}$ is oxygen atom or sulfur atom, R$^{29}$ and R$^{30}$ are the same or different and each is alkyl, R$^{31}$ is alkyl or hydrogen atom and v' is 0 or 1, when r=0 and q=1, Y is —CONR$^{10}$— or —CH$_2$NR$^{10}$—, and R and R$^{10}$ optionally form heteroaryl together with the adjacent nitrogen atom, and when p=q=r=O, R is a group of the formula (i)

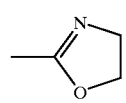

(i)

wherein said group is optionally substituted by alkyl or pyridyl; and a pharmaceutically acceptable salt thereof.

(3) A compound of the formula (Ia)

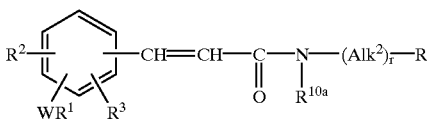

(Ia)

wherein

W is —O—, —S(O)$_t$—, —CR$^5$R$^6$—, —NR$^7$—, —NR$^7$CO—, —CONR$^7$—, —COO— or —OCO— wherein

R$^5$ and R$^6$ are the same or different and each is hydrogen atom or allyl, R$^7$ is hydrogen atom or allyl, and t is 0, 1 or 2;

R$^1$ is an alkyl, an alkenyl, an alkynyl, an aryl, an arylalkyl, a heteroaryl, a heteroarylalkyl, a cycloalkyl or a cycloalkylalkyl wherein each group at R$^1$ is optionally substituted by alkyl, alkylamino, amino, hydroxy, alkoxy, alkoxycarbonyl, acyl, acyloxy, acylthio, mercapto, allylthio, alkylsulfinyl or alkylsulfonyl;

R$^2$ is a hydrogen atom, an alkyl, —OR$^{15}$ wherein R$^{15}$ is hydrogen atom, alkyl, alkenyl, alkynyl, aryl, arylalkyl, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$,S(O)$_{u'}$R$^{12}$ wherein R$^{12}$ is hydrogen atom, alkyl, alkenyl or alkynyl, u is 0, 1 or 2 and u' is 0, 1 or 2 wherein each group at said R$^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;

R$^3$ is a hydrogen atom, an alkoxy, an alkyl, a carboxyl, an alkoxycarbonyl or a halogen atom, said alkyl being optionally substituted by alkoxy or hydroxy;

R$^{10a}$ is a hydrogen atom, an alkyl, an alkenyl or an amino-protecting group, said alkyl being optionally substituted by heteroaryl or arylsulfinyl;

Alk$^2$ is an alkylene, an alkenylene, —COCH$_2$— or —CONH(CH$_2$)$_v$— wherein v is 0, 1 or 2 wherein alkylene and alkenylene at said Alk$^2$ are each optionally substituted by hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl, or R$^{13}$ and R$^{14}$ optionally form heteroaryl together with the adjacent nitrogen atom;

R is an aryl, a heteroaryl, a cycloalkyl or a benzene-condensed cycloalkyl wherein said aryl and heteroaryl are each optionally substituted by alkyl optionally substituted by hydroxy, hydroxy, alkoxy, alkenyloxy, acyl, acyloxy, halogen atom, nitro, amino, sulfonamide, alkylamino, cyano, aralkyloxy or pyridyl, said cycloalkyl is optionally substituted by hydroxy, alkoxy or =O, and said benzene-condensed cycloalkyl is optionally substituted by hydroxy or alkoxy; and r is 0 or 1,
provided that when r=0, R and $R^{10a}$ optionally form heteroaryl together with the adjacent nitrogen atom;
[hereinafter also referred to as Compound (Ia)] and a pharmaceutically acceptable salt thereof.
(4) A compound of (3) above, which is represented by the formula (Ia)

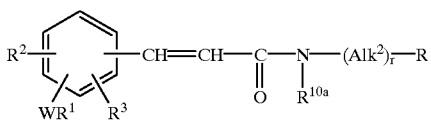

(Ia)

wherein
W is —O—, —S(O)$_t$—, —CR$^5$R$^6$— or —NR$^7$—
wherein
R$^5$ and R$^6$ are the same or different and each is hydrogen atom or alkyl, R$^7$ is hydrogen atom or alkyl, and t is 0, 1 or 2;
R$^1$ is an alkyl, an alkenyl, an alkynyl, an arylalkyl or a cycloalkylalkyl
wherein
each group at R$^1$ is optionally substituted by alkyl or alkylamino;
R$^2$ is a hydrogen atom, an alkyl, —OR$^{15}$ wherein R$^{15}$ is hydrogen atom, alkyl, alkenyl, alkynyl, arylalkyl or cycloalkylalkyl, —NR$^8$R$^9$ wherein R$^8$ and R$^9$ are the same or different and each is hydrogen atom or alkyl, or —(CH$_2$)$_u$, S(O)$_u$R$^{12}$ wherein R$^{12}$ is alkyl, u is 0, 1 or 2 and u' is 0, 1 or 2
wherein
each group at said R$^2$ except hydrogen atom is optionally substituted by alkyl or alkylamino;
R$^3$ is a hydrogen atom or an alkoxy,
R$^{10a}$ is a hydrogen atom or an alkyl, said alkyl being optionally substituted by heteroaryl;
Alk$^2$ is an alkylene
wherein
said alkylene is optionally substituted by alkoxycarbonyl, alkyl optionally substituted by hydroxy, or —CONR$^{13}$R$^{14}$ wherein R$^{13}$ and R$^{14}$ are the same or different and each is hydrogen atom or alkyl;
R is an aryl, a heteroaryl, a cycloalkyl or a benzene-condensed cycloalkyl
wherein
said aryl and heteroaryl are each optionally substituted by alkyl, hydroxy, alkoxy, alkenyloxy, acyloxy, halogen atom, nitro, amino, sulfonamide, alkylamino or cyano, said cycloalkyl is optionally substituted by hydroxy, and said benzene-condensed cycloalkyl is optionally substituted by hydroxy or alkoxy, and
r is 0 or 1,
provided that when r=0, R and R$^{10a}$ optionally form morpholino or imidazolyl together with the adjacent nitrogen atom;
and a pharmaceutically acceptable salt thereof.
(5) The compound of (4), wherein R$^3$ is hydrogen atom, R$^2$ is —OR$^{15}$, —NR$^8$R$^9$ or —(CH$_2$)$_u$S(O)$_u$R$^{12}$, and R$^2$ is substituted at the para position on the benzene ring and —WR$^1$ is substituted at the meta position on the benzene ring, both relative to the binding site of —CH=CH—CO—NR$^{10a}$—(Alk$^2$)$_r$—R on the benzene ring, and a pharmaceutically acceptable salt thereof.
(6) The compound of (5), wherein R$^1$ is alkyl having 4 to 6 carbon atoms, and a pharmaceutically acceptable salt thereof.

(7) The compound of (6), wherein Alk$^2$ is ethylene, and a pharmaceutically acceptable salt thereof.
(8) The compound of (4), wherein, when r=0, R and R$^{10a}$ form morpholino together with the adjacent nitrogen atom, and a pharmaceutically acceptable salt thereof.
(9) The compound of (7), which is selected from the group consisting of (E)-N-[2-(4-hydroxyphenyl)ethyl]-3-(4-methoxy-3-pentyloxyphenyl)-acrylamide, 3-(4-ethoxy-3-pentyloxyphenyl)-(E)-N-[2-(4-hydroxyphenyl)ethyl]-acrylamide, 3-(3,4dipentyloxyphenyl) -(E)-N-[2-(4-hydroxyphenyl)ethyl]acrylamide, (E)-N-[2-(4-hydroxyphenyl)ethyl]-3-(4-methoxy-3-butyloxyphenyl)-acrylamide, (E)-N-[2-(4-hydroxyphenyl)ethyl]-3-(4-methoxy-3-hexyloxyphenyl)-acrylamide, (E)-N-[2-(4-hydroxyphenyl)ethyl]-3-(4-methoxy-3-heptyloxyphenyl)-acrylamide, (E)-N-[2-(3-hydroxyphenyl)ethyl]-3-(4-methoxy-3-pentyloxyphenyl)-acrylamide, (E)-N-[2-(2-hydroxyphenyl)ethyl]-3-(4-methoxy-3-pentyloxyphenyl)-acrylamide, (E)-N-[2-(4-hydroxycyclohexyl)ethyl]-3-(4-methoxy-3-pentyloxyphenyl)-acrylamide, (E)-N-[2-(4-hydroxyphenyl)ethyl]-N-methyl-3-(4-methoxy-3-pentyloxyphenyl)acrylamide, (E)-N-[2-(4-hydroxyphenyl)ethyl]-3-(3-isopentyloxy-4-methoxyphenyl)-acrylamide, 3-[3-(2-ethylbutyloxy)-4-methoxyphenyl]-(E)-N-[2-(4-hydroxyphenyl)-ethyl]acrylamide, (E)-N-[2-(4-hydroxy-3-methoxyphenyl)ethyl]-3-(4-methoxy-3-pentyloxy-phenyl)acrylamide, 3-[3-(1,1-dimethylheptyl)-4-methoxyphenyl]-(E)-N-[2-(4-hydroxyphenyl)-ethyl]acrylamide, (E)-N-[2-(3,4-dihydroxyphenyl)ethyl]-3-[3-(1,1-dimethylheptyl)-4-methoxyphenyl]acrylamide, 3-(3-hexyl-4-methoxyphenyl)-(E)-N-[2-(4hydroxyphenyl)ethyl]acrylamide, (E)-N-(4-amino-3-pentyloxyphenyl)-N-[2-(4-hydroxyphenyl)ethyl]acrylamide, (E)-N-(4-amino-3-pentyloxyphenyl)-N-[2-(4-nitrophenyl)ethyl]acrylamide, 3-(4-methoxy-3-pentyloxyphenyl)-(E)-N-[2-(4-pentyloxyphenyl)ethyl]-acrylamide, (E)-N-[2-(4-methoxyphenyl)ethyl]-3-(4-methoxy-3-pentyloxyphenyl)-acrylamide, 3-(4-methoxy-3-pentyloxyphenyl)-(E)-N-(2-morpholinoethyl)acrylamide, (E)-N-[2-(3,4-dihydroxyphenyl)ethyl]-3-(4-methoxy-3-pentyloxyphenyl)-acrylamide, 2-[2-{3-(3-pentyloxy-4-methoxyphenyl)acryloylamino}ethyl]pyridine-N-oxide, (E)-N-[2-(4-hydroxyphenyl)ethyl]-3-(4-methoxy-3-pentylaminophenyl)-acrylamide, 3-[3-(N',N'-dipentylamino)-4-methoxyphenyl]-(E)-N-[2-(4-hydroxyphenyl)ethyl]acrylamide, (E)-N-[2-(4-hydroxyphenyl)ethyl]-3-(3-pentylamino-4-pentyloxyphenyl)-acrylamide, (E)-N-[2-(4-hydroxyphenyl)ethyl]-3-[3-(N'-methyl-N'-pentylamino)-4-methoxyphenyl]acrylamide, (E)-N-[2-(4-hydroxyphenyl)ethyl]-3-(4-methoxy-3-pentylthiophenyl)-acrylamide, (E)-N-[2-(4-hydroxyphenyl)ethyl]-3-(4-pentyloxy-3-pentylthiophenyl)-acrylamide, (E)-N-[2-(4-aminophenyl)ethyl]-3-(4-methoxy-3-pentyloxyphenyl)acrylamide, (E)-N-[2-(4-hydroxyphenyl)ethyl]-3-(3-pentyloxy-4-pentylthiophenyl)-acrylamide,
(E)-N-[2-(4-hydroxyphenyl)ethyl]-3-(3-pentyloxy-4-methylthiophenyl)-acrylamide,
(E)-N-[2-(4-aminophenyl)ethyl]-3-(4-methoxy-3-pentylthiophenyl)-acrylamide,
(E)-N-[2-(4-nitrophenyl)ethyl]-3-(4-methoxy-3-pentylthiophenyl)-acrylamide,
(E)-N-[2-(imidazol-4-yl)ethyl]-3-(4-methoxy-3-pentylthiophenyl)-acrylamide,
(E)-N-[2-(4-nitrophenyl)ethyl]-3-(4-methoxy-3-pentylaminophenyl)-acrylamide,
(E)-N-[2-(imidazol-4-yl)ethyl]-3-(4-methoxy-3-pentylaminophenyl)-acrylamide,
(E)-N-[2-(4-hydroxyphenyl)ethyl]-3-(4-methylamino-3-pentyloxy-phenyl)acrylamide,
(E)-N-[2-(4-aminophenyl)ethyl]-3-(4-methoxy-3-pentylaminophenyl)-acrylamide,
(E)-N-[2-(4-nitrophenyl)ethyl]-3-(4-methylamino3-pentyloxyphenyl)-acrylamide,
3-(4-methoxy-3-pentyloxyphenyl)-(E)-N-[2-(4-thiophen-2-yl)ethyl]-acrylamide,
(E)-N-[2-(4-hydroxyphenyl)ethyl]-3-[(N'-methyl-N'-pentylamino)-4-pentyloxyphenyl]acrylamide,
(E)-N-[2-(4-hydroxyphenyl)ethyl]-3-(4-pentylamino-3-pentyloxyphenyl)-acrylamide,
(E)-N-[2-(4-cyanophenyl)ethyl]-3-(4-methoxy-3-pentyloxyphenyl)-acrylamide and
(E)-N-[2-(4-carbamoylphenyl)ethyl]-3-(4-methoxy-3-pentyloxyphenyl)-acrylamide,
and a pharmaceutically acceptable salt thereof.
(10) A compound of the formula (Ib)

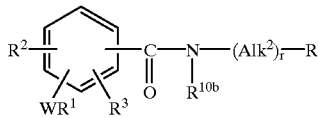

(Ib)

wherein
W is —O—, —S(O)$_t$—, —CR$^5$R$^6$—, —NR$^7$—, —NR$^7$CO—, —CONR$^7$—, —COO— or —OCO—
wherein
R$^5$ and R$^6$ are the same or different and each is hydrogen atom or alkyl, R$^7$ is hydrogen atom or alkyl, and t is 0, 1 or 2;
R$^1$ is an alkyl, an alkenyl, an alkynyl, an aryl, an arylalkyl, a heteroaryl, a heteroarylalkyl, a cycloalkyl or a cycloalkylalkyl
wherein
each group at R$^1$ is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
R$^2$ is a hydrogen atom, an alkyl, —OR$^{15}$ wherein R$^{15}$ is hydrogen atom, alkyl, alkenyl, alkynyl, aryl, arylalkyl, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$,S(O)$^u$R$^{12}$ wherein R$^{12}$ is hydrogen atom, alkyl, alkenyl or alkynyl, u is 0, 1 or 2 and u' is 0, 1 or 2
wherein
each group at said R$^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
R$^3$ is a hydrogen atom, an alkoxy, an alkyl, a carboxyl, an alkoxycarbonyl, nitro or a halogen atom, said alkyl being optionally substituted by alkoxy or hydroxy;
R$^{10b}$ is a hydrogen atom, an alkyl, an alkenyl or an amino-protecting group, said alkyl being optionally substituted by heteroaryl, arylsulfinyl or alkoxycarbonyl, and said alkenyl being optionally substituted by phenylthio;
Alk$^2$ is an alkylene, an alkenylene, —COCH$_2$— or —CONH(CH$_2$)$_v$— wherein vis 0, 1 or 2
wherein
alkylene and alkenylene at said AlK$^2$ are each optionally substituted by hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl, or R$^{13}$ and R$^{14}$ optionally form heteroaryl together with the adjacent nitrogen atom;
R is an aryl, a heteroaryl, a cycloalkyl or a benzene-condensed cycloalkyl
wherein
said aryl and heteroaryl are each optionally substituted by alkyl optionally substituted by hydroxy, hydroxy, alkoxy, alkenyloxy, acyl, acyloxy, halogen atom, nitro, amino, sulfonamide, alkylamino, aralkyloxy or pyridyl, said cycloalkyl is optionally substituted by hydroxy, alkoxy or =O, and said benzene-condensed cycloalkyl is optionally substituted by hydroxy or alkoxy, and
r is 0 or 1,
provided that when r=0, R and R$^{10b}$ optionally form heteroaryl together with the adjacent nitrogen atom;
[hereinafter also referred to as Compound (b)], and a pharmaceutically acceptable salt thereof.
(11) A compound of (10) above, which is represented by the formula (Ib)

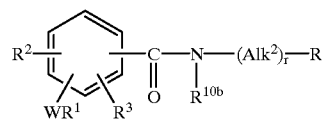

(Ib)

wherein
W is —O—, —S(O)$_t$—, —CR$^5$R$^6$—, —NR$^7$— or —NR$^7$CO—
wherein
R$^5$ and R$^6$ are the same or different and each is hydrogen atom or alkyl, R$^7$ is hydrogen atom or alkyl, and t is 0, 1 or 2;
R$^1$ is an alkyl, an alkenyl, an alkynyl, an arylalkyl or a cycloalkylalkyl
wherein
each group at R$^1$ is optionally substituted by alkyl, alkylamino or hydroxy;
R$^2$ is a hydrogen atom, an alkyl, —OR$^{15}$ wherein R$^{15}$ is hydrogen atom, alkyl, alkenyl, alkynyl, arylalkyl or cycloalkylalkyl, —NR$^8$R$^9$ wherein R$^8$ and R$^9$ are the same or different and each is hydrogen atom, alkyl or acyl, or —(CH$_2$)$_u$,S(O)$_u$R$^{12}$ wherein R$^{12}$ is alkyl, u is 0, 1 or 2 and u' is 0, 1 or 2
wherein
each group at said R$^2$ except hydrogen atom is optionally substituted by alkyl, alkylamino or hydroxy;
R$^3$ is a hydrogen atom, an alkoxy, an alkyl, a nitro or a halogen atom, said amyl being optionally substituted by hydroxy;

$R^{10b}$ is a hydrogen atom, an alkyl or an alkenyl, said alkyl being optionally substituted by heteroaryl, arylsulfinyl or alkoxycarbonyl, and said alkenyl being optionally substituted by phenylthio;

$Alk^2$ is an alkylene or an alkenylene
wherein
said alkylene and alkenylene are each optionally substituted by hydroxy, carboxyl, alkoxycarbonyl, alkyl optionally substituted by hydroxy, alkoxy or alkylthio, or —$CONR^{13}R^{14}$ wherein $R^{13}$ and $R^{14}$ are the same or different and each is hydrogen atom or alkyl;

R is an aryl, a heteroaryl, a cycloalkyl or a benzene-condensed cycloalkyl
wherein
said aryl and heteroaryl are each optionally substituted by alkyl, hydroxy, alkenyloxy, acyloxy, halogen atom, nitro, amino, sulfonamide, alkylamino or aralkyloxy, said cycloalkyl is optionally substituted by hydroxy, and said benzene-condensed cycloalkyl is optionally substituted by hydroxy; and r is 0 or 1,
provided that when r=0, R and $R^{10b}$ optionally form morpholino or imidazolyl together with the adjacent nitrogen atom;

and a pharmaceutically acceptable salt thereof.

(12) The compound of (11), wherein $R^3$ is hydrogen atom, $R^2$ is —$OR^{15}$, —$NR^8R^9$ or —$(CH_2)_u$$S(O)_u$$R^{12}$, and $R^2$ is substituted at the para-position on the benzene ring and —$WR^1$ is substituted at the meta-position on the benzene ring, both relative to the binding site of —CO—$NR^{10b}$—$(Alk^2)_x$—R on the benzene ring, and a pharmaceutically acceptable salt thereof.

(13) The compound of (12), wherein $R^1$ is alkyl having 4 to 6 carbon atoms, and a pharmaceutically acceptable salt thereof.

(14) The compound of (13), wherein $Alk^2$ is ethylene, and a pharmaceutically acceptable salt thereof.

(15) The compound of (14), which is selected from the group consisting of

N-[2-(4-hydroxyphenyl)ethyl]-4-methoxy-3-pentyloxybenzamide,
4-ethoxy-N-[2-(4-hydroxyphenyl)ethyl]-3-pentyloxybenzamide,
3,4-dipentyloxy-N-[2-(4-hydroxyphenyl)ethyl]benzamide,
4-dimethylamino-N-[2-(4-hydroxyphenyl)ethyl]-3-pentyloxybenzamide,
N-[2-(4-hydroxyphenyl)ethyl]-3-pentylamino-4-methoxybenzamide,
3-butyloxy-N-[2-(4-hydroxyphenyl)ethyl]-4-methoxybenzamide,
3-hexyloxy-N-[2-(4-hydroxyphenyl)ethyl]-4-methoxybenzamide,
3-heptyloxy-N-[2-(4-hydroxyphenyl)ethyl]-4-methoxybenzamide,
N-[2-(3-hydroxyphenyl)ethyl]-methoxy-3-pentyloxybenzamide,
N-[2-(2-hydroxyphenyl)ethyl]-4-methoxy-3-pentyloxybenzamide,
N-[2-(4-hydroxycyclohexyl)ethyl]-4-methoxy-3-pentyloxybenzamide,
N-[2-(4-hydroxyphenyl)ethyl]-N-methyl-4-methoxy-3-pentyloxybenzamide,
3-isopentyloxy-N-[2-(4-hydroxyphenyl)ethyl]-4-methoxybenzamide,
3-(2-ethylbutyloxy)-N-[2-(4-hydroxyphenyl)ethyl]-4-methoxybenzamide,
N-[2-(4-hydroxy-3-methoxyphenyl)ethyl]-4-hydroxy-3-pentyloxybenzamide,
N-[2-(4-hydroxyphenyl)ethyl]-hydroxy-3-pentyloxybenzamide,
N-[2-(4-hydroxyphenyl)ethyl]-4-hydroxy-N-methyl-3-pentyloxybenzamide,
3-(1,1-dimethylheptyl)-N-[2-(4-hydroxyphenyl)ethyl]-4-methoxybenzamide,
N-[2-(3,4-dihydroxyphenyl)ethyl]-3-(1,1-dimethylheptyl)-4-methoxybenzamide,
3-(1,1-dimethylheptyl)-N-[2-(4-hydroxy-3-methoxyphenyl)ethyl]-4-methoxybenzamide,
3-(1,1-dimethylheptyl)-N-[2-(4-hydroxyphenyl)ethyl]-4-hydroxybenzamide,
N-[2-(3,4-dihydroxyphenyl)ethyl]-3-(1,1-dimethylheptyl)-4-hydroxybenzamide,
3-hexyl-N-[2-(4-hydroxyphenyl)ethyl]-4-methoxybenzamide,
N-[2-(4-aminophenyl)ethyl]-3,4-dipentyloxybenzamide,
3,4-dihexyloxy-N-[2-(4-hydroxyphenyl)ethyl]benzamide,
4-methoxy-N-[2-(4-pentyloxyphenyl)ethyl]-3-pentyloxybenzamide,
4-methoxy-N-(2-morpholinoethyl)-3-pentyloxybenzamide,
4-methoxy-N-[2-(4-propen-2-yloxyphenyl)ethyl]-3-pentyloxybenzamide,
N-[2-(4-hydroxyphenyl)ethyl]-methoxy-N-[2-(phenylsulfinyl)ethyl]-3-pentyloxybenzamide,
N-[2-(3,4-dihydroxyphenyl)ethyl]-4-methoxy-3-pentyloxybenzamide,
N-[2-(4-acetoxyphenyl)ethyl]-4-methoxy-3-pentyloxy-N-(E)-phenylthiovinylbenzamide,
N-[2-(4-acetoxyphenyl)ethyl]-N-ethyl-4-methoxy-3-pentyloxybenzamide,
4-[2-{N-(4-methoxy-3-pentyloxybenzoyl)amino}ethyl]pyridine-N-oxide,
3-[2-{N-(4-methoxy-3-pentyloxybenzoyl)amino}ethyl]pyridine-N-oxide,
3-dipentylamino-N-[2-(4-hydroxyphenyl)ethyl]methoxybenzamide,
N-[2-(4-hydroxyphenyl)ethyl]-3-isohexyl-4-methoxybenzamide,
N-[2-(4-hydroxyphenyl)ethyl]-4-methoxy-3-(N'-methyl-N'-pentylamino)-benzamide,
N-[2-(4-hydroxyphenyl)ethyl]-3-pentylamino-4-pentyloxybenzamide,
N-[2-(4-hydroxyphenyl)ethyl]-4-pentylamino-3-pentyloxybenzamide,
3,4-dipentyloxy-N-[2-(4-sulfamoylphenyl)ethyl]benzamide,
3,4-dipentyloxy-N-[2-(imidazol-4-yl)ethyl]benzamide,
3,4-pentyloxy-N-[2-(4-nitrophenyl)ethyl]benzamide,
3,4-dipentyloxy-N-[2-(4-fluorophenyl)ethyl]benzamide,
N-[2-(4-hydroxyphenyl)ethyl]-3-pentyloxy-4-propen-2-ylbenzamide,
N-[2-(4-hydroxyphenyl)ethyl]-4-propyloxy-3-pentyloxybenzamide,
3,4-dibutyloxy-N-[2-(4-hydroxyphenyl)ethyl]benzamide,
3,4-diheptyloxy-N-[2-(4-hydroxyphenyl)ethyl]benzamide,
N-[2-(4-hydroxyphenyl)ethyl]-4-methylamino-3-pentyloxybenzamide,
N-[2-(4-hydroxyphenyl)ethyl]-3,4-dipentylaminobenzamide,
N-[2-(4-hydroxyphenyl)ethyl]-3-(N'-methyl-N'-pentylamino)-4-pentyloxybenzamide, 4-amino-N-[2-(4-hydroxyphenyl)ethyl]-3-pentyloxybenzamide,
N-[2-(4-hydroxyphenyl)ethyl]-4-methoxy-3-pentylthiobenzamide,
N-[2-(4-hydroxyphenyl)ethyl]-4-pentyloxy-3-pentylthiobenzamide,
3,4-dipentyloxy-N-[2-(2-thienyl)ethyl]benzamide,
3,4-dipentyloxy-N-[2-(5-hydroxyindol-3-yl)ethyl]benzamide,
3,4-dipentyloxy-N-[2-(4-methylamiophenyl)ethyl]benzamide,
N-[2-(4-dimethylamninophenyl)ethyl]-3,4-dipentyloxybenzamide,
4-butyrylamino-N-[2-(4-hydroxyphenyl)ethyl]-3-pentyloxybenzamide,
N-[2-(4-hydroxyphenyl)ethyl]-4-formylamino-3-pentylthiobenzamide,
N-[2-(4-hydroxyphenyl)ethyl]-4-methylthio-3-pentyloxybenzamide,
N-[2-(4-hydroxyphenyl)ethyl]-3-pentyloxy-4-pentylthiobenzamide,
N-[2-(4-hydroxyphenyl)ethyl]-3-(4-hydroxybutyloxy)-4-methoxybenzamide, N-[2-(4-aminophenyl)ethyl]-4-methoxy-3-pentylthiobenzamide,
4-methoxy-N-[2-(4-nitrophenyl)ethyl]-3-pentylthiobenzamide,
N-[2-(imidazol-4-yl)ethyl]-4-methoxy-3-pentylthiobenzamide,
N-[2-(4-aminophenyl)ethyl]-4pentyloxy-3-pentylthiobenzamide,
N-[2-(4-nitrophenyl)ethyl]-4-pentyloxy-3-pentylthiobenzamide and
N-[2-(imidazol-4-yl)ethyl]-4-pentyloxy-3-pentylthiobenzamide,
and a pharmaceutically acceptable salt thereof.

(16) A compound of the formula (Ic)

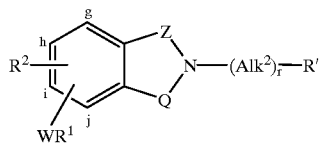

(Ic)

wherein
W is —O—, —S(O)$_t$—, —CR$^5$R$^6$—, —NR$^7$—, —NR$^7$CO—, —CONR$^7$—, —COO— or —OCO—
  wherein
  R$^5$ and R$^6$ are the same or different and each is hydrogen atom or alkyl, R$^7$ is hydrogen atom or alkyl, and t is 0, 1 or 2;
R$^1$ is an alkyl, an alkenyl, an allyl, an aryl, an arylalkyl, a heteroaryl, a heteroarylalkyl, a cycloalkyl or a cycloalkylalkyl
  wherein
    each group at R$^1$ is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
R$^2$ is a hydrogen atom, an alkyl, —OR$^{15}$ wherein R$^{15}$ is hydrogen atom, alkyl, alkenyl, alkynyl, aryl, arylalkyl, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$S(O)$_u$R$^{12}$ wherein R$^{12}$ is hydrogen atom, alkyl, alkenyl or alkynyl, u is 0, 1 or 2 and u' is 0, 1 or 2
  wherein
    each group at said R$^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
Z is —CH$_2$— or —CO—;
Q is —CH═CH—, —CH$_2$CHR$^{27}$—, —CH$_2$—, —S—, —CHOH—, —CO—, —CH$_2$CO—, —NHCR$^{28}$(CH$_2$)$_v$—, —NHCR$^{29}$R$^{30}$— or —N═CR$^{31}$—
  wherein
    R$^{27}$ is hydrogen atom or hydroxy, R$^{28}$ is oxygen atom or sulfur atom, R$^{29}$ and R$^{30}$ are the same or different and each is alkyl, R$^{31}$ is alkyl or hydrogen atom and v' is 0 or 1;
Alk$^2$ is an alkylene, an alkenylene, —COCH$_2$— or —CONH(CH$_2$)$_v$— wherein v is 0, 1 or 2
  wherein
    alkylene and alkenylene at said Alk$^2$ are each optionally substituted by hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl, or R$^{13}$ and R$^{14}$ optionally form heteroaryl together with the adjacent nitrogen atom;
R' is an aryl, a heteroaryl, a cycloalkyl or a benzene-condensed cycloalkyl
  wherein
    said aryl and heteroaryl are each optionally substituted by alkyl optionally substituted by hydroxy, hydroxy, alkoxy, alkenyloxy, acyl, acyloxy, halogen atom, nitro, amino, sulfonamide, alkylamino, aralkyloxy, acylamino, piperidino or pyridyl, said cycloalkyl is optionally substituted by hydroxy, alkoxy or =O, and said benzene-condensed cycloalkyl is optionally substituted by hydroxy or alkoxy; and
r is 0 or 1,
[hereinafter also referred to as Compound (Ic)], and a pharmaceutically acceptable salt thereof.

(17) A compound of (16) above, which is represented by the formula (Ic)

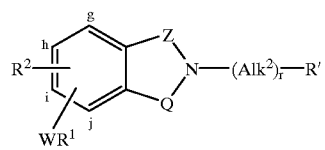

(Ic)

wherein
W is —O—, —S(O)$_t$—, —CR$^5$R$^6$—, —NR$^7$— or —NR$^7$CO—
  wherein
  R$^5$ and R$^6$ are the same or different and each is hydrogen atom or alkyl, R$^7$ is hydrogen atom or alkyl, and t is 0, 1 or 2;
R$^1$ is an alkyl;
R$^2$ is a hydrogen atom, an alkyl or —OR$^{15}$ wherein R$^{15}$ is hydrogen atom or alkyl;
Z is —CH$_2$— or —CO—;
Q is —CH═CH—, —CH$_2$CHR$^{27}$—, —CH$_2$—, —S—, —CHOH—, —CO—, —CH$_2$CO—, —NHCR$^{28}$(CH$_2$)$_v$—, —NHCR$^{29}$R$^{30}$— or —N═CR$^{31}$— wherein
R²⁷ is hydrogen atom or hydroxy, R²⁸ is oxygen atom or sulfur atom, R²⁹ and R³⁰ are the same or different and each is alkyl, R³¹ is alkyl or hydrogen atom and v' is 0 or 1;

Alk² is an alkylene, —COCH₂— or —CONH(CH₂)ᵥ—
wherein v is 0, 1 or 2;

R' is an aryl, a heteroaryl or a cycloalkyl
wherein
said aryl and heteroxryl are each optionally substituted by alkyl, hydroxy, acyloxy, nitro, amino, alkylamino, aralkyloxy, acylamino or piperidino, and said cycloalkyl is optionally substituted by =O;

r is 0 or 1,
and a pharmaceutically acceptable salt thereof.

(18) The compound of (17), wherein Z is —CO— and Q is —CH₂—, and a pharmaceutically acceptable salt thereof.

(19) The compound of (18), wherein R² is —OR¹⁵, W is —O—, —NR⁷— or —NR⁷CO—, R² is substituted at the i-position on the benzene ring, and —WR¹ is substituted at the j-position on the benzene ring, and a pharmaceutically acceptable salt thereof.

(20) The compound of (19), wherein R¹ is alkyl having 4 to 6 carbon atoms, and a pharmaceutically acceptable salt thereof.

(21) The compound of (20), which is selected from the group consisting of
2-[2-(4-hydroxyphenyl)ethyl]-5-methoxy-4-pentyloxy-2,3-dihydroisoindol-1-one,
2-[2-(4-benzyloxyphenyl)ethyl]-5-methoxy-4-pentyloxy-2,3-dihydroisoindol-1-one,
5-methoxy-2-[2-(4-nitrophenyl)ethyl]-4-pentyloxy-2,3-dihydroisoindol-1-one,
2-[2-(4-methylphenyl)ethyl]-5-methoxy-4-pentyloxy-2,3-dihydroisoindol-1-one,
4,5-dipentyloxy-2-[2-(imidazol-4-yl)ethyl]-2,3-dihydroisoindol-1-one,
2-[2-(4-benzyloxyphenyl)ethyl]-4,5-dipentyloxy-2,3-dihydroisoindol-1-one,
4,5-dipentyloxy-2-[2-(4-nitrophenyl)ethyl]-2,3-dihydroisoindol-1-one,
2-[2-(4-aminophenyl)ethyl]-4,5-dipentyloxy-2,3-dihydroisoindol-1-one,
4,5-dipentyloxy-2-[2-(4-hydroxyphenyl)ethyl]-2,3-dihydroisoindol-1-one,
4,5-dipentyloxy-2-[2-(4-methylaminophenyl)ethyl]-2,3-dihydroisoindol-1-one,
2-[2-(4-dimethylaminophenyl)ethyl]-4,5-dipentyloxy-2,3-dihydroisoindol-1-one,
2-[2-(4-aminophenyl)ethyl]-5-methoxy-4-pentyloxy-2,3-dihydroisoindol-1-one,
2-[2-(4-hydroxyphenyl)ethyl]-5-methoxy-4-pentylamino-2,3-dihydroisoindol-1-one,
5-methoxy-4-pentyloxy-2-[2-(4-pyridine)ethyl]-2,3-dihydroisoindol-1-one,
2-[2-(4-dimethylaminophenyl)ethyl]-5-methoxy-4-pentyloxy-2,3-dihydroisoindol-1-one and
5-methoxy-2-[2-(4-methylaminophenyl)ethyl]-4-pentyloxy-2,3-dihydroisoindol-1-one,
and a pharmaceutically acceptable salt thereof.

(22) The compound of (17), wherein Z is —CO— and Q is —CH=CH—, and a pharmaceutically acceptable salt thereof.

(23) The compound of (22), wherein R² is —OR¹⁵, W is —O—, —NR⁷— or —NR⁷CO—, R² is substituted at the i-position on the benzene ring, and —WR¹ is substituted at the j-position on the benzene ring, and a pharmaceutically acceptable salt thereof.

(24) The compound of (23), wherein R¹ is alkyl having 4 to 6 carbon atoms, and a pharmaceutically acceptable salt thereof.

(25) The compound of (24), which is selected from the group consisting of
2-[2-(4-benzyloxyphenyl)ethyl]-6-methoxy-5-pentyloxy-2H-isoquinolin-1-one,
2-[2-(4-hydroxyphenyl)ethyl]-6-methoxy-5-pentyloxy-2H-isoquinolin-1-one,
2-[2-(4-pyridyl)ethyl]-6-methoxy-5-pentyloxy-2H-isoquinolin-1-one,
4-[2-(6-methoxy-1-oxo-5-pentyloxy-1H-isoquinolin-2-yl)ethyl]phenyl acetate,
6-methoxy-2-[2-(4-nitrophenyl)ethyl]-5-pentyloxy-2H-isoquinolin-1-one,
2-[2-(4-methylphenyl)ethyl]-6-methoxy-5-pentyloxy-2H-isoquinolin-1-one,
6-methoxy-5-pentyloxy-2-(2-phenylethyl)-2H-isoquinolin-1-one,
2-[2-(4-acetylaminophenyl)ethyl]-6-methoxy-5-pentyloxy-2H-isoquinolin-1-one,
5,6-dipentyloxy-2-[2-(4-hydroxyphenyl)ethyl]-2H-isoquinolin-1-one,
2-[2-(4-aminophenyl)ethyl]-6-methoxy-5-pentyloxy-2H-isoquinolin-1-one,
2-[2-(4-aminophenyl)ethyl]-6-methoxy-5-pentyloxy-2H-isoquinolin-1-one hydrochloride,
2-[2-(4-dimethylaminophenyl)ethyl]-6-methoxy-5-pentyloxy-2H-isoquinolin-1-one,
2-[2-(4-methylaminophenyl)ethyl]-6-methoxy-5-pentyloxy-2H-isoquinolin-1-one,
6-methoxy-2-[2-(4-piperidinophenyl)ethyl]-5-pentyloxy-2H-isoquinolin-1-one and
6-methoxy-2-[2-(4-pyridyl)ethyl]-5-pentyloxy-2H-isoquinolin-1-one hydrochloride,
and a pharmaceutically acceptable salt thereof.

(26) The compound of (17), wherein Z is —CO— and Q is —CH₂CHR²⁷— wherein R²⁷ is hydrogen atom, and a pharmaceutically acceptable salt thereof.

(27) The compound of (26), wherein R² is —OR¹⁵, W is —O—, —NR⁷— or —NR⁷CO—, R² is substituted at the i-position on the benzene ring, and —WR¹ is substituted at the j-position on the benzene ring, and a pharmaceutically acceptable salt thereof.

(28) The compound of (27), wherein R¹ is alkyl having 4 to 6 carbon atoms, and a pharmaceutically acceptable salt thereof.

(29) The compound of (28), which is selected from the group consisting of
6-methoxy-2-[2-(4-oxocyclohexyl)ethyl]-5-pentyloxy-3,4-dihydro-2H-isoquinolin-1-one,
4-[2-(6-methoxy-1-oxo-5-pentyloxy-3,4-dihydro-1H-isoquinolin-2-yl)-ethyl]phenyl aceate,
2-[2-(4-hydroxyphenyl)ethyl]-6-methoxy-5-pentyloxy-3,4-dihydro-2H-isoquinolin-1-one,
2-(2-phenylethyl)-6-methoxy-5-pentyloxy-3,4-dihydro-2H-isoquinolin-1-one,
2-[2-(4-acetylaminophenyl)ethyl]-6-methoxy-5-pentyloxy-3,4-dihydro-2H-isoquinolin-1-one,
6-hydroxy-2-[2-(4-hydroxyphenyl)ethyl]-5-pentyloxy-3,4-dihydro-2H-isoquinolin-1-one,
2-[2-(4-methylphenyl)ethyl]-6-methoxy-5-pentyloxy-3,4dihydro-2H-isoquinolin-1-one,
2-[2-(4-aminophenyl)ethyl]-6-methoxy-5-pentyloxy-3,4-dihydro-2H-isoquinolin-1-one,
6-methoxy-5-pentyloxy-2-[2-(4-pyridyl)ethyl]-3,4-dihydro-2H-isoquinolin-1-one, 6-methoxy-1-oxo-5-pentyloxy-3,4-dihydro-1H-isoquinolin-2-carboxylic acid N-(4-aminophenyl)amide, 6-methoxy-1-oxo-5-pentyloxy-3,4-dihydro-1H-isoquinolin-2-carboxylic acid N-[(4-aminophenyl)methyl]amide and 6-methoxy-1-oxo-5-pentyloxy-3,4-dihydro-1H-isoquinolin-2-carboxylic acid N-(4-nitrophenyl)amide, and a pharmaceutically acceptable salt thereof.

(30) The compound of (17), wherein Z is —CO— and Q is —NHCR$^{28}$(CH$_2$)$_v$,— wherein R$^{28}$ is oxygen atom and v' is 0, and a pharmaceutically acceptable salt thereof.

(31) The compound of (30), wherein R$^2$ is —OR$^{15}$, W is —O—, —NR$^7$— or —NR$^7$CO—, R$^2$ is substituted at the i-position on the benzene ring, and —WR$^1$ is substituted at the j-position on the benzene ring, and a pharmaceutically acceptable salt thereof.

(32) The compound of (31), wherein R$^1$ is alkyl having 4 to 6 carbon atoms, and a pharmaceutically acceptable salt thereof.

(33) The compound of (32), which is selected from the group consisting of 7-methoxy-3-[2-(4-nitrophenyl)ethyl]-8-pentyloxy-(1H,3H)-quinazoline-2,4-dione, 7-methoxy-3-[2-(4-pyridyl)ethyl]-8-pentyloxy-(1H,3H)-quinazoline-2,4-dione, 3-[2-(4-aminophenyl)ethyl]-7-methoxy-8-pentyloxy-(1H,3H)-quinazoline-2,4-dione, 3-[2-(4-hydroxyphenyl)ethyl]-7-methoxy-8-pentyloxy-(1H,3H)-quinazoline-2,4-dione, 3-[2-(4-methylaminophenyl)ethyl]-7-methoxy-8-pentyloxy-(1H,3H)-quinazoline-2,4-dione and 3-[2-(4-dimethylaminophenyl)ethyl]-7-methoxy-8-pentyloxy-(1H,3H)-quinazoline-2,4-dione, and a pharmaceutically acceptable salt thereof.

(34) A compound of the formula (Id)

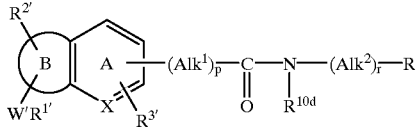

(Id)

wherein
X is CH or N;
W' is —O—,—S(O)$_t$—, —CR$^5$R$^6$—, —NR$^7$—, —NR$^7$CO—, —CONR$^7$—, —COO— or —OCO—
  wherein
  R$^5$ and R$^6$ are the same or different and each is hydrogen atom or alkyl, R$^7$ is hydrogen atom or alkyl, and t is 0, 1 or 2;
R$^{1'}$ is an alkyl, an alkenyl, an alkynyl, an aryl, an arylalkyl, a heteroaryl, a heteroarylalkyl, a cycloalkyl or a cycloalkylalkyl
  wherein
    each group at R$^{1'}$ is optionally substituted by alkyl, 1 alkylamino, amino, hydroxy, alkoxy, alkoxycarbonyl, acyl, acyloxy, acylthio, mercapto, alkylthio, alkylsulfinyl or alkylsulfonyl;
R$^{2'}$ is a hydrogen atom, an alkyl,—OR$^{15}$ wherein R$^{15}$ is hydrogen atom, alkyl, alkenyl, alkynyl, aryl, arylalkly, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$,S(O)$_u$ R$^{12}$ wherein R$^{12}$ is hydrogen atom, alkyl, alkenyl or alkynyl, u is 0, 1 or 2 and u' is 0, 1 or 2
  wherein
    each group at said R$^{2'}$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;
R$^{3'}$ is a hydrogen atom, an alkoxy, an alkyl, a carboxyl, an alkoxycarbonyl or a halogen atom, said alkyl being optionally substituted by alkoxy or hydroxy;
W'R$^{1'}$, R$^{2'}$ and R$^{3'}$ are substituted at an optional position of A ring or B ring, and B ring is a benzene ring, pyridine ring or furan ring,
Alk$^1$ is —CH═CH—, —CH$_2$CH$_2$— or —C≡C—;
R$^{10d}$ is a hydrogen atom, an alkyl, an alkenyl or an amino-protecting group, said alkyl being optionally substituted by heteroaryl or arylsulfinyl, and said alkenyl being optionally substituted by phenylthio;
Alk$^2$ is an alkylene, an alkenylene, —COCH$_2$— or —CONH(CH$_2$)$_v$— wherein v is 0, 1 or 2
  wherein
    alkylene and alkenylene at said Alk$^2$ are each optionally substituted by hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl, or R$^{13}$ and R$^{14}$ optionally form heteroaryl together with the adjacent nitrogen atom;
R is an aryl, a heteroaryl, a cycloalkyl or a benzene-condensed cycloalkyl
  wherein
    said aryl and heteroaryl are each optionally substituted by alkyl optionally substituted by hydroxy, hydroxy, alkoxy, alkenyloxy, acyl, acyloxy, halogen atom, nitro, amino, sulfonamide, alkylamino, aralkyloxy or pyridyl, said cycloalkyl is optionally substituted by hydroxy, alkoxy or =O, and said benzene-condensed cycloalkyl is optionally substituted by hydroxy or alkoxy; and
p and r are each independently 0 or 1,
  provided that when r=0, R and R$^{10d}$ optional form heteroaryl together with the adjacent nitrogen atom;

[hereinafter also referred to as Compound (Id)] and a pharmaceutically acceptable salt thereof.

(35) A compound of (34) above, which is represented by the formula (Id)

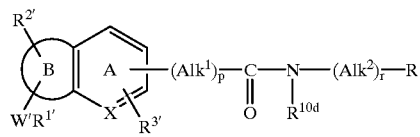

(Id)

wherein
X is CH or N;
W' is —O—,—S(O)$_t$—, —CR$^5$R$^6$—, —NR$^7$— or —NR$^7$CO—
  wherein
  R$^5$ and R$^6$ are the same or different and each is hydrogen atom or alkyl, R$^7$ is hydrogen atom or alkyl, and t is 0, 1 or 2;
R$^{1'}$ is an alkyl;
R$^{2'}$ is a hydrogen atom, an alkyl or —OR$^{15}$ wherein R$^{15}$ is hydrogen atom or alkyl;
R$^{3'}$ is a hydrogen atom or a halogen atom;

W'R$^{1'}$, R$^{2'}$ and R$^{3'}$ are substituted at an optional position of A ring or B ring, and B ring is a benzene ring or furan ring;

Alk$^1$ is —CH=CH— or —CH$_2$CH$_2$—;

R$^{10d}$ is a hydrogen atom;

Alk$^2$ is an alkylene;

R is an aryl or a heteroaryl wherein said aryl and heteroaryl are each optionally substituted by hydroxy, nitro or amino; and p and r are each independently 0 or 1, and a pharmaceutically acceptable salt thereof.

(36) The compound of (35), wherein X is N, and a pharmaceutically acceptable salt thereof.

(37) The compound of (36), wherein R$^{3'}$ is hydrogen atom, R$^{2'}$ is —OR$^{15}$, W is —O—, and a pharmaceutically acceptable salt thereof.

(38) The compound of (37), wherein R$^{1'}$ is alkyl having 4 to 6 carbon atoms, and a pharmaceutically acceptable salt thereof.

(39) The compound of (38), which is selected from the group consisting of 7-methoxy-8-pentyloxyquinoline-3-carboxylic acid N-[2-(4-pyridyl)-ethyl]amide, 7-methoxy-8-pentyloxyquinoline-3-carboxylic acid N-[2-(4-hydroxy-phenyl)ethyl]amide, 7-methoxy-8-pentyloxyquinoline-3-carboxylic acid N-[2-(4-aminophenyl)-ethyl]amide, 7-methoxy-8-pentyloxyquinoline-3-carboxylic acid N-[2-(4-nitrophenyl)-ethyl]amide and 7-methoxy-8-pentyloxyquinoline-3-carboxylic acid N-[2-(imidazol-4-yl)ethyl]amide, and a pharmaceutically acceptable salt thereof.

(40) A compound of the formula (Ie)

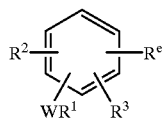

(Ie)

wherein

W is —O—, —S(O)$_t$—, —CR$^5$R$^6$—, —NR$^7$—, —NR$^7$CO—, —CONR$^7$—, —COO— or —OCO— wherein

R$^5$ and R$^6$ are the same or different and each is hydrogen atom or alkyl, R$^7$ is hydrogen atom or alkyl, and t is 0, 1 or 2;

R$^1$ is an alkyl, an alkenyl, an alkynyl, an aryl, an arylalkyl, a heteroaryl, a heteroarylalkyl, a cycloalkyl or a cycloalkylalkyl wherein each group at R$^1$ is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;

R$^2$ is a hydrogen atom, an alkyl, —OR$^{15}$ wherein R$^{15}$ is hydrogen atom, alkyl, alkenyl, alkynyl, aryl, arylalkyl, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$S(O)$_u$R$^{12}$ wherein R$^{12}$ is hydrogen atom, alkyl, alkenyl or alkynyl, u is 0, 1 or 2 and u' is 0, 1 or 2 wherein each group at said R$^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;

R$^3$ is a hydrogen atom, an alkoxy, an alkyl, a carboxyl, an alkoxycarbonyl or a halogen atom, said alkyl being optionally substituted by alkoxy or hydroxy; and R$^e$ is a group of the formula (i)

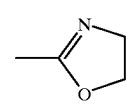

(i)

wherein said group is optionally substituted by alkyl optionally substituted by hydroxy, hydroxy, alkoxy, alkenyloxy, acyl, acyloxy, halogen atom, nitro, amino, sulfonamide, alkylamino, aralkyloxy or pyridyl,

[hereinafter also referred to as Compound (Ie)], and a pharmaceutically acceptable salt thereof.

(41) A compound of (40) above, which is represented by the formula (Ie)

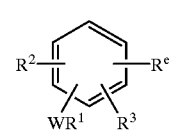

(Ie)

wherein

W is —O— or —S(O)$_t$— wherein t is 0, 1 or 2;

R$^1$ is an alkyl;

R$^2$ is a hydrogen atom, an alkyl,—OR$^{15}$ wherein R$^{15}$ is hydrogen atom or alkyl, or —(CH$_2$)$_u$S(O)$_u$R$^{12}$ wherein R$^{12}$ is alkyl, u is 0, 1 or 2 and u' is 0, 1 or2;

R$^3$ is a hydrogen atom, an alkoxy, an alkyl, an alkoxycarbonyl or a halogen atom, said alkyl being optionally substituted by hydroxy; and R$^e$ is a group of the formula (i)

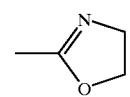

(i)

wherein said group is optionally substituted by alkyl or pyridyl, and a pharmaceutically acceptable salt thereof.

(42) The compound of (41), wherein R$^2$ is —OR$^{15}$, or —(CH$_2$)$_u$S(O)$_u$R$^{12}$, R$^2$ is substituted at the para-position on the benzene ring, and —WR$^1$ is substituted at the meta-position on the benzene ring, both relative to the binding site of R$^e$ on the benzene ring, and a pharmaceutically acceptable salt thereof.

(43) The compound of (42), wherein R$^{1'}$ is alkyl having 4 to 6 carbon atoms, and a pharmaceutically acceptable salt thereof.

(44) The compound of (43), which is selected from the group consisting of 2-(4-methoxy-3-pentyloxyphenyl)-4,4-dimethyl-4,5-dihydrooxazole, 2-(4-methoxy-3-pentylthiophenyl)-4,4-dimethyl-4,5-dihydrooxazole, 2-(3,4-dipentyloxyphenyl)-4,4-dimethyl-4,5-dihydrooxazole, 2-(4-methylthio-3-pentyloxyphenyl)-4,4-dimethyl4,5-dihydrooxazole,
2-(3-pentyloxy-4-pentylthiophenyl)-4,4-dimethyl-4,5-dihydrooxazole,
2-(4-pentyloxy-3-pentylthiophenyl)-4,4-dimethyl-4,5-dihydrooxazole and
2-(4-methoxy-3-pentyloxyphenyl)-5-(2-pyridyl)-4,5-dihydrooxazole,
and a pharmaceutically acceptable salt thereof.
(45) A pharmaceutical composition comprising, as an active ingredient, any one of the compounds of (3) to (44), or a pharmaceutically acceptable salt thereof.
(46) A cannabinoid receptor activator or antagonist of (1) or (2), wherein the cannabinoid receptor is a peripheral cannabinoid receptor.
(47) The cannabinoid receptor activator or antagonist of any one of (1), (2) and (46), which is an immunoregulator.
(48) The cannabinoid receptor activator or antagonist of any one of (1), (2) and (46), which is a therapeutic agent for autoimmune diseases.
(49) The cannabinoid receptor activator or antagonist of any one of (1), (2) and (46), which is an antiinflammatory agent.
(50) The cannabinoid receptor activator or antagonist of any one of (1), (2) and (46), which is an antiallergic agent
(51) The cannabinoid receptor activator or antagonist of any one of (1), (2) and (46), which is a therapeutic agent for nephritis.

The groups used in the present specification are explained in the following.

Alkyl may be linear or branched and exemplified by methyl, ethyl, propyl, isopropyl, butyl, isobutyl, s-butyl, t-butyl, pentyl, isopentyl, neopentyl, t-pentyl hexyl, isohexyl, neohexyl, heptyl and the like. The alkyl at $R^2$, $R^{2'}$, $R^3$, $R^{3'}$, $R^7$, $R^8$, $R^9$, $R^{12}$, $R^{15}$, $R^{29}$, $R^{30}$ and $R^{31}$ preferably has 1 to 7 carbon atoms; that at $R^{29}$, $R^{30}$ and $R^{31}$ more preferably has 1 or 2 carbon atoms; that at $R^2$ and $R^{2'}$ more preferably has 1 or 5 carbon atoms; that at $R^5$, $R^6$, $R^{10}$, $R^{10a}$, $R^{10b}$, $R^{10d}$, $R^{11}$, $R^{13}$ and $R^{14}$ preferably has 1 to 4 carbon atoms; and that at $R^1$ and $R^{1'}$ preferably has 4 to 6 carbon atoms.

The alkenyl may be linear or branched and is exemplified by vinyl, allyl, crotyl, 2-pentenyl, 3-pentenyl, 2-hexenyl, 3-hexenyl, heptenyl and the like. The alkenyl at $R^8$, $R^9$, $R^{12}$ and $R^{15}$ preferably has 2 to 7 carbon atoms; that at $R^{10}$, $R^{10a}$, $R^{10b}$, $R^{10d}$ and $R^{11}$ preferably has 2 to 4 carbon atoms; and that at $R^1$ and $R^{1'}$ preferably has 4 to 7 carbon atoms.

The alkynyl may be linear or branched and is exemplified by ethynyl, propynyl, butynyl, 2-pentynyl, 3-pentynyl, 2-hexynyl, 3-hexynyl, heptynyl and the like. The alkynyl at $R^8$, $R^9$, $R^{12}$ and $R^{15}$ preferably has 2 to 7 carbon atoms; and that at $R^1$ and $R^{1'}$ preferably has 4 to 7 carbon atoms.

The alkylene at $Alk^2$ may be linear or branched and preferably has 1 to 4 carbon atoms. Examples thereof include methylene, ethylene, trimethylene, tetramethylene and the like, with preference given to that having 2 carbon atoms.

The alkenylene at $Alk^2$ may be linear or branched and preferably has 2 to 4 carbon atoms. Examples thereof include vinylene, propenylene, butenylene and the like.

The alkoxy at $R^3$ and $R^{3'}$ may be linear or branched and preferably has 1 to 7 carbon atoms. Examples thereof include methoxy, ethoxy, propoxy, isopropoxy, butoxy, isobutoxy, s-butoxy, t-butoxy, pentyloxy, isopentyloxy, neopentyloxy, hexyloxy, heptyloxy and the like.

The alkoxycarbonyl at $R^3$ and $R^{3'}$ preferably has 2 to 5 carbon atoms, and is exemplified by the above-mentioned alkoxy having 1 to 4 carbon atoms plus carbonyl. Specific examples thereof include methoxycarbonyl, ethoxycarbonyl, propoxycarbonyl, butoxycarbonyl and the like.

The acyl at $R^8$ and $R^9$ preferably has 1 to 5 carbon atoms and is exemplified by formyl, acetyl, propionyl, butyryl, isobutyryl, valeryl, isovaleryl pivaloyl and the like.

The cycloalkyl is exemplified by cyclopropyl, cyclobutyl, cyclopentyl, cyclohexyl, cycloheptyl and the like. The cycloalkyl at $R^1$, $R^{1'}$, $R^8$, $R^9$ and $R^{15}$ preferably has 3 to 6 carbon atoms; and that at R preferably has 3 to 7 carbon atoms, and more preferably has 6 carbon atoms.

With regard to the cycloalkylalkyl at $R^1$, $R^{1'}$, $R^8$, $R^9$ and $R^{15}$, the cycloalkyl moiety is that exemplified above which has 3 to 6 carbon atoms, and the alkyl moiety is that exemplified above which has 1 to 4 carbon atoms. Specific examples include cyclopropylmethyl, cyclobutylmethyl, cyclopentylmethyl, cyclohexylmethyl, cyclopropylethyl, cyclopropylpropyl, cyclopropylbutyl and the like.

The aryl at $R^1$, $R^{1'}$, $R^8$, $R^9$, $R^{15}$ and R is exemplified by phenyl, naphthyl, biphenyl and the like, with preference given to phenyl.

With regard to the arylalkyl at $R^1$, $R^{1'}$, $R^8$, $R^9$ and $R^{15}$, the aryl moiety is that exemplified above and the alkyl moiety is that exemplified above which has 1 to 4 carbon atoms. Specific examples include benzyl, phenethyl, phenylpropyl, phenylbutyl, naphthylmethyl, biphenylmethyl and the like, with preference given to benzyl.

The heteroaryl at $R^1$, $R^{1'}$, $R^8$, $R^9$, $R^{15}$ and R may be saturated with hydrogen atom, and is exemplified by pyrimidyl, pirazinyl, pyridazinyl, pirazolyl, imidazolyl, thiazolyl, isothiazolyl, oxazolyl, isoxazolyl, tetrazolyl, thiadiazolyl, oxadiazolyl, triazinyl, triazolyl, thienyl, pyrrolyl, pyrrolinyl, furyl, azepinyl, benzopyranyl, benzothienyl, benzotriazolyl, indolyl, isoindolyl, quinolyl, isoquinolyl, cinnolinyl, phthalazinyl, quinazolinyl, quinoxalinyl, 1,8-naphthyridyl, 1,7-naphthyridyl 1,6-naphthyridyl, 1,5-naphthyridyl, pyrido[2,3-d]pyimidyl, thieno[2,3-b]pyridyl, pyrrolidinyl, imidazolidinyl, piperidyl, piperidino, piperazinyl, morpholino, hydroazepinyl, hydroindolyl, hydroisoindolyl, hydroquinolyl, hydroisoquinolyl and the like, with preference given to thienyl, imidazolyl and morpholino.

The heteroaryl at R' may be those exemplified above for heteroaryl and pyridyl, with preference given to pyridyl, thienyl, imidazolyl and morpholino.

The heteroaryl formed by $R^8$ and $R^9$ together with the adjacent nitrogen atom, the heteroaryl formed by $R^{13}$ and $R^{14}$ together with the adjacent nitrogen atom, and the heteroaryl formed by R and $R^{10}$ ($R^{10a}$, $R^{10b}$, $R^{10d}$) together with the adjacent nitrogen atom may be, of the above-mentioned heteroaryl, that having one or more nitrogen atoms. Specific examples include pyrrolidinyl, imidazoildinyl, piperidino, piperadinyl, morpholino, pyrazolyl, imidazolyl, tetrazolyl, triazolyl, pyrrolyl, pyrrolinyl, indolyl, hydroazepinyl, hydroindolyl, hydroisoindolyl, hydroquinolyl, hydroisoquinolyl and the like, with preference given to morpholino, piperidino, pyrrolidinyl and imidazolyl.

With regard to the heteroarylalkyl at $R^1$, $R^{1'}$, $R^8$, $R^9$ and $R^{15}$, the heteroaryl moiety is that exemplified above and the alkyl moiety is that exemplified above which has 1 to 4 carbon atoms. Specific examples include 2-thienylmethyl, 3-furylmethyl, 4-pyridylmethyl, 2-quinolylmethyl, 3-isoquinolylmethyl and the like, with preference given to 4-pyridylmethyl.

The benzene-condensed cycloalkyl at R is specifically tetrahydronaphthalene, indane and the like, with preference given to tetrahydronaphthalene.

The halogen atom at $R^3$ and $R^{3'}$ may be fluorine, chlorine, bromine or iodine.

The amino-protecting group at $R^{10}$, $R^{10a}$, $R^{10b}$, $R^{10d}$, and $R^{11}$ may be an optionally substituted aralkylidene such as benzylidene, 4-chlorobenzylidene, 4-nitrobenzylidene, salicylidene, α-naphthylidene, β-naphthylidene and the like;

an optionally substituted aralkyl such as benzyl, 4-methoxybenzyl, 3,4-dimethoxybenzyl, 2-nitrobenzyl, 4-nitrobenzyl, benzhydryl, bis(4-methoxyphenyl)methyl, trityl and the like;

an optionally substituted acyl such as formyl, acetyl, propionyl, butyryl, pivaloyl, 2-chloroacetyl, 2-bromoacetyl, 2-iodoacetyl, 2,2-dichloroacetyl, 2,2,2-trichloroacetyl, 2,2,2-trifluoroacetyl, phenylacetyl, phenoxyacetyl, benzoyl, 4-chlorobenzoyl, 4-methoxybenzoyl, 4-nitrobenzoyl, naphthylcarbonyl, adamantylcarbonyl and the like;

an optionally substituted alkoxycarbonyl such as methoxycarbonyl, ethoxycarbonyl, propoxycarbonyl, isopropoxycarbonyl, t-butoxycarbonyl, pentyloxycarbonyl, isopentyloxycarbonyl, cyclohexyloxycarbonyl, 2-chloroethoxycarbonyl, 2-iodoethoxycarbonyl, 2,2,2-trichloroethoxycarbonyl, 2,2,2-trichloro-t-butoxycarbonyl, benzhydryloxycarbonyl, bis-(4methoxyphenyl)methoxycarbonyl, phenacyloxycarbonyl, 2-trimethylsilylethoxycarbonyl, 2-triphenylsilylethoxycarbonyl, fluorenyl-9-methoxycarbonyl and the like;

an optionally substituted alkenyloxycarbonyl such as vinyloxycarbonyl, 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl, cinnamyloxycarbonyl and the like;

phenoxycarbonyl;

an optionally substituted aralkyloxycarbonyl such as benyloxycarbonyl, 4-bromobenzyloxycarbonyl, 2 chlorobenzyloxycarbonyl, 3-chlorobenzyloxycarbonyl, 3,5-dimethoxybenzyloxycarbonyl, 4-methoxybenzyloxycarbonyl, 2-nitrobenzyloxycarbonyl, 4-nitrobenzyloxycarbonyl, 2-nitro-4,5-dimethoxybenzyloxycarbonyl, 3,4,5-trimethoxybenzyloxycarbonyl, phenethyloxycarbonyl and the like;

an optionally substituted lower alkylsilyl such as trimethylsilyl, t-butyldimethylsilyl and the like;

an optionally substituted alkylthiocarbonyl such as methylthiocarbonyl, ethylthiocarbonyl, butylthiocarbonyl, t-butyltiocarbonyl and the like;

an optionally substituted aralkylthiocarbonyl such as benzylthiocarbonyl;

an optionally substituted phosphoryl such as dicyclohexylphosphoryl, diphenylphosphoryl, dibenzylphosphoryl, di-(4-nitrobenryl)phosphoryl, phenoxyphenylphosphoryl and the like; and an optionally substituted phosphinyl such as diethylphosphinyl, diphenylphosphinyl and the like. It may be phthaloyl where appropriate.

Preferred is aralkyloxycarbonyl and more preferred is benzyloxycarbonyl.

Each of the optionally substituted groups may be substituted by one or more substituents. The groups to be used as the substituents are explained in the following.

The alkyl may be that exemplified above which has 1 to 4 carbon atoms.

The alkoxy may be that exemplified above which has 1 to 4 carbon atoms.

The alkoxycarbonyl and halogen atom may be those exemplified above.

The heteroaryl may be those exemplified above for R'.

The alkylamino is that wherein the alkyl moiety is the above-mentioned alkyl having 1 to 4 carbon atoms. Specific examples of the alkylamino include methylamino, ethylamino, propylamino, butylamino, dimethylamino, diethylamino and the like.

The alkylthio is that wherein the alkyl moiety is the above-mentioned alkyl having 1 to 4 carbon atoms. Specific examples of the alkylthio include methylthio, ethylthio, propylthio, butylthio and the like.

The alkylsulfinyl is that wherein the alkyl moiety is the above-mentioned alkyl having 1 to 4 carbon atoms. Specific examples of the alkylsulfinyl include methylsulfinyl, ethylsulfinyl, propylsulfinyl, butylsufinyl and the like.

The alkylsulfonyl is that wherein the alkyl moiety is the above-mentioned alkyl having 1 to 4 carbon atoms. Specific examples of the alkylsulfonyl include methylsulfonyl, ethylsulfonyl, propylsulfonyl, butylsulfonyl and the like.

The alkenyloxy is that wherein the alkenyl moiety is the above-mentioned alkenyl having 2 to 4 carbon atoms. Specific examples of the alkenyloxy include ethenyloxy, propenyloxy, butenyloxy and the like.

The acyl may be those exemplified above which has 1 to 4 carbon atoms.

The acyloxy is that wherein the acyl moiety is the above-mentioned acyl having 1 to 4 carbon atoms. Specific examples of the acyloxy include formyloxy, acetyloxy, propionyloxy, butyryloxy, isobutyryloxy and the like, with preference given to acetyloxy.

The acylthio is that wherein the acyl moiety is the above-mentioned acyl having 1 to 4 carbon atoms. Specific examples of the acylthio include formylthio, acetylthio, propionylthio, butylylthio, isobutyrylthio and the like, with preference given to acetylthio.

The acylamino is that wherein the acyl moiety is the above-mentioned acyl having 1 to 4 carbon atoms. Specific examples of the acylamino include formylamino, acetylamino, propionylamino, butyrylamino and the like, with preference given to acetylamino.

The alkoxycarbonyl is that wherein the alkoxy moiety is the above-mentioned alkoxy having 1 to 4 carbon atoms. Specific examples of the alkoxycarbonyl include methoxycarbonyl, ethoxycarbonyl, propoxycarbonyl, butoxycarbonyl and the like, with preference given to ethoxycarbonyl.

The arylsulfinyl is that wherein the aryl moiety is the above-mentioned aryl. Specific examples of the arylsulfinyl include phenylsulfinyl, naphthylsulfinyl, biphenylsulfinyl and the like.

The aralkyloxy is that wherein the arylalkyl moiety is the above-mentioned arylalkyl. Specific examples of the aralkyloxy include benzyloxy, phenethyloxy, phenylpropyloxy, phenylbutyloxy, naphthylmethyloxy, biphenylmethyloxy and the like.

The pharmaceutically acceptable salts include, but not limited to, a metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The present invention encompasses various isomers of respective compounds, prodrugs and the like.

In the present invention, Compounds (Ia), (Ib), (Ic), (Id) and (Ie) are encompassed in Compound (I). These compounds are explained together as Compound (I) in the following.

While the Compound (I) can be produced as in the following, the production method is not limited to those exemplified below.

PRODUCTION METHOD 1

Compound of the formula (I) wherein q is 1 and Y is —$CONR^{10}$—

The present method comprises conversion of Compound (11) to an activated carboxylic acid derivative and reaction of the thus-obtained derivative with Compound (12) to give Compound (I-2).

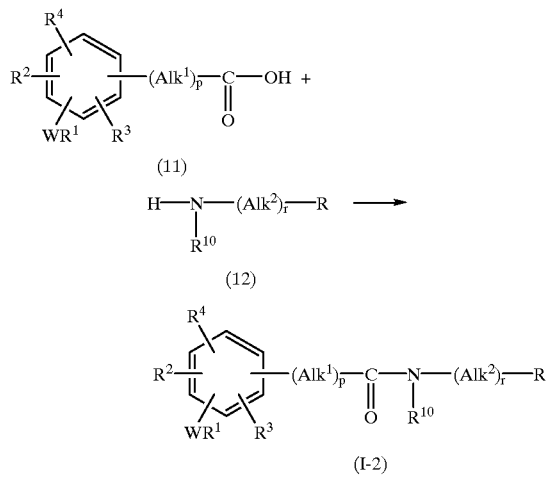

wherein each symbol is as defined above.

Examples of the activated carboxylic acid derivative include acid halides obtained by the treatment of the carboxylic acids with thionyl chloride, phosphorus oxychloride, phosphorus pentachloride, oxalyl chloride and the like; activated esters obtained by condensation of the carboxylic acids with N-hydroxybenzotriazole, N-hydroxysuccinimide and the like using a condensation agent such as dicyclohexylcarbodiimide (DCC), 1-ethyl-3-(3-dimethylaminopropyl)carbodimide (WSC) hydrochloride and the like; and mixed acid anhydrides obtained by reaction of the carboxylic acid with ethyl chlorocarbonate, pivaloyl chloride, isobutyl chlorocarbonate and the like. Active esters derived from acids by the treatment with N-hydroxybenzotriazole using a condensing agent such as WSC hydrochloride are preferably used.

In the above reactions, a base may be used if necessary.

As the base, usable are, for example, organic amines such as triethylamine, pyridine, N-methylmorpholine and the like, with preference given to triethylamine.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to dimethylformamide.

The reaction temperature is generally 0° C.–100° C., preferably 0° C.–30° C., and the reaction time is generally 15 min-24 hr, preferably 1–12 hr.

PRODUCTION METHOD 2

Compound of the formula (I) wherein q is 1 and Y is —$NR^{11}CO$—

The present method comprises conversion of Compound (14) to an activated carboxylic acid derivative and reaction of the thus-obtained derivative with Compound (13) in a suitable solvent in the presence of a suitable base to give Compound (I-3).

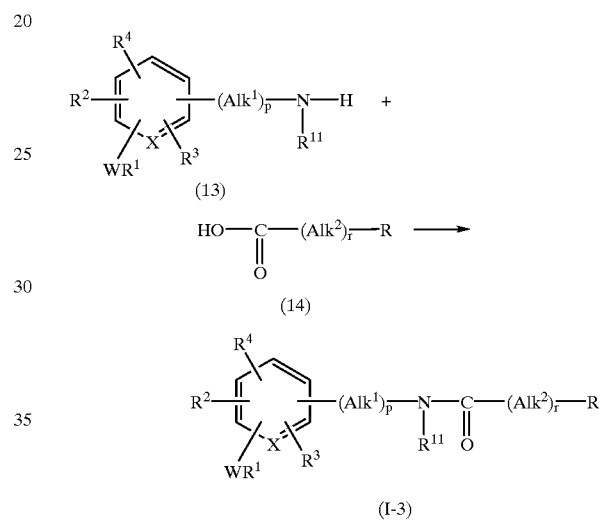

wherein each symbol is as defined above.

The activated carboxylic acid derivative, base, solvent and respective reaction temperature and time in the instant method are the same as those in Production Method 1.

PRODUCTION METHOD 3

Compound of the formula (I) wherein q is 1 and Y is —COO—

The present method comprises conversion of Compound (11) to activated carboxlic acid derivatives and reaction of the thus-obtained derivatives with Compound (15) to give Compound (I-4).

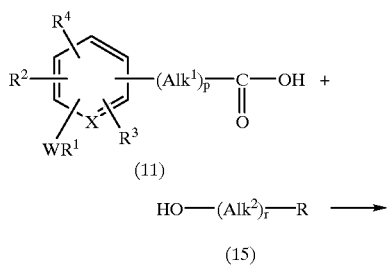

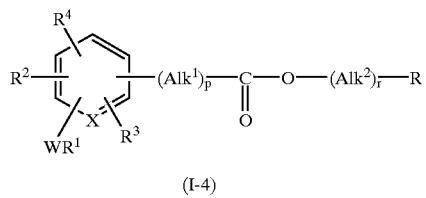

(I-4)

wherein each symbol is as defined above.

Examples of the activated carboxylic acid derivative include acid halides obtained by the treatment of the carboxylic acid with thionyl chloride, phosphorus oxychloride, phosphorus pentachloride, oxalyl chloride and the like; active esters obtained by the treatment of the carboxylic acid with N-hydroxybenzotriazole, N-hydroxysuccinimide and the like, in the presence of a condensation agent such as DCC, WSC hydrochloride and the like; and mixed acid anhydrides obtained by the treatment of the carboxylic acid with ethyl chlorocarbonate, pivaloyl chloride, isobutyl chlorocarbonate and the like. An active ester obtained by using a condensing agent such as WSC hydrochloride is preferably used.

In the above reaction, a base may be used if necessary.

The representative bases are, for example, organic amines such as triethylamine, pyridine, N-methylmorpholine and the like, with preference given to pyridine.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to the use of the above-mentioned base as a solvent.

The reaction temperature is generally 0° C.–100° C., preferably 0° C.–30° C., and the reaction time is generally 15 min-24 hr, preferably 1–12 hr.

Alternatively, Compound (I-4) is produced by the condensation of Compound (11) with Compound (15) by the action of acid catalysts.

The representative acid catalysts are, for example, a mineral acid such as hydrochloric acid, sulfuric acid, nitric acid and the like, or an organic acid such as acetic acid, methanesulfonic acid, p-toluenesulfonic acid and the like.

PRODUCTION METHOD 4

Compound of the formula (I) wherein q is 1 and Y is —CH$_2$NR$^{10}$—

The present method comprises reduction of Compound (I-2) obtained in Production Method 1, using a suitable reducing agent in a suitable solvent to give Compound (I-5).

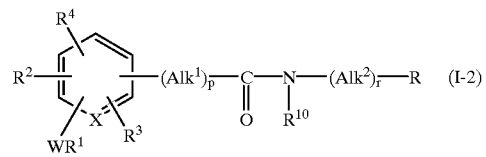

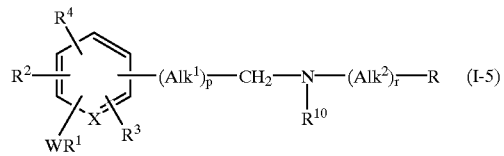

wherein each symbol is as defined above.

Examples of the reducing agents include, for example, LiAlH$_4$, LiBH$_4$, NABH$_4$, diisobutylaluminum hydride (PIBAL), reduced aluminum (Red-Al) and the like, with preference given to LiAlH$_4$.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to ether solvents which is more preferably tetrahydrofuran.

The reaction temperature is generally from −30° C. to 100° C., preferably 0° C.–50° C., and the reaction time is generally 15 min-24 hr, preferably 1–6 hr.

PRODUCTION METHOD 5

Compound of the formula (I) wherein q is 1 and Y is —NHCONH—

The present method comprises Curtius rearrangement of acid azide derived from Compound (11) and reaction of the thus-obtained isocyanate with Compound (25) to give Compound (I-6).

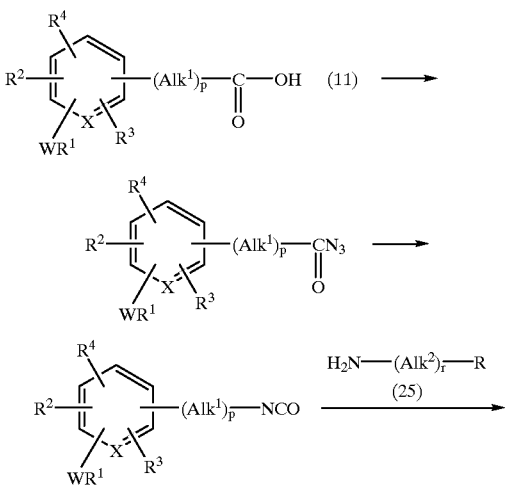

-continued

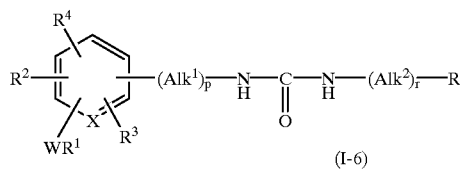

(I-6)

wherein each symbol is as defined above.

The Curtius rearrangement converts acyl azide to isocyanate by thermal rearrangement.

The acyl aside may be synthesized by ① a method wherein carboxylic acid is reacted with diphenylphosphoric azide in the presence of a base, ② a method wherein carboxylic acid is converted to hydrazide via ester and the thus-obtained hydrazide is reacted with nitrous acid or alkyl ester thereof, ③ a method wherein carboxylic acid is converted to acid chloride and the thus-obtained acid chloride is reacted with sodium aside, ④ a method wherein mixed acid anhydride is reacted with sodium azide, or other method.

As the base, exemplified are triethylamine, pyridine, potassium hydride, sodium hydride, N-methylmorpholine and the like, with preference given to triethylamine.

Examples of the solvent include hydrocarbon solvents such as benzene, toluene, hexane, xylene and the like; ether solvents such as diethyl ether, 1,2-dimethoxyethane, tetrahydrofuran, diglyme, dioxane and the like; and halogen solvents such as dichloromethane, chloroform, carbon tetrachloride, 1,2-dichloroethane and the like, with preference given to an ether solvent which is more preferably dioxane.

The reaction temperature is generally 0° C.–150° C., preferably 0° C.–80° C., and the reaction time is generally 15 min-6 hr, preferably 1–3 hr.

PRODUCTION METHOD 6

Compound of the formula (I) wherein p=q=r=0 and R is a group of the formula (i) which may be substituted by one or more substituent(s)

The compound wherein R is 4,4-dimethyl4,5-dihydrooxazolinyl is exemplified here.

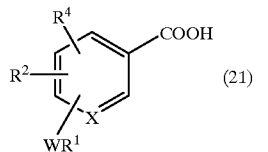

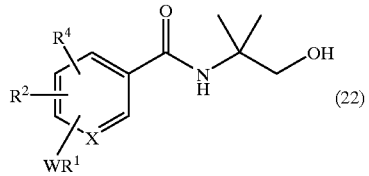

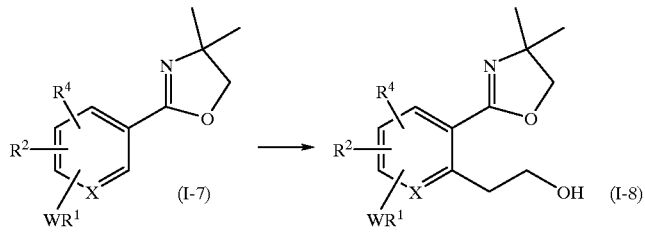

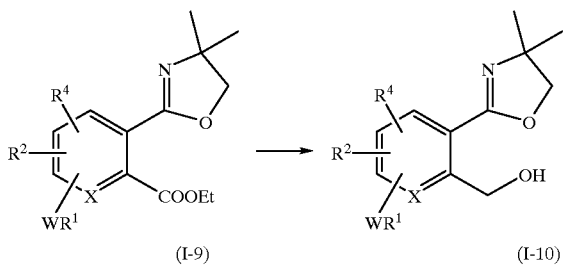

wherein each symbol is as defined above.

(1) According to the present method, Compound (21) is converted to the acid halide by thionyl halide, and the thus-obtained acid halide is then reacted with 2-amino-2-methylpropanol to give Compound (22).

Examples of thionyl halide include thionyl chloride, thionyl bromide and the like.

The instant step can be performed, besides conversion to acid halide, by using a suitable condensing agent.

Examples of the condensing agent include DCC, WSC hydrochloride, pivaloyl chloride, ethoxycarbonyl chloride and the like. As an additive, hydroxybenzotriazole (HOBT), N-hydroxysuccinimide (NBS), pyridine, triethylamine and the like may be used as appropriate upon selection.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the lie; and polar solvents such as dimethylformamide, dimethyl sulfoxide, acetonitrile, acetone and the like, with preference given to a halogen solvent which is more preferably dichloromethane.

The reaction temperature is generally 0° C.–100° C., preferably 0° C.–40° C., and the reaction time is generally 15 min-24 hr, preferably 1–6 hr.

(2) The Compound (22) obtained in (1) is reacted with a suitable dehydrating agent to give Compound (I-7).

Examples of the dehydrating agent include thionyl chloride, $POCl_3$, phosphorus pentachloride, diphosphorus pentaoxide, acetic anhydride, zinc chloride, titanium tetrachloride and the like, with preference given to thionyl chloride.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to the reaction without solvent.

The reaction temperature is generally 0° C.–100° C., preferably 10° C.–50° C., and the reaction time is generally 15 min-24 hr, preferably 1–6 hr.

(3) The Compound (I-7) obtained in (2) is treated with a suitable base and reacted with ethylene oxide to give Compound (I-8).

The base may be, for example, lithium diisopropylamide (LDA), n-butyllithium, s-butyllithium, t-butyllithium, lithium hexamethyldisilazane (LiHMDS), sodium hexamethyldisilazane (NaHMDS), potassium hexamethyldisilazane (KHMDS), sodium hydride, potassium hydride, EtMgBr, (i-Pr)$_2$NMgBr and the like, with preference given to n-butyllithium.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably 1,2-dimethoxyethane.

The reaction temperature is generally from –100° C. to 100° C., preferably from –100° C. to 0° C., and the reaction time is generally 15 min-24 hr, preferably 1–6 hr.

(4) The Compound (I-7) obtained in (2) is treated with a suitable base and reacted with a suitable carbonic acid ester to give Compound (I-9).

The base may be, for example, LDA, n-butyllithium, s-butyllithium, t-butyllithium, LiHMDS, NaHMDS, KHMDS, sodium hydride, potassium hydride, EtMgBr, (i-Pr)$_2$NMgBr and the like, with preference given to n-butyllithium.

The carbonic acid ester may be, for example, ethyl chlorocarbonate, diethyl carbonate and the like, with preference given to ethyl chlorocarbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably 1,2-dimethoxyethane.

The reaction temperature is generally from –100° C. to 100° C., preferably from –78° C. to 30° C., and the reaction time is generally 15 min-24 hr, preferably 1–6 hr.

(5) The Compound (I-9) obtained in (4) is reacted with a suitable reducing agent to give Compound (I-10).

Examples of the reducing agent include LiAlH$_4$, LiBH$_4$, NaBH$_4$, DIBAL, Red-Al and the like, with preference given to LiAlH$_4$.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably tetrahydrofuran.

The reaction temperature is generally –30° C.–100° C., preferably 0° C.–50° C., and the reaction time is generally 15 min-24 hr, preferably 1–6 hr.

33
PRODUCTION METHOD 7

Compound of the formula (I) wherein p=0, q=1, Y is —$CONR^{10}$— or —$CH_2NR^{10}$— and $R^3$ and $R^{10}$ in combination form a condensed ring together with A ring This production method is explained in the following Production Methods 7-1–7-6.

34
PRODUCTION METHOD 7-1

Compound of the formula (I) wherein p=0, q1, Y is —$CONR^{10}$— and $R^3$ and $R^{10}$ in combination form —$CH_2CH_2$—, —$CH_2$—, —CH=CH—, —CHOH— or —$CH_2CHOH$—

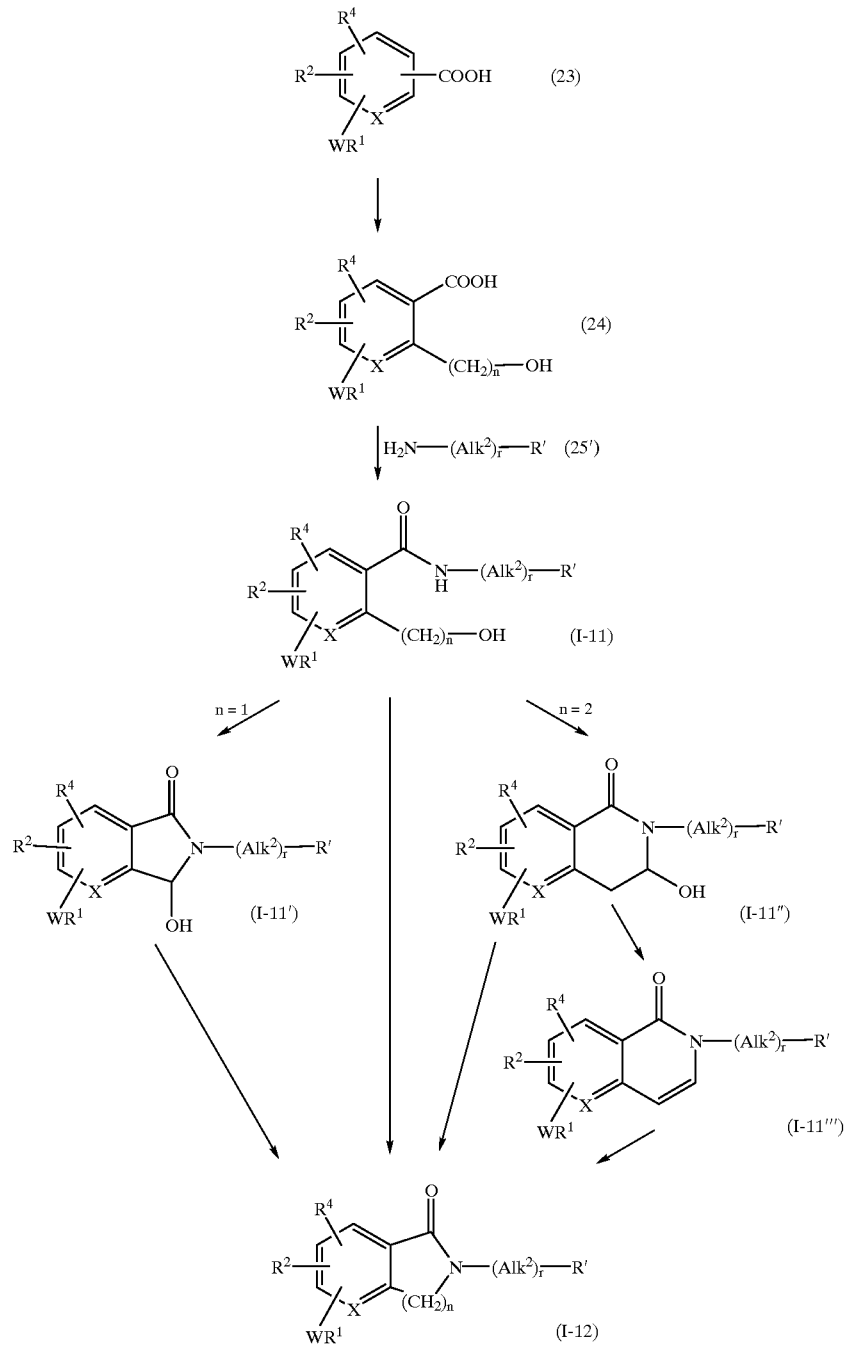

wherein n is 1 or 2 and other symbols are as defined above.
(1) According to this method, the carbon adjacent to the carbon bonded to the carboxyl group of Compound (23) is alkylated to give Compound (24).

The carboxylic acid is converted to oxazoline (I-7), treated with a suitable base and alkylated with ethylene oxide to give Compound (-8). The hydrolysis of the thus-obtained compound by a conventional method gives Compound (24) wherein n is 2.

When the Compound (I-7) is alkylated with a base and ethyl chlorocarbonate to give Compound (I-9), and this compound is treated with a suitable reducing reagent, Compound (I-10) is obtained. By hydrolysis of Compound (I-10) by a conventional method, Compound (24) wherein n is 1 is derived.

The reaction conditions are the same as those in Production Method 6, (3), (4) and (5).
(2) Then, Compound (24) is converted to an activated carboxylic acid derivative and condensed with Compound (251 to give Compound (I-11).

Examples of the activated carboxylic acid derivative include acid halides obtained by treatment of the carboxylic acid with thionyl chloride, phosphorus oxychioride, phosphorus pentachloride, oxalyl chloride and the like; active esters obtained by the treatment of the carboxylic acid with N-hydroxybenzotriazole, N-hydroxysuccinimide and the like, in the presence of a condensing agent such as DCC, WSC hydrochloride and the like; and mixed acid anhydrides obtained by the treatment of the carboxylic acid with ethyl chlorocarbonate, pivaloyl chloride, isobutyl chlorocarbonate and the like. An active ester derived from the carboxylic acid by the treatment with N-hydroxybenzotiazole and WSC hydrochloride as the condensing agent is preferably used.

In the above reaction, a base may be present as necessary.

As the base, usable are, for example, organic amine such as triethylamine, pyridine, N-methylmorpholine and the like, with preference given to triethylamine.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to dimethylformamide.

The reaction temperature is generally 0° C.–100° C., preferably 0° C.–30° C., and the reaction time is generally 15 min-24 hr, preferably 1–12 hr.
(3) The Compound (I-11) can be dehydrated to give Compound (I-12).

The dehydration is performed in the presence of an acid which is exemplified by Lewis acid such as aluminum chloride, tin chloride, zinc chloride, copper chloride, copper bromide, iron chloride, boron trifluoride-diethyl ether, titanium tetrachloride and the like; mineral acid such as hydrochloric acid, sulfuric acid, nitric acid and the like; and organic acid such as trifluoroacetic acid, trichloroacetic acid, acetic acid, methanesulfonic acid, p-toluenesulfonic acid and the like, with preference given to p-toluenesulfonic acid.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; and polar solvents such as dimethylformamide, dimethyl sulfoxide, acetonitrile, acetone and the like, with preference given to toluene.

The reaction temperature is generally 0° C.–200° C., preferably 60° C.–120° C., and the reaction time is generally 3–48 hr, preferably 6–12 hr.
(3) When the aforementioned dehydration using an acid catalyst does not proceed smoothly, the hydroxyl group of the 2-position alkyl of Compound (I-11) may be oxidized to give an animal (I-11' when n is 1) or an animal (I-11" when n is 2). A following reduction of the thus-obtained animal with a suitable reducing agent gives Compound (I-12).

An electrophile for oxidation may be, for example, acetic anhydride, trfluoroacetic anhydride, sulfur trioxide-pyridine complex ($SO_3$—Py), diphosphorus pentaoxide, $(COCl)_2$ and the like, with preference given to $SO_3$—Py.

In addition, an additive such as dimethyl sulfoxide, triethylamine and the like may be used. Moreover, a chromic oxidizing agent such as pyridinium chlorochromate (PCC), pyridinium dichromate (PDC) and the like may be used.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to dimethyl sulfoxide.

The reaction temperature is generally −78° C.–30° C., preferably 10° C.–20° C., and the reaction time is generally 15 min-24 hr, preferably 1–3 hr.

Examples of the reducing reagent include sodium borohydride, sodium cyanoborohydride, lithium borohydride, triethylsilane, trimethylsilane, diphenylsilane, phenylsilane, trichlorosilane, trimethylsilane and the like, with preference given to triethylsilane.

The reduction may be carried out in the presence of a suitable acid. Examples of the acid include trifluoroacetic acid, trichloroacetic acid, acetic acid, methanesulfonic acid, p-toluenesulfonic acid and the like, with preference given to trifluoroacetic acid.

The reaction temperature is generally from −10° C. to 100° C., preferably 0° C.–30° C., and the reaction time is generally 15 min-48 hr, preferably 30 min-3 hr.

This reduction may be also performed by catalytic hydrogenation.
(3") In the above-mentioned case wherein n is 2, animal (I-11") is treated with an acid in a solvent and dehydrated to give Compound (I-11") which is one of the objective compounds. The Compound (I-11''') is successively reduced in a suitable solvent to give Compound (I-12) wherein n is 2.

The acid to be used in the above-mentioned dehydration is exemplified by Lewis acid such as aluminum chloride, tin chloride, zinc chloride, copper chloride, copper bromide, iron chloride, boron trifluoride-diethyl ether, titanium tetrachloride and the like; mineral acid such as hydrochloric acid, sulfuric acid, nitric acid and the like;
and organic acid such as trifluoroacetic acid, trichloroacetic acid, acetic acid, methanesulfonic acid, p-toluenesulfonic acid and the like, with preference given to hydrochloric acid.

Examples of the solvent include hydrocarbon solvents such as benzene, toluene, hexane, xylene and the like; ether solvents such as diethyl ether, 1,2-dimethoxyethane, tetrahydrofuran, diglyme and the like;
halogen solvents such as dichloromethane, chloroform, carbon tetrachloride, 1,2-dichloroethane and the like; and polar solvents such as dimethylformamide, dimethyl sulfoxide, acetonitrile, acetone and the like, with preference given to chloroform.

The reaction temperature is generally 0° C.–200° C., preferably 60° C.–120° C., and the reaction time is generally 3–48 hr, preferably 6–12 hr.

The reduction catalyst to be used in the above-mentioned reduction may be, for example, palladium-carbon, palladium hydroxide-carbon, Raney nickel and the like, which is preferably palladium-carbon.

Examples of the suitable solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, acetonitrile, acetone and the like; alcohol solvents such as methanol, ethanol and the like; and acids such as hydrochloric acid, acetic acid and the like, with preference given to acetic acid.

The reaction is performed under high pressure conditions in a hydrogen atmosphere, which is generally 1–4 kgf/cm², preferably 3 kgf/cm².

The reaction temperature is generally 0° C.–100° C., preferably 50° C.–60° C., and the reaction time is generally 1–48 hr, preferably 1–20 hr.

PRODUCTION METHOD 7-2

Compound of the formula (I) wherein p=0, q=1, Y is —CONR$^{10}$— and R$^3$ and R$^{10}$ in combination show —CO— and form a condensed ring with A ring

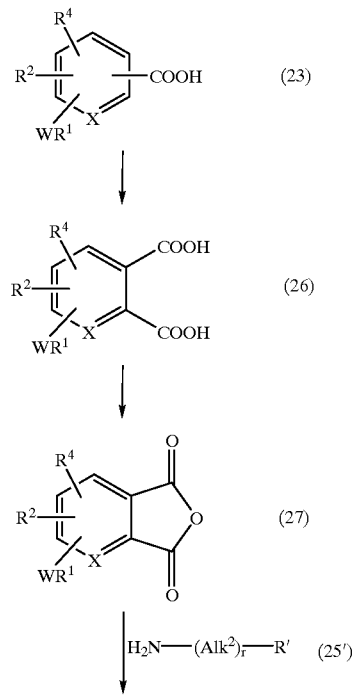

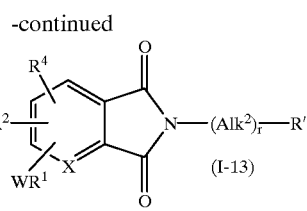

wherein each symbol is as defined above.

(1) In the same manner as in Production Method 7-1, the carbon adjacent to the carbon bearing carboxyl group of Compound (23) is acylated to give Compound (26).

The acylating agent may be, for example, ethyl chlorocarbonate, carbon dioxide and the like, with preference given to ethyl chlorocarbonate.

When oxazoline is used as a carboxylic acid equivalent, carboxylic acid can be regenerated by a conventional method after acylation.

(2) The Compound (26) obtained in (1) can be converted to Compound (27) by a conventional method.

(3) The Compound (27) obtained in (2) is subjected to thermal dehydration condensation with Compound (25') to give Compound (I-13).

Examples of the solvent include hydrocarbon solvents such as benzene, toluene, hexane, xylene and the like; ether solvents such as diethyl ether, 1,2-dimethoxyethane, tetahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropyl alcohol, t-butanol and the like, with preference given to toluene.

The reaction temperature is generally 0° C.–200° C., preferably 100° C.–130° C., and the reaction time is generally 15 min-24 hr, preferably 1–6 hr.

PRODUCTION METHOD 7-3

Compound of the formula (I) wherein p=0, q=1, Y is —CONR$^{10}$— and R$^3$ and R$^{10}$ in combination show —S— and form a condensed ring with A ring

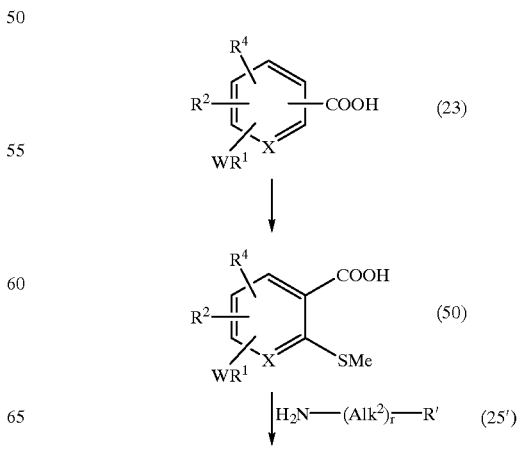

-continued

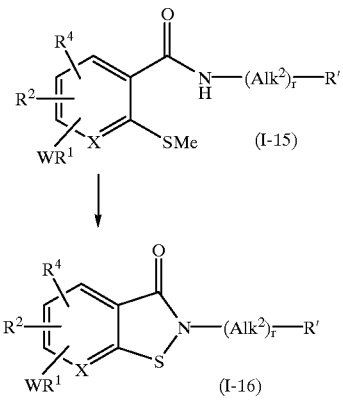

wherein each symbol is as defined above.

(1) With this procedure, in the ring, methylthio group is introduced into the carbon adjacent to the carbon bearing carboxyl group of Compound (23) to give Compound (50).

When, for example, carboxylic acid is converted to oxazoline (I-7) and oxazoline (I-7) is treated with a suitable base and reacted with dialkylsulfide, Compound (50) is obtained. When oxazoline is used as a carboxylic acid equivalent, carboxylic acid can be regenerated by a conventional method after introduction of methylthio group.

The base to be used may be, for example, LDA, n-butyllithium, s-butyllithium, t-butyllithium, LiHMDS, NaHMDS, KHMDS, sodium hydride, potassium hydride, EtMgBr, (i-Pr)$_2$NMgBr and the like, with preference given to n-butyllithium.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably 1,2-dimethoxyethane.

(2) Then, Compound (50) is converted to an activated carboxylic acid derivative and condensed with Compound (25') to give Compound (I-15).

Examples of the activated carboxylic acid derivative include acid halides obtained by treatment of the carboxylic acid with thionyl chloride, phosphorus oxychloride, phosphorus pentachloride, oxalyl chloride and the like; active esters obtained by condensation of the carboxylic acid with N-hydroxybenzotriazole, N-hydroxysuccinimide and the like using a condensing agent such as DCC, WSC hydrochloride and the like; and mixed acid anhydrides obtained by reaction of the the carboxylic acid with ethyl chlorocarbonate, pivaloyl chloride, isobutyl chlorocarbonate and the like. An active ester obtained by condensation of the carboxylic acid with N-hydroxybenzotriazole using WSC hydrochloride as a condensing agent is preferably used.

In the above reaction, a base may be present as necessary.

As the base, usable are, for example, organic amine such as triethylamine, pyridine, N-methylmorpholine and the like, with preference given to triethylamine.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to dimethylformamide.

The reaction temperature is generally 0° C.–100° C., preferably 0° C.–30° C., and the reaction time is generally 15 min-24 hr, preferably 1–12 hr.

(3) The Compound (I-15) is cyclized in the presence of N-chlorosuccinimide to give Compound (I-16).

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to dichloromethane.

The reaction temperature is generally 0° C.–200° C., preferably 0° C.–30° C., and the reaction time is generally 3–48 hr, preferably 6–12 hr.

PRODUCTION METHOD 7-4

Compound of the formula (I) wherein p=0, q=1, Y is —CONR$^{10}$— and R$^3$ and R$^{10}$ in combination show —NHCR$^{28}$—, —NHCR$^{29}$R$^{30}$— or —N=CR$^{31}$— and form a condensed ring with A ring

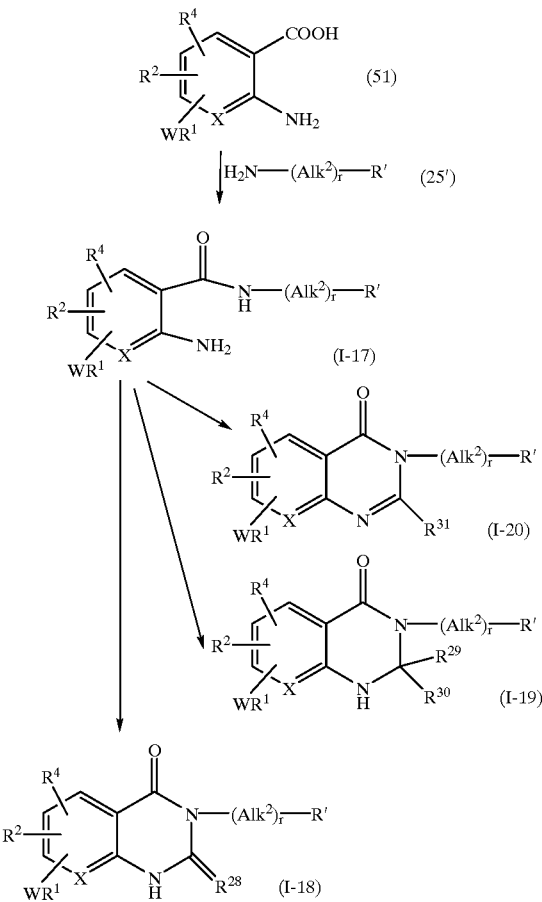

wherein each symbol is as defined above.

(1) The activated carboxylic acid derivative (51) is condensed with Compound (25') to give Compound (I-17).

Examples of the activated carboxylic acid derivative include acid halides obtained by treatment of the carboxylic acids with thionyl chloride, phosphorus oxychloride, phosphorus pentachloride, oxalyl chloride and the like; activated esters obtained by condensation of the carboxylic acids with N-hydroxybenzotriazole, N-hydroxysuccinimide and the like using a condensation agent such as DCC, WSC hydrochloride and the like; and mixed acid anhydrides obtained by the reaction of the carboxylic acid with ethyl chlorocarbonate, pivaloyl chloride, isobutyl chlorocarbonate and the like. Active esters derived from the carboxylic acid by treatment with N-hydroxybenzotriazole and WSC hydrochloride as a condensing agent is preferably used.

In the above reactions, a base may be used if necessary.

As the base, usable are, for example, organic amines such as triethylamine, pyridine, N-methylmorpholine and the like, with preference given to triethylamine.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone and the like, with preference given to dimethylformamide.

The reaction temperature is generally 0° C.–100° C., preferably 0° C.–30° C., and the reaction time is generally 15 min-24 hr, preferably 1–12 hr.

(2) Then Compound (I-17) can be converted to Compound (I-18), Compound (I-19) or Compound (I-20) by condensing with a carbon unit compound in the presence of an acid.

The carbon unit compound is, for example, triphosgene when $R^{28}$ in Compound (I-18) is oxygen atom, and carbon disulfide when $R^{28}$ is sulfur atom. It is acetone when $R^{29}$ and $R^{30}$ in Compound (I-19) are both methyl, dimethylformamide dimethylacetal when $R^{31}$ in Compound (I-20) is hydrogen atom, and acetylacetone when $R^{31}$ is methyl.

Examples of the acid include Lewis acid such as aluminum chloride, tin chloride, zinc chloride, copper chloride, copper bromide, iron chloride, boron trifluoride-diethyl ether, titanium tetrachloride and the like; mineral acid such as hydrochloric acid, sulfuric acid, nitric acid and the like; and organic acid such as trifluoroacetic acid, trichloroacetic acid, acetic acid, methanesulfonic acid, p-toluenesulfonic acid and the like, with preference given to hydrochloric acid.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; and polar solvents such as dimethylformamide, dimethyl sulfoxide, acetonitrile, acetone and the like, with preference given to chloroform.

The reaction temperature is generally 0° C.–200° C., preferably from room temperature to 100° C., and the reaction time is generally 3–48 hr, preferably 6–12 hr.

PRODUCTION METHOD 7-5

Compound of the formula U) wherein p=0, q=1, Y is —CONR$^{10}$— and $R^3$ and $R^{10}$ in combination show —CH$_2$CO— or —CH=CH— and form a condensed ring with A ring

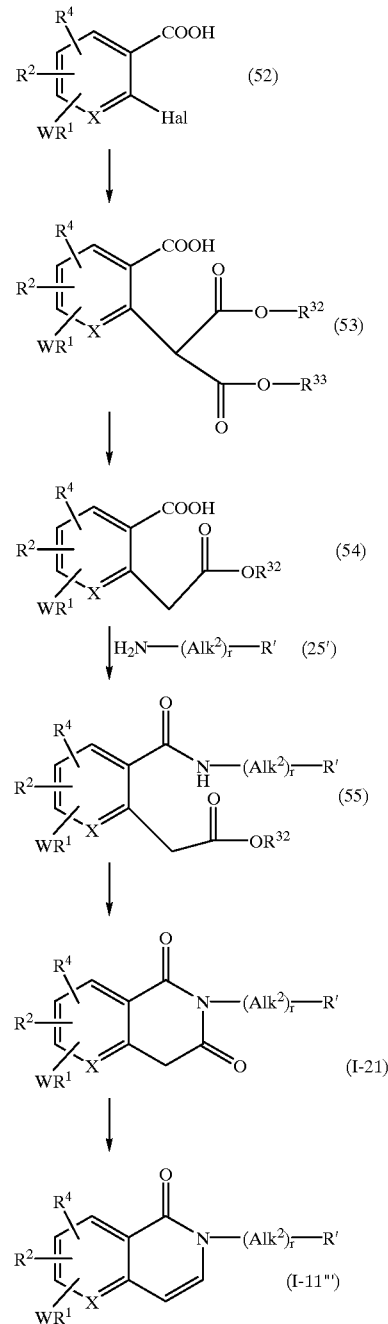

wherein Hal is halogen atom, $R^{32}$ and $R^{33}$ are the same or different and each is al having 1 to 6 carbon atoms or benzyl and other symbols are as defined above.

(1) The Compound (52) is reacted with an activated ester compound in a suitable solvent in the presence of a metallic catalyst to give Compound (53).

Examples of the solvent include hydrocarbon solvents such as benzene, toluene, hexane, xylene and the like; and ether solvents such as diethyl ether, 1,2dimethoxyethane, tetrahydrofuran, diglyme and the like, with preference given to toluene.

The metallic catalyst is exemplified by copper halide and the like, which is preferably copper bromide.

The activated ester can be formed by mixing alkyl malonate and the like with a suitable base.

A suitable base in this case is, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to sodium hydride.

The reaction temperature is generally from $-10°$ C. to $200°$ C., preferably $0°$ C.–$100°$ C., and the reaction time is generally 15 min48 hr, preferably 30 min-3 hr.

(2) The Compound (53) is decarboxylated in a suitable solvent in the presence of a salt to give Compound (54).

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; and polar solvents such as dimethylformamide, dimethyl sulfoxide, acetonitrile, acetone, water and the like, with preference given to a polar solvent which is more preferably a mixed solvent of water and dimethyl sulfoxide.

Examples of the salt include sodium chloride, sodium cyanide, lithium fluoride, lithium chloride, lithium iodide, lithium carbonate, potassium bromide, potassium chloride, potassium iodide, potassium cyanide, magnesium chloride and the like.

The reaction temperature is generally from $0°$ C. to $300°$ C., preferably $100°$ C.–$200°$ C., and the reaction time is generally 15 min-24 hr, preferably 30 min-3 hr.

(3) Using Compound (54) and Compound (25'), Compound (55) can be obtained in the same manner as in Production Method 7-1(2) by amide condensation.

(4) The Compound (55) is cyclized in a suitable solvent in the presence of a base to give Compound (I-21).

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; and alcohol solvents such as methanol, ethanol, isopropyl alcohol, t-butanol and the like, with preference given to an alcohol solvent which is more preferably ethanol.

A suitable base is, for example, sodium carbonate, potassium carbonate, lithium carbonate, sodium hydrogencarbonate, potassium hydrogencarbonate, potassium hydroxide, lithium hydroxide, sodium methoxide, sodium ethoxide, potassium t-butoxide and the like, with preference given to sodium ethoxide.

The reaction temperature is generally $0°$ C.–$200°$ C., preferably $0°$ C.–$150°$ C., and the reaction time is generally 15 min-24 hr, preferably 30 min-3 hr.

(5) The Compound (I-21) is reduced and dehydrated to give Compound (I-11''').

Examples of the reducing agent include $LiAlH_4$, $LiBH_4$, $NaBH_4$, DIBAL, Red-Al and the like, with preference given to $LiAlH_4$.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably tetrahydrofuran.

The reaction temperature is generally $-30°$ C.–$100°$ C., preferably $0°$ C.–$50°$ C., and the reaction time is generally 15 min-24 hr, preferably 1–6 hr.

PRODUCTION METHOD 7-6

Compound of the formula (I) wherein p=0, q=1, Y is —$CONR^{10}$— and $R^3$ and $R^{10}$ in combination form —$NHCOCH_2$—

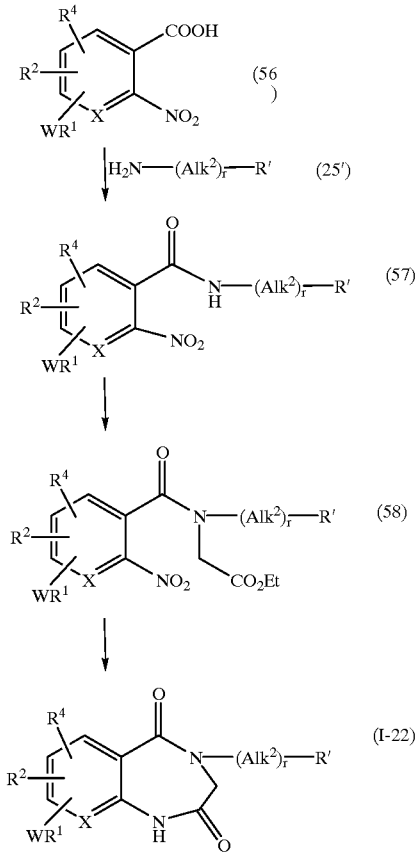

wherein each symbol is as defined above.

(1) Using Compound (56) and Compound (25'), Compound (57) can be obtained in the same manner as in Production Method 7-1(2) by amide condensation.

(2) The Compound (57) is alkylated at the amide group with ethyl haloacetate such as ethyl bromoacetate in the presence of a base to give Compound (58).

A suitable base is, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to sodium hydride.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2- dichloroethane and the like; ester solvents such as ethyl acetate, methyl acetate, butyl acetate and the like; and polar solvents such as dimethylformamide, dimethyl sulfoxide, acetonitrile, acetone and the like, with preference given to tetrahydrofuran.

The reaction temperature is generally from −10° C. to 200° C., preferably 0° C.–100° C., and the reaction time is generally 15 min-48 hr, preferably 1–8 hr.

(3) The Compound (58) is converted to Compound (I-22) by reduction of nitro group by a conventional method followed by cyclization.

The cyclization is performed in the presence of an acid which is exemplified by Lewis acid such as aluminum chloride, tin chloride, zinc chloride, copper chloride, copper bromide, iron chloride, boron trifluoride-diethyl ether, titanium tetrachloride and the like; mineral acid such as hydrochloric acid, sulfuric acid, nitric acid and the like; and organic acid such as trifluoroacetic acid, trichloroacetic acid, acetic acid, methanesulfonic acid, p-toluenesulfonic acid and the like, with preference given to p-toluenesulfonic acid.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; and polar solvents such as dimethylformamide, dimethyl sulfoxide, acetonitrile, acetone and the like, with preference given to toluene.

The reaction temperature is generally 0° C.–200° C., preferably 60° C.–120° C., and the reaction time is generally 3–48 hr, preferably 6–12 hr.

PRODUCTION METHOD 8

Compound of the formula (I) wherein r=0, q=1, Y is —$CONR^{10}$— or —$CH_2NR^{10}$— and R and $R^{10}$ in combination form heteroamyl together with the adjacent nitrogen atom The compound of the formula (I) wherein r=0, q=1, Y is —$CONR^{10}$— and R and $R^{10}$ in combination form morpholino together with the adjacent nitrogen atom is exemplified here.

The present method comprises converting Compound (11) to an activated carboxylic acid derivative and reacting the derivative with morpholine in a suitable solvent in the presence of a base to give Compound (I-14).

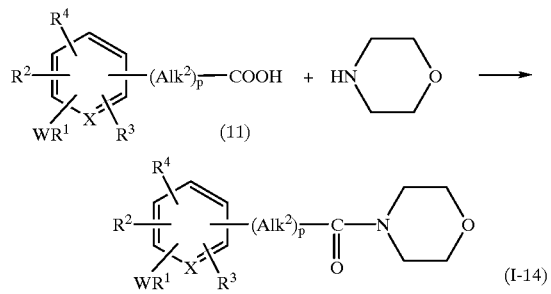

wherein each symbol is as defined above.

The activated carboxylic acid derivative, base, solvent and respective conditions of reaction temperature and reaction time in the instant method are the same as in Production Method 1.

The compound wherein R and $R^{10}$ in combination form other heteroaryl together with the adjacent nitrogen atom can be synthesized in the same manner as above except that the heteroaryl ring is used instead of morpholine as the starting compound.

The compound wherein Y is —$CH_2NR^{10}$— can be synthesized by reducing the compound wherein Y is —$CONR^{10}$— according to Production Method 4.

While Production Methods 1–8 have been explained in the above, a compound wherein $R^2$ and $R^4$ in combination form a condensed ring of the formula (II) with the A ring in the above Production Method can be synthesized in the same manner as in the above Production Method except that a compound having the condensed ring is used as a starting compound.

The Compound (11) to be used as the starting compound in Production Method 1 can be obtained, for example, as in the following Production Methods 1-A to 1-F.

PRODUCTION METHOD 1-A

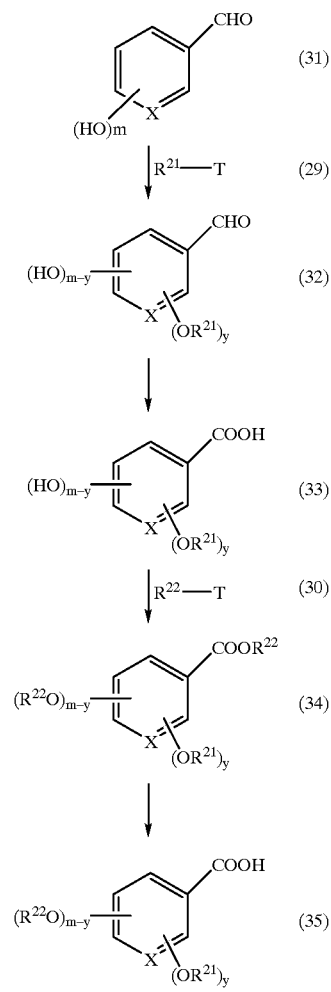

wherein $R^{21}$ and $R^{22}$ are each the same as those shown with regard to $R^1$, T is halogen atom, m and y are each 1, 2 or 3 and m-y≧0.

(1) Using Compound (31) as the starting material, the hydroxyl group is subjected to etherification with Compound (29) in the presence of a base to give Compound (32).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to lithium carbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropyl alcohol, t-butanol and the like, with preference given to dimethylformamide.

The reaction temperature is generally from −10° C. to 200° C., preferably 0° C.–60° C., and the reaction time is generally 15 min-48 hr, preferably 1–8 hr.

(2) Then, the Compound (32) obtained in (1) is oxidized to give Compound (33).

The oxidizing agent to be used is exemplified by $NaClO_2$, $CrO_3$, $K_2Cr_2O_7$, $KMnO_4$ and the like.

As an additive, $NaHPO_4$, $KHPO_4$, amylene and the like may be used as appropriate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone, acetic acid, water and the like; and alcohol solvents such as methanol, ethanol, isopropyl alcohol, t-butanol and the like, with preference given to t-butanol.

(3) Then, the Compound (33) obtained in (2) is subjected to etherification with Compound (30) in the presence of a base to give Compound (34).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to potassium carbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropyl alcohol, t-butanol and the like, with preference given to dimethylformamide.

The reaction temperature is generally from −10° C. to 200° C., preferably 0° C.–60° C., and the reaction time is generally 15 min-48 hr, preferably 1–8 hr.

(4) The Compound (34) obtained in (3) is hydrolzed in the presence of a base by a conventional method to give Compound (35).

PRODUCTION METHOD 1-B

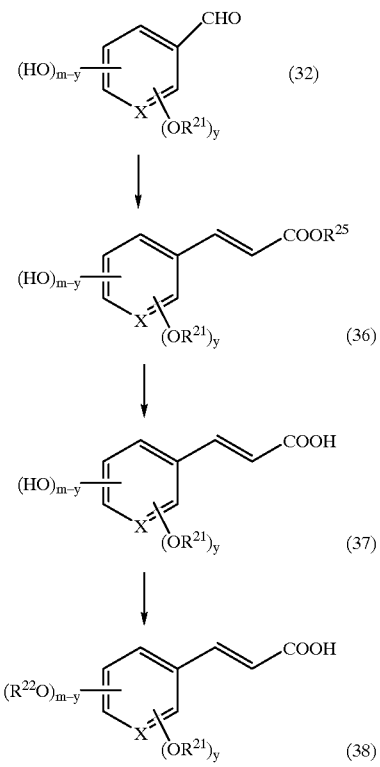

wherein $R^{25}$ is alkyl having 1 to 6 carbon atoms and other symbols are as defined above.

(1) The Compound (32) obtained in Production Method 1-A(l) is subjected to Wittig reaction to give Compound (36).

Examples of Wittig reagent include methyl (triphenylphosphoranylidene)acetate, ethyl (triphenylphosphoranylidene)acetate, and the like, preferably methyl (triphenylphosphoranylidene)acetate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone, acetic acid, water and the like; and alcohol solvents such as methanol, ethanol, isopropyl alcohol, t-butanol and the like, with preference given to an ether solvent which is more preferably tetrahydrofuran.

The reaction temperature is generally 0° C.–100° C., preferably 0° C.–70° C., and the reaction time is generally 15 min- 12 hr, preferably 30 min-3 hr.

(2) Then, the Compound (36) obtained in (1) is hydrolyzed in the presence of a base to give Compound (37).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to lithium carbonate.

(3) The Compound (37) obtained in (2) is reacted in the same manner as in Production Method 1-A(3) and (4) to give Compound (38).

PRODUCTION METHOD 1-C

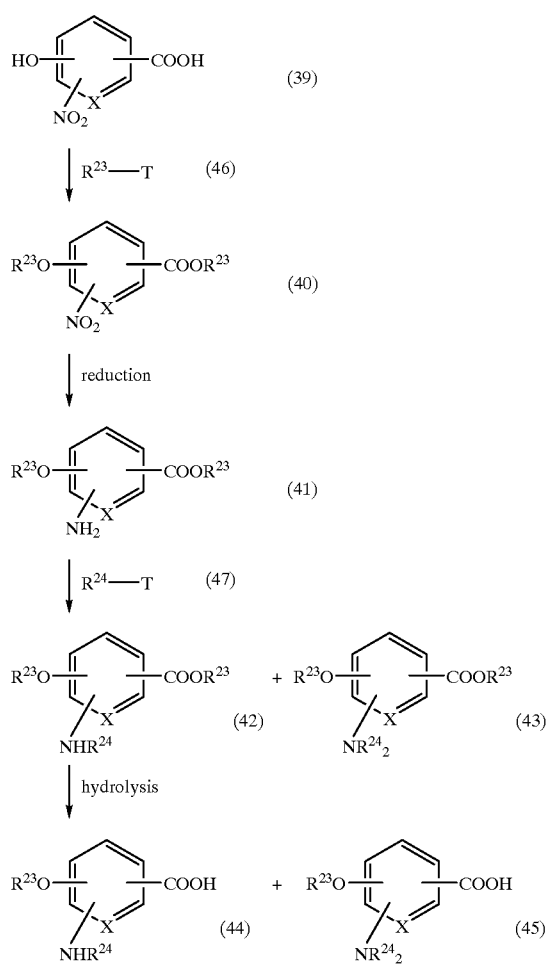

wherein $R^{23}$ and $R^{24}$ are each the same as those shown with regard to $R^1$ and other symbols are as defined above.

The Compound (39) is reacted with Compound (46) to give Compound (40). Then, Compound (40) is reduced by a conventional method to give Compound (41). Further, Compound (41) is reacted with Compound (47) to give Compound (42) and Compound (43). Then, Compound (42) and Compound (43) are hydrolyzed to give Compound (44) and Compound (45).

The reagent and conditions of the aforementioned reactions and the like are the same as those in Production Method 1-A.

PRODUCTION METHOD 1-D

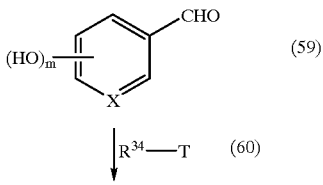

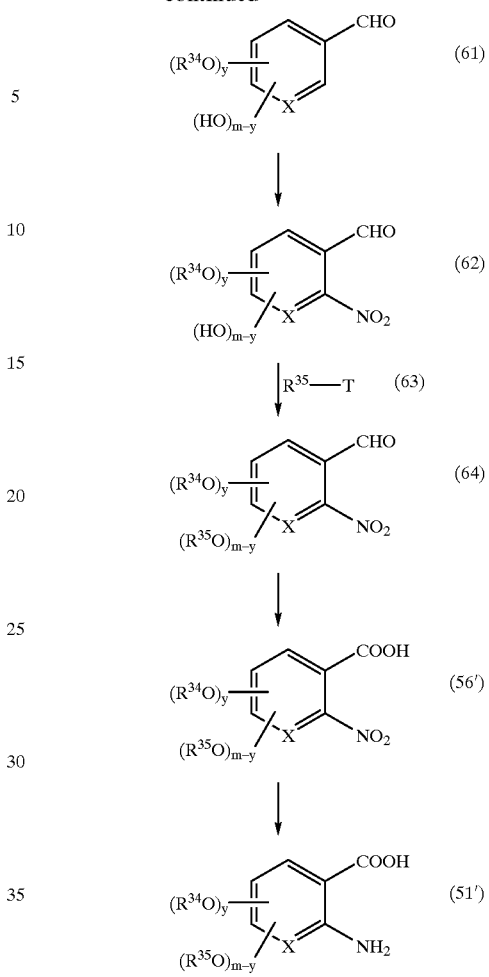

wherein $R^{34}$ and $R^{35}$ are respectively similar to those exemplified for $R^1$ and other symbols are as defined above.

(1) Using Compound (59) as a starting material, the hydroxy group is converted to ether with Compound (60) in the presence of a base to give Compound (61).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to lithium carbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropyl alcohol, t-butanol and the like, with preference given to dimethylformamide.

The reaction temperature is generally from $-10°$ C. to $200°$ C., preferably $0°$ C.$-60°$ C., and the reaction time is generally 15 min-48 hr, preferably 1-8 hr.

(2) The Compound (61) is reacted with fuming nitric acid in the presence of conc. sulfuric acid to give Compound (62).

Examples of the solvent include ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; alcohol solvents such as methanol, ethanol, isopropyl alcohol, t-butanol and the like; and acid solvents such as acetic acid, acetic anhydride and the like, with preference given to acetic acid.

The reaction temperature is generally from −50° C. to 200° C., preferably from −10° C. to 60° C., and the reaction time is generally 15 min48 hr, preferably 1–8 hr.

(3) The hydroxy group of Compound (62) is subjected to etherification with Compound (63) in the presence of a base to give Compound (64).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to potassium carbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropyl alcohol, t-butanol and the like, with preference given to dimethylformamide.

The reaction temperature is generally from −10° C. to 200° C., preferably 0° C.–60° C., and the reaction time is generally 15 min48 hr, preferably 1–8 hr.

(4) The Compound (64) is oxidized to give Compound (56').

The oxidizing agent to be used is, for example, NaClO$_2$, CrO$_3$, K$_2$Cr$_2$O$_7$, KMnO$_4$ and the like.

As an additive, for example, NaHPO$_4$, KHPO$_4$, amylene and the like may be used as appropriate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone, acetic acid, water and the like; and alcohol solvents such as methanol, ethanol, isopropyl alcohol, t-butanol and the like, with preference given to isopropyl alcohol and t-butanol.

The reaction temperature is generally from 0° C. to 100° C., preferably 0° C.–30° C., and the reaction time is 10 min-6 hr, preferably 15 min-3 hr.

(5) The Compound (56') is reduced to Compound (51') by a conventional method.

PRODUCTION METHOD 1-E

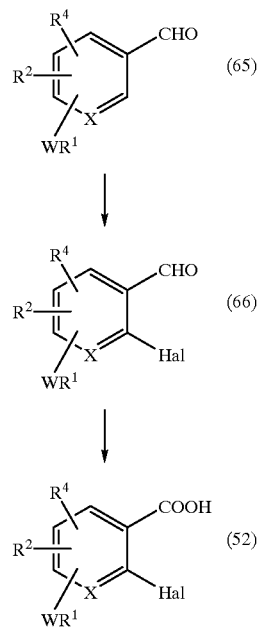

wherein each symbol is as defined above.

(1) The Compound (65) obtained by the method of Production Methods 1-A–1-D is reacted with a halogenizing agent in a suitable solvent or a mixed solvent to give Compound (66).

Examples of the suitable solvent include hydrocarbon solvents such as benzene, toluene, hexane, xylene and the like; ether solvents such as diethyl ether, 1,2-dimethoxyethane, tetrahydrofuran, diglyme, dioxane and the like; halogen solvents such as dichloromethane, chloroform, carbon tetrachloride, 1,2-dichloroethane and the like; ester solvents such as ethyl acetate, methyl acetate, butyl acetate and the like; and polar solvents such as dimethylformamide, dimethyl sulfoxide, acetonitrile, acetone, water and the like, with preference given to halogen solvents and a mixed solvent of dioxane and water.

The halogenizing agent is exemplified by N-bromosuccinimide, bromine and the like.

The reaction temperature is generally from 0° C. to 200° C., preferably 0° C.–60° C., and the reaction time is generally 15 min-24 hr, preferably 30 min-3 hr.

(2) The Compound (66) is oxidized in a conventional manner in a suitable solvent to give Compound (52).

The oxidizing agent to be used is, for example, NaClO$_2$, CrO$_3$, K$_2$Cr$_2$O$_7$, KMnO$_4$ and the like.

As an additive, NaHPO$_4$, KHPO$_4$, amylene and the like may be used as appropriate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone, acetic acid, water and the like; and alcohol solvents such as methanol, ethanol, isopropyl alcohol, t-butanol and the like, with preference given to t-butanol.

The reaction temperature is generally from −30° C. to 100° C., preferably 0° C.–30° C., and the reaction tine is generally 10 min-12 hr, preferably 30 min-3 hr.

PRODUCTION METHOD 1-F

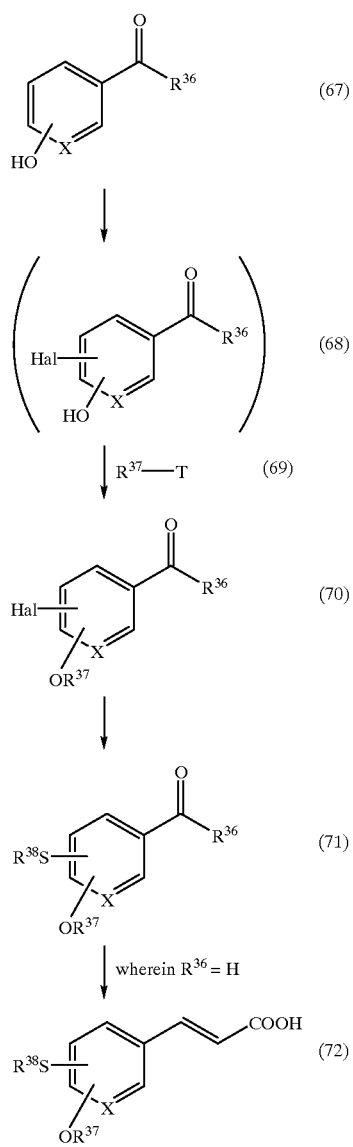

wherein $R^{36}$ is hydroxy or hydrogen atom, $R^{37}$ is the same as $R^1$ and $R^{38}$ is the same as $R^2$.

In this method, alkylthio group is introduced onto the carbon adjacent to the carbon bearing substituent OH of Compound (67) to give Compound (71) or Compound (72).

For an improved reactivity of the carbon adjacent to the carbon bearing substituent OH, in the ring, the compound is halogenized to give Compound (68). A treatment of Compound (68) with a suitable base followed by addition of a suitable sulfur reagent affords a sulfide.

When converting to an alkylthio compound, the carboxyl group or carbonyl group of Compound (67) may be protected with oxzolidine, imidazolidine and the like by a conventional method. After the reaction, these protecting groups may be removed to regenerate the carboxyl group or carbonyl group by a conventional method.

(1) The Compound (67) is treated with a halogenizing agent in a suitable solvent to give Compound (68).

Examples of the halogenizing agent include bromine, N-bromosuccimide, hydrogen bromide, hydrobromic acid, copper bromide and the like.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone, water and the like; and acid solvents such as acetic acid, hydrochloric acid, sulfuric acid and the like, with preference given to acetic acid.

The reaction temperature is generally from 0° C. to 200° C., preferably 0° C.–60° C., and the reaction time is generally 10 min-18 hr, preferably 30 min-3 hr.

(2) Using Compound (68) and Compound (69), Compound (70) can be obtained in the same manner as in Production Method 1-A(1).

(3) The Compound (70) is treated with a sulfur agent in a suitable solvent in the presence of a base to give an alkylthio compound (71).

As the base, usable are, for example, LDA, n-butyllithium, s-butyllithium, t-butyllithium, LiHMDS, NaHMDS, KHMDS, sodium hydride, potassium hydride, EtMgBr, (i-Pr)$_2$NMgBr and the like, with preference given to n-butyllithium.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably tetrahydrofuran.

Examples of the sulfur agent include n-alkyldisulfide and the like. Using this agent, the compound is converted to the n-alkyl($C_1$-$C_7$)thio.

The reaction temperature is generally from -100° C. to 50° C., preferably from -78° C. to 30° C., and the reaction time is generally 15 min-24 hr, preferably 1–6 hr.

(4) When Compound (71) is an aldehyde derivative wherein $R^{36}$ is hydrogen atom, aldehyde Compound (71) can be converted to Compound (72) in the same manner as in Production Method 1-B.

The Compound (11) having optional substituent(s) can be obtained by the above-mentioned Production Methods 1-A–1-F.

PRODUCTION METHOD 1-G

The Compound (12) to be used as a starting compound in Production Method 1 can be obtained, for example, as in the following.

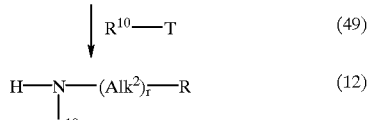

wherein Alk$^2$ has one less carbons than Alk$^2$ and other symbols are as defined above.

(1) The Compound (48) is reduced with a suitable reducing agent to give Compound (25).

Examples of the reducing agent include $BH_3$, $BH_3 SMe_2$, $LiBH_4$, $NaBH_4$, $KBH_4$, $NaBH_3OH$, $LiAlH_4$ and the like, with preference given to $LiAlH_4$.

Examples of the solvent include hydrocarbon solvents such as benzene, toluene, hexane, xylene and the like; ether solvents such as diethyl ether, 1,2-dimethoxyethane, tetrahydrofuran, diglyme and the like; and halogen solvents such as dichloromethane, chloroform, carbon tetrachloride, 1,2-dichloroethane and the like, with preference given to an ether solvent which is more preferably tetrahydrofuran.

The reaction temperature is generally from −30° C. to 100° C., preferably 0° C.–80° C., and the reaction time is generally 15 min-24 hr, preferably 1–6 hr.

(2) The Compound (25) obtained in (1) is reacted with Compound (49) in the presence of a base to give Compound (12).

As the base, usable are, for example, sodium carbonate, potassium carbonate, lithium carbonate, sodium hydrogencarbonate, potassium hydrogencarbonate, sodium hydroxide, potassium hydroxide, lithium hydroxide, sodium hydride, n-butyllithium, s-butyllithium, t-butyllithium, lithium diisopropylamide and the like, with preference given to potassium carbonate.

Examples of the solvent include hydrocarbon solvents such as benzene, toluene, hexane, xylene and the like; ether solvents such as diethyl ether, 1,2-dimethoxyethane, tetrahydrofuran, diglyme and the like; halogen solvents such as dichloromethane, chloroform, carbon tetrachloride, 1,2-dichloroethane and the like; ester solvents such as ethyl acetate, methyl acetate, butyl acetate and the like; polar solvents such as dimethylformamide, dimethyl sulfoxide, acetonitrile, acetone and the like; and alcohol solvents such as methanol, ethanol, isopropanol, t-butanol and the like, with preference given to dimethylformamide.

The reaction temperature is generally 0° C.–150° C., preferably 20° C.–100° C., and the reaction time is generally 1–48 hr, preferably 3–24 hr.

The Compound (I) produced as above can be separated and purified by a known method such as concentration, concentration under reduced pressure, solvent extraction, crystallization, recrystallization, chromatography and the like.

The pharmaceutically acceptable salt of Compound (I) and various isomers of Compound (I) can be produced by a conventionally known method.

The Compound (I) and pharmaceutically acceptable salts thereof show pharmaceutical effects on mammals against the medical condition which is known to involve cannabinoid receptor, particularly, the medical condition in which peripheral cell tissues are involved (e.g., immune diseases, various inflammations, allergic diseases, nephritis and the like).

To be specific, the Compound at) and pharmaceutically acceptable salts thereof selectively act on a cannabinoid receptor, particularly on peripheral receptors, cause less central side effects and have superior immunoregulating action, anti-inflammatory action, antiallergic action and therapeutic effect on nephritis.

Thus, the Compound (I) and pharmaceutically acceptable salts thereof are useful as cannabinoid receptor (particularly, peripheral cannabinoid receptor) activators and antagonists, immunoregulators, therapeutic agents for autoimmune diseases, antiinflammatory agents, antiallergic agents and therapeutic agents for nephritis.

When the Compound (I) and pharmaceutically acceptable salts thereof are used as pharmaceutical preparations, they are generally admixed with pharmacologically acceptable carriers, excipients, diluents, extenders, disintegrants, stabilizers, preservatives, buffering agents, emulsifiers, aromatics, colorants, sweeteners, thickeners, corrigents, solubilizers and other additives, all of which are known per se, such as water, vegetable oil, alcohols such as ethanol and benzyl alcohol, polyethylene glycol, glycerol triacetate, gelatin, lactose, carbohydrates such as starch and the like, magnesium stearate, talc, lanolin, petrolatum and the like and formulated by a conventional method into tablets, pills, powders, granules, suppositories, injections, eye drops, liquids, capsules, troches, aerosols, elixirs, suspensions, emulsions, syrups and the like, which can be administered orally or parentally.

The dose varies depending on the kind of disease, severity thereof, the compound to be administered, administration route, age, sex and body weight of patients, and the like. In the case of oral administration, the dose is generally 0.1–1, 000 mg, preferably 1–300 mg of Compound (I) daily for an adult, which is administered in one to several doses.

The present invention is described in detail by illustrative Examples in the following, to which the present invention is not limited.

PREPARATIVE EXAMPLE 1

4-Methoxytoluene (100 ml, 0.793 mol) and methylene chloride (300 ml) were mixed, and this solution was cooled to 0° C. To this solution was added aluminum chloride (190.3 g, 1.44 mol), and then heptanoyl chloride (123 ml, 0.8 mol) was added dropwise to this solution over 2 hours. The reaction mixture was heated to room temperature, and stirred for 2 hours. The reaction mixture was poured onto ice (400 g) to stop the reaction. The aqueous layer was extracted with chloroform (300 ml). The organic layers were combined, washed successively with water, a saturated aqueous sodium hydrogencarbonate solution and saturated brine (100 ml each), and dried over anhydrous magnesium sulfate. The drying agent was filtered off, the filtrate was concentrated under reduced pressure, and the obtained residue was purified by distillation (120 pa, 125–140° C.) to give 1-(2-hydroxy-5-methylphenyl)heptan-1-one (127.8 g, 77%/) as a colorless oil.

$^1$H-NMR (CDCl$_3$)δ: 12.2(1H, s), 7.53(1H, s), 7.26(1H, d, J=8.47 Hz), 6.88(1H, d, J=8.47 Hz), 2.96(2H, t, J=7.31 Hz), 1.79-1.67(2H, m), 1.47-1.25(6H, m), 0.90(3H, t, J=6.90 Hz). FABMS (m/z): 235[M$^+$H$^+$] (10), 221(100), 202(40). IR (Neat, cm$^{-1}$): 3500-3100, 1642.

PREPARATIVE EXAMPLE 2

1-(2-Hydroxy-5-methylphenyl)heptan-1-one (127 g, 0.61 mol), a 2.5N aqueous sodium hydroxide solution (250 ml) and ethanol (250 ml) were mixed, and this solution was cooled to 0° C. Dimethyl sulfate (60 ml) was added, and the mixture was refluxed under heating for 2 hours. Dimethyl sulfate (40 ml) and a 2.5N aqueous sodium hydroxide solution (170 ml) were further added, and the mixture was refluxed under heating for 2 hours. The reaction mature was concentrated under reduced pressure and the obtained residue was extracted twice with ether (200 ml). The organic layers were combined, washed twice with a 2.5N aqueous sodium hydroxide solution and saturated brine (100 ml1 each), and dried over anhydrous magnesium sulfate. The drying agent was filtered off, and the filtrate was concentrated under reduced pressure. The obtained residue was purified by column chromatography (n-hexane/ethyl acetate=95/5) to give 1-(2-methoxy-5-methylphenyl) heptan-1-one (82 g, 57%) as a colorless oil.

¹H-NMR (CDCl₃)δ: 7.42(1H, s), 7.22(1H, d, J=8.42 Hz), 6.83(1H, d, J=8.42 Hz), 3.84(3H, s), 2.93(2H, t, J=7.56 Hz), 2.28(3H, s), 1.70-1.59(2H, m), 1.45-1.20(6H, m), 0.87(3H, t, J=6.2 Hz).

PREPARATIVE EXAMPLE 3

1-(2-Methoxy-5-methylphenyl)heptan-1-one (81.6 g, 0.348 mol), ethyl chloroacetate (64 g, 0.522 mol) and benzene (100 ml) were mixed, and this solution was cooled to 0° C. Potassium t-butoxide (58.6 g, 0.522 mol) was added, and the mixture was stirred at room temperature for 0.5 hour. This solution was cooled again to 0° C. Then ethyl chloroacetate (32 g, 0.261 mol) and potassium t-butoxide (29.3 g, 0.261 mol) were added, and the mixture was stirred at room temperature for 0.5 hour. The reaction mixture was poured onto ice (200 g) to stop the reaction and the aqueous layer was extracted 3 times with toluene (120 ml). The organic layer was washed successively with water, an aqueous acetic acid solution (water/acetic acid=50/1) and water (100 ml each), and dried over anhydrous magnesium sulfate. The drying agent was filtered off, and the filtrate was concentrated under reduced pressure. To the obtained residue were added ethanol (90 ml) and sodium ethoxide previously prepared from sodium (13.1 g, 0.567 mol) and ethanol (260 ml), and the mixture was stirred at room temperature for 1.5 hours. Water (17 ml) was added to the reaction mixture, and the mixture was stirred for 0.5 hour. Ethanol was evaporated under reduced pressure. To this residue, water (350 ml) and conc. hydrochloric acid (63 ml) were added, and the mixture was refluxed under heating for 1.5 hours. The aqueous layer was extracted 3 times with ether (200 ml). The organic layers were combined, washed successively with water, a saturated aqueous sodium hydrogencarbonate solution and saturated brine (100 ml each), and dried over anhydrous magnesium sulfate. The drying agent was filtered off, the filtrate was concentrated under reduced pressure, and the obtained residue was distilled under reduced pressure (450 pa, 155–160° C.) to give 2-(2-methoxy-5-methylphenyl) octanal (64.5 g, 74.6%) as a colorless oil.

¹-H-NMR (CDCl₃)δ: 9.65(1H, s), 7.06(1H, d, J=8.32 Hz), 6.88(1H, s), 6.80(1H, d, J=8.32 Hz), 3.79(3H, s), 3.74(2H, t, J=8.46 Hz), 2.29(3H, s), 2.17-2.00(1H, m), 1.75-1.60(1H, m), 1.45-1.20(8H, m), 0.87(3H, t, J=6.78 Hz). FABMS (m/z): 249[M⁺H⁺] (80), 219(60).

PREPARATIVE EXAMPLE 4

2-(2-Methoxy-5-methylphenyl)octanal (63.8 g, 0.257 mol), methyl iodide (160 ml, 2.57 mol) and benzene (300 ml) were mixed, and this solution was cooled to −5° C. Potassium t-butoxide (31.3 g, 0.279 mol) was added in such a manner that the temperature of the reaction mixture does not exceed 0° C., and the mixture was stirred at −2° C. for 0.5 hour. The reaction mixture was poured into ice water (200 ml) to stop the reaction. The aqueous layer was erected twice with ether (150 ml), and the organic layers were combined, washed with saturated brine (100 ml) and dried over anhydrous magnesium sulfate. The drying agent was filtered off, and the filtrate was concentrated under reduced pressure. Methanol (400 ml), an aqueous solution (110 ml) of semicarbazide hydrochloride (28.6 g, 0.257 mol) and pyridine (20.4 ml, 0.257 mol) were added to the obtained residue, and the mixture was stirred at room temperature for 0.75 hour. The precipitated crystals were collected by filtration, and washed with hexane. The crystals were dried to give 2-(2-methoxy-5-methylphenyl)octanal semicarbazide (64.7 g, 79%) as colorless crystals.

¹H-NMR (CDCl₃)δ: 7.97(1H, s), 7.32(1H, s), 7.00(1H, s), 6.96(1H, d, J=8.22 Hz), 6.73(1H, d, J=8.22 Hz), 5.10(2H, bs), 3.71(3H, s),2.26(3H, s), 2.08-1.93(1H, m), 1.84-1.72 (1H, m), 1.42(3H, s), 1.28-0.9(8H, m), 0.82(3H, t, J=6.66 Hz).

PREPARATIVE EXAMPLE 5

2-(2-Methoxy-5-methylphenyl)octanal semicarbazide (64.7 g, 0.203 mol), potassium t-butoxide (47.8 g, 0.43 mol) and xylene (600 ml) were mixed, and this solution was refluxed under heating for 2.5 hours. This reaction mixture was poured into ice water (200 ml) to stop the reaction. The aqueous layer was extracted 3 times with toluene (120 ml). The organic layer was washed 3 times with saturated brine (100 ml) and dried over anhydrous magnesium sulfate. The drying agent was filtered off, and the filtrate was concentrated under reduced pressure. The obtained residue was purified by column chromatography (chloroform) to give 2-(1,1-dimethylheptyl)-1-methoxymethylbenzene (51 g, overweight) as a mixture with xylene. The mixture was used for the next reaction.

¹H-NMR (CDCl₃)δ: 6.99(1H, s), 6.97(1H, d, J=8.03 Hz), 6.75(1H, d, J=8.03 Hz), 3.78(3H, s), 2.28(3H, s), 1.82-1.73 (2H, m), 1.31(6H, s), 1.25-1.13(6H, m), 1.05-0.91(2H, m), 0.84(3H, t, J=5.68 Hz).

PREPARATIVE EXAMPLE 6

2-(1,1-Dimethylheptyl)-1-methoxy-4-methylbenzene (a mixture with xylene: calculated as 51 g, 0.203 mol), N-bromosuccinimide (38A4 g, 0.215 mol), benzoyl peroxide (0.97 g, 4 mmol) and carbon tetrachloride (500 ml) were mixed, and this solution was refluxed under heating for 3.5 hours. N-Bromosuccimide (2.1 g, 12 mmol) was further added, and the was refluxed under healing for 0.5 hour. N-Bromosuccimide (36 g, 0.2 mol) was added, and this reaction mixture was refluxed under heating for 2 hours. The crystals were filtered off, and the mother liquor obtained was washed twice with saturated brine (100 ml) and dried over anhydrous magnesium sulfate. The drying agent was filtered off, and the filtrate was concentrated under reduced pressure. The obtained residue was purified by column chromatography (hexane/ethyl acetate=20/1) to give 3-(1,1-dimethylheptyl)-4-methoxybenaaldehyde (33.4 g, 50% in 2 steps) as a pale-yellow oil.

¹H-NMR (CDCl₃)δ: 9.87(1H, s), 7.77(1H, s), 7.74(1H, d, J=8.32 Hz), 6.96(1H, d, J=8.32 Hz), 3.91(3H, s), 1.83-1.70 (2H, m), 1.37(6H, s), 1.35-1.06(6H, m), 1.04-0.85(2H, m), 0.83(3H, t, J=6.74 Hz). FABMS (m/z): 263[M⁺H⁺] (100), 247(95), 163(50).

PREPARATIVE EXAMPLE 7

3-(1,1-Dimethylheptyl)-4-methoxybenzaldehyde (13 g, 49.5 mmol), t-butanol (65 ml) and 2-methyl-2-butene (35.2 ml, 332 mmol) were mixed, and to this solution was added dropwise a solution prepared by mixing sodium chlorite (7.37 g, 64.4 mmol), sodium dihydrogenphosphate (7.73 g, 64.4 mmol) and water (50 ml). The mixture was stirred at room temperature for 12 hours. A 1N sodium hydroxide solution (100 ml) was added, and t-butanol was evaporated under reduced pressure. Conc. hydrochloric acid was added to make the mixture acidic. The aqueous layer was extracted 3 times with ethyl acetate (150 ml). The organic layers were combined, washed with saturated brine (100 ml), and dried over anhydrous magnesium sulfate. The drying agent was filtered off, and the filtrate was concentrated under reduced pressure. The obtained residue was purified by column chromatography (n-hexane/ethyl acetate=5/1-2/1) to give 3-(1,1-dimethylheptyl)-4-methoxybenzoic acid (10.7 g, 77%) as colorless crystals.

$^1$H-NMR (CDCl$_3$)δ: 7.98(1H, d, J=2.15 Hz), 7.97(1H, dd, J=9.12, 2.15 Hz), 6.89(1H, d, J=9.12 Hz), 3.89(3H, s), 1.83-1.74(2H, m), 1.36(6H, s), 1.24-1.10(6H, m), 1.00-0.94 (2H, m), 0.83(3H, t, J=6.49 Hz). FABMS (m/z): 279[M$^+$H$^+$] (65), 261(70), 193(100).

PREPARATIVE EXAMPLE 8

3-(1,1-Dimethylheptyl)-4-methoxybenzaldehyde (1.5 g, 5.39 mmol), methanol (25 ml) and methyl (triphenylphosphoranylidene)acetate (3.24 g, 9.7 mmol) were mixed, and this solution was refluxed under heating for 7 hours. Saturated saturated brine was added to stop the reaction. The aqueous layer was extracted 3 times with ethyl acetate (10 ml). The organic layers were combined and dried over anhydrous magnesium sulfate. The drying agent was filtered off, and the filtrate was concentrated under reduced pressure. The obtained residue was purified by column chromatography (n-hexane/ethyl acetate=20/1-10/1) to give methyl 3-[3-(1,1-dimethylheptyl)-4-methoxyphenyl] cinnamate (0.80 g, 47%) as a colorless oil.

$^1$H-NMR (CDCl$_3$)δ: 7.65(1H, d, J=16 Hz), 7.39(1H, s), 7.37(1H, d, J=9.0 Hz), 6.85(1H, d, J=9.0 Hz), 6.30(1H, d, J=16 Hz), 3.85(3H, s), 3.79(3H, s), 1.84-1.73(2H, m), 1.34 (6H, s), 1.28-1.12(6H, m), 1.01-0.85(2H, m), 0.83(3H, t, J=6.45 Hz). FABMS (m/z): 319[M$^+$H$^+$] (55), 287(65), 233 (100).

PREPARATIVE EXAMPLE 9

Methyl 3-[3-(1,1-dimethylheptyl)-4-methoxyphenyl] cinnamate (334.5 mg, 1.05 mmol), methanol (4 ml) and a 1N aqueous sodium hydroxide solution (1.2 ml, 1.2 mmol) were mixed, and this solution was refluxed under heating for 1 hour. Methanol was evaporated under reduced pressure. Conc. hydrochloric acid (0.3 ml) and saturated brine (5 ml) were added, and the aqueous layer was extracted 4 times with ethyl acetate (5 ml). The organic layers were combined, washed twice with saturated brine (5 ml), and dried over anhydrous magnesium sulfate. The drying agent was filtered off, and the filtrate was concentrated under reduced pressure. The obtained crystals were washed with hexane to give 3-[3-(1,1-dimethylheptyl)-4-methoxyphenyl]cinnamic acid (0.33 g, quant.) as colorless crystals.

$^1$H-NMR (CDCl$_3$)δ: 7.75(1H, d, J=15.9 Hz), 7.44-7.38(2H, m), 6.86(1H, d, J=6.45 Hz), 6.32(1H, d, J=15.9 Hz), 3.86 (3H, s), 1.82-1.73(2H, m), 1.34(6H, s), 1.27-1.10(6H, m), 1.00-0.87(2H, m), 0.84(3H, t, J=6.45 Hz).

PREPARATIVE EXAMPLE 10

3-[3-(1,1-Dimethylheptyl)-4-methoxyphenyl]cinnamic acid (600 mg, 2.16 mmol) and methylene chloride (6 ml) were mixed in a reaction vessel replaced with nitrogen, and this solution was cooled to 0° C. To this solution was added dropwise a methylene chloride solution (4 ml) of boron tribromide (0.82 ml, 8.64 mmol), and the mixture was stirred at room temperature for 20 hours. A methylene chloride solution (5 ml) of boron tribromide (0.82 ml, 8.64 mmol) was further added dropwise, and the mixture was stirred at room temperature for 18 hours. This reaction mixture was poured into water (20 ml) to stop the reaction. Ether (20 ml) was added, and the organic layer was extracted 3 times with a 1N aqueous sodium hydroxide solution (20 ml). Conc. hydrochloric acid was added to make the mixture acidic. The aqueous layer was extracted 3 times with ethyl acetate (40 ml). The organic layers were combined, washed twice with saturated brine (20 ml), and dried over anhydrous magnesium sulfate. The drying agent was filtered off, and the filtrate was concentrated under reduced pressure. The residue obtained was purified by column chromatography (hexane/ethyl acetate=6/1-1/2) to give 3-(1,1-dimethylheptyl)-4H-hydroxybenzoic acid (457 mg, 80%) as colorless crystals.

$^1$H-NMR (CDCl$_3$)δ: 8.00(1H, s), 7.86(1H, d, J=8.4 Hz), 6.72(1H, d, J=8.4 Hz), 5.85-5.28(1H, bs), 1.87-1.77(2H, m), 1.40(6H, s), 1.30-1.14(6H, m), 1.07-0.93(2H, m), 0.83(3H, t, J=6.8 Hz). FABMS (m/z): 265[M$^+$H$^+$] (100), 247(40), 179(60).

PREPARATIVE EXAMPLE 11

Chromic acid (105.4 mg, 1.05 mmol, 1.2 eq) was dissolved in acetic acid (2 ml), and a solution of 3-(1,1-dimethylheptyl)benzaldehyde (205 mg, 0.878 mmol) in acetic acid (2 ml) was added to the solution under ice-cooling, which was followed by stirring for 2 minutes. The mixture was further stirred at room temperature for 30 minutes. Conc. sulfuric acid (2 drops) was added, and the mixture was stirred for 3 hours. To this reaction mixture, water (10 ml) was added, and the mixture was extracted twice with ethyl acetate (10 ml). The organic layers were combined, washed with saturated brine (20 ml), and dried over anhydrous sodium sulfate. The drying agent was filtered off, and the filtrate was concentrated under reduced pressure. The obtained residue was purified by column chromatography (n-hexane/ethyl acetate=2/1) to give 3-(1,1-dimethylheptyl) benzoic acid (205 mg, 99.0%).

$^1$H-NMR (DMSO-d$_6$)δ: 8.08(1H, s), 7.92(1H, d, J=7.7 Hz), 7.58(1H, d, J=7.7 Hz), 7.39(1H, t, J=7.7 Hz), 1.7-1.5(2H, m), 1.33(3H, s), 1.4-1.1(6H, m), 1.1-1.0(2H, m), 7.58(3H, t, J=6.7 Hz). FABMS (m/z): 249[M$^+$H$^+$] (100), 163(80). IR (Neat, cm$^{-1}$): 2927, 1689.

PREPARATIVE EXAMPLE 12

2-Methyl-[1,4]-naphthoquinone (5 g, 29 mmol) and ether (200 ml) were mixed in a reaction vessel replaced with argon, and this solution was cooled to −10° C. A suspension (40 ml) of lithium aluminum hydride (1.0 g, 26.3 mmol) in ether was added dropwise to this solution over 40 minutes, and the mixture was stirred at room temperature for 0.5 hour. To the reaction mixture was added dropwise 1N hydrochloric acid (100 ml) to stop the reaction. The aqueous layer was extracted twice with ethyl acetate (100 ml). The organic layers were combined, washed twice with saturated brine (50 ml), 3 times with a saturated aqueous sodium hydrogencarbonate solution (30 ml) and twice with saturated brine (50 ml), and dried over anhydrous magnesium sulfate. The drying agent was filtered off, and the filtrate was concentrated under reduced pressure. Water (10 ml) and conc. hydrochloric acid (10 ml) were added to the obtained residue, and the mixture was refluxed under heating for 2 hours. Water (50 ml) was added to this reaction mixture, and the aqueous layer was extracted twice with ether (50 ml). The organic layer was washed with water (30 ml), washed twice with a saturated aqueous sodium hydrogencarbonate solution (30 ml) and twice with saturated brine (30 ml), and dried over anhydrous magnesium sulfate. The drying agent was filtered off, and the filtrate was concentrated under reduced pressure. The obtained residue was purified by column chromatography (hexane/ethyl acetate=30/1-10/1) to give 3-methylnaphthalen-1-ol in a mixture of compounds structurally unidentified. The mixture was not further purified, but used for the next reaction.

PREPARATIVE EXAMPLE 13

The crude product of 3-methylnaphthalen-1-ol, dimethylformamide (DMF, 20 ml), potassium carbonate (3 g, 21.7 mmol) and pentyl bromide (4.0 ml, 32.3 mmol) were mixed in a reaction vessel replaced with argon, and this solution was stirred at 90° C. for 3 hours. DMF was evaporated under reduced pressure, and water (20 ml) was added. The aqueous layer was extracted with ethyl acetate (20 ml) 3 times. The organic layer was washed with saturated brine (20 m1l) and dried over anhydrous magnesium sulfate. The drying agent was filtered off, and the filtrate was concentrated under reduced pressure. The obtained residue was purified by column chromatography (hexane/ethyl acetate=100/0-50/1) to give 3-methyl-1-pentyloxynaphthalene (827 mg, 12% in 3 steps) as a colorless oil.

$^1$H-NMR (CDCl$_3$)δ: 8.23(1H, d, J=8.07 Hz), 7.69(1H, d, J=8.07 Hz), 7.48-7.36(2H, m), 7.19(1H, s), 6.65(1H, s), 4.13(2H, t, J=6.42 Hz), 2.49(3H, s), 1.98-1.87(2H, m), 1.53-1.37(4H, m), 0.98 (3H, t, J=7. 19 Hz).

PREPARATIVE EXAMPLE 14

A crude product of 3-methyl-1-pentyloxynaphthalene, carbon tetrachloride (15 ml) and N-bromosuccinimide (2.11 g, 11.9 mmol) were mixed. A solution (3 ml) of benzoyl peroxide (72.7 mg, 0.3 mmol) in carbon tetrachloride was added, and this solution was stirred at 100° C. for 4 hours. The crystals were filtered off, and the mother liquor was washed twice with saturated brine (20 ml) and dried over anhydrous magnesium sulfate. The drying agent was filtered off, and the filtrate was concentrated under reduced pressure. The obtained residue was purified by column chromatography (hexane/ethyl acetate=25/1) to give 1-bromo-2-dibromomethyl-4-pentyloxynaphthalene (1.16 g, 69%) as colorless crystals.

$^1$H-NMR (CDCl$_3$)δ: 8.35-8.25(2H, m), 7.73-7.57(2H, m), 7.55(1H, s), 7.42(1H, s), 4.31(2H, t, J=6.41 Hz), 2.10-1.97 (2H, m), 1.82-1.45(4H, m), 1.04(3H, t, J=7.19 Hz). FABMS (m/z): 466[M$^+$H$^+$] (20), 385(100), 315(40).

PREPARATIVE EXAMPLE 15

1-Bromo-2-dibromomethyl-4-pentyloxynaphthalene (1.13 g, 2.43 mmol), acetic acid (8 ml) and sodium acetate (0.8 g, 9.72 mmol) were mixed, and this solution was refluxed under heating for 4 hours. Acetic acid was evaporated under reduced pressure. Water (5 ml) was added, and the aqueous layer was extracted twice with ethyl acetate (20 ml). The organic layers were combined, washed with saturated brine (10 ml), a saturated aqueous sodium hydrogencarbonate solution (10 ml) and saturated brine (10 ml), and dried over anhydrous magnesium sulfate. The drying agent was filtered off, and the filtrate was concentrated under reduced pressure. The obtained residue was purified by column chromatography (hexane/ethyl acetate=25/1) to give 1-bromo4-pentyloxynaphthalene-2-carbaldehyde (0.647 g, 83%) as colorless crystals.

$^1$H-NMR (CDCl$_3$)δ: 10.64(1H, s), 8.50-8.42(1H, m), 8.38-8.30(1H, m), 7.75-7.62(2H, m), 7.27(1H, s), 4.20(2H, t, J=6.5 Hz), 2.00-1.88(2H, m), 1.60-1.36(4H, m), 0.97(3H, t, J=7.2 Hz). FABMS (m/z): 322[M$^+$H$^+$] (100), 251(65), 144 (40).

PREPARATIVE EXAMPLE 16

1-Bromo-4-pentyloxynaphthalene-2-carbaldehyde (0.77 g, 2.4 mmol), t-butanol (4.8 ml) and 2-methyl-2-butene (1.71 ml, 16.1 mmol) were mixed, and a solution prepared by mixing sodium chlorite (360 mg, 3.12 mmol), sodium dihydrogenphosphate (374 mg, 3.12 mmol) and water (2.4 ml) was added dropwise. The mixture was stirred at room temperature for 16.5 hours. A 1N aqueous sodium hydroxide solution (5 ml) was added, and t-butanol was evaporated under reduced pressure. Conc. hydrochloric acid was added to make the mixture acidic. Saturated saturated brine (5 ml) was added, and the aqueous layer was extracted 3 times with ethyl acetate (10 ml). The organic layer was dried over anhydrous magnesium sulfate, and the drying agent was filtered off. The filtrate was concentrated under reduced pressure. The obtained residue was recrystallized from ethyl acetate to give 1-bromo-4-pentyloxynaphthalene-2-carboxylic acid (619 mg, 76%) as pale-yellow crystals.

$^1$H-NMR (CDCl$_3$)δ: 8.47(1H, d, J=8.4 Hz), 8.33(1H, d, J=8.4 Hz), 7.72-7.58(2H, m), 7.24(1H, s), 4.18(2H, t, J=6.48 Hz), 1.62-1.37(6H, m), 0.97(3H, t, J=7.2 Hz). FABMS (m/z): 338[M$^+$H$^+$] (90), 339(70), 268(50).

PREPARATIVE EXAMPLE 17

1-Bromo-4-pentyloxynaphthalene-2-carboxylic acid (400 mg, 1.19 mmol) and tetrahydrofuran (THF, 3 ml) were mixed in a reaction vessel replaced with argon, and this solution was cooled to −78° C. A hexane solution (1.6M, 1.63 ml) of n-butyllithium (2.61 mmol) was added, and the mixture was stirred for 1 hour. Water (0.5 ml) and saturated brine (2 ml) were added, and the aqueous layer was extracted 4 times with ethyl acetate (5 ml). The organic layers were combined and dried over anhydrous magnesium sulfate. The drying agent was filtered off, and the filtrate was concentrated under reduced pressure. The obtained residue was purified by column chromatography (hexane/ethyl acetate=3/1-1/2) to give 4-pentyloxynaphthalene-2-carboxylic acid (149.6 mg, 49%) as colorless crystals.

$^1$H-NMR (CDCl$_3$)δ: 8.32(1H, d, J=7.47 Hz), 8.31(1H, s), 7.93(1H, d, J=7.47 Hz), 7.68-7.52(2H, m), 7.42(1H, s), 4.23(2H, t, J=6.48 Hz), 2.04-1.90(2H, m), 1.65-1.39(4H, m), 0.98(3H, t, J=7.2 Hz). FABMS (m/z): 259[M$^+$H$^+$] (50), 258(100), 188(70).

PREPARATIVE EXAMPLE 18

1-Bromo-4-pentyloxynaphthalene-2-carbaldehyde (0.644 g, 2.0 mmol), THF (5 ml) and methyl (triphenylphosphoranylidene)acetate (1.0 g, 3.0 mmol) were mixed, and this solution was refluxed under heating for 4 hours. THF was evaporated under reduced pressure, and the obtained residue was purified by column chromatography (hexane/ethyl acetate=25/1) to give methyl 3-(1-bromo-4-pentyloxynaphthalene-2-yl)cinnamate (592 mg, 78%) as pale-yellow crystals.

$^1$H-NMR (CDCl$_3$)δ: 8.38(1H, d, J=15.9 Hz), 8.34(1H, d, J=8.0 Hz), 8.27(1H, d, J=8.0 Hz), 7.67-7.52(2H, m), 6.94 (1H, s), 6.45(1H, d, J=15.9 Hz), 4.15(2H, t, J=6.44 Hz), 3.86(3H, s), 2.03-1.90(2H, m), 1.64-1.30(4H, m), 0.97(3H, t, J=7.17 Hz). FABMS (m/z): 378[M$^+$H$^+$] (100), 379(60), 226(60).

PREPARATIVE EXAMPLE 19

Methyl 3-(1-bromo-4-pentyloxynaphthalene-2-yl) cinnamate (588 mg, 1.56 mmol), ethanol (4 ml) and a 1N aqueous sodium hydroxide solution (4 ml) were mixed, and this solution was refluxed under heating for 1 hour. Ethanol was evaporated under reduced pressure and conc. hydrochloric acid was added to make the reaction mixture acidic. THF (5 ml) and ethyl acetate (20 ml) were added to dissolve the precipitated crystals. The organic layer was separated and the aqueous layer was extracted twice with ethyl acetate (20 ml). The organic layers were combined, washed 3 times with saturated brine (20 ml), and dried over anhydrous sodium sulfate. The drying agent was filtered off and the filtrate was concentrated under reduced pressure. The obtained residue was purified by washing with hexane to give 3-(1-bromo4-pentyloxynaphthalene-2-yl)cinnamic acid (540 mg, 95%) as pale-yellow crystals.
$^1$H-NMR (DMSO-d$_6$)δ: 12.6(1H, bs), 8.26(1H, d, J=7.76 Hz), 8.22(1H, d, J=7.76 Hz), 7.03(2H, d, J=8.4 Hz), 8.15 (1H, d, J=15.8 Hz), 7.75-7.60(2H, m), 7.34(1H, s), 6.84(1H, d, J=15.8 Hz), 4.27(2H, t, J=6.41 Hz), 1.93-1.80(2H, m), 1.59-1.33(4H, m), 0.93(3H, t, J=7.15 Hz). FABMS (m/z): 364[M$^+$H$^+$] (20), 169(100).

PREPARATIVE EXAMPLE 20

3-(1-Bromo-4-pentyloxynaphthalene-2-yl)cinnamic acid (100 mg, 0.275 mmol) and THF (2 ml) were mixed in a reaction vessel replaced with argon, and this solution was cooled to −78° C. A hexane solution (1.6M, 0.38 ml) of n-butyllithium (0.6 mmol) was added, and the mixture was stirred for 1 hour. Water (1 ml) and conc. hydrochloric acid were added to make this solution acidic (pH=1), and the aqueous layer was extracted 4 times with ethyl acetate (5 ml). The organic layers were combined, washed 3 times with saturated brine (5 ml), and dried over anhydrous magnesium sulfate. The drying agent was filtered off, and the filtrate was concentrated under reduced pressure. The obtained residue was purified by column chromatography (hexane/ethyl acetate=2/1) to give 3-(4-pentyloxynaphthalene-2-yl) cinnamic acid (46.2 mg, 59%) as colorless crystals.
$^1$H-NMR (DMSO-d$_6$)δ: 12.4(1H, bs), 8.16-8.10(1H, m), 7.91-7.86(1H, m), 7.71(1H, s), 7.69(1H, d, J=15.9 Hz), 7.59-7.50(2H, m), 7.28(1H, s), 6.70(1H, d, J=15.9 Hz), 4.23(2H, t, J=6.42 Hz), 1.94-1.8(2H, m), 1.60-1.35(4H, m), 0.93(3H, t, J=7.16 Hz). FABMS (m/z): 285[M$^+$H$^+$] (10), 284(300), 169(100).

PREPARATIVE EXAMPLE 21

2-Hydroxy-3-methoxybenzoic acid (15.66 g, 93 mmol), DMF (200 ml), potassium carbonate (51.4 g, 372 mmol) and pentyl bromide (29 ml, 233 mmol) were mixed, and this solution was stirred at 90° C. for 1 hour. DMF was evaporated under reduced pressure, and water (100 ml) was added. The aqueous layer was extracted 3 times with ethyl acetate (150 ml). The organic layers were combined, washed twice with saturated brine (70 ml), and dried over anhydrous magnesium sulfate. The drying agent was filtered off and the filtrate was concentrated under reduced pressure. To the obtained residue were added a 1N aqueous sodium hydroxide solution (70 ml) and ethanol (70 ml), and the mixture was refluxed under heating for 1 hour. A 1N aqueous sodium hydroxide solution (70 ml) and ethanol (70 ml) were further added, and the mixture was refluxed under heating for 2 hours. Ethanol was evaporated under reduced pressure, and conc. hydrochloric acid was added to make this solution acidic. The aqueous layer was extracted 3 times with ethyl acetate (100 ml). The organic layers were combined, washed twice with saturated brine (100 ml), and dried over anhydrous magnesium sulfate. The drying agent was filtered off, and the filtrate was concentrated under reduced pressure. The obtained residue was purified by column chromatography (hexane/ethyl acetate=2/1-1/1) to give 3-methoxy-2-pentyloxybenzoic acid (20.5 g, 97%) as a pale-yellow oil.
$^1$H-NMR (CDCl$_3$)δ: 7.22(1H, d, J=7.35 Hz), 7.20-7.09(2H, m), 4.26(2H, t, J=6.96 Hz), 3.91(3H, s), 1.90-1.79(2H, m), 1.50-1.30(4H, m), 0.92(3H, t, J=7.0 Hz).

PREPARATIVE EXAMPLE 22

3-Methoxy-2-pentyloxybenzoic acid (1.5 g, 6.3 mmol), methanol (10 ml) and conc. sulfuric acid (1 drop) were mixed, and this solution was refluxed under heating for 7 hours. Methanol was evaporated under reduced pressure, and a saturated aqueous sodium hydrogencarbonate solution (3 ml) was added. The aqueous layer was extracted twice with ethyl acetate (20 ml). The organic layers were combined, washed twice with a saturated aqueous sodium hydrogencarbonate solution (5 ml) and once with saturated brine (5 ml), and dried over anhydrous magnesium sulfate. The drying agent was filtered off, and the filtrate was concentrated under reduced pressure. THF (15 ml) was added to the obtained residue in a stream of argon, and the mixture was cooled to 0° C. Lithium aluminum hydride (0.49 g, 13 mmol) was added to this solution, and the mixture was stirred for 1 hour. Water (0.4 ml), a 1N aqueous sodium hydroxide solution (0.4 ml) and water (1.2 ml) were successively added dropwise to the reaction mixture. Ether (60 ml) was added, and the mixture was vigorously stirred for 1 hour. The inorganic salt was filtered off, and the filtrate was concentrated under reduced pressure to give a crude product of (3-methoxy-2-pentyloxyphenyl)methanol. The product was not further purified, and used in the next reaction.

PREPARATIVE EXAMPLE 23

The crude product of (3-methoxy-2-pentyloxyphenyl) methanol (1.2 g), dimethyl sulfoxide (DMSO, 25 ml) and triethylamine (6.72 ml, 48.2 mmol) were mixed, and this solution was cooled to 0° C. Sulfur trioxide—pyridine complex (2.56 g, 16.1 mmol) was added, and the mixture was stirred at room temperature for 1 hour. The reaction mixture was poured into water to stop the reaction, and the aqueous layer was extracted 3 times with ethyl acetate (30 ml). The organic layers were combined, washed with 2N hydrochloric acid (30 ml), water (30 ml) and saturated brine (30 ml), and dried over anhydrous magnesium sulfate. The drying agent was filtered off, and the filtrate was concentrated under reduced pressure. The obtained residue was purified by column chromatography (hexane/ethyl acetate= 15/1-10/1) to give 3-methoxy-2-pentyloxybenzaldehyde (1.16 g, 83% in 3 steps) as a colorless oil.
$^1$H-NMR (CDCl$_3$)δ: 7.42(1H, d, J=6.69 Hz), 7.20-7.09(3H, m, involving a singlet at 7.13), 4.12(2H, t, J=6.73 Hz), 3.89(3H, s), 1.90-1.75(2H, m), 1.52-1.32(4H, m), 0.93(3H, t, J=7.08 Hz). FABMS (m/z): 223[M$^+$H$^+$] (60), 164(20).

PREPARATIVE EXAMPLE 24

3-Methoxy-2-pentyloxybenzaldehyde (1.15 g, 5.17 mmol), THF (20 ml) and methyl (triphenylphosphoranylidene)acetate (3.34 g, 10 mmol) were mixed, and this solution was refluxed under heating for 4 hours. THF was evaporated under reduced pressure, and the obtained residue was purified by column chromatography (hexane/ethyl acetate=3/1) to give methyl 3-(3-methoxy-2-pentyloxyphenyl)cinnamate (1.48 g, over weight) as a colorless oil.
$^1$H-NMR (CDCl$_3$)δ: 7.35(1H, d, J=2.0 Hz), 7.15(1H, dd, J=8.3, 2.0 Hz), 7.03(2H, d, J=8.4 Hz), 6.80(2H, d, J=8.4 Hz), 6.80(1H, d, J=8.3 Hz), 6.62(1H, bs), 6.19(1H, t, J=12.9 Hz), 3.98(2H, t, J=6.9 Hz), 3.86(3H, s), 3.64(2H, q, J=6.9 Hz), 2.82(2H, t, J=6.9 Hz), 1.9-1.7(2H, m), 1.5-1.3(4H, m), 0.90(3H, t, J=7.0 Hz). FABMS (m/z) : 358[M$^+$H$^+$] (100), 221(80), 154(60).

PREPARATIVE EXAMPLE 25

Methyl 3-(3-methoxy-2-pentyloxyphenyl)cinnamate (1.47 g, 5.28 mmol), ethanol (10 ml) and a 1N aqueous sodium hydroxide solution (10 ml) were mixed, and this solution was refluxed under heating for 0.5 hour. Ethanol was evaporated under reduced pressure, and conc. hydrochloric acid was added to make the mixture acidic (pH=1). The precipitated crystals were extracted 3 times with ethyl acetate (20 ml). The organic layers were combined, washed 3 times with saturated brine (20 ml), and dried over anhydrous sodium sulfate. The drying agent was filtered off, and the filtrate was concentrated under reduced pressure. The obtained residue was purified by recrystallization from ethanol to give 3-(3-methoxy-2-pentyloxyphenyl)cinnamic acid (1.09 g, 78%) as colorless crystals.
$^1$H-NMR (CDCl$_3$)δ: 8.16(1H, d, J=16.2 Hz), 7.19(1H, d, J=7.99 Hz), 7.06(1H, d, J=7.99 Hz), 6.95(1H, d, J=7.99 Hz), 6.48(1H, d, J=16.2 Hz), 3.99(2H, t, J=6.88 Hz), 3.87(3H, s), 1.89-1.75(2H, m), 1.57-1.35(4H, m), 0.94(3H, t, J=7.14 Hz). FABMS (m/z): 265[M$^+$H$^+$] (40), 264(70), 177(100).

PREPARATIVE EXAMPLE 26

2-Hydroxy-3-methoxybenzoic acid (7.15 g, 30 mmol), toluene (60 ml), triethylamine (4.6 ml, 33 mmol) and diphenylphosphoryl azide (7.11 ml, 33 mmol) were mixed in a reaction vessel replaced with argon, and this solution was stirred at room temperature for 1 hour and then for 2.5 hours while heating from 45° C. to 100° C. Benzyl alcohol (3.41 ml, 33 mmol) was added, and the mixture was refluxed under heating for 2 hours. To this reaction mixture was added ice water (60 ml) to stop the reaction, and the aqueous layer was extracted 3 times with ethyl acetate (50 ml). The organic layers were combined, washed twice with saturated brine (50 ml), and dried over anhydrous magnesium sulfate. The drying agent was filtered off, and the filtrate was concentrated under reduced pressure. The obtained residue was purified by column chromatography (hexane/ethyl acetate=9/1) to give benzyl (3-methoxy-2-pentyloxyphenyl) carbonate (8.41 g, 82%) as a pale-yellow oil.
$^1$H-NMR (CDCl$_3$)δ: 7.73(1H, d, J=8.1 Hz), 7.42-7.31(6H, m), 7.01(1H, t, J=8.4 Hz), 7.0 (1H, d, J=8.4 Hz), 5.21(2H, s), 3.99(2H, t, J=6.8 Hz), 3.84(3H, s), 1.80-1.67(2H, m), 1.5-1.3(4H, m), 0.90(3H, t, J=7.1 Hz). FABMS (m/z): 344 [M$^+$H$^+$] (45), 343(100), 300(65).

PREPARATIVE EXAMPLE 27

Benzyl (3-methoxy-2-pentyloxyphenyl)carbonate (2 g, 5.82 mmol), ethanol (50 ml) and 10% palladiumcarbon catalyst (160 mg) were mixed, and this solution was stirred at room temperature for 4.5 hours in a stream of hydrogen. The palladium-carbon catalyst was filtered off, and ethanol was evaporated under reduced pressure. Ethanol (10 ml) and diethyl ethoxymethylenemalonate (1.29 ml, 6.4 mmol) were added to the obtained residue, and this solution was refluxed under heating for 2 hours. Ethanol was evaporated under reduced pressure, and liquid paraffin (10 ml) was added to the obtained residue. The mixture was stirred at 250° C. for 1 hour, and cooled to room temperature. A brown oil was separated from liquid paraffin, and ethyl acetate (3 ml) and hexane (10 ml) were added to this brown oil. The mixture was stirred and the obtained crystals were purified by washing with hexane and ether to give ethyl 7-methoxy-4-oxo-8-pentyloxy-1,4-dihydroquinoline-3-carboxylate (589 mg, 30% in 3 steps) as pale-brown crystals.
$^1$H-NMR (CDCl$_3$)δ: 9.15(1H, bs), 8.55(1H, s), 8.12(1H, d, J=9.1 Hz), 7.03(1H, d, J=9.1 Hz), 4.36(2H, q, J=7.1 Hz), 4.17(2H, t, J=6.9 Hz), 3.96(3H, s), 1.85-1.69(2H, m), 1.50-1.32(7H, m), 0.91(3H, t, J=7.0 Hz). FABMS (m/z): 334[M$^+$H$^+$] (100), 288(30), 218(20).

PREPARATIVE EXAMPLE 28

Ethyl 7-methoxy-4-oxo-8-pentyloxy-1,4-dihydroquinoline-3-carboxylate (580 mg, 1.74 mmol) and phosphorus oxychloride (3 ml) were mixed, and this solution was refluxed under heating for 1 hour. This reaction mixture was poured onto ice (30 g) to stop the reaction. A 30% aqueous sodium hydroxide solution (20 ml) was gradually added dropwise under ice-cooling. The aqueous layer was extracted 4 times with ether (20 ml). The organic layers were combined, washed twice with saturated brine (10 ml), and dried over anhydrous magnesium sulfate. The drying agent was filtered off, and the filtrate was concentrated under reduced pressure. The obtained residue was purified by column chromatography (hexane/ethyl acetate=2/1) to give ethyl 4-chloro-7-methoxy-8-pentyloxyquinoline-3-carbamate (561 mg, 92%) as pale-yellow crystals.
$^1$H-NMR (CDCl$_3$)δ: 9.21(1H, s), 8.16(1H, d, J=9.0 Hz), 7.47(1H, d, J=9.0 Hz), 4.48(2H, q, J=7.2 Hz), 4.26(2H, t, J=7.1 Hz), 4.05(3H, s), 1.94-1.74(2H, m), 1.51-1.30(7H, m), 0.92(3H, t, J=7.1 Hz). FABMS (m/z): 352[M$^+$H$^+$] (100), 294(60).

PREPARATIVE EXAMPLE 29

Ethyl 4-chloro-7-methoxy-8-pentyloxyquinoline-3-carbamate (311 mg, 0.84 mmol), ethanol (3 ml) and a 1N aqueous sodium hydroxide solution (3 ml) were mixed, and this solution was refluxed under heating for 0.5 hour. Ethanol was evaporated under reduced pressure, and conc. hydrochloric acid was added to make the reaction mixture acidic. THF (10 ml) and ethyl acetate (10 ml) were added to dissolve the precipitated crystals. The organic layer was separated, washed 3 times with saturated brine (10 ml) and dried over anhydrous magnesium sulfate. The drying agent was filtered off, and the filtrate was concentrated under reduced pressure. The obtained residue was recrystallized from ethanol to give 4-chloro-7-methoxy-8-pentyloxyquinoline-3-carbamic acid (229 mg, 80%) as pale-yellow crystals.
$^1$H-NMR (DMSO-d$_6$)δ: 13.8(1H, bs), 9.07(1H, s), 8.10(1H, d, J=9.6 Hz), 7.75(1H, d, J=9.6 Hz), 4.13(2H, t, J=6.5 Hz), 3.99(3H, s), 1.78-1.67(2H, m), 1.50-1.28(4H, m), 0.88(3H, t, J=7.4 Hz). FABMS (m/z) 324[M$^+$H$^+$] (85), 307(25), 266(25).

PREPARATIVE EXAMPLE 30

4-Chloro-7-methoxy-8-pentyloxyquinoline-3-carbamic acid (101 mg, 0.312 mmol) and methanol (10 ml) were mixed, and 10% palladium-carbon catalyst (30 mg) was added to this solution. The mixture was stirred at room temperature for 5 hours in a stream of hydrogen. The palladium-carbon catalyst was filtered off, and the filtrate was concentrated under reduced pressure. The obtained residue was purified by column chromatography (hexane/ethyl acetate=10/1-6/4) to give 7-methoxy-8-pentyloxyquinoline-3-carbamic acid (74.6 mg, 83%) as yellow crystals.
$^1$H-NMR (DMSO-d$_6$) δ: 9.32(1H, s), 8.70(1H, s), 7.80(1H, d, J=4.52 Hz), 7.54(1H, d, J=4.52 Hz), 4.16(2H, t, J=6.53 Hz), 3.95(3H, s), 1.83-1.68(2H, m), 1.57-1.30(4H, m), 0.90 (3H, t, J=7.18 Hz). FABMS (m/z): 290[M$^+$H$^+$] (100), 258 (35), 220(60).

PREPARATIVE EXAMPLE 31

3-Bromo-4-methoxybenzaldehyde (15 g, 70 mmol), t-butanol (140 ml), 2-methyl-2-butene (50 ml, 469 mmol)

were mixed, and to this solution was added dropwise a solution prepared by mixing sodium chlorite (10.42 g, 91 mmol), sodium dihydrogenphosphate dihydrate (14.2 g, 91 mmol) and water (70 nil). The mixture was stirred at room temperature for 16 hours. A 1N aqueous sodium hydroxide solution (50 ml) was added, and t-butanol was evaporated under reduced pressure. Conc. hydrochloric acid was added to make the mixture acidic. The precipitated crystals were collected by filtration and washed with hexane. The obtained crystals were dissolved in ethyl acetate (200 ml), and this solution was dried over anhydrous magnesium sulfate. The drying agent was filtered off, and the filtrate was concentrated under reduced pressure to give 3-bromo-4-methoxybenzoic acid (10.5 g, 65%) as colorless crystals.
$^1$H-NMR (CDCl$_3$)δ: 12.9(1H, bs), 8.06(1H, s), 7.94(1H, d, J=8.5 Hz), 7.20(1H, d, J=8.5 Hz), 3.93(3H, s). FABMS (m/z): 232[M$^+$H$^+$] (800),233(90),231(100).

PREPARATIVE EXAMPLE 32

3-Bromo-4-methoxybenzoic acid (8.75 g, 37.9 mmol), toluene (80 ml), ethyl acetate (20 m11), methylene chloride (20 ml) and DMF (1 drop) were mixed, and to this solution was added thionyl chloride (6.5 ml, 90 mmol). The mixture was stirred at 70° C. for 0.5 hour. The reaction mixture was concentrated under reduced pressure, and toluene was added. The mixture was further concentrated under reduced pressure. Methylene chloride (160 ml) was added to the obtained residue, and this solution was cooled to 0° C. 2-Amino-2-methyl-1-propanol (7.64 nil, 80 mmol) was added dropwise, and the mixture was stirred at room temperature for 14 hours. The precipitated crystals were filtered off, and the filtrate was concentrated under reduced pressure. The obtained residue was diluted with ethyl acetate (200 ml), and this solution was washed with 1N hydrochloric acid (50 ml). This solution was dried over anhydrous magnesium sulfate, and the drying agent was filtered off. The filtrate was concentrated under reduced pressure. The obtained residue and methylene chloride (150 ml) were mixed, and thionyl chloride (10.9 ml, 150 mmol) was added under ice-cooling. The mixture was stirred at room temperature for 2 hours. To this reaction mixture were successively added water (13 ml) and a 50% aqueous sodium hydroxide solution (40 ml) under ice-cooling. The aqueous layer was extracted 3 times with ethyl acetate (100 ml). The organic layers were combined, washed twice with saturated brine (100 ml). This solution was dried over anhydrous magnesium sulfate, and the drying agent was filtered off. The filtrate was concentrated under reduced pressure, and the obtained residue was purified by column chromatography (hexane/ethyl acetate= 2/1-1/2) to give 2-(3-bromo-4-methoxyphenyl)4,4-dimethyl-4,5-dihydrooxazole (7.10 g, 66%) as a colorless oil.
$^1$H-NMR (CDCl$_3$)δ: 8.15(1H, s), 7.85(1H, d, J=8.5 Hz), 6.90(1H, d, J=8.5 Hz), 4.09(2H, s), 3.93(3H, s), 1.37(6H, s). FABMS (m/z): 285[M$^+$H$^+$] (200), 286(90), 284(100).

PREPARATIVE EXAMPLE 33

2-(3-Bromo-4-methoxyphenyl)-4,4-dimethyl-4,5-dihydrooxazole (2.1 g, 7.4 mmol) and THF (15 ml) were mixed, and this solution was cooled to −78° C. A hexane solution (1.6M, 4.75 ml) of n-butyllithium (7.6 mmol) was added, and the mixture was stirred for 2 hours. DMF (1.16 ml, 15 mmol) was added and the mixture was stirred for 20 minutes. Water (20 ml) was added to stop the reaction. The aqueous layer was extracted twice with ethyl acetate (20 ml). The organic layers were combined, and washed with satu-rated brine (30 ml). This solution was dried over anhydrous magnesium sulfate, and the drying agent was filtered off. The filtrate was concentrated under reduced pressure, and the obtained residue was purified by column chromatography (hexane/ethyl acetate=3/1-1/3) to give 5-(4,4-dimethyl-4,5-dihydrooxazole-2-yl)-2-methoxybenzaldehyde (0.71 g, 41%) as colorless transparent crystals.
$^1$H-NMR (CDCl$_3$)δ: 8.36(1H, d, J=2.3 Hz), 8.15(1H, dd, J=8.8,2.3 Hz), 7.01(1H, d, J=8.8 Hz), 4.09(2H, s), 3.97(3H, s), 1.37(6H, s).

PREPARATIVE EXAMPLE 34

Pentyltriphenylphosphonium bromide (1.17 g, 2.83 mmol) and ether (5 ml) were mixed, and to this solution was added a hexane solution (1.6M, 1.77 ml) of n-butyllithium (2.83 mmol). The mixture was stirred at room temperature for 2 hours. A THF solution (3 ml) of 5-(4,4-dimethyl-4,5-dihydrooxazol-2-yl)-2-methoxybenzaldehyde (600.8 mg, 2.58 mmol) was added to this solution, and the mixture was stirred for 1.5 hours. Water (5 ml) was added to stop the reaction. The aqueous layer was extracted 3 times with ethyl acetate (5 ml). The organic layers were combined, and washed twice with saturated brine (20 ml1). This solution was dried over anhydrous magnesium sulfate, and the drying agent was filtered off. The filtrate was concentrated under reduced pressure, and the obtained residue was purified by column chromatography (hexane/ethyl acetate=2/1) to give 2-[3-(1-hexenyl)-4-methoxyphenyl]-4,4-dimethyl-4,5-dihydrooxazole (583.3 mg, 79%) as a mixture (a colorless oil) of geometrical isomers (1:1).
$^1$H-NMR (CDCl$_3$)
E-isomer
δ: 7.99(1H, s), 7.75(1H, d, J=8.4 Hz), 6.87(1H, d, J=8.4 Hz), 6.66(1H, d, J=15.9 Hz), 6.32(1H, dt, J=15.9, 6.9 Hz), 4.08(2H, s), 3.87(3H, s), 2.28-2.18(2H, m), 1.51-1.26(10H, m, involving a singlet at 1.37), 0.87(3H, t, J=7.2 Hz).
Z-isomer
δ: 7.83(1H, d, J=8.4 Hz), 7.77(1H, s), 6.84(1H, d, J=8.4 Hz), 6.44(1H, d, J=11.7 Hz), 5.75(1H, dt, J=11.7, 7.26 Hz), 4.08(2H, s), 3.86(3H, s), 2.30-2.21(2H, m), 1.51-1.30(4H, m), 0.92(3H, t, J=7.5 Hz).

PREPARATIVE EXAMPLE 35

6N Hydrochloric acid (20 ml) was added to 2-[3-(1-hexenyl)-4-methoxyphenyl]-4,4-dimethyl-4,5-dihydrooxazole (583 mg, 2.03 mmol), and the mixture was refluxed under heating for 4 hours. Saturated saturated brine (30 ml) was added to this solution, and the aqueous layer was extracted 3 times with ethyl acetate (50 ml). The organic layers were combined, and dried over anhydrous magnesium sulfate. The drying agent was filtered off, and the filtrate was concentrated under reduced pressure. The obtained residue was purified by column chromatography (hexane/ethyl acetate=2/1) to give 3-(1-hexenyl)-4-methoxybenzoic acid (164.3 mg, 35%) as a mixture (colorless crystals) of geometrical isomers (1:1).
$^1$H-NMR (CDCl$_3$)
E-isomer
δ: 8.17(1H, d, J=2.13 Hz), 7.95(1H, dd, J=8.31, 2.13 Hz), 6.92(1H, d, J=8.31 Hz), 6.67(1H, d, J=16.0 Hz), 6.32(1H, dt, J=16.0, 6.95 Hz), 3.92(3H, s), 2.30-2.21(2H, m), 1.51-1.30 (4H, m), 0.89(3H, t, J=7.18 Hz).
Z-isomer
δ: 8.02(1H, dd, J=8.66, 2.18 Hz), 8.00(1H, d, J=2.13 Hz), 6.89(1H, d, J=8.66 Hz), 6.47(1H, d, J=1 1.6 Hz), 5.79(1H, dt, J=11.6, 7.36 Hz), 3.91(3H, s), 2.30-2.21(2H, m), 1.51-1.30(4H,m), 0.93(3H, t, J=7.28 Hz).

PREPARATIVE EXAMPLE 36

3-(1-Hexenyl)-4-methoxybenzoic acid (160 mg, 0.683 mmol) and ethanol (7 ml) were mixed, and to this solution was added 10% palladium-carbon catalyst (30 mg). The mixture was stirred at room temperature for 3 hours in a steam of hydrogen. The palladium-carbon catalyst was filtered off, and the filtrate was concentrated under reduced pressure. The obtained residue was purified by washing with hexane to give 3-hexyl-4-methoxybenzoic acid (116 mg, 72%) as colorless crystals.
$^1$H-NMR (CDCl$_3$)$\delta$: 7.97(1H, d, J=8.63 Hz), 7.88(1H, s), 6.88(1H, d, J=8.63 Hz), 3.89(3H, s), 2.63(2H, t, J=7.72 Hz), 1.67-1.50(2H, m), 1.42-1.21(6H, m), 0.89(3H, t, J=6.88 Hz). FABMS (m/z): 237[M$^+$H$^+$] (100), 236(90), 219(80).

PREPARATIVE EXAMPLE 37

A crude product of 3-hexyl-4-methoxybenzoic acid and methanol (4 ml) were mixed. To this solution was added conc. sulfuric acid (2 drops), and the mixture was refluxed under heating for 20 hours. Water (10 ml) was added and methanol was evaporated under reduced pressure. The aqueous layer was extracted 3 times with ethyl acetate (20 ml). The organic layers were combined, and washed 3 times with saturated brine (20 ml). This solution was dried over anhydrous magnesium sulfate, and the drying agent was filtered off. The filtrate was concentrated under reduced pressure, and the obtained residue was purified by column chromatography (hexane/ethyl acetate=10/1) to give methyl 3-hexyl-4-methoxybenzoate (96.2 g) as a colorless oil.
$^1$H-NMR (CDCl$_3$)$\delta$: 7.88(1H, dd, J=8.55, 2.20 Hz), 7.82 (1H, d, J=2.20 Hz), 6.84(1H, d, J=8.55 Hz), 3.90(3H, s), 3.87(3H, s), 2.61(2H, t, J=7.74 Hz), 1.65-1.50(2H, m), 1.42-1.24(4H, m), 0.88(3H, t, J=6.89 Hz). FABMS (m/z): 251[M$^+$H$^+$] (100), 219(45), 179(45).

PREPARATIVE EXAMPLE 38

Methyl 3-hexyl-4-methoxybenzoate (93.2 mg, 0.372 mmol) and THF (2 ml) were mixed in a stream of argon. To this solution was added LAH (19 mg, 0.5 mmol) under ice-cooling, and the mixture was stirred for 1 hour. To this reaction mixture were successively added dropwise water (0.019 ml), a 1N aqueous sodium hydroxide solution (0.019 ml) and water (0.06 ml). Ether (20 ml) was added, and the mixture was vigorously stirred for 1 hour. The inorganic salt was filtered off, and the filtrate was concentrated under reduced pressure to give a crude product of (3-hexyl4-methoxyphenyl)methanol. The obtained product was not further purified, and used in the next reaction.

PREPARATIVE EXAMPLE 39

A crude product of (3-hexyl-4methoxyphenyl)methanol, dimethyl sulfoxide (DMSO, 1.5 ml) and triethylamine (0.46 ml, 3.3 mmol) were mixed in a stream of argon. To this solution was added sulfur trioxide-pyridine complex (159 mg, 1 mmol) under ice-cooling, and the mire was stirred at room temperature for 1 hour. This reaction mixture was poured into water (20 ml) to stop the reaction. The aqueous layer was extracted 3 times with ethyl acetate (20 ml). The organic layer was washed successively with 2N hydrochloric acid (20 ml), water (20 ml) and saturated brine (30 ml). This solution was dried over anhydrous magnesium sulfate, and the drying agent was filtered off. The filtrate was concentrated under reduced pressure, and the obtained residue was purified by column chromatography (hexane/ethyl acetate=1/1) to give 3-hexyl-4-methoxybenzaldehyde (75.4 mg, 92% in 2 steps) as a colorless oil.
$^1$H-NMR (CDCl$_3$)$\delta$: 9.87(1H, s), 7.72(1H, d, J=8.1 Hz), 7.69(1H, s), 6.94(1H, d, J=8.1 Hz), 3.91(3H, s), 2.64(2H, t, J=7.7 Hz), 1.70-1.46(2H, m), 1.42-1.23(6H, m), 0.89(3H, t, J=6.9 Hz). FABMS (m/z): 221[M$^+$H$^+$] (100), 149(30).

PREPARATIVE EXAMPLE 40

3-Hexyl-4-methoxybenzaldehyde (70 mg, 0.318 mmol), THF (1.5 ml) and methyl (triphenylphosphoranylidene) acetate (201 mg, 0.6 mmol) were mixed, and this solution was refluxed under heating for 5 hours. THF was evaporated under reduced pressure, and the obtained residue was purified by column chromatography (hexane/ethyl acetate=10/1) to give methyl 3-(3-hexyl-4-methoxyphenyl)cinnamate (84 mg, 96%) as colorless crystals.
$^1$H-NMR (CDCl$_3$)$\delta$: 7.64(1H, d, J=15.6 Hz), 7.34(1H, d, J=8.4 Hz), 7.32(1H, s), 6.93(1H, d, J=8.4 Hz), 6.30(1H, d, J=15.6 Hz), 3.85(3H, s), 3.79(3H, s), 2.59(2H, t, J=7.7 Hz), 1.64-1.50(2H, m), 1.42-1.21(6H, m), 0.97-0.83(3H, m). FABMS (m/z): 277[M$^+$H$^+$] (60), 276(100), 245(60).

PREPARATIVE EXAMPLE 41

Methyl 3-(3-hexyl-4-methoxyphenyl)cinnamate (80 mg, 0.29 mmol), ethanol (1 ml) and a 1N aqueous sodium hydroxide solution (1 ml) were mixed, and this solution was refluxed under heating for 1.5 hours. Ethanol was evaporated under reduced pressure, and conc. hydrochloric acid was added to make the solution acidic. Ethyl acetate (5 ml) was added to dissolve the precipitated crystals. The organic layer was separated, and the aqueous layer was extracted twice with ethyl acetate (5 ml). The organic layers were combined, washed 3 times with saturated brine (8 ml), and dried over anhydrous magnesium sulfate. The drying agent was filtered off, and the filtrate was concentrated under reduced pressure. The obtained residue was recrystallized from ethyl acetate to give 3-(3-hexyl-4-methoxyphenyl) cinnamic acid (58 mg, 76%) as colorless crystals.
$^1$H-NMR (CDCl$_3$)$\delta$: 7.73(1H, d, J=15.9 Hz), 7.37(1H, d, J=8.1 Hz), 7.35(1H, s), 6.84(1H, d, J=8.1 Hz), 6.56(1H, d, J=15.9 Hz), 2.60(2H, t, J=8.0 Hz), 1.73-1.50(2H, m), 1.43-1.22(6H,m), 0.89(3H, t, J=6.6 Hz). FABMS (m/z): 263[M$^+$H$^+$] (60), 262(100), 191(40).

PREPARATIVE EXAMPLE 42

Bromoacetyl bromide (7.73 g, 0.0383 mol, 1.0 eq) was dissolved in carbon disulfide (35 ml), and the solution was cooled with an ice salt Anhydrous aluminum chloride (10.2 g, 0.077 mol, 2.0 eq) and 2-pentyloxyphenol (6.9 g, 0.0383 mol, 1.0 eq) were successively added, and the mixture was stirred for 1 hour. The mixture was further stirred at room temperature for 4 hours, and water (10 ml) and dilute hydrochloric acid (10 ml) were carefully added under ice-cooling. The reaction mixture was extracted twice with ether (10 ml). The organic layers were combined, washed with saturated brine (30 ml), and dried over anhydrous sodium sulfate. The drying agent was filtered off, and the filtrate was concentrated under reduced pressure. The obtained residue was purified by column chromatography (n-hexane/ethyl acetate=5/1) to give 1-(4-hydro-3-pentyloxyphenyl)-2-bromoethanone (6.58 g, 57.0%).
$^1$H-NMR (CDCl$_3$)$\delta$: 7.55(1H, d, J=8.1 Hz), 7.54(1H, s), 6.97(2H, d, J=8.1 Hz), 6.19(1H, s), 4.40(2H, s), 4.12(2H, t, J=6.6 Hz), 1.9-1.8(2H, m), 1.5-1.4(4H, m), 0.94(3H, t, J=7.0 Hz). FABMS (m/z): 302[M$^+$H$^+$] (80), 301(85).

PREPARATIVE EXAMPLE 43

A solution of sodium hydroxide (680 mg), water (21ml) and antiformin (34 ml) was heated to 55° C. 1-(4-Hydroxy- 3-pentyloxyphenyl)-2-bromoethanone (3.01 g, 0.01 mol, 1.0 eq) was added, and the mixture was stirred at 60° C.–70° C. for 40 minutes. An aqueous solution (10 ml) of sodium thiosulfate (1.2 g) was added, and the mixture was cooled to room temperature. Conc. hydrochloric acid (5 ml) was added to adjust the mixture to pH 5–6. Water (50 ml) was added to this reaction mixture, and the mixture was extracted twice with ethyl acetate (100 ml). The organic layers were combined, washed with saturated brine (200 ml) and dried over anhydrous sodium sulfate. The drying agent was filtered off, and the filtrate was concentrated under reduced pressure. The obtained residue was purified by column chromatography (n-hexane/ethyl acetate/acetic acid=2/1/0.01) to give 4-hydroxy-3-pentyloxybenzoic acid (1.24 g, 55.3%).

$^1$H-NMR (CDCl$_3$)δ: 8.0-6.8(3H, m), 6.3(1H, bs), 4.2-4.0 (2H, m), 2.0-1.8(2H, m), 1.6-1.4(4H, m), 0.9(3H, t, J=7.5 Hz). FABMS (m/z): 225[M$^+$H$^+$] (80), 207(50).

PREPARATIVE EXAMPLE 44

3-Hydroxy-4-methoxybenzoic acid (9.6 g, 0.057 mol) was dissolved in DMF (90 ml), and to this solution were successively added 1-bromopentane (25.9 g, 0.17 mol, 3.0 eq) and anhydrous potassium carbonate (47.4 g, 0.34 mol, 6.0 eq). The mixture was stirred under heating at 90° C. for 3 hours. This reaction mixture was cooled to room temperature, and anhydrous potassium carbonate was filtered off. Water (200 ml) was added to the filtrate, and the mixture was extracted twice with ethyl acetate (200 ml). The organic layers were combined, washed with saturated brine (300 ml) and dried over anhydrous sodium sulfate. The drying agent was filtered off, and the filtrate was concentrated under reduced pressure. The obtained residue was purified by column chromatography (n-hexane/ethyl acetate=15/1-10/1) to give pentyl 4-methoxy-3-pentyloxybenzoate (17.4 g, 98.8%) as a colorless oil.

$^1$H-NMR (CDCl)δ: 7.7(1 H, dd, J=9, 3 Hz), 7.6(1 H, d, J=3 Hz), 6.9(1 H, d, J=9 Hz), 4.3(2 H, t, J=9 Hz), 4.1(2 H, t, J=8 Hz), 3.9(3 H, s), 2.0-1.7(4 H, m), 1.5-1.3(8 H, m), 0.9(6 H, t, J=8.0 Hz).

FABMS (m/z): 309[M$^+$H$^+$] (80), 308(100), 239(42).

IR (Neat, cm$^{-1}$):2956, 1712.

Elemental analysis: C$_{18}$H$_{28}$O$_4$ Calculated C 70.10, H 9.15 Found C 70.19, H 9.25

PREPARATIVE EXAMPLE 45

Pentyl 4-methoxy-3-pentyloxybenzoate (17.4 g, 0.056 mol) was dissolved in methanol (85 ml). A 1N aqueous sodium hydroxide solution (85 ml, 0.085 mol, 1.5 eq) was added, and the mixture was refluxed under heating for 1.5 hours. This reaction mixture was cooled to room temperature, and washed with n-hexane (100 ml). A 10% aqueous hydrochloric acid solution (ca. 120 ml) was added to the aqueous layer under ice-cooling to make the same acidic. This was extracted twice with ethyl acetate (220 ml). The organic layers were combined, washed with saturated brine (400 ml) and dried over anhydrous sodium sulfate. The drying agent was filtered off, and the filtrate was concentrated under reduced pressure. The obtained residue was purified by recryst azation from ethyl acetate to give 4-methoxy-3-pentyloxybenzoic acid (10.7 g, 79.6%) as colorless crystals.

m.p.: 124.6–125.0° C.

$^1$H-NMR (CDCl$_3$)δ:7.76(1 H, d, J=2.1 Hz), 7.60(1 H, dd, J=8.6, 2.1 Hz), 6.92(1 H, d, J=8.6 Hz), 4.08(2 H, t, J=7.0 Hz), 4.05(3 H, s), 2.1–1.8(2 H, m), 1.6–1.3(4 H, m), 0.94(3 H, t, J=7.2 Hz).

FABMS (m/z): 239[M+H$^+$] (80), 238(100), 168(57).

IR (KBr, cm$^{-1}$): 3432, 2951, 1678.

Elemental analysis: C$_{13}$H$_{18}$O$_4$ Calculated C 65.53, H 7.61 Found C 65.65, H 7.74

PREPARATIVE EXAMPLE 46

3-Hydroxy-4-methoxycinnamic acid (9.7 g, 0.050 mol, 1.0 eq) was dissolved in DMF (90 ml). 1-Bromopentane (22.7 g, 0.150 mol, 3.0 eq) and anhydrous potassium carbonate (41.5 g, 0.30 mol, 6.0 eq) were successively added to this solution, and the mixture was stirred under heating at 90° C. for 3 hours. This reaction mixture was cooled to room temperature, and anhydrous potassium carbonate was filtered off. Water (200 ml) was added to the filtrate, and the mixture was exracted twice with ethyl acetate (200 ml). The organic layers were combined, washed with saturated brine (300 ml) and dried over anhydrous sodium sulfate. The drying agent was filtered off, and the filtrate was concentrated under reduced pressure. The obtained residue was purified by column chromatography (n-hexane/ethyl acetate=15/1-10/1) to give pentyl 4-methoxy-3-pentyloxycinnamate (18.2 g, 100%) as a colorless oil.

$^1$H-NMR (CDCl$_3$)δ:7.62(1 H, d, J=15.0 Hz), 7.08(1 H, dd, J=10.3, 1.9 Hz), 7.06(1 H, d, J=1.9 Hz), 6.86(1 H, d, J=10.3 Hz), 6.30(1 H, d, J=15.0 Hz), 4.19(2 H, t, J=9.0 Hz), 4.03(2 H, t, J=6.0 Hz), 3.89(3 H, s), 1.9-1.6(4 H, m), 1.5-1.3(8 H, m), 1.0-0.9(6 H, m).

FABMS (m/z): 335[M$^+$H$^+$] (55), 334(100), 247(62).

IR (Neat, cm$^{-1}$): 2954, 1710.

Elemental analysis: C$_{20}$H$_{30}$O$_4$ Calculated C 71.82, H 9.04 Found C 71.99, H 9.28

PREPARATIVE EXAMPLE 47

Pentyl 4-methoxy-3-pentyloxycinna inate (18.0 g, 0.050 mol) was dissolved in methanol (75 ml). A 1N aqueous sodium hydroxide solution (75 ml, 0.075 mol, 1.5 eq) was added, and the mixture was re fluxed under heating for 1 hour. This reaction mixture was cooled to room temperature, and a 10% aqueous hydrochloric acid solution (ca. 100 ml) was added under ice-cooling to make the mixture acidic. This was extracted twice with ethyl acetate (150 ml). The organic layers were combined, washed with saturated brine (300 ml) and dried over anhydrous sodium sulfate. The drying agent was fltered off, and the filtrate was concentrated under reduced pressure. The obtained residue was purified by recrystallization from ethyl acetate to give 4-methoxy-3-pentyloxycinnamic acid (12.2 g, 93%) as colorless crystals.

m.p.: 150.0–150.3° C.

$^1$H-NMR (CDCl$_3$)δ: 7.73(1 H, d, J=16.0 Hz), 7.13(1 H, dd, J=8.1, 1.9 Hz), 7.09(1 H, d, J=1.9 Hz), 6.88(1 H, d, J=8.1 Hz), 6.31(1 H, d, J=16.0 Hz), 4.04(2 H, t, J=6.8 Hz), 3.91(3 H, s), 2.1-1.8(2 H, m), 1.5-1.3(4 H, m), 0.94(3 H, t, J=7.0 Hz).

FABMS (m/z): 265 [M$^+$H$^+$] (62), 264(100), 247(40).

IR (KBr, cm$^{-1}$): 2934, 1679.

Elemental analysis: C$_{15}$H$_{20}$O$_4$ Calculated C 68.16, H 7.63 Found C 68.20, H 7.78

PREPARATIVE EXAMPLE 48

3,4-Dihydroxybenzoic acid (462 mg, 3 mmol) was dissolved in DMF (10 ml). Potassium carbonate (3.73 g, 27 mmol, 9 eq) and 1-bromopentane (1.70 ml, 13.5 mmol, 4.5 eq) were successively added to this solution at room temperature, and the mixture was stirred at 110° C. for 24 hours. This reaction mixture was filtered, and the residual potassium carbonate was washed with ethyl acetate (50 ml). The filtrate was washed with water (15 ml×3) and saturated brine (15 ml). The organic layer was dried over anhydrous sodium sulfate. After the drying agent was filtered off, the filtrate was concentrated under reduced pressure. The obtained residue was purified by column chromatography (heaxane/ethyl acetate=95/5) to give pentyl 3,4-dipentyloxybenzoate (912 mg, 83%).

$^1$H-NMR (CDCl$_3$, 300 MHz)δ: 7.66(1 H, d, J=8.4, 1.9 Hz), 7.57(1 H, d, J=1.9 Hz), 6.89(1 H, d, J=8.4 Hz), 4.31(2 H, t, J=6.7 Hz), 4.07(4 H, 2t, J=6.6 Hz), 1.90-1.76(6 H, m), 1.52-1.38(12 H, m), 0.98-0.94(9 H, m).

FABMS (+) (m/z): 465[M+1] (61), 364[M](100), 295 (45), 276(42).

PREPARATIVE EXAMPLE 49

Pentyl 3,4-dipentyloxybenzoate (911 mg, 2.50 mmol) was dissolved in methanol (15.0 ml). To this solution was added a 1N aqueous potassium hydroxide solution (7.5 ml, 7.5 mmol, 3 eq), and the mixture was stirred with reflux for 5 hours. A 3N aqueous hydrochloric acid solution was added to this reaction mixture to make the same acidic (pH <2). The mixture was extracted with chloroform (20 ml×3). The organic layer was washed with saturated brine (20 ml). The organic layer was d ried over anhydrous magnesium sulfate, and the drying agent was filtered off. The filtrate was concentrated under reduced pressure to give a colorless solid. This was recrystallized from ethyl acetate-hexane to give 3,4-dipentyloxybenzoic acid (512 mg, 70%) as colorless crystals.

$^1$H-NMR (CDCl$_3$, 300 MHz)δ: 7.71(1 H, dd, J=8.4, 2.0 Hz), 7.58(1 H, d, J=2.0 Hz), 6.88(1 H, d, J=8.4 Hz), 4.06(2 H, t, J=6.6 Hz), 4.04(2 H, t, J=6.6 Hz), 1.87-1.79(4 H, m), 1.49-1.35(8 H, m), 0.95-0.90(6 H, m).

FABMS (+) (m/z): 295[M+1] (52), 294[M](80), 277(29), 224(32).

PREPARATIVE EXAMPLE 50

3-Hydroxy-4-nitrobenzoic acid (5 g, 27.4 mmol), DMF (40 ml), potassium carbonate (13.8 g, 100 mmol) and pentyl bromide (8.7 ml, 70 mmol) were mixed, and this solution was stirred at 100° C. for 1.5 hours. The reaction mixture was filtered to remove the inorganic salt, and DMF was evaporated under reduced pressure. Ethyl acetate (100 ml) was added to the obtained residue, and the mixture was washed 3 times with saturated brine (30 ml) and dried over anhydrous magnesium sulfate. The drying agent was filtered off, and the filtrate was concentrated under reduced pressure. Ethanol (150 ml) and 10% palladium carbon catalyst (0.5 g) were added to the obtained residue, and the mixture was stirred at room temperature for 5.5 hours in a stream of hydrogen. The palladium-carbon catalyst was filtered off, and the filtrate was concentrated under reduced pressure. The obtained residue was purified by column chromatography (hexane/ethyl acetate=5/1) to give pentyl 4-amino-3-pentyloxybenzoate (5.72 g, 70% in 2 steps) as a pale-yellow oil.

$^1$H-NMR (CDCl$_3$)δ: 7.53(1 H, dd, J=8.2, 1.7 Hz), 7.44(1 H, d, J=1.7 Hz), 6.66(1 H, d, J=8.2 Hz), 4.26(2 H, t, J=6.7 Hz), 4.20(2 H, bs), 4.05(2 H, t, J=6.5 Hz), 1.86-1.65(4 H, m), 1.50-1.30(8 H, m), 1.0-0.85(6 H, m).

FABMS (m/z): 294[M$^+$H$^+$] (80), 224(50), 206(50).

PREPARATIVE EXAMPLE 51

Pentyl 4-amino-3-pentyloxybenzoate (1 g, 3.41 mmol), acetone (5 ml), potassium carbonate (0.83 g, 6 mmol) and methyl iodide (4 ml) were mixed, and this solution was refluxed under heating for 9 hours. The reaction mixture was filtered to remove the inorganic salt, and acetone was evaporated under reduced pressure. Ethanol (10 ml) and a 1N aqueous sodium hydroxide solution (10 ml) were added to the obtained residue, and the mixture was refluxed under heating for 2.5 hours. Ethanol was evaporated under reduced pressure, and conc. hydrochloric acid was added to make this solution acidic. The aqueous layer was extracted 3 times with ethyl acetate (20 ml). The organic layers were combined, washed 3 times with saturated brine (20 ml), and dried over anhydrous magnesium sulfate. The drying agent was filtered off, and the filtrate was concentrated under reduced pressure. The obtained residue was purified by column chromatography (hexane/ethyl acetate=1/1) to give 4-dimethylamino-3-pentyloxybenzoic acid (146 mg, 17% in 2 steps) as a pale-yellow oil.

$^1$H-NMR (CDCl$_3$)δ: 7.68(1 H, dd, J=8.1, 1.5 Hz), 7.53(1 H, d, J=1.8 Hz), 6.85(1 H, d, J=8.1 Hz), 4.06(2 H, t, J=6.8 Hz), 2.93(6 H, s), 1.93-1.80(2 H, m), 1.50-1.30(4 H, m), 0.94(3 H, t, J=7.2 Hz).

FABMS (m/z): 252[M$^+$H$^+$1(100), 181(30).

PREPARATIVE EXAMPLE 52

4Methoxy-3-nitrobenzoic acid (5 g, 25.4 mmol), DMF (30 ml), potassium carbonate (5.53 g, 40 mmol) and pentyl bromide (4 ml, 32.3 mmol) were mixed, and this solution was stirred at 100° C. for 1.5 hours. The reaction mixture was filtered to remove the inorganic salt, and DMF was evaporated under reduced pressure. Ethyl acetate (100 ml) was added to the obtained residue. The mixture was washed 3 times with saturated brine (30 ml) and dried over anhydrous magnesium sulfate. The drying agent was filtered off, and the filtrate was concentrated under reduced pressure. Ethanol (150 ml) and 10% palladium-carbon catalyst (0.5 g) were added to the obtained residue, and the mixture was stirred at room temperature for 5.5 hours in a stream of hydrogen. The palladium-carbon catalyst was filtered off, and the filtrate was concentrated under reduced pressure. The obtained residue was purified by column chromatography (hexane/ethyl acetate=3/1) to give 3-amino-4-methoxybenzoic acid (5.98 g, 99% in 2 steps) as colorless crystals.

$^1$H-NMR (CDCl$_3$)δ: 7.48(1 H, dd, J=8.3, 1.9 Hz), 7.38(1 H, d, J=2.1 Hz), 6.79(1 H, d, J=8.3 Hz), 4.26(2 H, t, J=6.7 Hz), 4.09(3 H, s), 3.86(2 H, bs), 1.78-1.66(2 H, m), 1.47-1.29(4 H, m), 0.93(3 H, t, J=7.1 Hz).

FABMS (m/z): 238[M$^+$H$^+$ (60), 237(100).

PREPARATIVE EXAMPLE 53

3-Amino-4-methoxybenzoic acid (1.53 g, 6.45 mmol), DMF (15 ml), potassium carbonate (2.07 g, 15 mmol) and pentyl bromide (1.86 ml, 15 mmol) were mixed, and the solution was stirred at 100° C. for 10.5 hours. The reaction mixture was filtered to remove the inorganic salt, and DMF was evaporated under reduced pressure. The obtained residue was purified by column chromatography on silica gel (hexane/ethyl acetate=10/1) to give pentyl 4-methoxy-3-pentylaminobenzoate (1.32 g, 67%) and pentyl 3-dimethylamino-4-methoybenzoate (334 mg, 14%) as colorless oils. pentyl 4-methoxy-3-pentylaminobenzoate ¹H-NMR (CDCl₃)δ: 7.41(1 H, dd, J=8.1, 2.1 Hz), 7.24(1 H, d, J=2.1 Hz), 6.75(1 H, d, J=8.1 Hz), 4.27(2 H, t, J=6.6 Hz), 4.20(1 H, bs), 3.90(3 H, s), 3.17(2 H, t, J=7.2 Hz), 1.82-1.62(4 H, m), 1.5-1.3(8 H, m), 0.93(3 H, t, J=7.2 Hz).

FABMS (m/z): 308[M⁺H⁺] (50), 307(100), 250(50). pentyl 3-dimethylamino-4-methoxybenzoate ¹H-NMR (CDCl₃)δ: 7.67(1 H, dd, J=8.5, 2.1 Hz), 7.66(1 H, d, J=2.0 Hz), 6.84(1 H, d, J=8.5 Hz), 4.28(2 H, t, J=6.7 Hz), 3.89(3 H, s), 3.08(4 H, t, J=7.7 Hz), 1.80-1.70(2 H, m), 1.5-1.18(16 H, m), 0.93(3 H, t, J=7.1 Hz), 0.86(3 H, t, J=7.0 Hz).

FABMS (m/z): 378[M⁺H⁺] (100), 320(100), 264(40).

PREPARATIVE EXAMPLE 54

Ethanol (3 ml) and a 1N aqueous sodium hydroxide solution (3 ml) were added to pentyl 4-methoxy-3-pentylaminobenzoate (500 mg, 1.63 mmol), and the mixture was refluxed under heating for 2 hours. Ethanol was evaporated under reduced pressure. Conc. hydrochloric acid was added to neutralize this solution, and the aqueous layer was etacted 3 times with ethyl acetate (5 ml). The organic layers were combined, washed 3 times with saturated brine (5 ml) and dried over anhydrous magnesium sulfate. The drying agent was filtered off, and the filtrate was concentrated under reduced pressure. The obtained crude crystals were purif ied by washing with hexane to give 4methoxy-3-pentylaminobenzoic acid (356 mg, 71%) as colorless crystals.

¹H-NMR (CDCl₃)δ: 7.51(1 H, dd, J=8.1, 2.1 Hz), 7.29(1 H, d, J=2.1 Hz), 6.78(1 H, d, J=8.1 Hz), 3.92(3 H, s), 3.18(2 H, t, J=7.2 Hz), 1.75-1.6(2 H, m), 1.5-1.3(4 H, m), 0.93(3 H, t, J=6.5 Hz).

FABMS (m/z): 238[M⁺H⁺] (80), 180(70).

PREPARATIVE EXAMPLE 55

(4-Hydroxyphenyl)acetonitrile (12.6 g, 0.094 mol, 1 eq) was dissolved in DMF (60 ml), and to this solution were successively added ben zyl bromide (12.4 ml, 0.104 mol, 1.1 eq) and anhydrous potassium carbonate (19.6 g, 0.14 mol, 1.5 eq). The mixture was stirred under heating at 90° C. for 1.5 hours. This reaction mixture was cooled to room temperature. Water (200 ml) was added, and the mixture was extracted twice with ethyl ether (400 ml). The organic layers were combined, washed with saturated brine (800 ml), and dried over anhydrous sodium sulfate. The drying agent was filtered off, and the filtrate was concentrated under reduced pressure and recrystllized from ethyl ether to give 4-benzyloxyphenylacetonitrile (11.1 g, 52.7%) as colorless needles.

m.p.: 67.9–68.2° C.

¹H-NMR (CDCl₃)δ: 7.5-7.3(5 H, m), 7.23(2 H, d, J=8.7 Hz), 6.97(2 H, d, J=8.7 Hz), 5.06(2 H, s), 3.67(2 H, s).

FABMS (m/z): 223[M⁺H⁺] (40).

IR (KBr, cm⁻¹): 3438, 2247, 1615, 1514, 1247, 1014.

Elemental analysis: C₁₅H₁₃NO₄ Calculated C 80.69, H 5.87, N 6.27 Found C 80.48, H 5.83, N 6.33

PREPARATIVE EXAMPLE 56

LAH (2.82 g, 0.15 mol, 1.5 eq) was dissolved in THF (50 ml), and to this solution was added dropwise a THF solution (50 ml) of 4-benzyloxyphenyl-acetonitrile (11.1 g, 0.05 mol, 1.0 eq) under ice-cooling. After the completion of the dropwise addition, the mixture was refluxed under heating for 1.5 hours. The reaction mixture was cooled to room temperature, and a saturated aqueous sodium sulfate solution (about 40 ml) was added under ice-cooling. After filtration through Celite, the filtrate was concentrated under reduced pressure. The obtained residue was purified by column chromatography (chloroform/methanol=10/1) to give 2-(4-benzyloxyphenyl)ethylamine (2.02 g, 17.9%) as colorless needles.

m.p.: 58.7°–59.6° C.

¹H-NMR (CDCl₃)δ: 7.5-7.3(5 H, m), 7.11(2 H, d, J=8.6 Hz), 6.92(2 H, d, J=8.6 Hz), 5.04(2 H, s), 2.93(2 H, t, J=6.8 Hz), 2.69(2 H, t, J=6.8 Hz), 1.57(2 H, bs).

FABMS (m/z): 228[M⁺H⁺] (40).

IR (KBr, cm⁻¹): 3360, 2864, 1611, 1513, 1248.

PREPARATIVE EXAMPLE 57

3-Hydroxyphenylacetonitrile (834 mg, 6.26 mmol) was dissolved in DMF (10 ml), and to this solution were successively added benzyl bromide (0.82 ml, 6.89 mmol, 1.1 eq) and anhydrous potassium carbonate (1.30 g, 9.40 mmol, 1.5 eq). The mixture was stirred under heating at 90° C. for 1.5 hours. This reaction mixture was cooled to room temperature, and water (20 ml) was added. The mixture was extracted twice with ethyl acetate (40 ml). The organic layers were combined, washed with saturated brine (80 ml) and dried over anhydrous sodium sulfate. The drying agent was filtered off, and the filtrate was concentrated under reduced pressure. The obtained residue was purified by column chromatography (hexane/ethyl acetate=1/1) to give (3-benzyloxyphenyl)acetonitrile (1.21 g, 86.8%).

¹H-NMR (CDCl₃)δ: 7.5-7.3(6 H, m), 7.0-6.9(3 H, m), 5.09(2 H, s), 3.72(2 H, s).

PREPARATIVE EXAMPLE 58

LAH (0.615 g, 0.0162 mol, 3.0 eq) was dissolved in THF (20 ml), and to this solution was added dropwise a THF solution (20 ml) of (3-benzyloxyphenyl)-acetonitrile (1.2 g, 0.0054 mol, 1.0 eq) under ice-cooling. After the completion of the dropwise addition, the mixture was refluxed under heating for 3 hours. The reaction mixture was cooled to room temperature, and a saturated aqueous sodium sulfate solution (about 3040 ml) was added under ice-cooling. After filtration through Celite, the filtrate was concentrated under reduced pressure. The obtained residue was purified by column chromatography (chloroform/methanol=10/1) to give 2-(3-benzyloxyphenyl)ethylamine (0.434 g, 35.3%) as a pale-yellow amorphous.

¹H-NMR (CDCl₃)δ: 7.5-7.2(6 H, m), 6.8-6.7(3 H, m), 5.09(2 H, s), 2.95(2 H, t, J=7.0 Hz), 2.70(2 H, t, J=7.0 Hz), 2.01(2 H, bs).

FABMS (m/z): 228M⁺H⁺] (90).

PREPARATIVE EXAMPLE 59

10% Palladium-carbon catalyst (water content 50%, 86 mg) was added to a solution of 2-(3-benzyloxyphenyl) ethylamine (434 mg, 1.91 mmol, 1.0 eq) in THF (10 ml), and the mixture was stirred at room temperature for 3 hours in a stream of hydrogen. The reaction ma ire was filtered through Celite, and the filtrate was concentrated under reduced pressure to give 2-(3-hydroxyphenyl)ethylamine (250 mg, 95.5%).

¹H-NMR (CDCl₃)δ: 8.26(1 H, bs), 7.1-6.9(1 H, m), 6.7-6.6(1 H, m), 6.6-6.4(2 H, m), 2.7-2.6(2 H, m), 2.6-2.5(2 H, m), 3.5(2 H, bs).

FABMS (m/z): 138[M⁺H⁺] (30).

PREPARATIVE EXAMPLE 60

(2-Hydro xyphenyl)acetonitrile (1.01 g, 0.0076 mol) was dissolved in DMF (10 ml), and to this solution were successively added benzyl bromide (0.90 ml, 0.0076 mol, 1.0 eq) and anhydrous potassium carbonate (2.1 g, 0.015 mol, 3.0 eq). The mixture was stirred with heating at 90° C. for 1.5 hours. The reaction mixture was cooled to room temperature, and water (10 ml) was added. The mixture was extracted twice with ethyl acetate (30 ml). The organic layers were combined, washed with saturated brine (60 ml) and dried over anhydrous sodium sulfate. The drying agent was filtered off, and the filtrate was concentrated under reduced pressure to give (2-benzyloxyphenyl)acetonitrile (2.04 g, 100%) as a colorless solid.

PREPARATIVE EXAMPLE 61

LAH (1.04 g, 0.0273 mol, 3.0 eq) was dissolved in THF (25 ml), and to this solution was added dropwise a THF solution (25 ml) of (2-benzyloxyphenyl)-acetonitrile (2.04 g, 0.0091 mol, 1.0 eq) under ice-cooling. After the completion of the dropwise addition, the mixture was stirred at room temperature for 15 minutes and refluxed under heating for 2 hours. This reaction mixture was cooled with ice-cold water, and a saturated aqueous sodium sulfate solution (about 30–40 ml) was added. After filtration through Celite, the filtrate was concentrated under reduced pressure. The obtained residue was purified by column chromatography (chloroforn/methanol=5/1) to give 2-(2-benzyloxyphenyl) ethylamine (0.415 g, 20.0%) as a pale-yellow amorphous compound.

FABMS (m/z): 228[M$^+$H$^+$] (100).

PREPARATIVE EXAMPLE 62

10% Palladium-carbon catalyst (water content 50%, 42 mg) was added to a solution of 2-(2-benzyloxyphenyl) ethylamine (415 mg, 1.826 mmol, 1.0 eq) in THF (10 ml), and the mixture was stirred for 2 hours at room temperature in a stream of hydrogen. The reaction mixture was filtered through Celite, and the filtrate was concentrated under reduced pressure to give 2-(2-hydroxyphenyl)ethylamine (230 mg, 91.8%).

PREPARATIVE EXAMPLE 63

3-(4-Hydroxyphenyl)propionitrile (1.47 g, 0.01 mol) was dissolved in DMF (24 ml), and to this solution were successively added benzyl bromide (1.31 ml, 0.011 mol, 1.1 eq) and anhydrous potassium carbonate (4.15 g, 0.030 mol, 3.0 eq). The mixture was stirred under heating at 90° C. for 3 hours. This reaction mixture was cooled to room temperature, and water (100 ml) was added. The mixture was extracted twice with ethyl acetate (100 ml). The organic layers were combined, washed with saturated brine (200 ml) and dried over anhydrous sodium sulfate. The drying agent was filtered off, and the filtrate was concentrated under reduced pressure to give 3-(4-benzyloxyphenyl) propionitrile (2.39 g, 100%) as a colorless solid.

PREPARATIVE EXAMPLE 64

LAH (570 mg, 0.015 mol, 1.5 eq) was dissolved in THF (30 ml), and to this solution was added dropwise a THF solution (50 ml) of 3-(4-benzyloxyphenyl)-propionitrile (2.37 g, 0.01 mol, 1.0 eq) under ice-cooling. After the completion of the dropwise addition, the mixture was stirred at room temperature for 2 hours. This reaction mixture was cooled with ice-cold water, and a saturated aqueous sodium sulfate solution (about 30–40 ml) was added. After filtration through Celite, the filtrate was concentrated under reduced pressure. The obtained residue was purified by column chromatography (chloroform/metanol=10/1-5/1) to give 3-(4-benzyloxyphenyl)propylamine (1.2 g, 49.7%) as a pale-yellow amorphous compound.

$^1$H-NMR (CDCl$_3$)δ:7.4-7.3(5 H, m), 7.10(2 H, d, J=8.6 Hz), 6.90(2 H, d, J=8.6 Hz), 5.04(2 H, s), 3.48(2 H, s), 2.72(2 H, d, J=7.1 Hz), 2.60(2 H, t, J=7.7 Hz), 1.8-1.7(2 H, m).

FABMS (m/z): 242[M$^+$H$^+$] (100).

PREPARATIVE EXAMPLE 65

100% Palladium-carbon catalyst (water content 50%, 120 mg) was added to a solution of 3-(4-benzyloxyphenyl) propylamine (620 mg, 2.57 mmol, 1.0 eq) in THF (10 ml), and the mixture was stirred for 2 hours at room temperature in a stream of hydrogen. The reaction mixture was filtered through Celite, and the filtrate was concentrated under reduced pressure to give 3-(4-hydroxyphenyl)propylamine (354 mg, 91.1%).

$^1$H-NMR (CDCl$_3$)δ: 7.0(2 H, d, J=9 Hz), 6.7(2 H, d, J=9 Hz), 3.0(3 H, bs), 2.7(2 H, t, J=7.5 Hz), 2.6(2 H, t, J=7.5 Hz), 1.8-1.7(2 H, m).

FABMS (m/z): 152[M$^+$H$^+$] (100).

PREPARATIVE EXAMPLE 66

LAH (570 mg, 0.015 mol, 1.5 eq) was dissolved in THF (30 ml), and to this solution was added dropwise a THF solution (30 ml) of 4-benzyloxybenzonitrile (2.09 g, 0.01 mol, 1.0 eq) under ice-cooling. After the completion of the dropwise addition, the mixture was heated to room temperature and refluxed under heating for 3 hours. This reaction mire was cooled with ice-cold water, and a saturated aqueous sodium sulfate solution (about 30–40 ml) was added. After filtration through Celite, the filtrate was concentrated under reduced pressure to give 4-benzylobenzylamine (2.03 g, 95.1%) as a pale-yellow amorphous compound.

$^1$H-NMR (CDCl$_3$)δ: 7.4-7.3(5 H, m), 7.22(2 H, d, J=8.6 Hz), 6.94(2 H, d, J=8.6 Hz), 5.05(2 H, s), 3.80(2 H, s), 1.50(2 H, s).

FABMS (m/z): 214[M$^+$H$^+$] (60), 197(100).

PREPARATIVE EXAMPLE 67

10% Palladium-carbon catalyst (water content 50%, 50 mg) was added to a solution of 4-benzyloxybenzylamine (530 mg, 2.485 mmol, 1.0 eq) in THF (10 ml), and the mixture was stirred for 3 hours at room temperature in a stream of hydrogen. The reaction mixture was filtered through Celite, and the filtrate was concentrated under reduced pressure. The obtained residue was purified by column chromatography (n-hexane/ethyl acetate=1/1) to give 4-hydroxybenzylamine (260 mg, 85.0%).

$^1$H-NMR (CDCl$_3$)δ: 7.1(2 H, d, J=9 Hz), 6.77(2 H, d, J=9 Hz), 3.8(2 H, s), 2.9(3 H, bs).

FABMS (m/z): 124M$^+$H$^+$] (80).

PREPARATIVE EXAMPLE 68

2-(4-Hydroxyphenyl)ethylamine (1.37 g, 10.0 mmol, 1.0 eq ) was dissolved in acetic acid (10 ml), and platinum dioxide catalyst (137 mg) was added. The mixture was stirred at 3 kgf/cm$^2$ in a stream of hydrogen at 70° C. for 5 hours. The reaction mixture was filtered through Celite and the catalyst was washed with toluene. The filtrate was concentrated under reduced pressure to give 2-(4-hydroxycylohexyl)ethylamine (1.8 g).

$^1$H-NMR (CDCl$_3$)δ: 8.76(1 H, bs), 3.9(0.5 H, bs), 3.6-3.5(0.5 H, m), 3.0-2.8(4 H, m), 2.2-0.8(9 H, m).

FABMS (m/z): 144[M$^+$H$^+$] (20), 128(100).

PREPARATIVE EXAMPLE 69

LAH (1.90 g, 50 mmol) was suspended in diethyl ether (150 ml), and a solution of 3-pyridylacetonitrile (5.91 g, 50 mmol, 1.0 eq) in diethyl ether (150 ml) was added at room temperature. The mixure was stirred at room temperature for 14 hours. To this reaction mixture were successively added water (1.9 ml), a 15% aqueous sodium hydroxide solution (1.9 ml) and water (5.7 ml). The resulting precipitate was filtered through Celite and washed with diethyl ether, which was followed by concentration under reduced pressure. The obtained residue was subjected to column chromatography (chloroform/methanol=30/1-chloroform/methanol/triethylamine=8/2/0.1) to give 2-(3-pyridyl)ethylamine (2.39 g, 39%) as a colorless oil.

$^1$H-NMR (CDCl$_3$, 300 MHz)δ: 8.48-8.46(2 H, m), 7.55-7.52(1 H, m), 7.25-7.16(1 H, m), 2.99(2 H, t, J=7.5 Hz), 2.76(2 H, t, J=7.5 Hz).

FABMS (+) (m/z): 123[M+1] (100).

PREPARATIVE EXAMPLE 70

4-Vinylpyridine (5.26 ml, 50 mmol) and ammonium chloride (5.35 g, 100 mmol, 2.0 eq) were dissolved in methanol (2.5 ml) and water (15 ml), and the mixture was stirred with reflux for 23 hours. This reaction mixture was poured into ice water, and a 15% aqueous sodium hydroxide solution was added to make the same strong alkaline. The mixture was extracted 3 times with chloroform (50 ml). The organic layers were combined, washed with saturated brine and dried over anhydrous sodium sulfate. The drying agent was filtered off, and the filtrate was concentrated under reduced pressure. The obtained residue was distilled under reduced pressure to give 2-(4-pyridyl)ethylamine (①) (1.80 g, 30%; 87° C./6 mmHg) as a colorless oil. The residue from the distillation was subjected to column chromatography (chloroform/methanol=30/1-9/1) to give bis[2-(4-pyridyl)ethyl]amine (②) (1.11 g, 20%) as a pale-yellow oil.

①: $^1$H-NMR (CDCl$_3$, 300 MHz)δ: 8.53-8.51(2 H, m), 7.15-7.13(2 H, m), 3.04-2.98(2 H, m), 2.75(2 H, t, J=8.4 Hz).

FABMS (+) (m/z): 123[M+1] (100).

②: $^1$H-NMR (CDCl$_3$, 300 MHz)δ: 8.47-8.42(4 H, m), 7.11-7.09(4 H, m), 2.95-2.90(4 H, m), 2.77(4 H, t, J=7.1 Hz).

FABMS (+) (m/z): 228[M+1] (100).

PREPARATIVE EXAMPLE 71

2-Vinylpyridine (5.26 g, 50 mmol) and ammonium chloride (13.4 g, 250 mmol, 5.0 eq) were dissolved in methanol (2.5 ml) and water (15 ml), and the mixture was stirred with reflux for 7 hours. This reaction mixture was poured into ice water, and a 15% aqueous sodium hydroxide solution was added to make the same strong alkaline. The mixture was extracted 3 times with chloroform (50 ml). The organic layers were combined, washed with saturated brine and dried over anhydrous sodium sulfate. The drying agent was filtered off, and the filtrate was concentrated under reduced pressure. The obtained residue was distilled under reduced pressure to give 2-(2-pyridine)ethylamine.

(①) (2.55 g, 42%; 77–78° C./6 mmHg) as a colorless oil. The residue from the distillation was subjected to column chromatography (chloroform/methanol=10/1) to give bis[2-(2-pyridyl)ethyl]amine ((②)) (2.04 g, 36%) as a pale-yellow oil ①: $^1$H-NMR (CDCl$_3$, 300 MHz)δ: 8.56-8.52(4 H, m), 7.60(1 H, td, J=7.60, 1.80 Hz), 7.17(1 H, d, J=7.6 Hz), 7.16-7.09(1 H, m), 3.12(2 H, t, J=6.7 Hz), 2.93(2 H, t, J=6.7 Hz).

FABMS (+) (m/z): 123[M+1] (100), 106(45).

②: $^1$H-NMR (CDCl$_3$, 300 MHz)δ: 8.48(2 H, d, J=4.8 Hz), 7.57(2 H, td, J=7.6, 1.7 Hz), 7.14(2 H, d, J=7.6 Hz), 7.12-7.08(2 H, m), 3.10-2.96(8 H, m), 2.41(1 H, brs).

FABMS (+) (m/z): 228[M+1] (100), 135(80).

PREPARATIVE EXAMPLE 72

2-(4-Hydroxyphenyl)ethylamine (5.0 g, 0.0364 mol, 1 eq) was dissolved in formic acid (77 ml, 2.04 mol, 56 eq), and acetic anhydride (25.4 ml, 0.27 mol, 7.4 eq) was added to this solution at 5–15° C. The mixture was stirred at room temperature for 3 hours. Ice-cold water (30 ml) was added to this reaction mixture, and the mixture was concentrated under reduced pressure. Water (50 ml) was added to the residue, and the mixture was extracted twice with ethyl acetate (50 ml). The organic layers were combined, washed with saturated brine (100 ml) and dried over anhydrous sodium sulfate. The drying agent was filtered off, and the filtrate was concentrated under reduced pressure to give 2-(4-hydroxyphenyl)ethyl-N-formamide (6.6 g, 100%) as an oil.

$^1$H-NMR (CDCl$_3$)δ: 8.69(1 H, s), 8.09(1 H, s), 7.41(2 H, d, J=8.7 Hz), 6.60(2 H, d, J=8.7 Hz), 3.83(2 H, t, J=4.9 Hz), 3.51(2 H, t, J=4.9 Hz).

FABMS (m/z): 166(100).

PREPARATIVE EXAMPLE 73

LAH (2.14 g, 0.056 mol, 3 eq) was dissolved in THF (30 ml), and to this solution was added dropwise a THF solution (30 ml) of 2-(4-hydroxyphenyl)ethyl-N-formamide (3.1 g, 0.0188 mol, 1 eq) under ice-cooling. After the completion of the dropwise addition, the mixture was heated to room temperature and refluxed under heating for 5 hours. This reaction mixture was cooled with ice-cold water, and a saturated aqueous sodium sulfate solution (about 10–20 ml) was added. After filtration of this reaction mixture through Celite, the filtrate was concentrated under reduced pressure to give 2-(4-hydroxyphenyl)ethyl-N-methylamine (2.81 g, 99.0%).

$^1$H-NMR (CDCl$_3$)δ: 7.1-6.9(2 H, m), 6.7-6.6(2 H, m ), 4.0(1 H, bs), 2.9-2.7(2 H, m), 2.7-2.6(2 H, m), 2.31(3 H, m).

FABMS (m/z): 152(60), 121(80).

PREPARATIVE EXAMPLE 74

(1) Benzene (20 ml) and N,N'-dimethylethylenediamine (1.56 ml, 14.7 mmol) were added to 4-methoxybenzaldehyde (2 g, 14.7 mmol), and the m tture was refluxed under heating for 5 hours while removing the generated water. Benzene was evaporated to give a crude product of 2-(4-methoxyphenyl)-1,3-dimethylimidazolidine.

(2) The above crude product (0.5 g, 2.42 mmol), THF (6 ml) and tetramethylethylenediamine (0.73 ml, 4.84 mmol) were mixed, and this solution was cooled to −78° C. n-Butyllithium (3 ml of 1.6M hexane solution, 4.84 mmol) was added and the mixture was stirred at 0° C. for 2 hours. This solution was cooled to −78° C., and di-n-amyldisulfide (1.07 ml, 4.84 mmol) was added. The mixture was stirred at room temperature for 11.5 hours. Water (5 ml) was added and the aqueous layer was extracted 3 times with ethyl acetate (5 ml). The organic layers were combined and washed with saturated brine (5 ml). The filtrate was concentrated under reduced pressure. A 10% aqueous sulfuric acid solution was added to the obtained residue and the mixture was stirred for 2 days. The aqueous layer was extracted 4 times with ethyl acetate (10 ml). The organic layers were combined and washed twice with saturated brine (5 ml). The filtrate was concentrated under reduced. The obtained residue was purified by column chromatography (hexane/ethyl acetate=20/1-10/1) to give 4-methoxy-3-pentylthiobenzaldehyde (437 mg, 76%) as a pale-yellow oil.

$^1$-H-NMR (CDCl$_3$, 300 MHz)δ: 9.87(1 H, s), 7.74(1 H, d, J=2.1 Hz), 7.66(1 H, dd, J=8.1, 1.8 Hz), 6.95(1 H, d, J=8.1 Hz), 3.98(3 H, s), 2.95(2 H, t, J=7.4 Hz), 1.62-1.80(2 H, m), 1.20-1.55(4H m), 0.91(3 H, t, J=7.2 Hz).

FABMS (m/z): 289[M$^+$H$^+$] (100), 237(70).

PREPARATIVE EXAMPLE 76

A suspension of isovanillin (200 g, 1.341 mmol), acetic acid (700 ml) and concentrated sulfuric acid (0.2 ml) was cooled to 0° C., a solution (200 ml) of fuming nitric acid (57.2 ml, 1.38 mol) in acetic acid was added dropwise over 30 minutes. After stirring for 40 minutes, water (400 ml) was added, and the generated crystals were collected by filtration to give a mixture of 3-hydroxy-4-methoxy-2-nitrobenzaldehyde and 3-hydroxy-4-methoxy-6-nitrobenzaldehyde (156.4 g, 60.4%).

$^1$H-NMR (CDCl$_3$, 300 MHz)δ: 10.1(1 H, s), 7.46(1 H, d, J=8.4 Hz), 7.12(1 H, d, J=8.4 Hz), 4.03(3 H, s).

PREPARATIVE EXAMPLE 77

A mixture of 3-hydroxy4-methoxy-2-nitrobenzaldehyde and 3-hydroxy4-methoxy-6-nitrobenzaldehyde, and DMF (700 ml) were mixed, and potassium carbonate (136.7 mg, 989 mmol) and bromopentane (122.7 ml, 989 mmol) were successively added to this solution. The reaction mixture was stirred at 100° C. for 4 hours and fltered. Water (600 ml) and hexane-ethyl acetate (1:1, 600 ml) were added to the filtrate for separation. The aqueous layer was extracted with hexane-ethyl acetate (1:1, 600 ml). The organic layers were combined, and dried over anhydrous magnesium sulfate. The drying agent was filtered off, and the filtrate was evaporated. The precipitated crystals were collected by filtration to give 4-methoxy-6-nitro-3-pentyloxybenzaldehyde (②)) (90.1 g, 44%) as yellow crystals. The filtrate after filtration of said crystals was further evaporated to give 4-methoxy-2-nitro-3-pentyloxybenzaldehyde (①) (117 g, 58%) as a red oil.

①: $^1$H-NMR (CDCl$_3$, 300 MHz)δ: 9.80(1 H, s), 7.64(1 H, d, J=8.6 Hz), 7.09(1 H, d, J=8.6 Hz), 4.11(2 H, t, J=6.6 Hz), 3.99(3 H, s), 1.60-1.80(2 H, m), 1.28-1.47(4 H, m), 0.92(3 H, t, J=7.1 Hz).

FABMS (m/z): 268[M$^+$H$^+$] (80), 198(100).

②: $^1$H-NMR (CDCl$_3$, 300 MHz)δ: 10.4(1 H, s), 7.61(1 H, s), 7.39(1 H, s), 4.16(2 H, t, J=6.8 Hz), 1.82-1.95(2 H, m), 1.30-1.50(4 H, m), 0.94(3 H, t, J=7.2 Hz).

PREPARATIVE EXAMPLE 78

4-Methoxy-2-nitro-3-pentyloxybenzaldehyde (70 g, 261.9 mmol), amidosulfuric acid (76.3 g, 785.7 mmol) and isopropanol (210 ml) were mixed, an aqueous sodium chlorite (38.5 g, 340.5 mmol) solution (350 ml) was added dropwise to this solution while cooling in a water bath. After stirring for 20 minutes, ethyl acetate (300 ml) was added to separate the organic layer. The aqueous layer was extracted with ethyl acetate (200 ml). The organic layers were combined, washed with saturated brine (150 ml), and dried over anhydrous magnesium sulfate. The drying agent was filtered off and the filtrate was concentrated under reduced pressure. The precipitated crystals were collected by filtration to give 4-methoxy-2-nitro-3-pentyloxybenzoic acid (59.02 g, 80%) as pale-yellow crystals.

$^1$H-NMR (CDCl$_3$, 300 MHz)δ: 7.85(1 H, d, J=8.8 Hz), 7.02(1 H, d, J=8.8 Hz), 4.08(2 H, t, J=6.7 Hz), 3.98(3 H, s), 1.95-1.80(2 H, m), 1.30-1.45(4 H, m), 0.93(3 H, t, J=7.0 Hz).

FABMS (m/z): 284[M$^+$H$^+$](30), 266(30), 196(100).

PREPARATIVE EXAMPLE 79

4-Methoxy-2-nitro-3-pentyloxybenzoic acid (26.8 g, 94.6 mmol) and ethanol (350 ml) were mixed, and 10% palladium-carbon catalyst (2.6 g) was added to this solution. The reaction miture was stirred at room temperature for 7.5 hours in a hydrogen gas stream (3 kgf/cm$^2$) and filtered. The filtrate was concentrated under reduced pressure, and the precipitated crystals were collected by filtration to give 2-amino-4-methoxy-3-pentyloxybenzoic acid (22.7 g, 95%) as gray crystals.

$^1$H-NMR (CDCl$_3$, 300 MHz)δ: 7.87(1 H, d, J=9.0 Hz), 6.31(1 H, d, J =9.0 Hz), 3.94(2 H, t, J=6.8 Hz), 3.89(3 H, s), 1.70-1.88(2 H, m), 1.30-1.54(4 H, m), 0.94(3 H, t, J=7.1 Hz).

PREPARATIVE EXAMPLE 80

Pentyl 3-amino-4-methoxybenzoate (0.744 g, 4.45 mmol), methylene chloride (15 ml) and dimethylsulfide (0.33 ml, 4.50 mmol) were mixed, and after cooling to −30° C., N-chlorosuccinimide (601 mg, 4.5 mmol) was added to this solution. After sti ring for 1 hour, triethylamine (0.627 ml, 4.5 mmol) was added, and the mixture was refluxed under heating for 0.5 hour. Saturated brine (0.5 ml) was added to stop the reaction, the reaction mixture was concentrated under reduced pressure. The obtained residue was purified by column chromatography (hemne/ethyl acetate=4/1) to give pentyl 3-amino-4-methoxy-2-methylthiomethylbenzoate (0.83 g, 82%) as a brown oil.

$^1$H-NMR (CDCl$_3$, 300 MHz)δ: 7.40(1 H, d, J=8.6 Hz), 6.74(1 H, d, J=8.6 Hz), 4.40(2 H, bs), 4.26(2 H, t, J=6.7 Hz), 4.22(2 H, s), 3.90(3 H, s), 2.05(3 H, s), 1.65-1.80(2 H, m), 1.30-1.50(4 H, m), 0.93(3 H, t, J=7.1 Hz).

FABMS (m/z): 298[M$^+$H$^+$] (10), 297(50), 250(50).

PREPARATIVE EXAMPLE 81

Pentyl 3-amino-4-methoxy-2-methylthiomethylbenzoate (830 mg, 2.79 mmol) and DMF (4.0 ml) were mixed, and potassium t-butoxide (470 mg, 4.19 mmol) and bromopentane (0.62 ml, 5.0 mmol) were successively added to this solution. The mixture was stirred at 100° C. for 1 hour and filtered. The filtrate was concentrated under reduced pressure. The obtained residue was purified by column chromatography (hexane/ethyl acetate=15/1) to give pentyl 4methoxy-2-methylthiomethyl-3-pentylaminobenzoate (178 mg, 17%) as a pale-yellow oil.

$^1$H-NMR (CDCl$_3$, 300 MHz)δ: 7.54(1 H, d, J=8.7 Hz), 6.75(1 H, d, J=8.7 Hz), 4.27(2 H, t, J=6.7 Hz), 4.23(2 H, s), 3.88(3 H, s), 3.73(1 H, bs), 3.05(2 H, t, J=7.1 Hz), 2.02(3 H, s), 1.70-1.85(2 H, m), 1.30-1.50(1OH, m), 0.83-0.97(6 H, m).

PREPARATIVE EXAMPLE 82

Pentyl 4-methoxy-2-methylthiomethyl-3-pentylaminobenzoate (173 mg, 0.47 mmol) was hydrolyzed in the same manner as in Preparative Example 45 to give 4-methoxy-2-methylthiomethyl-3-pentylaminobenzoic acid (93 mg, 66%) as colorless crystals.

$^1$H-NMR (CDCl$_3$, 300 MHz)δ: 7.74(1 H, d, J=8.6 Hz), 6.80(1 H, d, J=8.6 Hz), 4.31(2 H, s), 3.92(3 H, s), 3.09(2 H, t, J=7.1 Hz), 2.08(3 H, s), 1.50-1.65(2 H, m), 1.30-1.45(4 H, m), 0.94(3 H, t, 7.0 Hz).

FABMS (m/z): 298[M$^+$H$^+$] (50), 250(50), 185(85).

PREPARATIVE EXAMPLE 83

2-(4-Methoxy-3-pentyloxyphenyl)-4,4-dimethyl-4,5-dihydrooxazole (500 mg, 1.76 mmol) and DMF (8 ml) were mixed, and this solution was cooled to −60° C. n-Butyllithium (1.6M hexane solution, 2.42 ml, 3.87 mmol) was added and the mixture was stirred for 1 hour. Dimethyl disulfide (0.35 ml, 3.87 mmol) was added to this solution, and the mitxure was stirred at room temperature for 1 hour. Water (5 ml) was added, and the aqueous layer was extracted 3 times with ethyl acetate (10 ml). The organic layers were combined and concentrated under reduced pressure. A 3N hydrochloric acid (4 ml) was added to the obtained residue and the mixture was under heating for 3 hours. A 10N aqueous sodium hydroxide solution (4 ml) was added and the mixture was refluxed under heating for 2 hours. A concentrated hydrochloric acid (3 ml) was added to make the reaction mixture acidic, and the aqueous layer was extracted 4 times with ethyl acetate (20 ml). The organic layers were combined, washed 3 times with saturated brine (10 ml) and dried over anhydrous magnesium sulfate. The drying agent was filtered off and the filtrate was concentrated under reduced pressure. The obtained crude crystals were purified by washing with hexane to give 4-methoxy-2-methylthio-3-pentyloxybenzoic acid (370 mg, 74%) as pale-brown crystals.

$^1$H-NMR (CDCl$_3$, 300 MHz )δ: 8.10(1 H, d, J=8.9 Hz), 6.99(1 H, d, J=8.9 Hz), 4.02(2 H, t, J=6.6 Hz), 3.93(3 H, s), 2.50(3 H, s), 1.75-1.90(2 H, m), 1.30-1.58(4 H, m), 0.95(3 H, t, 7.1 Hz).

FABMS (m/z): 285[M$^+$H$^+$] (40), 267(100).

PREPARATIVE EXAMPLE 84

4-Amino-3-pentyloxybenzoic acid (200 mg, 0.90 mmol), methylene chloride (5 ml) and pyridine (0.081 ml, 1.0 mmol) were mixed, and valeryl chloride (0.11 ml, 0.90 mmol) was added to this solution. The mixture was stirred at room temperature for 0.5 hour. Water was added to the reaction mixture, and the aqueous layer was extracted 3 times with ethyl acetate (5 ml). The organic layers were combined, washed with saturated brine (10 ml), and dried over anhydrous magnesium sulfate. The drying agent was filtered off and the filtrate was concentrated under reduced pressure. The obtained crude crystals were washed with hexane to give 4-pentanoylamino-3-pentyloxybenzoic acid (109.5 mg, 400%) as colorless crystals.

$^1$H-NMR (CDCl$_3$, 300 MHz)δ: 8.50(1 H, d, J=8.4 Hz), 7.98(1 H, s), 7.73(1 H, d, J=8.4 Hz), 7.55(1 H, s), 4.11(2 H, t, J=6.6 Hz), 2.43(2 H, t, J=7.5 Hz), 1.80-1.95(2 H, m), 1.35-1.55(6 H, m), 0.96(6 H, t, 7.2 Hz).

FABMS (m/z): 308[M$^+$H$^+$] (40), 206(100).

PREPARATIVE EXAMPLE 85

(1) 2-Hydroxy-3-methoxybenzaldehyde (3.00 g, 19.7 mmol) and DMF (25 ml) were mixed, and potassium carbonate (3.00 g, 22.0 mmol) and bromopentane (2.73 ml, 22.0 mmol) were successively added to this solution. The reaction mixture was stirred at 100° C. for 2 hours and the obtained solid was filtered. Water (20 ml) and ethyl acetate (50 ml) were added for separation. The aqueous layer was extracted twice with ethyl acetate (25 ml). The organic layers were combined, washed twice with saturated brine (20 ml) and dried over anhydrous magnesium sulfate. The drying agent was filtered off, and the filtrate was concentrated under reduced pressure to give a crude product of 3-methoxy-2-pentyloxybenzaldehyde. (2) THF (30 ml) and methyl (triphenylphosphoranilidene)acetate (7.36 g, 22.0 mmol) were added to the above-mentioned compound. The mixture was re iuxed under heating for 5.5 hours and THF was evaporated under reduced pressure. Hexane (100 ml) was added to the obtained residue, and the precipitated crystals were filtered off. The filtrate was concentrated under reduced pressure. To the obtained residue were added ethanol (40 ml) and a 1N aqueous sodium hydroxide solution (40 ml). The mixture was refluxed under heating for 1 hour. After removing ethanol by evaporation under reduced pressure, concentrated hydrochloric acid was added to make the aqueous layer acidic. The aqueous layer was extracted twice with ethyl acetate (70 ml). The organic layers were combined, washed 3 times with saturated brine (40 ml) and dried over anhydrous magnesium sulfate. The drying agent was filtered off, and the filtrate was concentrated under reduced pressure. The obtained crude crystals were recrystallized from ethyl acetate to give 3- (3-methoxy-2-pentyloxyphenyl)cinnamic acid (3.82 g, 73% in 3 steps) as colorless needles.

$^1$H-NMR (CDCl$_3$, 300 MHz)δ: 8.17(1 H, d, J=16.2 Hz), 7.18(1 H, d, J=7.8 Hz), 7.06(1 H, t, J=7.8 Hz), 6.95(1 H, d, J=7.8 Hz), 6.48(1 H, d, J=16.2 Hz), 3.99(2 H, t, J=6.7 Hz), 3.86(3 H, s), 1.75-1.85(2 H, m), 1.37-1.49(4 H, m), 0.94(3 H, t, 7.2 Hz).

FABMS (m/z): 265[M$^+$H$^+$] (20), 177(100).

PREPARATIVE EXAMPLE 86

3-(3-Methoxy-2-pentyloxyphenyl)cinnamic acid (3.80 g, 14.4 mmol) was dissolved in ethanol (100 ml), and 10% palladium-carbon catalyst (0.38 g) was added to this solution. The reaction mixture was stirred for 1 hour in a stream of hydrogen and filtered. The Mtrate was concentrated under reduced pressure to give 3-(3-methoxy-2-pentyloxyphenyl) propionic acid (3.42 g, 89%) as gray crystals.

$^1$H-NMR (CDCl$_3$, 300 MHz)δ: 6.96(1 H, t, J=7.9 Hz), 6.98(2 H, d, J=7.9 Hz), 3.95(2 H, t, J=6.7 Hz), 3.83(3 H, s), 2.95(2 H, t, J=7.9 Hz), 2.66(2 H, t, J=7.9 Hz), 1.70-1.85(2 H, m), 1.35-1.50(4 H, m), 0.92(3 H, t, 7.0 Hz).

FABMS (m/z): 267[M$^+$H$^+$] (20), 179(100).

PREPARATIVE EXAMPLE 87

3-(3-Methoxy-2-pentyloxyphenyl)propionic acid (1.00 g, 3.75 mmol), thionyl chloride (0.72 ml, 10 mmol) and one drop of DMF were mixed, and the mixture was stirred at room temperature for 15 minutes. Toluene (10 ml) was added and the mixture was filtered. The filtrate was concentrated under reduced pressure. Acetone (5 ml) and a solution of sodium azide (0.33 g, 5.0 mmol) in water (0.5 ml) were added to the obtained residue, and the mixture was stirred at room temperature for 20 minutes. Water (5 ml) was add, and the aqueous layer was extracted twice with toluene (20 ml). The organic layers were combined, washed twice with saturated brine (10 ml) and dried over anhydrous magnesium sulfate. The drying agent was filtered off, and the filtrate was concentrated under reduced pressure. Toluene (10 ml) was added to the obtained residue. The mixture was refluxed under heating for 2.5 hours, and toluene was evaporated under reduced pressure. Polyphosphoric acid (3 ml) was added to the obtained residue and the mixture was stirred for 40 minutes. Water (20 ml) and ethyl acetate (50 ml) were added to separate the organic layer. The organic layer was washed successively with water (10 ml) and saturated brine (10 ml), and dried over anhydrous magnesium sulfate. The drying agent was filtered off, and the filtrate was concentrated under reduced pressure. Hexane (10 ml) was added to the obtained residue, and the precipitated crystals were collected by filtration to give 6-methoxy-5-pentyloxy-3,4-dihydro-2H-isoquinolin-1-one (829 mg, 84%) as colorless needles.

$^1$H-NMR (CDCl$_3$, 300 MHz)δ: 7.84(1 H, d, J=8.4 Hz), 6.88(1 H, d, J=8.4 Hz), 6.04(1H, bs), 3.93(2 H, t, J=6.9 Hz), 3.90(3 H, s), 3.49-3.55(2 H, m), 3.02(2 H, t, J=6.6 Hz), 1.70-1.81(2 H, m), 1.30-1.50(4 H, m), 0.94(3 H, t, 7.2 Hz).

FABMS (m/z): 264[M$^+$H$^+$] (100).

PREPARATIVE EXAMPLE 88

3-Hydroxy-4-methoxybenzaldehyde (200 g, 1.31 mol), dioxane (1000 ml) and water (400 ml) were mixed, and N-bromosuccinimide (245.7 g, 1.38 mol) was added over 10 minutes. After 60 and 70 minutes, N-bromosuccinimide was further added in an amount of 16.4 g (92.1 mmol) and 7.02 g (39.4 mmol), respectively, and the mixture was further stirred for 30 minutes. Water (1600 ml) was added, and the precipitated crystals were collected by filtration. The crystals were washed with water (1000 ml) to give 2-bromo-3-hydroxy-4-methoxybenzaldehyde (227.1 g, 74.8%) as pale-red crystals.

$^1$H-NMR (DMSO-d$_6$, 300 MHz) δ: 10.1(1 H, s), 9.59(1 H, s), 7.40(1 H, d, J=8.4 Hz), 7.14(1 H, d, J=8.4 Hz), 3.92(3 H, s).

FABMS (m/z): 232[M$^+$H$^+$] (20), 185(100).

PREPARATIVE EXAMPLE 89

(1) 2-Bromo-3-hydroxy-4-methoxybenzaldehyde (225.2 g, 975 mmol) and DMF (660 ml) were mixed, and potassium carbonate (148.2 g, 1.07 mol) and bromopentane (133 ml, 1.07 mol) were successively added to this solution. The mixture was stirred at 90° C. for 1.5 hours and cooled to room temperature. Water (800 ml) was added to stop the reaction. The aqueous layer was extracted successively with diethyl ether (1000 ml, 500 ml) and ethyl acetate (500 ml). The organic layers were combined, washed successively with water (200 ml) and saturated brine (200 ml) and dried over anhydrous sodium sulfate. The drying agent was filtered off, and the filtrate was concentrated under reduced pressure to give a crude product of 2-bromo4-methoxy-3-pentyloxybenzaldehyde.

(2) The above crude product, isopropanol (440 ml) and sulfamic acid (283.9 g, 2.92 mol) were mixed, and an aqueous sodium chlorite (purity 80%, 143.3 g, 1.27 mol) solution (1320 ml) was added dropwise to this solution under ice-cooling. The mixture was stirred at 40° C. for 30 minutes, and water (1000 ml) was added. The precipitated crystals were collected by filtration and washed with water (2000 ml) to give 2-bromo4-methoxy-3-pentyloxybenzoic acid (238.98 g, 77%) as colorless crystals.

$^1$H-NMR (CDCl$_3$, 300 MHz)δ: 7.83(1 H, d, J=8.7 Hz), 6.90(1 H, d, J=8.7 Hz), 3.98(2 H, t, J=6.7 Hz), 3.92(3 H, s), 1.82-1.90(2 H, m), 1.30-1.53(4 H, m), 0.94(3 H, t, 7.2 Hz).

FABMS (m/z): 318[M$^+$H$^+$] (10), 185(100).

PREPARATIVE EXAMPLE 90

(1) 2-bromo4-methoxy-3-pentyloxybenzoic acid (80.1 g, 253 mmol), toluene (480 ml), copper (I) bromide (3.62 g, 25.3 mmol) and diethyl malonate (153.4 ml, 1.01 mol) were mixed, and sodium hydride (60% dispersion, 30.3 g, 758 mmol) was added to this suspension. The mixture was stirred at 78° C.–83° C. for 1 hour. Said reaction mixture was combined with a reaction mixture in which 2-bromo-4-methoxy-3-pentyloxybenzoic acid (49.43 g, 156 mmol) had been reacted in the same manner, and the resulting reaction mixture was extracted with water (1000 ml, 500 ml). The aqueous layer was washed with hexane (500 ml). Concentrated hydrochloric acid was added to make the aqueous layer acidic. The aqueous layer was extracted with ethyl acetate (1000 ml, 500 ml). The organic layers were combined, and dried over anhydrous sodium sulfate. The drying agent was filtered off, and the filtrate was concentrated under reduced pressure to give a crude product of diethyl 2-(6-carboxy-3-methoxy-2-pentyloxyphenyl)-malonate.

(2) The above crude product, lithium chloride (51.93 g, 1.23 mol), water (7.35 ml, 408 mmol) and DMSO (405 ml) were mixed, and the mixture was stirred at 140° C. for 1 hour. Water (600 ml) and ethyl acetate (800 ml) were added to the reaction mixture, and the organic layer was separated and extracted twice with water (300 ml) and dried over anhydrous sodium sulfate. The drying agent was filtered off, and the filtrate was concentrated under reduced pressure. Hexane (250 ml) was added to the obtained residue. The precipitated crystals were collected by filtration and washed with hexane (150 ml) to give 2-ethoxycarbonylmethyl-4-methoxy-3-pentyloxybenzoic acid (99.93 g, 75.3% in 2 steps) as pale-brown crystals.

$^1$H-NMR (CDCl$_3$, 300 MHz)δ: 7.93(1 H, d, J=8.7 Hz), 6.88(1 H, d, J=8.7 Hz), 4.12-4.22(4 H, m), 3.93(2 H, t, J=6.6 Hz), 3.93(3 H, s), 1.70-1.88(2 H, m), 1.35-1.55(4 H, m), 1.26(3 H, t, 7.2 Hz), 0.93(3 H, t, 6.9 Hz).

FABMS (m/z): 323[M$^+$H$^+$] (70),227(90).

PREPARATIVE EXAMPLE 91–131

The compounds shown in Preparative Examples 91–131 were obtained in the same manner as in the above-mentioned Preparative Examples 1–90. The properties of said compounds are shown in Tables 1–14.

Example 1—1

4-Methoxy-3-pentyloxycinnamic acid (5.29 g, 0.02 mol, 1.0 eq) and 1-hydroxybenzotriazole hydrate (2.7 g, 0.024 mol, 1.0 eq) were dissolved in DMF (50 ml), and to this solution were successively added 2-(4-hydroxyphenyl) ethylamine (4.1 g, 0.03 mol, 1.5 eq) and 1-ethyl-3-(3-dimethylaminopropyl)carbomiide (WSC) hydrochloride (4.6 g, 0.024 mol, 1.2 eq) under ice-cooling. The mixture was stirred at room temperature for 12 hours. To this reaction mixture were successively added ice water (50 ml) and a saturated aqueous sodium hydrogencarbonate solution (50 ml), and the mixture was extracted twice with ethyl acetate (200 ml). The organic layers were combined, washed with saturated brine (200 ml) and dried over anhydrous sodium sulfate. The d rying agent was filtered off, and the filtrate was concentrated under reduced pressure. The obtained residue was purified by column chromatography (n-hexane/ethyl acetate=5/1-2/1) to give (E)-N-[2-(4-hydroxyphenyl)ethyl]-3-(4-methoxy-3-pentyloxyphenyl) acrylamide (8.61 g, 100%) as a colorless solid. This was further purified by recrystalization from ethyl acetate to give colorless crystals (6.28 g, 81.9%).

The properties of this compound are shown in Table 15.

Examples 1-2 to 1-33

In the same manner as in the above Example 1—1, the compounds shown in Tables 15–25 were obtained.

Example 1-34

In the same manner as in Example 1—1 using 3-(4-methoxy-3-pentylthiophenyl)cinnamic acid (100 mg, 0.357 mmol) obtained in Preparative Example 103, N-[2-(4-hydroxyphenyl)ethyl]-3-(4-methoxy-3-pentylthiophenyl)acrylamide (118 mg, 83%) was obtained as colorless crystals.

Example 1-35

In the same manner as in Example 1—1 using 3-(4-methoxy-3-pentylaminophenyl)cinnamic acid (100 mg, 0.380 mmol) obtained in Preparative Example 97, N-[2-(4-aminophenyl)ethy]-3-(4methoxy-3-pentylaminophenyl)-acrylamide (31.1 mg, 21%) was obtained as pale-yellow crystals.

The properties of the compounds obtained in the above Example 1-34 and 1-35 are shown in Table 26.

Examples 1-36 to 1-92

In the same manner as in Example 1—1 to 1-35, the compounds of Example 1-36 to 1-92 were obtained. The properties of the compounds are shown in Tables 26–45.

Example 2-1

4-Methoxy-3-pentyloxybenzoic acid (4.77 g, 0.02 mol, 1 eq) and 1-hydroxybenzotriazole hydrate (2.7 g, 0.024 mol, 1.0 eq) were dissolved in DMF (50 ml), and to this solution were successively added 2-(4-hydroxyphenyl)ethylamine (4.1 g, 0.03 mol, 1.5 eq) and WSC hydrochloride (4.6 g, 0.024 mol, 1.2 eq) under ice-cooling. In the same manner as in Example 1—1, N-[2-(4-hydroxyphenyl)ethyl]-(4-methoxy-3-pentyloxy)benzamide (5.6 g, 79%) was obtained as colorless crystals.

The properties of this compound are shown in Table 46.

Examples 2—2 to 2-43

In the same manner as in the above Example 2-1, the compounds shown in Tables 46–60 were obtained.

Example 2-44

3,4-Dipentyloxy-[2-(4-nitrophenyl)ethyl]benzanide (110 mg, 0.25 mmol, 1.0 eq) was dissolved in methanol (11 ml), and 10% palladium-carbon catalyst (10 mg, water content 50%) was added. The mixture was stirred for 2 hours in a stream of hydrogen. The reaction mixture was cooled to room temperature, and filtered through Celite. The filtrate was concentrated under reduced pressure, and the obtained residue was purified by column chromatography on silica gel (ethyl acetate/hexane=1/1) to give [2-(4-aminophenyl)ethyl]-3,4-dipentyloxybenzamide (94.1 mg, 91.7%) as colorless crystals.

Example 2-45

3,4-Dihexyloxybenzoic acid (161 mg, 0.5 mmol) and 1-hydroxy-benzotriazole hydrate (45.9 mg, 0.3 mmol, 0.6 eq) were dissolved in DMF (5 ml), and to this solution were successively added 2-(4-hydroxyphenyl)ethylamine (82 mg, 0.6 mmol, 1.2 eq) and WSC hydrochloride (114 mg, 0.6 mmol, 1.2 eq) at room temperature. The mixture was stirred at room temperature for 15 hours. This reaction mixture was poured into ethyl acetate (75 ml), washed with water (5 ml×3) and saturated brine (15 ml). The organic layerwas dried over anhydrous sodium sulfate. The drying agent was filtered off, and the filtrate was concentrated under reduced pressure. The obtained residue was purified by column chromatography on silica gel (chloroform/methanol=50/1) to give 3,4-dihexyloxy-N-[2-(4-hydroxyphenyl)ethyl]benzamide (230 mg). The obtained solid was recrystallized from ethyl acetate-hexane to give 3,4-dihexyloxy-N-[2-(4-hydroxyphenyl)ethyl]benzamide (194 mg, 88%) as colorless crystals.

Example 2-46

In the same manner as in Example 2-1 using 2-aminomethoxy-3-pentyloxybenzoic acid (45.0 g, 177.6 mmol) obtained in Preparative Example 79, 2-amino-4-methoxy-N-[2-(4-nitrophenyl)ethyl]-3-pentyloxybenzamide (67.85 g, 95%) was obtained as pale-yellow crystals.

Example 2-47

In the same manner as in Example 2-1 using 4-methoxy-2-nitro-3-pentyloxybenzoic acid (500 mg, 1.76 mmol) obtained in Preparative Example 78, 4-methoxy-2-nitro-N-[2-(4-nitrophenyl)ethyl]-3-pentyloxybenzamide (738 mg, 97%) was obtained as colorless crystals.

Example 2-48

4-Methoxy-2-nitro-N-[2-(4nitrophenyl)ethyl]-3-pentyloxybenzamide obtained in Example 2–47, THF (1 ml) and sodium hydride (13.3 mg, 0.556 mmol) were mixed, and the mixture was stirred for 5 minutes. Ethyl bromoacetate (0.0617 ml, 0.556 mmol) was added, and the mixture was stirred at 90° C. for 5.5 hours. Then, sodium hydride (6.7 mg, 0.278 mmol) and ethyl bromoacetate (6.7 mg, 0.278 mmol) were further added, and the mixture was stirred at 90° C. for 6.5 hours. To the mixture was added water (3 ml) to stop the reaction, and the organic layer was extracted 3 times with ethyl acetate (5 ml). The organic layers were combined and dried over anhydrous magnesium sulfate. The drying agent was fitered off, and the filtrate was concentrated under reduced pressure. The obtained residue was purified by column chromatography on silica gel (hexane/ethyl acetate= 4/1-2/3) to give ethyl{ (4-methoxy-2-nitro-3-pentyloxybenzoyl)-[2-(4nitrophenyl)ethyl]amino}acetate (0.137 g, 68%) as a pale-yellow oil.

Example 2-49

In the same manner as in Example 2-1 using 4-methoxy-2-methylthiomethyl-3-pentylaminobenzoic acid (90 mg, 0.30 mmol) obtained in Preparative Example 82, N-[2-(4-hydroxyphenyl)ethyl]-4-methoxy-2-methylthiomethyl-3-pentylamino-benzamide (113 mg, 90%) was obtained as colorless crystals.

Example 2-50

In the same manner as in Example 2-1 using 4-methoxy-2-methylthio-3-pentyloxybenzoic acid obtained in Preparatrve Example 83, N-[2-(4-hydroxyphenyl)ethyl]-4-methoxy-2-methylthio-3-pentyloxybenzamide was obtained as colorless crystals.

Example 2-51

In the same manner as in Example 2-1 using 2-ethoxycarbonylmethyl-4-methoxy-3-pentyloxybenzoic acid (45.01 g, 138.8 mmol) obtained in Preparative Example 90, ethyl{3-methoxy-2-pentyloxy-[2-(pyridin-4-yl)ethylcarbamoyl]-phenyl}acetate was obtained as a crude product This product was used in the next reaction.

Example 2-52

In the same manner as in Example 2-1 using 4-pentyloxy-3-pentylthiobenzoic acid obtained in Preparative Example 112, N-[2-(4-aminophenyl)ethyl]4-pentyloxy-3-pentylthiobenzamide was obtained as colorless crystals.

The properties of the compounds obtained in the above Examples 2-44 to 2-52 are shown in Tables 60-63.

Examples 2-53 to 2-161

In the same manner as in Examples 2-1 to 2-52, the compounds of Examples 2-53 to 2-161 were obtained. The properties of the compounds are shown in Tables 63–99.

Example 3-1

4-Methoxy-3-pentyloxycinnamic acid (529 mg, 2.0 mmol, 1 eq) was dissolved in pyridine (10 ml), and to this solution were successively added 2-(4-hydroxyphenyl)ethyl alcohol (484 mg, 3.5 mmol, 1.5 eq) and WSC hydrochloride (460 mg, 2.4 mmol, 1.2 eq) under ice-cooling. In the same manner as in Example 1≦1, 2-(4-hydroxyphenyl)ethyl-3-(4-methoxy-3-pentyloxy)cinnamate (61 mg, 7.9%) was obtained as colorless crystals.

The properties of this compound are shown in Table 100.

Examples 3-2 to 3—3

In the same manner as in the above Example 3-1, the compounds of Example 3-2 and 3—3 were obtained. The properties of the compounds are shown in Table 100.

Example 4-1

3-(1-Bromo-4-pentyloxynaphthalen-2-yl)cinnamic acid (51.2 mg, 0.141 mmol) and 1-hydroxybenzotriazole hydrate (19.1 mg, 0.141 mmol) were dissolved in DMF (1 ml), and to this solution were successively added 2-(4-hydroxyphenyl)-ethylamine (23.2 mg, 0.169 mmol) and WSC hydrochloride (32.4 mg, 0.169 mmol) under ice-cooling. In the same manner as in Example 1—1, (E)-3-(1-bromo-4-pentyloxynaphthalen-2-yl)-N-[2-(4-hydroxyphenyl)ethyl]acrylamide (52.3 mg, 77%) was obtained as colorless crystals.

The properties of this compound are shown in Table 101.

Examples 4-2 to 4-1

In the same manner as in the above Example 4-1, the compounds shown in Tables 101–102 were obtained.

Example 5-1

7-Methoxy-8-pentyloxyquinoline-3-carbamic acid (24 mg, 0.083 mmol), chloroform (1.0 ml) and DMF (0.3 ml) were mixed, and to this solution were successively added a DMF solution (0.1 ml) of 2-(4-pyridinyl)ethylamine (12.2 mg, 0.1 mmol), WSC hydrochloride (19.2 mg, 0.1 mmol), and dimethylaminopyridine (1 mg, 0.0082 mmol). In the same manner as in Example 1—1, 7-methoxy-8-pentyloxyquinoline-3-carbamic acid (2-pyridin-4-ylethyl) amide (11.4 mg, 35%) was obtained as colorless crystals.

The properties of this compound are shown in Table 103.

Examples 5-2 to 5-9

In the same manner as in the above Example 5-1, the compounds of Example 5-2 to 5-9 were obtained. The properties of the compounds are shown in Tables 103–105.

Example 6-1

(1) 4-Methoxy-3-pentyloxybenzoic acid (5.96 g, 0.025 mol, 1 eq) was dissolved in thionyl chloride (7.3 ml, 0.100 mol, 4 eq), and the solution was stirred at room temperature for 24 hours. Excess thionyl chloride was evaporated under reduced pressure. Dichloromethane (10 ml) was added to the residue. 2-Amino-2-methylpropanol (5.01 ml, 0.053 mol, 2.1 eq) was added under ice-cooling, and the mixture was stirred at room temperature for 2 hours. Water (200 ml) was added to this reaction mixture, and the mixture was extracted twice with ethyl acetate (200 ml). The organic layers were combined, washed with saturated brine (400 ml) and dried over anhydrous sodium sulfate. The drying agent was filtered off, and the filtrate was concentrated under reduced pressure. The obtained residue was purified by column chromatography on silica gel (n-hexane/ethyl acetate=3/1-1/1) to give N-(2-hydroxy-1,1-dimethylethyl)-4-methoxy-3-pentyloybenzanmide (5.75 g, 74.4%) as a colorless oil.

$^1$H-NMR (CDCl$_3$)δ: 7.38(1 H, d, J=2.1 Hz), 7.20(1 H, dd, J=8.3, 2.1 Hz), 6.84(1 H, d, J=8.3 Hz), 6.13(1 H, bs), 4.79(1 H, t, J=6.1 Hz), 4.06(2 H, t, J=6.9 Hz), 3.90(3 H, s), 3.69(2 H, d, J=6.1 Hz), 2.0-1.8(2 H, m), 1.5-1.3(4 H, m), 1.41(3 H, s), 1.41(3 H, s), 0.93(3 H, t, J=7.1 Hz).

FABMS (m/z): 310[M$^+$H$^+$(100), 221(100), 238(50).

IR (Neat, cm$^{-1}$): 3385, 2955, 1638, 1505.

(2) N-(2-Hydroxy-1,1-dimethylethyl)-4-methoxy-3-pentyloxybenzamide (5.498 g, 0.0178 mol, 1 eq) was dissolved in thionyl chloride (4.29 ml, 0.0214 mol, 3.3 eq), and the solution was stirred at room temperature for 1 hour. The reaction mixture was poured into diethyl ether (40 ml). The obtained hydrochloride compound was collected by filtration, and excess thionyl chloride was removed. A 1N aqueous sodium hydroxide solution (about 20 ml) was added to this hydrochloride compound under ice-cooling, whereby the mixture was alkalized (pH=10). The solution was extracted twice with diethyl ether (30 ml). The organic layers were combined, washed with saturated brine (60 ml) and dried over anhydrous sodium sulfate. The drying agent was filtered off, and the filtrate was concentrated under reduced pressure to give 2-(4-methoxy-3-pentyloxyphenyl)-4,4-dimethyl-4,5-dihydrooxazole (4.46 g, 86%) as colorless crystals.

Example 6-2

2-(4-Methoxy-3-pentyloxyphenyl)-4,4-dimethyl-4,5-dihydrooxazole (373 mg, 1.28 mmol, 1 eq) was dissolved in dimethoxyethane (7 ml). The solution was cooled to −60° C., and n-butyllithium (1.6M hexane solution)(1.76 ml, 2.82 mmol, 2.2 eq) was added dropwise. The mixture was stirred at said temperature for 1.5 hours. Ethylene oxide was added dropwise, and the mixture was stirred for 1.0 hour. The mixture was heated to room temperature, and further stirred for 2 hours. Water (50 ml) was added to the reaction mixture, and the mixture was extracted twice with ethyl acetate (50 ml). The organic layers were combined, washed with saturated brine (100 ml) and dried over anhydrous sodium sulfate. The drying agent was filtered off, and the filtrate was concentrated under reduced pressure. The obtained residue was purified by column chromatography on silica gel (n-hexane/ethyl acetate=3/1-2/1) to give [6-(4,4-dimethyl-4,5-dihydrooxazol-2-yl)-3-methoxy-2-pentyloxyphenyl] ethanol (164 mg, 38.2%) as an oil.

Example 6-3

2-(4-Methoxy-3-pentyloxyphenyl)-4,4-dimethyl-4,5-dihydrooxazole (0.74 g, 2.54 mmol, 1 eq) was dissolved in dimethoxyethane (7 ml). The solution was cooled to −60° C., and n-butyllithium (1.6M hexane solution)(3.5 ml, 5.59 mmol, 2.2 eq) was added dropwise. The mixture was stirred at said temperature for 1.5 hours. Ethyl chlorocarbonate was added dropwise, and the mixture was stirred for 1.0 hour. The mixture was heated to room temperature, and further stirred for 2 hours. Water (50 ml) was added to the reaction mixture, and the mixture was extracted twice with ethyl acetate (50 ml). The organic layers were combined, washed with saturated brine (100 ml) and dried over anhydrous sodium sulfate. The drying agent was filtered off, and the filtrate was concentrated under reduced pressure. The obtained residue was purified by column chromatography on silica gel (n-hexane/ethyl acetate=3/1) to give ethyl 6-(4,4-dimethyl-4,5-dihydrooxazol-2-yl)-3-methoxy-2-pentyloxy benzoate (814 mg, 88.2%) as an oil.

Example 6-4

Lithium aluminum hydride (255 mg, 6.72 mol, 3.0 eq) was dissolved in THF (30 ml), and to this solution was added dropwise a THF solution (50 ml) of ethyl 6-(4,4dimethyl-4,5-dihydrooxazol-2-yl)-3-methoxy-2-pentyloxy benzoate (814 mg, 2.24 mmol, 1.0 eq) under ice-cooling. After the completion of the dropwise addition, the mixture was stirred at room temperature for 1.5 hours. This reaction mixture was cooled with ice-cold water, and a saturated aqueous sodium sulfate solution (about 20 ml) was added. After filtration through Celite, the filtrate was concentrated under reduced pressure. The obtained residue was purified by column chromatography on silica gel (n-hexane/ethyl acetate=3/1) to give 16-(4,4-dimethyl-4,5-dihydrooxazol-2-yl)-3-methoxy-2-pentyloxyphenyl]methanol (677 mg, 94.1%).

Example 6-5

2-[2-(4-Methoxy-3-pentyloxybenzoylamino)ethyl] pyridine N-oxide (200 mg, 0.558 mmol) was dissolved in acetic anhydride (2 ml), and the solution was stirred at 100° C. for 30 minutes. This reaction mixture was concentrated under reduced pressure, and the obtained residue was subjected to column chromatography on silica gel (n-hexane/ethyl acetate=1/1) to give 2-[2-(4-methoxy-3-pentyloxyphenyl)-4,5-diydrooxazol-5-yl]pyridine (①, 14.8 mg), and 163.5 mg of a mixture of N-(2-acetoxy-2-pyridin-2-ylethyl)-4-methoxy-3-pentyloxybenzamide (②) and N-[2-(5-acetoxypyridin-2-yl)ethyl]-4-methoxy-3-pentyloxybenzamide (③). ① was further purified by preparative thin layer chromatography to give a colorless oil (11.6 mg, 6.1%). The mixture of ② and ③ was separated and purified by preparative HPLC (ethyl acetate only, recycled) [② 95.7 mg, 42.7%, ③ 12.4 mg, 5.5%].

②¹H-NMR (CDCl₃, 300 MHz)δ: 8.64-8.59(1 H, m), 7.73(1 H, td, J=7.7, 1.8 Hz), 7.45-7.40(2 H, m), 7.30-7.23(2 H, m), 6.96(1 H, t), 6.87(1 H, d, J=8.5 Hz), 6.03(1 H, t, J=5.7 Hz), 4.16-4.02(4 H, m), 3.90(3 H, s), 2.15(3 H, s), 1.91-1.82(2 H, m), 1.50-1.36(4 H, m), 0.93(3 H, t, J=7.0 Hz).

FABMS (+) (m/z): 402[M+1] (26), 401(93), 341(67), 221(100).

③: ¹H-NMR (CDCl₃, 300 MHz)δ: 8.40-8.32(1 H, m), 7.43-7.40(2 H, m), 7.27-7.22(2 H, m), 6.85(1 H, d, J=8.4 Hz), 4.06(2 H, t, J=7.8 Hz), 3.89(3 H, s), 3.84(2 H, q, J=5.9 Hz), 3.10(2 H, t, J=6.3 Hz), 2.34(3 H, s), 1.91-1.80(2 H, m), 1.49-1.33(4 H, m), 0.93(3 H, t, J=7.0 Hz).

FABMS (+) (m/z): 401[M+1] (82), 221(73), 154(100).

Example 6-6

2-(3-Bromo-4-methoxyphenyl)-4,4-dimethyl-4,5-dihydrooxazole (400 mg, 1.41 mmol) obtained in the same manner as in Example 6-1 and THF (4 ml) were mixed, and this solution was cooled to −60° C. n-Butyllithium (1.6M hexane solution, 1.94 ml, 3.1 mmol) was added and the mixture was stirred for 1.5 hours. Di-n-amyldisulfide (0.69 ml, 3.1 mmol) was added to this reaction mixture, and the mixture was stirred for 4 hours at room temperature. To the mixture was added 1N hydrochloric acid (2 ml), and the aqueous layer was extracted 3 times with ethyl acetate (5 ml). The organic layer was concentrated under reduced pressure. The obtained residue was purified by column chromatography on silica gel (hexane/ethyl acetate=4/1) to give 2-(4-methoxy-3-pentylthiophenyl)-4,4-dimethyl-4,5-dihydrooxazole (422 mg, 97%) as a colorless oil.

The properties of the compounds obtained in the above Example 6-1 to 6—6 are shown in Tables 106 and 107.

Examples 6-7 to 6-13

In the same manner as in Examples 6-1 to 6—6, the compounds of Examples 6-7 to 6-13 were obtained. The properties of the compounds are shown in Tables 108–110.

Example 7-1

3-Nitrophthalic anhydride (1.93 g, 0.01 mol, 1 eq) and 2-(4-hydroxyphenyl)-ethylamine (2.06 g, 0.015 mol, 1.5 eq) were refluxed under heating in toluene (20 ml) for 3 hours. The reaction mixture was cooled to room temperature, and ethyl acetate (100 ml) was added to this reaction mixture. The organic layer was washed twice with dil. aqueous hydrochloric acid solution (30 ml), further washed with saturated brine (100 ml), and dried over anhydrous sodium sulfate. After the drying agent was filtered off, the filtrate was concentrated under reduced pressure. The obtained residue was purified by column chromatography on silica gel (n-hexane/ethyl acetate=1/1) to give N-[2-(4-hydroxyphenyl)ethyl]-3-nitrophthalimide (2.92 g, 92.8%) as a colorless solid. This was further purified by recrystallization from methanol to give colorless crystals (1.9 g, 60.8%).

Example 7-2

10% Palladium-carbon catalyst (water content 50%, 200 mg) was added to a mixed solution of N-[2-(4-hydroxyphenyl)ethyl]-3-nitrophthalimide (1.67 g, 0.0053 mol, 1 eq) in methanol (20 ml)-ethanol (50 ml)-acetic acid (20 ml), and the mixture was stirred for 3 hours at room temperature in a stream of hydrogen. The reaction mixture was filtered through Celite, and the filtrate was concentrated under reduced pressure. The obtained residue was purified by column chromatography on silica gel (chloroform/methanol=50/1) to give 3-amino-N-[2-(4-hydroxyphenyl) ethyl]phthalimide (360 mg, 24.1%) as a colorless solid.

Example 7-3

3-Amino-N-[2-(4-hydroxyphenyl)ethyl]phthalimide (110 mg, 0.390 mol, 1 eq) was dissolved in acetone (30 ml), and to this solution were added 1-chloro-1-pentanone (70.5 mg, 0.585 mmol, 1.5 eq) and triethylamine (0.081 ml, 0.585 mol, 1.5 eq) in this order. The mire was refluxed under heating for 30 minutes. This reaction mixture was cooled to room temperature. Ice water (10 ml) and citric acid (10 ml) were added, and the mixture was extracted twice with ethyl acetate (20 ml). The organic layers were combined, washed with saturated brine (30 ml) and dried over anhydrous sodium sulfate. After the drying agent was filtered off, filtrate was concentrated under reduced pressure. The obtained residue was purified by column chromatography on silica gel (n-hexane/ethyl acetate=5/1) to give 4-[2-(1,3- dioxo4-pentanoylamino-1,3-dihydroisoindol-2-yl)ethyl] phenyl pentanoate (80.2 mg, 56.2%) as colorless crystals.

Example 7-4

(1) Ethyl 6-(4,4-dimethyl-4,5-dihydrooxazol-2-yl)-3-methoxy-2-pentyloxybenzoate (200 mg, 0.55 mmol, 1 eq) was dissolved in a 3N aqueous hydrochloric acid solution (20 ml), and the solution was refluxed under heating for 11 hours. After the completion of the reaction, the mixture was cooled to room temperature and extracted twice with ethyl acetate (20 ml). The organic layers were combined, washed with saturated brine (40 ml) and dried over anhydrous sodium sulfate. After the drying agent was filtered off, the filtrate was concentrated under reduced pressure. The obtained residue was dissolved in a 1N aqueous potassium hydroxide solution (10 ml), and the mixture was stirred for 1.5 hours at room temperature. Ice water and a 3N aqueous hydrochloric acid solution (30 ml) were added to the reaction mixture to make the same acidic. The mixture was extracted twice with ethyl acetate (20 ml). The organic layers were combined, washed with saturated brine (40 ml) and dried over anhydrous sodium sulfate. The drying agent was filtered off, and the filtrate was concentrated under reduced pressure to give 4-methoxy-3-pentyloxyphthalic acid (178 mg, 100%).

(2) 2-Methoxy-3-pentyloxyphthalic acid (155 mg, 0.55 mmol, 1 eq) and 2-(4-hydroxyphenyl)ethylamine (101.6 mg, 0.74 mmol, 1.4 eq) were dissolved in acetic acid (10 ml), and the solution was refluxed under heating for 2 hours. The mixture was cooled to room temperature and extracted twice with ethyl acetate (40 ml). The organic layers were combined, washed with a 1N aqueous hydrochloric acid solution (40 ml) and further with saturated brine (40 ml), and dried over anhydrous sodium sulfate. The drying agent was Eltered off, and the filtrate was concentrated under reduced pressure and purified by column chromatography on silica gel (n-hexane/ethyl acetate=4/1) to give 2-[2-(4-hydroxyphenyl)ethyl]-5-methoxy-4-pentyloxyisoindole-1,3-dione (67 mg, 31.8%).

Example 7-5

[6-(4,4-Dimethyl-4,5-dihydrooxamzol-2-yl)-3-methoxy-2-pentyloxyphenyl]methanol (344 mg, 1.07 mmol, 1.0 eq) was dissolved in DMSO (4 ml), and triethylamine (1.4 ml, 9.63 mmol, 9.0 eq) was added to this solution. The mixture was cooled with coldwater. Sulfur trioxide-pyridine complex (511 mg, 3.21 mmol, 3.0 eq) was added, and the mixture was stirred at room temperature for 1.5 hours. Water (5 ml) was added to this reaction mixture, and the m lxture was extracted twice with ethyl acetate (20 ml). The organic layers were combined, washed with saturated brine (200 ml) and dried over anhydrous sodium sulfate. The drying agent was filtered off, and the filtrate was concentrated under reduced pressure. The obtained residue was dissolved in methanol (16 ml), and 2-(4-hydroxyphenyl)ethylamine (146.8 mg, 1.07 mmol, 1.0 eq) and cyanoborohydride (67.3 mg, 1.07 mmol, 1.0 eq) were added. The mixture was stirred at room temperature for 10 hours. The reaction mixture was concentrated under reduced pressure and purified by column chromatography on silica gel (n-hexane/ethyl acetate=5/1) to give 2-12-(4-hydroxyphenyl)ethyl]- 5-methoxy-4-pentyloxy-2,3dihydroisoindol-1-one (6.7 mg, 1.7%).

Example 7-6

3-Hydroxyphthalic anhydride (1.0 g, 6.6 mmol) was dissolved in methanol (20 ml), and a catalytic amount of p-toluene sulfonic acid was added to this solution. The mixture was stirred with refluxing under heating for 5 hours, and concentrated under reduced pressure to give a crude product of dimethyl 3-hydroxyphthalate. The crude product of dimethyl 3-hydroxyphthalate was dissolved in DMF (20 ml), and potassium carbonate (6 g, 43 mmol) and n-amyl bromide (3 ml, 24 mmol) were added to this solution. The mixture was stirred at 90° C. for 1.5 hours, and solids were removed by filtration through Celite. The filtrate was concentrated under reduced pressure to give a crude product of dimethyl 3-pentyloxyphthalate. The crude product of dimethyl 3-pentyloxyphthalate was dissolved in methanol (10 ml), and a 1N aqueous sodium hydroxide solution (20 ml) was added to this solution. The mixture was stirred at 90° C. for 2 hours, and a 3N aqueous hydrochloric acid solution (15 ml) was added to the reaction nixture. The mixture was extracted with ethyl acetate (30 ml×3), and washed with saturated brine (20 ml). The organic layer was dried over anhydrous magnesium sulfate. The drying agent was filtered off, and the filtrate was concentrated under reduced pressure to give a crude product of 3-pentyloxyphthalic acid. The crude product of 3-pentyloxyphthalic acid was dissolved in acetic acid (20 ml), and a mine hydrochloride (1.0 g, 7.3 mmol) was added. The mixture was stirred at 90° C. for 2 hours and concentrated under reduced pressure. The obtained residue was purified by column chromatography on silica gel (hexane/ethyl acetate=4/1) to give N-2-(4-hydroxyphenyl)ethyl-3-pentyloxyphthalimide (0.8 g, 2.3 mmol, 35%) as colorless crystals.

Example 7—7

N-2-(4-Hydroxyphenyl)ethyl-3-pentyloxyphthalimide (412 mg, 1.17 mmol) was dissolved in THF (1 ml), and a 1.0M THF solution (4 ml) of BH3·THF (4.0 mmol) was added to this solution. The mixture was stirred with refluxing under heating for 8 hours. A 3N aqueous hydrochloric acid solution (10 ml) was added to the reaction mixture. The mixture was further stirred for 0.5 hour at the same temperature, and water (20 ml) was added. The mixture was extracted with ethyl acetate (20 ml×3), and washed with a saturated aqueous sodium hydrogencarbonate solution (20 ml) and saturated brine (30 ml). The organic layer was dried over anhydrous magnesium sulfate. The drying agent was filtered off, and the filtrate was concentrated under reduced pressure. The obtained residue was purified by column chromatography on silica gel (hexane/ethyl acetate=2/1) to give N-2-(4-hydroxyphenyl)ethyl-7-pentyloxyisoindol-1-one (232 mg, 0.68 mmol, 59%) as colorless crystals.

Example 7-8

A suspension of lithium aluminum hydride (LAH, 74 mg, 2 mmol) in THF (1 ml) was added to a solution of N-2-(4-hydroxyphenyl)ethyl-3-pentyloxyphthalimide (351 mg, 0.99 mmol) in THF (1 ml) at 0° C. The mixture was stirred at room temperature for 5 hours. This reaction mixture was poured into a 3N aqueous hydrochloric acid solution (20 ml). The mixture was extracted with ethyl acetate (20 ml×3), and washed with a saturated aqueous sodium hydrogencarbonate solution (20 ml) and saturated brine (30 ml). The organic layer was combined, and dried over anhydrous magnesium sulfate. The drying agent was filtered off, the filtrate was concentrated under reduced pressure and the obtained residue was purified by column chromatography on silica gel (hexane/ethyl acetate-2/1) to give N-2-(4-hydroxyphenyl)ethyl-3-pentyloxisoindoline (130 mg, 40%) as colorless crystals.

Example 7-9

(1) Dimethyl 4-hydroxyphthalate (10.0 g, 47 mmol) was dissolved in DMF (100 ml), and potassium carbonate (30 g, 217 mmol) and n-amyl bromide (10 ml, 80 mmol) were added to this solution. The mixture was stirred at 90° C. for 2 hours, and the solid was removed by filtration through Celite. The filtrate was concentrated under reduced pressure. The obtained residue was purified by column chromatography on silica gel (hexane/ethyl acetate=4/1) to give dimethyl 4-pentyloxyphthalate (12.7 g, 45.4 mmol, 97%) as a colorless oil.

$^1$H-NMR (CDCl$_3$, 300 MHz)δ: 7.80(1 H, d, J=8.40 Hz), 7.05(1 H, d, J=2.70 Hz), 6.97(1 H, dd, J=8.40, 2.70 Hz), 4.00(2 H, t, J=6.90 Hz), 3.91(3 H, s), 3.87(3 H, s), 1.80(2 H, quint, J=6.98 Hz), 1.47-1.34(4 H, m), 0.93(3 H, t, J=7.20 Hz).

FABMS (+) (m/z): 281[M+1] (42), 249(100), 179(78).

(2) Dimethyl 4-pentyloxyphthalate (3.0 g, 10.7 mmol) was dissolved in methanol (20 ml), and a 1N aqueous sodium hydroxide solution (25 ml) was added to this solution. The mixture was stirred at room temperature for 6.5 hours. A 3N aqueous hydrochloric acid solution (20 ml) was added to this reaction mixture. The mixture was extracted with ethyl acetate (40 ml×3), and washed with saturated brine (30 ml). The organic layer was dried over anhydrous magnesium sulfate. The drying agent was filtered off, and the filtrate was concentrated under reduced pressure to give a crude product of 4-pentyloxyphthalic acid. This crude product was not further purified, but used in the next reaction.

The crude product of 4-pentyloxyphthalic acid was dissolved in acetic acid (20 ml), and tyramine hydrochloride (2.74 g, 20 mmol) was added. The mixture was stirred at 96° C. for 4 hours, and concentrated under reduced pressure. The obtained residue was purified by column chromatography on silica gel (hexane/ethyl acetate=6/1) to give N-2-(4-hydroxyphenyl)ethyl-4-pentyloxyphthalimide (2.6 g, 9.4 mmol, 88%) as colorless crystals.

Example 7-10

N-2-(4-Hydroxyphenyl)ethyl-4-pentyloxyphthalimide (330 mg, 0.93 mmol) was dissolved in THF (1 ml), and a 1.0M THF solution (1.5 ml) of BH$_3$·THF (1.5 mmol) was added to this solution. The mixture was stirred with refluxing under heating for 1.5 hours. A 3N aqueous hydrochloric acid solution (2 ml) was added to this reaction mixture. The mixture was further stirred for 0.5 hour at the same temperature, and water (20 ml) was added. The mixture was extracted with ethyl acetate (20 ml×3), and washed with a saturated aqueous sodium hydrogencarbonate solution (20 ml) and saturated brine (30 ml). The organic layer was dried over anhydrous magnesium sulfate. The drying agent was filtered off, and the filtrate was concentrated under reduced pressure. The obtained residue was purified by column chromatography on silica gel (hexane/ethyl acetate=2/1) to give N-2-(4-hydroxyphenyl)ethyl-4-pentyloxyisoindol-1-one (①) (139 mg, 0.41 mmol, 44%, colorless crystals) and N-2-(4-hydroxyphenyl)ethyl-5-pentyloxyisoindol-1-one (②) (111 mg, 0.33 mmol, 35%, colorless crystals).

Example 7-11

A suspension of LAH (40 mg, 1.1 mmol) in THF (1 ml) was added to a solution of N-2-(4-hydroxyphenyl)ethyl-4-pentyloxyphthalimide (208 mg, 0.59 mmol) in THF (1 ml) at 0° C. The mixture was stirred at room temperature for 3.5 hours. This reaction mixture was poured into a 3N aqueous hydrochloric acid solution (20 ml). The mixture was extracted with ethyl acetate (20 ml×3), and washed with a saturated aqueous sodium hydrogencarbonate solution (20 ml) and saturated brine (30 ml). The organic layer was dried over anhydrous magnesium sulfate. The drying agent was filtered of, and the filtrate was concentrated under reduced pressure. The obtained residue was purified by column chromatography on silica gel (chloroform/methanol=30/1) to give N-2-(4-hydroxyphenyl)ethyl-4-pentyloxyisoindoline (181 mg, 94%) as colorless crystals.

Example 7-12

(1) [6-(4,4-Dimethyl-4,5-dihydrooxazol-2-yl)-3-methoxy-2-pentyloxyphenyl]-methanol (4.69 g, 0.014 mmol, 1 eq) was dissolved in 3N hydrochloric acid (50 ml), and the solution was stirred under heating for 3 hours. After the completion of the reaction, the mixture was cooled to room temperature and extracted twice with diethyl ether (50 ml). The organic layers were combined, washed with saturated brine (100 ml) and dried over anhydrous sodium sulfate. The drying agent was filtered off, and the filtrate was concentrated under reduced pressure. The obtained residue was purified by column chromatography on silica gel (n-hexane/ethyl acetate=2/1) to give 5-methoxy-4-pentyloxy-3H-isobenzofuran-1-one (3.4 g, 82.4%) as a colorless oil.

$^1$H-NMR (CDCl$_3$)δ: 7.61(1 H, d, J=8.3 Hz), 7.07(1 H, d, J=8.3 Hz), 5.28(2 H, s), 4.09(2 H, t, J=6.6 Hz), 3.95(3 H, s), 1.8-1.7(2 H, m), 1.5-1.3(4 H, m), 0.93(3 H, t, J=6.9 Hz).

FABMS (m/z): 251[M$^+$H$^+$] (100).

(2) 2-(4-Benzyloxyphenyl)ethylamine (377 mg, 1.66 mmol, 2 eq) was dissolved in dichloromethane (3 ml), and trimethylaluminum (15% hexane solution, 0.88 ml, 1.825 mmol, 2.2 eq) was added. The mire was stirred for 30 minutes. A dichloromethane solution (3 ml) of 5-methoxy-4pentyloxy-3H-isobenzofuran-1-one (207.6 mg, 0.83 mmol, 1 eq) was added dropwise thereto, and the mixture was stirred for 24 hours. 3N Hydrochloric acid (20 ml) was added to this solution, and the mixture was extracted 3 times with chloroform (10 ml). The organic layers were combined, washed with saturated brine (50 ml) and dried over anhydrous sodium sulfate. The drying agent was filtered off, and the filtrate was concentrated under reduced pressure. The obtained residue was purified by column chromatography on silica gel (n-hexane/ethyl acetate=2/1-1/1) to give 2 -(2-hydroxymethyl)-4-methoxy-3-pentyloxy-N-[2-(4-benzyloxyphenyl)-ethyl]benzamide (204 mg, 51.5%) as colorless crystals.

$^1$H-NMR (CDCl$_3$)δ: 7.5-7.3(5 H, m), 7.15(2 H, d, J=8.5 Hz), 7.11(1 H, d, J=8.5 Hz), 6.93(2 H, d, J=8.5 Hz), 6.79(1 H, d, J=8.5 Hz), 6.20(1 H, t, J=6.7 Hz), 5.05(2 H, s), 4.65(2 H, d, J=6.7 Hz), 4.20(1 H, t, J=6.7 Hz), 3.97(2 H, t, J=6.7 Hz), 3.85(3 H, s), 3.67(2 H, q, J=6.8 Hz), 2.88(2 H, t, J=6.8 Hz), 1.9-1.7(2 H, m), 1.5-1.3(4 H, m), 0.93(3 H, t, J=7.1 Hz).

FABMS (m/z): 478[M$^+$H$^+$] (30), 460(100).

IR (KBr, cm$^{-1}$): 3333, 2937, 1623, 1510, 1268, 1216, 1014.

Elemental analysis: C$_{29}$H$_{35}$NO$_5$ Calculated C 72.93, H 7.39, N 2.93 Found C 73.06, H 7.50, N 2.79

Example 7-13

2-(2-Hydroxymethyl)-4-methoxy-3-pentyloxy-N-[2-(4-benzyloxyphenyl)ethyl]benzamide (219.1 mg, 0.459 mmol, 1.0 eq) was dissolved in DMSO (3 ml), and t niethylamine (0.59 ml, 4.13 mmol, 9 eq) and sulfur trioxide-pyridine complex (219 mg, 1.38 mmol, 3 eq) were added under ice-cooling. The mixture was stirred at room temperature for 4 hours. A saturated aqueous sodium hydrogencarbonate solution (10 ml) was added to this reaction mixture, and the mixture was extracted twice with ethyl acetate (20 ml). The organic layers were combined, washed with saturated brine (30 ml) and dried over anhydrous sodium sulfate. The drying agent was filtered off, and the filtrate was concentrated under reduced pressure. The obtained residue was purified by column chromatography on silica gel (ethyl acetate/hexane= 3/1) to give 2-[2-(4-benzyloxyphenyl)ethyl]-3-hydroxy-5-methoxy-4-pentyloxy-2,3-dihydroisoindol-1-one (163 mg, 74.7%) as a colorless oil.

Example 7-14

2-[2-(4-Benzyloxyphenyl)ethyl]-3-hydroxy-5-methoxy-4pentyloxy-2,3-dihydroisoindol-1-one (142 mg, 0.30 mmol, 1.0 eq) was dissolved in dichloromethane (3 ml), and triethylsilane (0.095 ml, 0.60 mmol, 2.0 eq) was added. The mixture was stirred for 10 minutes at room temperature. Trifluoroacetic acid was added thereto, and the mixture was further stirred for 4 hours. A saturated aqueous sodium hydrogencarbonate solution (30 ml) was added to this reaction mixture. The mire was extracted twice with ethyl acetate (30 ml). The organic layers were combined, then washed with saturated brine (60 ml) and dried over anhydrous sodium sulfate. The drying agent was filtered off, and the filtrate was concentrated under reduced pressure to give 2-[2-(4-benzyloxyphenyl)ethyl]-5-methoxy-4-pentyloxy-2,3-dihydroisoindol-1-one (136 mg, 99.8%) as a colorless oil.

Example 7-15

2-[2-(4-Benzyloxyphenyl)ethyl]-5-methoxy-4-pentyloxy-2,3-dihydroisoindol-1-one (125.9 mg, 0.274 mmol, 1.0 eq) was dissolved in ethyl acetate (10 ml), and 100% palladium-carbon catalyst (80 mg, water content 50%) was added. The mixture was stirred in a stream of hydrogen for 3 hours. After the completion of the reaction, the mixture was filtered through Celite and the filtrate was concentrated under reduced pressure. The obtained residue was purified by column chromatography on silica gel (ethyl acetate/hexane=1/1) to give 2-[2-(4-hydroxyphenyl)ethyl]-5-methoxy-4-pentyloxy-2,3-dihydroisoindol-1-one (5 mg, 74.1%) as colorless crystals.

This compound and the compound of Example 7-5 are the same, and have the same properties.

Example 7-16

(1) [6-(4,4-Dimethyl-4,5-dihydrooxazol-2-yl)-3-methoxy-2-pentyloxyphenyl]-ethanol (4.69 g, 0.014 mmol, 1 eq) was dissolved in 3N hydrochloric acid (50 ml), and the solution was stirred under heating for 1.5 hours. The mixture was cooled to room temperature, and an aqueous sodium hydroxide solution was added under ice-cooling to make same alkaline (pH=13–14). The mixture was stirred for 1 hour at room temperature. Hydrochloric acid was added to this solution and the mixture was made acidic (pH=1–2). This mixture was extracted twice with diethyl ether (50 ml). The organic layers were combined, washed with saturated brine (100 ml) and dried over anhydrous sodium sulfate. The drying agent was filtered off, and the filtrate was concentrated under reduced pressure. The obtained residue was purified by column chromatography on silica gel (n-hexane/ethyl acetate=2/1) to give 6-methoxy-5-pentyloxy-3,4-diydroisocoumalin (3.36 g, 90.2%) as a colorless oil.

$^1$H-NMR (CDCl$_3$)δ: 7.86(1 H, d, J=8.6 Hz), 6.92(1 H, d, J=8.6 Hz), 4.48(2 H, t, J=6.0 Hz), 3.95(2 H, t, J=6.8 Hz), 3.92(3 H, s), 3.06(2 H, t, J=6.0 Hz), 1.8-1.7(2 H, m), 1.5-1.3(4 H, m), 0.93(3 H, t, J=7.1 Hz).

FABMS (m/z): 265[M$^+$H$^+$] (100).

(2) A solution (2 ml) of 2-(4-benzyloxyphenyl)ethylamine (1.15 g, 5.1 mmol, 1 eq) in dichloromethane was dissolved in dichloromethane (30 ml), and trimethylaluminum (15% hexane solution, 4.9 ml, 10.2 mmol, 2 eq) was added dropwise. The mixture was stirred at room temperature for 30 minutes. A dichloromethane solution (30 ml) of 6-methoxy-5-pentyloxy-3,4-dihydroisocoumalin (1.36 g, 5.1 mol, 1 eq) was added dropwise thereto, and the mixture was stirred at room temperature for 12 hours. 3N Hydrochloric acid (20 ml) was added to this solution, and the mixture was extracted twice with dichloromethane (20 ml). The organic layers were combined, washed with saturated brine (100 ml) and dried over anhydrous sodium sulfate. The drying agent was filtered off, and the filtrate was concentrated under reduced pressure. The obtained residue was purified by column chromatography on silica gel (n-hexane/ethyl acetate=1/1-ethyl acetate) to give 2-(2-hydroxyethyl)-4-methoxy-3-pentyloxy-N-[2-(4-benzyloxyphenyl)ethyl]benzamide (1.35 g, 53.7%) as colorless crystals.

m.p.: 93.4–93.7° C.

$^1$H-NMR (CDCl$_3$)δ: 7.5-7.3(5 H, m), 7.15(2 H, d, J=8.6 Hz), 7.05(1 H, d, J=8.5 Hz), 6.93(2 H, d, J=8.6 Hz), 6.75(1 H, d, J=8.5 Hz), 6.40(1 H, bs), 5.05(2 H, s), 3.96(1 H, bs), 3.94(2 H, t, J=6.7 Hz), 3.86(2 H, q, J=5.7 Hz), 3.84(3 H, s), 3.65(2 H, q, J=6.8 Hz), 2.94(2 H, t, J=5.7 Hz), 2.86(2 H, t, J=6.8 Hz), 1.8-1.7(2 H, m), 1.5-1.3(4 H, m), 0.92(3 H, t, J=7.1 Hz).

FABMS (m/z): 492 [M$^+$H$^+$] (100), 210(60).

IR (Br, cm$^{-1}$): 3291, 2932, 1614, 1512, 1243.

Elemental analysis: C$_{30}$H$_{37}$NO$_5$ Calculated C 73.29, H 7.59, N 2.85 Found C 73.51, H 7.72, N 2.80

Example 7-17

2-(2-Hydroxyethyl)-4-methoxy-3-pentyloxy-N-[2-(4-benzyloxyphenyl)-ethyl]benzamide (1.33 g, 2.7 mmol, 1.0 eq) was dissolved in DMSO (26 ml), and triethylamine (3.49 ml, 24.3 mmol, 9 eq) and sulfur trioxide-pyridine complex (1.29 g, 8.1 mmol, 3 eq) were successively added under ice-cooling. The mixture was stirred at room temperature for 2 hours. 3N Hydrochloric acid (35 ml) was added to this reaction mixture. The mixture was stirred at room temperature for 30 minutes and e xacted twice with ethyl acetate (40 ml). The organic layers were combined, washed with a saturated aqueous sodium carbonate solution (40 ml) and saturated brine (100 ml), and dried over anhydrous sodium sulfate. The drying agent was filtered off, and the filtrate was concentrated under reduced pressure. The obtained residue was purified by column chromatography on silica gel (ethyl acetate/hexane=2/1) to give 2-[2-(4-benzyloxyphenyl) ethyl]-6-methoxy-5-pentyloxy-2H-isoquinolin-1-one (1.275 g, 100%) as colorless crystals.

Example 7-18

10% Palladium hydroxide-carbon catalyst (300 mg, water content 50%) was added to a solution of 2-[2-(4-benzyloxyphenyl)ethyl]-6-methoxy-5-pentyloxy-2H-isoquinolin-1-one (1.18 g, 2.5 mmol, 1.0 eq) in acetic acid (20 ml), and the mixture was stirred with heating in a stream of hydrogen for 4 hours at 60–70° C. at 3 kgf/cm$^2$. The reaction mixture was cooled to room temperature, and filtered through Celite. The filtrate was concentrated under reduced pressure, and the obtained residue was purified by column chromatography on silica gel (ethyl acetate/hexane= 4/1) to give 6-methoxy-2-[2-(4-oxocyclohexyl)ethyl]-5-pentyloxy-3,4-dihydro-2H-isoquinolin-1-one (800 mg, 82.6%) as a pale-yellow oil.

Example 7-19

2-(2-Hydroxyethyl)-4-methoxy-3-pentyloxy-N-[2-(4-hydroxyphenyl)-ethyl]benzamide (121.9 mg, 0.304 mmol, 1.0 eq) was dissolved in DMSO (6 ml), and triethylamine (0.39 ml, 2.7 mmol, 9 eq) and sulfur troxide-pyridine complex (145 mg, 0.91 mmol, 3 eq) were successively added under ice-cooling. The mixture was stirred at room temperature for 2 hours. Water (20 ml) and a saturated aqueous sodium hydrogencarbonate solution (10 ml) were successively added to the reaction mixture, and the mixture was extracted twice with ethyl acetate (20 ml). The organic layers were combined, washed successively with a saturated aqueous ammonium chloride solution (40 ml) and saturated brine (40 ml), and dried over anhydrous sodium sulfate. The drying agent was filtered off, and the filtrate was concentrated under reduced pressure. The obtained residue was purified by column chromatography on silica gel (ethyl acetate/hexane=3/1) to give 2-[2-(4-hydroxyphenyl)ethyl]-6-methoxy-5-pentyloxy-2H-isoquinolin-1-one (①) (59 mg, 20.3%) as colorless crystals and 3-hydroxy-2-[2-(4-hydroxyphenyl)-ethyl]-6-methoxy-5-pentyloxy-3,4-dihydro-2H-isoquinolin-1-one (②) (103.1 mg, 82.5%) as a colorless oil.

②: $^1$H-NMR (CDCl$_3$)δ: 7.85(1 H, d, J=8.7 Hz), 7.09(2 H, d, J=8.5 Hz), 6.89(1 H, d, J=8.7 Hz), 6.77(2 H, d, J=8.5 Hz), 5.50(1 H, bs), 4.82(1 H, m), 4.1-4.0(1 H, m), 4.0-3.9(2 H, m), 3.88(3 H, s), 3.7-3.5(1 H, m), 3.3-3.2(1 H, m), 3.0-2.8(3 H, m), 2.3-2.2(1 H, bs), 1.8-1.7(2 H, m), 1.5-1.3(4 H, m), 0.92(3 H, t, J=7.1 Hz).

FABMS (m/z): 400[M$^+$H$^+$] (80), 382(60).

IR (Neat, cm$^{-1}$): 3304, 2934, 1631, 1597, 1468, 1281.

Example 7-20

2-(2-Hydroxyethyl)-4-methoxy-3-pentyloxy-N-(2-pyridin-4-ylethyl)-benzamide (90 mg, 233 mmol, 1.0 eq) was dissolved in DMSO (2 ml), and triethylamine (0.3 ml, 2.10 mmol, 9 eq) and sulfur trioxide-pyridine complex (111.2 mg, 0.70 mmol, 3 eq) were successively added under ice-cooling. The mixture was stirred at room temperature for 4 hours. 3N Hydrochloric acid (15 ml) was added to this reaction mixture, and the mixture was stirred at room temperature for 1 hour. Sodium hydroxide was added to make the same alkaline. The solution was extracted twice with ethyl acetate (20 ml). The organic layers were combined, washed with saturated brine (40 ml) and dried over anhydrous sodium sulfate. The drying agent was filtered off, and the filtrate was concentrated under reduced pressure. The obtained residue was purified by column chromatography on silica gel (ethyl acetate) and recrystallized from ethyl acetate to give 2-[2-(4-pyridyl)ethyl]-methoxy-5-pentyloxy-2H-isoquinolin-1-one (40.2 mg, 47.1%) as colorless crystals.

Example 7-21

2-[2-(4-Benzyloxyphenyl)ethyl]-6-methoxy-5-pentyloxy-2H-isoquinolin-1-one (1.21 g, 2.6 mmol, 1.0 eq) was dissolved in ethyl acetate (12 ml), and 10% palladium-carbon catalyst (300 mg, water content 50%) was added. The mixture was stirred in a stream of hydrogen for 4 hours. The reaction mixture was cooled to room temperature and filtered through Celite. The filtrate was concentrated under reduced pressure, and the obtained residue was purified by column chromatography on silica gel (ethyl acetate/hexane= 1/1-ethyl acetate) to give 2-[2-(4-hydroxyphenyl)ethyl]-6-methoxy-5-pentyloxy-2H-isoquinolin-1-one (681.8 mg, 68.7%) as colorless crystals.

This compound and the compound of Example 7-19 ① are the same, and have the same properties.

Example 7-22

2-[2-(4-Hydroxyphenyl)ethyl]-methoxy-5-pentyloxy-2H-isoquinolin-1-one (681.8 mg, 1.79 mmol, 1.0 eq) was dissolved in dichloromethane (7 ml), and 2,6-lutidine (575 mg, 5.36 mmol, 3 eq) and acetic anhydride (1.13 g, 5.36 mmol, 3 eq) were successively added under ice-cooling. The mixture was stirred at room temperature for 12 hours and refluxed under heating for 3 hours. The reaction mixture was cooled to room temperature, and water (10 ml) and a 10% aqueous hydrochloric acid solution (10 ml) were successively added. The miture was extracted twice with dichloromethane (30 ml). The organic layers were combined, washed with saturated brine (40 ml) and dried over anhydrous sodium sulfate. The drying agent was filtered off, and the filtrate was concentrated under reduced pressure. The obtained residue was purified by column chromatography on silica gel (ethyl acetate/ hexane=1/1) to give 4-[2-(6-methoxy-1-oxo-5-pentyloxy-1H-isoquinolin-2-yl)ethyl] phenyl acetate (734 mg, 97.0%) as colorless crystals.

Example 7-23

4[2-(6-Methoxy-1-oxo-5-pentyloxy-1H-isoquinolin-2-yl)ethyl]phenyl acetate (5.65 g, 13.0 mmol, 1.0 eq) was dissolved in acetic acid (60 ml), and 10% palladium-carbon catalyst (5.6 g, water content 50%) was added. The mixture was stirred with heating in a stream of hydrogen for 8 hours at 60–70° C. at a pressure of 3 kgf/cm$^2$. The reaction mixture was cooled to room temperature and filtered through Celite. The filtrate was concentrated under reduced pressure, and the obtained residue was purified by column chromatography on silica gel (ethyl acetate/hexane=1/1) to give 4-[2-(6-methoxy-1-oxo-5-pentyloxy-3,4-dihydro-1H-isoquinolin-2-yl)ethyl]phenylacetate (4.067 g, 73.5%) as colorless crystals.

Example 7-24

4-[2-(6-Methoxy-1-oxo-5-pentyloxy-3,4-dihydro-1H-isoquinolin-2-yl)ethyl]phenyl acetate (720 mg, 1.69 mmol, 1 eq) was dissolved in methanol (10 ml), and aqueous ammonia (10 ml) was added. The mixture was stirred for 2 hours at room temperature. The reaction mixture was concentrated under reduced pressure, and water (20 ml) was added to the residue. The mixture was extracted twice with ethyl acetate (30 ml). The organic layers were combined, washed with a 1N aqueous hydrochloric acid solution (10 ml) and saturated brine (50 ml), and dried over anhydrous sodium sulfate. The drying agent was filtered off, and the filtrate was concentrated under reduced pressure. The obtained residue was purified by column chromatography on silica gel (ethyl acetate/hexane=1/1) to give 2-[2-(4-hydroxyphenyl)ethyl]-6-methoxy-5-pentyloxy-3,4dihydro-2H-isoquinolin-1-one (396 mg, 61.0%) as colorless crystals.

Example 7-25

4-[2-(6-Methoxy-1-oxo-7-pentyloxy-3,4-dihydro-1H-isoquinolin-2-yl)ethyl]phenyl acetate (25 mg, 0.0588 mmol, 1.0 eq) was dissolved in methanol (1 ml), and aqueous ammonia (3 drops) was added. The mixture was strred for 1 hour at room temperature. The reaction mixture was concentrated under reduced pressure to give a colorless solid (21 mg, 93.1%). This was purified by recrystallization from a mixed solution of ethyl acetate and methanol to give 2-[2-(4-hydroxyphenyl)ethyl]-6-methoxy-7-pentyloxy-3,4-dihydro-2H-isoquinolin-1-one (15 mg, 66.5%) as colorless needles.

Example 7-26

4-{2-[(2-Acetoxy-2-benzenesulfanylethyl)-(4-methoxy-3-pentyloxybenzoylamino)]ethyl}phenyl acetate (1.575 g, 0.0027 mmol, 1 eq) was dissolved in benzene (15 ml), and trichloroacetic acid (3.65 g) was added. The miure was refluxed under heating for 2 hours. The reaction mixture was made acidic with a 3N aqueous hydrochloric acid solution (40 ml). The solution was extracted twice with dichloromethane (70 ml). The organic layers were combined, washed with saturated brine (140 ml) and dried over anhydrous sodium sulfate. The drying agent was filtered off, and the filtrate was concentrated under reduced pressure. The obtained residue was purified by column chromatography on silica gel (n-hexane/ethyl acetate=1/1) to give 2-[2-(4acetyloxyphenyl)ethyl]-(6-methoxy-7-pentyloxy)-2H-isoquinolin-1-one (500 mg, 43.7%) as a colorless solid.

Example 7-27

4-{2-[(2-Acetoxy-2-benzenesulfanylethyl)-(4-methoxy-3-pentyloxybenzoyl amino)]ethyl}phenyl acetate (565 mg, 1.02 mmol) was dissolved in toluene (12 ml), and p-toluenesulfonic acid monohydrate (390 mg, 2.05 mol, 2 eq) was added. The mixture was refluxed with heating for 1 hour. A 1N aqueous potassium hydroxide solution (20 ml) was added under ice-cooling. The mixture was stirred at room temperature for 30 minutes. In the same manner as in Example 7-26, 2-[2-(4-hydroxyphenyl)ethyl]-(6-methoxy-7-pentyloxy)-2H-isoquinolin-1-one (287 mg, 74%) was obtained as colorless crystals.

Example 7-28

In the same manner as in Example 7-27 using 4-{2-[(2-acetoxy-2-benzenesulfanylethyl)-(3-methoxy-4-pentyloxybenzoylamino)]ethyl} phenyl acetate, 2-[2-(4-hydroxyphenyl)ethyl]-(7-methoxy-6-pentyloxy)-2H-isoquinolin-1-one (31 mg, 7.9%) was obtained as colorless crystals.

Example 7-29

10% Palladium-carbon catalyst (water content 50%, 100 mg) was added to a solution of 2-[2-(4-acetyloxyphenyl) ethyl]-(6-methoxy-7-pentyloxy)-2H-isoquinolin-1-one (300 mg, 0.708 mmol, 1.0 eq) in acetic acid (5 ml), and the mixture was stirred in a stream of hydrogen at room temperature under a pressure of 3 kgf/cm² for 16 hours. The reaction mixture was filtered through Celite, and the filtrate was concentrated under reduced pressure to give 4-[2-(6-methoxy-1-oxo-7-pentyloxy-3,4-dihydro-2H-isoquinolin-2-yl)ethyl]phenyl acetate (90 mg, 47.7%) as colorless crystals.

Example 7-30

4,5-Dipentyloxy-3-hydroxy-2-[2-(4-nitrophenyl)ethyl]-2,3-dihydroisoindol-1 -one (1.04 g, 2.2 mmol, 1.0 eq) was dissolved in dichloromethane (20 ml), and triethylsilane (0.70 ml, 4.4 mmol, 2.0 eq) was added. The mixture was stirred for 10 minutes at room temperature. Trifluoroacetic acid (2.2 ml) was added dropwise thereto, and the mixture was further stirred for 4 hours. A saturated aqueous sodium hydrogencarbonate solution (40 ml) was added to this reaction mixture, and the mixture was extracted 3 times with ethyl acetate (30 ml). The organic layers were combined, washed with saturated brine (100 ml) and dried over anhydrous sodium sulfate. The drying agent was filtered off, and the filtrate was concentrated under reduced pressure to give 4,5-dipentyloxy-2-[2-(4-nitrophenyl)ethyl]-2,3-dihydroisoindol-1-one (868 mg, 86.8%) as pale-yellow crystals.

Example 7-31

N-[2-(4-Hydroxyphenyl)ethyl]-4-methoxy-2-methylthiomethyl-3-pentylaminobenzamide (93 mg, 0.223 mmol) obtained in Example 2-49, methylene chloride (1 ml) and molecular sieve 4A (100 mg) were mixed, and the mixture was cooled to 0° C. N-Chlorosuccinimide (44.7 mg, 0.33 mmol) was added, and the mixture was stirred at room temperature for 24 hours. Saturated saturated brine (0.5 ml) was add to the mixture, and the aqueous layer was extracted 5 times with ethyl acetate (5 ml). The organic layers were combined, and dried over anhydrous magnesium sulfate. The drying agent was filtered off, and the filtrate was concentrated under reduced pressure. The obtained residue was purified twice by column chromatography on silica gel (chloroform/methanol=50/1-10/1, hexane/ethyl acetate=1/2) to give 2- [2-(4-hydroxyphenyl)ethyl]-5-methoxy-4-pentylamino-2,3-dihydroindol-1-one (12.4 mg, 15%) as colorless crystals.

Example 7-32

N-[2-(4-Hydroxyphenyl)ethyl]-4-methoxy-2-methylthio-3-pentyloxybenzamide (85 mg, 0.21 mmol) obtained in Example 2-50, molecular sieve 4A (200 mg) and methylene chloride (1 ml) were mixed, and this mixture was cooled to 0° C. N-Chlorosuccinimide (29.4 mg, 0.22 mmol) was added, and the mixture was stirred at room temperature for 5 hours. The reaction mixture was filtered, ethyl acetate (20 ml) was added to the filtrate, and the mixture was washed twice with saturated brine (5 ml). The mixture was dried over anhydrous magnesium sulfate. The drying agent was filtered off, and the filtrate was concentrated under reduced pressure. The obtained residue was purified twice by column chromatography on silicagel (hene/ethyl acetate=1/1) to give apale-yellow oil. To allow reaction of the residual raw materials, this oil, molecular sieve 4A (200 mg) and methylene chloride (1 ml) were mixed, and cooled to 0° C. N-Chlorosuccinimide (17.4 mg, 0.13 mmol) was added, and the reaction mixture was stirred at room temperature for 2 hours, followed by filtration. Ethyl acetate (20 ml) was added to the filtrate, and the filtrate was washed once with saturated brine (5 ml) and dried over anhydrous magnesium sulfate. Th drying agent was filtered off and the filtrate was concentrated under reduced pressure. The obtained residue was purified by thin layer chromatography (chloroform/methanol=20/1) to give 2-[2-(4-hydroxyphenyl)ethyl]-6-methoxy-7-pentyloxybenzo[d]isothiazol-3-one (34 mg, 42%) as colorless crystals.

Example 7-33

2-(2-Hydroxymethyl)-3,4-bispentyloxy-N-[2-(4-nitrophenyl)ethyl]benzamide (19.83 g, 42.0 mmol, 1.0 eq) obtained in Example 2-120 was dissolved in DMSO (200 ml), and sulfur trioxide-pyridine complex (20.1 g, 12.6 mmol, 3 eq) and triethylamine (52.7 g, 37.8 mmol, 9 eq) were successively added under cooling with cold water. The mixture was allowed to warm up to room temperature and the mixture was stirred at the same temperature for 2 hours. After addition of saturated sodium hydrogencarbonate solution (300 ml), the mixture was extracted with ethyl acetate (400 ml). The organic layer was washed with saturated brine (300 ml), and dried over anhydrous magnesium sulfate. The drying agent was filtered off and the filtrate was concentrated under reduced pressure to give 3-hydroxy-2-[2-(4-nitrophenyl)ethyl]4,5-bispentyloxy-2,3-dihydroisoindol-1-one (32.2 g, over weight) as a yellow oil.

Example 7-34

4,5-Dipentyloxy-2-[2-(4-nitrophenyl)ethyl]-2,3-dihydroisoindol-1-one (19.69 g, 43.3 mmol, 1.0 eq) obtained in Example 7-30 was dissolved in ethanol (200 ml), and 5% palladium-carbon catalyst (3.8 g, water content 50%) was added. The reaction mixture was stirred in a stream of hydrogen at room temperature for 2.5 hours under the pressure of 3 kgf/cm$^2$, and filtered through celite. The filtrate was concentrated under reduced pressure, and the obtained residue was purified by column chromatography on silica gel (ethyl acetate/chloroform=1/2) to give 2-[2-(4-aminophenyl)ethyl]-4,5-bispentyloxy-2,3-dihydroisoindol-1-one (17.19 g, 93.5%) as pale-yellow crystals.

Example 7-35

2-[2-(4-Aminophenyl)ethyl]-4,5-bispentyloxy-2,3-dihydroisoindol-1-one (22.37 g, 52.7 mmol, 1.0 eq) obtained in Example 7-34 was dissolved in methanol (100 ml), and 10% HCl- methanol solution (86.0 g, 236 mmol, 4.4 eq) was added to this solution. The mixture was stired at room temperature for 30 minutes, and concentrated under reduced pressure to remove the solvent. The obtained residue was washed with hexane and dissolved in ethanol by heating. After cooling at room temperature for 1 hour, the mixture was stirred under ice-cooling. The precipitated crystals were collected by filtration, washed with cold ethanol and dried in vacuo at 40° C. overnight to give 2-[2-(4-aminophenyl) ethyl]-4,5-bispentyloxy-2,3-dihydroisoindol-1-one hydrochloride (17.451 g, 72%) as colorless needles.

Example 7-36

Using 3-hydroxy-5-methoxy-2-[2-(4-nitrophenyl)ethyl]-4-pentyloxy-2,3-dihydroisoindol-1-one obtained in the same manner as in Example 7-33, 5-methoxy-2-[2-(4-nitrophenyl)ethyl]4-pentyloxy-2,3-dihydroisoindol-1-one was obtained as pale-yellow solid in the same manner as in Example 7-30.

Example 7-37

Using 5-methoxy-2-[2-(4-nitrophenyl)ethyl]-4-pentyloxy-2,3-dihydroisoindol-1-one obtained in Example 7-36, 2-[2-(4-aminophenyl)ethyl]-5-methoxy-4-pentyloxy-2,3-dihydroisoindol-1-one was obtained as colorless crystals in the same manner as in Example 7-34.

Example 7-38

2-[2-(4-Acetanilyl)ethyl]-7-methoxy-8-pentyloxy-3,4-dihydro-2H-isoquinolin-1-one (239.4 mg, 3.88 mmol, 1.0 eq) obtained in the same manner as in Example 7-23 was dissolved in ethanol (20 ml), and 3N hydrochloric acid (20 ml) was added to this solution. The reaction mixture was refluxed under heating and concentrated under reduced pressure. The obtained residue was purified by recrystallization from ethanol-ethyl ether to give 2-[2-(aminophenyl) ethyl]-7-methoxy-8-pentyloxy-3,4-dihydro-2H-isoquinolin-1-one hydrochloride (165 mg, 70.0%) as colorless crystals.

Example 7-39

2-Amino-4-methoxy-N-[2-(4-nitrophenyl)ethyl]-3-pentyloxybenzamide (15.0 g, 37.4 mmol) obtained in Example 2-46, triethylamine (5.30 ml, 38.0 mmol) and chloroform (200 ml) were mixed, and a solution (10 ml) of triphosgene (4.75 g, 16.0 mmol) in chloroform was added dropwise to this solution. After stirring at 50° C. for 11.5 hours, ethanol (20 ml) was added to stop the reaction. The organic layer was washed successively with saturated aqueous sodium hydrogencarbonate solution (100 ml, 50 ml) and water (100 ml, 50 ml). This solution was dried over anhydrous magnesium sulfate, and the drying agent was filtered off. The filtrate was concentrated under reduced pressure. A hexane-chloroform solution (10:1, 110 ml) was added to the precipitated crystals, and the crystals were washed by stirring to give 7-methoxy-3-[2-(4-nitrophenyl)ethyl]-8-pentyloxy-1H-quinazoline-2,4-dione (12.56 g, 79%) as pale-yellow crystals.

Example 7-40

7-Methoxy-3-[2-(4-nitrophenyl)ethyl]-8-pentyloxy-1H-quinazoline-2,4-dione (45.0 g, 105 mmol) obtained in Example 7-39, ethanol (1300 ml) and dioxane (700 ml) were mixed, and 10% palladium-carbon catalyst (4.5 g) was added to this solution. The reaction mixture was stirred in a stream of hydrogen at room temperature for 16.5 hours, followed by filtration. Activated charcoal (2.6 g was added to the filtrate, and the reaction mixture was stirred at 50° C. for 1 hour and then filtered. The filtrate was concentrated under reduced pressure, and the obtained residue was purified by column chromatography on silica gel (chloroform/ ethyl acetate=3/1). The precipitated crude crystals were recrystallized from ethanol-hexane to give 3-[2-(4-aminophenyl)ethyl]-7-methoxy-8-pentyloxy-1H-quinazoline-2,4-dione (33.82 g, 81%) as pale-yellow crystals.

Example 7-41

3-[2-(4-Aminophenyl)ethyl]-7-methoxy-8-pentyloxy-1H-quinazoline-2,4-dione (28.0 g, 70.4 mmol) obtained in Example 7-40 and ethanol (500 ml) were mixed, and the mixture was refluxed under heating until the crystals were completely dissolved. Concentrated hydrochloric acid (5.93 ml, 70.4 mmol) was added dropwise to this solution, and ethanol (200 ml) was further added. The mixture was cooled to room temperature, and the precipitated crystals were collected by filtration to give 3-[2-(4-aminophenyl)ethyl]-7-methoxy-8-pentyloxy-1H-quinazoline-2,4-dione hydrochloride (28.24 g, 92%) as colorless crystals.

Example 7-42

Ethyl {(4-Methoxy-2-nitro-3-pentyloxybenzoyl)-[2-(4-nitrophenyl)-ethyl]amino}acetate (70.0 mg, 0.135 mmol) and ethanol (2 ml) were mixed, and 10% palladium-carbon catalyst was added. The reaction mixture was stirred in a stream of hydrogen at room temperature for 10.5 hours, and then filtered. The filtrate was concentrated under reduced pressure. Toluene (10 ml) and p-toluene sulfonate monohydrate (1 mg, 0.0053 mmol) were added to the precipitated crude crystals, and the mixture was refluxed under heating for 3.5 hours. Ethyl acetate (20 ml) was added to this reaction mixture, and the organic layer was washed with saturated aqueous sodium hydrogencarbonate solution (5 ml) and saturated brine (5 ml) and dried over anhydrous magnesium sulfate. The drying agent was filtered off and the filtrate was concentrated under reduced pressure. The obtained residue was purified by column chromatography on silica gel (chloroform/methanol=10/1) to give 4-[2-(4-aminophenyl)ethyl]-8-methoxy-9-pentyloxy-3,4-dihydro-1H-benzo[e][1,4]diazepine-2,5-dione (35 mg, 63% in 2 steps) as colorless crystals.

Example 7-43

2-Amino-4-methoxy-N-[2-(4-nitrophenyl)ethyl]-3-pentyloxybenzamide (300 mg, 0.747 mmol), acetone (3 ml) and acetic acid (1.5 ml) were mixed, and the mixture was stirred at 100° C. for 2 hours. Ethyl acetate (30 ml) and water (25 ml) were added to separate the organic layer. The organic layer was washed twice successively with saturated brine (20 ml), saturated aqueous sodium hydrogencarbonate solution (20 ml) and saturated brine (20 ml), and dried over anhydrous magnesium sulfate. The drying agent was filtered off and the filtrate was concentrated under reduced pressure to give a crude product of 7-methoxy-2,2-dimethyl-3-[2-(4-nitrophenyl)ethyl]-9-pentyloxy-2,3-dihydro-1H-quinazolin-4-one.

Example 7-44

2-Amino-4-methoxy-N-[2-(4-nitrophenyl)ethyl]-3-pentyloxydenzamide (200 mg, 0.498 mmol) obtained in Example 2-46, ethanol (3 ml) and acetyl acetone (0.13 ml, 1.25 mmol) were mixed, and one drop of concentrated hydrochloric acid was added to this solution. The mixture was refluxed under heating for 2.5 hours, and ethyl acetate (30 ml) and saturated brine (30 ml) were added to separate the organic layer. This organic layer was washed successively with saturated aqueous sodium hydrogencarbonate solution (20 ml) and saturated brine (20 ml), and dried over anhydrous magnesium sulfate. The drying agent was filtered off and the filtrate was concentrated under reduced pressure to give a crude product of 7-methoxy-2-methyl-3-[2-(4-nitrophenyl)ethyl]-8-pentyloxy-3H quinazolin A one.

Example 7-45

Using 2-amino-4-methoxy-3-pentyloxy-N-(2-pyridin-4-ylethyl)bezamide (100 mg, 0.280 mmol) obtained in Example 2-61, 7-methoxy-8-pentyloxy-3-(2-pyridin-4-ylethyl)-1H-quinazoline-2,4-dione (103 mg, 96%) was obtained as colorless crystals in the same manner as in Example 7-39.

Example 7-46

2-Amino-4-methoxy-3-pentyloxy-N-(2-pyridin-4-ylethyl)benzamide (200 mg, 0.560 mmol) obtained in Example 2-61, carbon disulfide (0.6 ml), 1,8-diazabicyclo[5.4.0]-7-undecene (0.0837 ml, 0.56 mmol) and DMF (1.0 ml) were mixed, and this mixture was refluxed under heating for 4 hours. Ethyl acetate (4 ml) and water were added to this reaction mixture. The organic layer was washed with saturated aqueous sodium hydrogencarbonate solution (5 ml) and saturated brine (5 ml), and dried over anhydrous magnesium sulfate. The drying agent was filtered off and the filtrate was concentrated under reduced pressure. The obtained residue was subjected to column chromatography on silica gel (chloroform/methanol=10/1) and recryst allization from ethyl acetate to give 7-methoxy-8-pentyloxy-3-(2-pyridin-4-ylethyl)-2-thioxo-2,3-dihydro-1H-quinazolin-4-one (24 mg, 11%) as colorless crystals.

Example 7-47

2-Amino-4-methoxy-3-pentyloxy-N-(2-pyridin-4-ylethyl)benzamide (100 mg, 0.280 mmol) obtained in Example 2-61, dimethyl formamide dimethyl acetal (0.19 ml, 1.4 mmol) and DMF (0.5 ml) were mixed, and p-toluene sulfonate monohydrate (2 mg, 0.011 mmol) was added to this solution. The mixture was stirred at 130° C. for 5 hours, and ethyl acetate (15 ml) and saturated aqueous sodium hydrogencarbonate solution (15 ml) were added to separate the organic layer. The organic layer was washed with saturated bnne (15 ml), and dried over anhydrous magnesium sulfate. The drying agent was filtered off and the filtrate was concentrated under reduced pressure. The obtained residue was purified by column chromatography on silica gel (chloroform/methanol=25/1) to give 7-methoxy-8-pentyloxy-3-(2-pyridin-4-ylethyl)-3H-quinazolin-4-one (57 mg, 55%) as a pale-yellow oil.

Example 7-48

The crude product of ethyl [3-methoxy-2-pentyloxy-6-(2-pyridin-4-ylethylcarbamoyl)phenyl]acetate obtained in Example 2-51, ethanol (400 ml) and sodium ethoxide (1.98 g, 29.1 mmol) were mixed and stirred at 90° C. for 30 minutes. The solvent was concentrated under reduced pressure, and 1N hydrochloric acid (100 ml), water (100 ml) and hexane-ethyl acetate solution (2:1 solution, 150 ml) were added to separate the aqueous layer. The organic layer was extracted with a mixed solution of water (100 ml) and 1N hydrochloric acid (100 ml). The aqueous layers were combined, and washed with hexane-ethyl acetate solution (2:1 solution, 150 ml). Sodium carbonate was added to the aqueous layer to make the solution alkaline under ice-cooling, and the aqueous layer was extracted twice with ethyl acetate (300 ml), and dried over anhydrous magnesium sulfate. The drying agent was filtered off and the filtrate was concentrated under reduced pressure. The obtained residue was purified by column chromatography on silica gel (hexane/ethyl acetate=1/4) to give 6-methoxy-5-pentyloxy-6-(2-pyridin-4-ylethyl)-4H-isoquinoline-1,3-dione (31.51 g, 67.5% in 2 steps) as pale-yellow crystals.

Example 7-49

6-Methoxy-5-pentyloxy-2-(2-pyridin-4-ylethyl)-4H-isoquinoline-1,3-dione (30.97 g, 80.98 mmol) obtained in Example 7-48, methylene chloride (150 ml) and methanol (150 ml) were mixed, and sodium borohydrate (6.127 g, 1623 mmol) was slowly added to this solution under ice-cooling. After stirring at room temperature for 2 hours, concentrated hydrochloric acid was added under ice-cooling to adjust the solution to pH 1, and the solution was stirred at room temperature for 30 minutes. Saturated aqueous sodium hydrogencarbonate solution was added to make the solution alkaline, and the aqueous layer was extracted with chloroform (500 ml) and the organic layer was dried over anhydrous magnesium sulfate. The drying agent was filtered off and the filtrate was concentrated under reduced pressure. The obtained residue was purified by column chromatography on silica gel (ethyl acetate), and 4N hydrochloric acid-dioxane solution (40 ml) was added to the residue. Ethyl acetate (200 ml) and hexane (100 ml) were further added, and the precipitated crystals were collected by filtration. These crystals were washed twice with ethyl acetate with heating to give 6-methoxy-5-pentyloxy-2-(2-pyridin-4-ylethyl)-2H-isoquinoin-1-one hydrochloride (22.412 g, 68.7%) as colorless crystals.

Example 7-50

6-Methoxy-5-pentyloxy-1,2,3,4-tetrahydroisoquinoline (116 mg, 0.465 mmol), (4-nitrophenyl)acetate (101.1 mg, 0.558 mmol) and 1-hydroxybenzotriazol hydrate (81.7 mg, 0.605 mmol) were dissolved in DMF (2 ml), and WSC hydrochloride (125 mg, 0.651 mmol) was added to this solution under ice-cooling. After stirring at room temperature for 3 hours, ethyl acetate (3 ml) and saturated aqueous sodium hydrogencarbonate solution (3 ml) were added to the reaction mixture to separate the organic layer. The organic layer was dried over anhydrous sodium sulfate. The drying agent was filtered off and the filtrate was concentrated under reduced pressure to give a crude product of 1-(6-methoxy-5-pentyloxy-3,4-dihydro-1H-isoquinolin-2-yl)-2-(4-nitrophenyl)ethanone. This product was used for the next reaction.

Example 7-51

The crude product of 1-(6-methoxy-5-pentyloxy-3,4-dihydro-1H-isoquinolin-2-yl)-$^2$-(4-nitrophenyl)ethanone obtained in Example 7-50 was dissolved in ethanol (4 ml), and 10% palladium-carbon catalyst (38 mg) was added to this solution. The reaction mixture was stirred in a stream of hydrogen for 3 hours, and then filtered. The solvent was concentrated under reduced pressure. The obtained residue was purified by column chromatography on silica gel (hexane/ethyl acetate=1/2) to give 2-(4-aminophenyl)-1-(6-methoxy-5-pentyloxy-3,4-dihydro-1H-isoquinolin-2-yl) ethanone (159 mg, 89% in 2 steps) as a colorless oil.

The properties of the compounds obtained in the above Examples 7-1 to 7-51 are shown in Tables 111–127.

Examples 7-52 to 7-102

In the same manner as in the above-mentioned Example 7-1 to 7-51, the compounds shown in Example 7-52 to 7-102 were obtained. The properties of said compounds are shown in Tables 127–144.

Example 8-1

7-Methoxycoumalin (300 mg, 2.78 mmol) was dissolved in morpholine (3 ml), and the solution was refluxed under heating for 2 hours. This reaction mixture was cooled to room temperature, and water (10 ml) and saturated citric acid (50 ml) were added. The mixture was extracted twice with ethyl acetate (50 ml). The organic layers were combined, washed with saturated brine (100 ml) and dried over anhydrous sodium sulfate. The drying agent was filtered off, and the filtrate was concentrated under reduced pressure. The obtained residue was purfied by column chromatography on silica gel (n-hexane/ethyl acetate=4/1-1/2) to give (E)-[3-(6-hydroxy-4-methoxyphenyl)-1-oxo-2-propenyl]-4-morpholine (37 mg, 12.0%) as colorless crystals.

Example 8-2

(E)-[3-(6-Hydroxy-4-methoxyphenyl)-1-oxo-2-propenyl]-4-morpholine (27 mg, 0.103 mmol) was dissolved in DMF (3 ml), and to this solution were successively added 1-bromopentane (20 mg, 0.132 mmol, 1.3 eq) and anhydrous potassium carbonate (40 mg, 0.29 mmol, 2.8 eq). The mixture was stirred with heating at 90° C. for 1 hour. This reaction mixture was cooled to room temperature, and water (30 ml) was added. The mixture was extracted twice with ethyl acetate (30 ml). The organic layers were combined, washed with saturated brine (30 ml) and dried over anhydrous sodium sulfate. The drying agent was filtered off, and the filtrate was concentrated under reduced pressure. The obtained residue was purified by column chromatography on silica gel (n-hexane/ethyl acetate=20/1) to give (E)-[3-(4-methoxy-2-pentyloxyphenyl)-1-oxo-2-propenyl]-4-morpholine (31 mg, 90.7%) as a colorless oil.

Example 8-3

4-Methoxy-3-pentyloxycinnamic acid (500 mg, 2.62 mmol, 1 eq) and 1-hydroxybenzotriazole hydrate (371 mg, 2.75 mmol, 1.05 eq) were dissolved in DMF (5 ml), and to this solution were successively added morpholine (684 mg, 7.85 mmol, 3.0 eq) and WSC hydrochloride (526 mg, 2.75 mmol, 1.05 eq) under ice-cooling. The mixture was stirred at room temperature for 12 hours. Ice water (5 ml) and a saturated aqueous sodium hydrogencarbonate solution (5 ml) were successively added to this reaction mixture. The mixture was exracted twice with ethyl acetate (20 ml). The organic layers were combined, washed with saturated brine (40 ml) and dried over anhydrous sodium sulfate. The drying agent was filtered off, and the filtrate was concentrated under reduced pressure. The obtained residue was purified by column chromatography on silica gel (n-hexane/ethyl acetate=1/2) to give (E)-3-(3-pentyloxy-4-methoxyphenyl)-1-morpholin-4-yl-prop-2-en-1-one (343 mg, 49.8%) as a colorless solid.

Example 8-4

4-Methoxy-3-pentyloxybenzoic acid (250 mg, 1.05 mmol, 1 eq) was dissolved in thionyl chloride (1.05 ml) in a stream of nitrogen, and the solution was stirred at 70° C. for 5 hours. The mixture was cooled to room temperature, and excess thionyl chloride was evaporated under reduced pressure. The residue was added to a solution of morpholine (274 mg, 3.15 mol, 3.0 eq) in DMF (3 ml) under ice-cooling. The mixture was stirred under ice-cooling for 30 minutes, and then further at room temperature for 1.5 hours. Water (30 ml) was added to this reaction mixture and the mixture was extracted twice with ethyl acetate (50 ml). The organic layers were combined, washed with saturated brine (50 ml) and dried over anhydrous sodium sulfate. The drying agent was fltered off, and the filtrate was concentrated under reduced pressure. The obtained residue was purified by column chromatography on silica gel (n-hexane/ethyl acetate=2/1) to give (4-methoxy-3-pentyloxyphenyl) morpholin-4-yl-methanone (219 mg, 67.9%) as an oil The properties of the compounds obtained in the above Example 8-1 to 8-4 are shown in Tables 145 and 146.

Examples 8-5 to 8-7

In the same manner as in the above Example 8-1 to 8-4, the compounds of Example 8-5 to 8-7 were obtained. The properties of obtained compounds are shown in Tables 146 and 147.

TABLE 1

| Prep. Ex. | Structural formula | 1H NMR (δ) ppm | MS |
|---|---|---|---|
| 91 | MeO-C6H3(OC5H11)-COOH<br>Colorless crystals | CDCl3, 300 MHz<br>10.72(1H, ba), 8.14(1H, d, J=8.8 Hz),<br>6.64(1H, dd, J=8.8, 2.3 Hz),<br>6.51(1H, d, J=2.3 Hz),<br>4.21(2H, t, J=6.6 Hz),<br>3.87(3H, s),<br>1.83–1.95(2H, m),<br>1.33–1.50(4H, m),<br>0.95(3H, t, J=7.0 Hz). | FAB+<br>239[M+H+]<br>(70),<br>221(30). |
| 92 | MeO-C6H3(NHPen)-CO2H<br>Colorless crystals | CDCl3, 300 MHz<br>7.51(1H, dd, J=8.1, 2.1 Hz),<br>7.29(1H, d, J=2.1 Hz),<br>6.78(1H, d, J=8.1 Hz),<br>3.92(3H, s),<br>3.18(2H, t, J=7.2 Hz),1.6–1.75 (2H, m),<br>1.3–1.5(4H, m),<br>0.93(3H, t, J=6.5 Hz). | |
| 93 | PenO-C6H2(OPen)(OPen)-COOH<br>Colorless crystals | CDCl3, 300 MHz<br>7.32(2H, s),<br>4.0–4.1(6H, m),<br>1.7–1.9(6H, m),<br>1.30–1.55(12H, m),<br>0.85–0.95(9H, m). | FAB+<br>381[M+H+]<br>(100), 310(60). |

TABLE 2

| Prep. Ex. | Structural formula | 1H NMR (δ) ppm | MS |
|---|---|---|---|
| 94 | MeO-C6H3(NPen2)-CO2H<br>Colorless crystals | CDCl3, 300 MHz<br>8.65(1H, bs),<br>8.22(1H, d, J=9.0 Hz),<br>7.14(1H, d, J=9.0 Hz),<br>4.06(3H, s),<br>3.54(4H, bt),<br>1.8–2.1(1H, m),<br>1.0–1.4(11H, m),<br>0.81(6H, bt). | FAB+<br>308[M+H+]<br>(100), 250(30). |
| 95 | PenO-C6H2(OPen)(OPen)-CH=CH-CO2H<br>Colorless crystals | CDCl3, 300 MHz<br>7.67(1H, d, J=16 Hz),<br>7.75(2H, s),<br>6.31(1H, d, J=16 Hz),<br>3.9–4.1(6H, m),<br>1.7–1.9(6H, m),<br>1.30–1.55(12H, m),<br>0.87–1.0(9H, m). | FAB+<br>407[M+H+]<br>(90), 336(60). |
| 96 | PenO-C6H3(NHPen)-CO2H<br>Colorless crystals | CDCl3, 300 MHz<br>7.47(1H, dd, J=8.4, 2.1Hz),<br>7.28(1H, d, J=2.0 Hz),<br>6.76(1H, d, J=8.4 Hz),<br>4.06(2H, t, J=6.6 Hz),<br>3.18(2H, t, J=7.1 Hz),<br>1.78–1.92(2H, m),<br>1.62‘1.74(2H, m),<br>1.30–1.53(8H, m),<br>0.94(3H, t, J=7.0 Hz),<br>0.93(3H, t, J=7.0 Hz). | FAB+<br>294[M+H+]<br>(50),<br>277(60),<br>185(100). |

TABLE 3

| Prep. Ex. | Structural formula | 1H NMR (δ) ppm | MS |
|---|---|---|---|
| 97 | MeO, NHPen, CO₂H (Yellow crystals) | CDCl3, 300 MHz<br>7.71(1H, d, J=16 Hz),<br>6.86(1H, dd, J=8.2, 2.0 Hz),<br>6.77(1H, s),<br>6.74(1H, d, J=8.2 Hz),<br>6.29(1H, d, J=16 Hz),<br>3.88(3H, s),<br>3.14(2H, t, J=7.1 Hz),<br>1.6–1.75(2H, m),<br>1.3–1.5(4H, m),<br>0.94(3H, t, J=7.0 Hz). | FAB+<br>264[M+H+]<br>(50),<br>237(100),<br>206(40). |
| 98 | MeO, NPen₂, CO₂H (Yellow crystals) | CDCl3, 300 MHz<br>7.72(1H, d, J=16 Hz),<br>7.18(1H, dd, J=8.4, 2.0 Hz),<br>7.12(1H, d, J=2.0 Hz),<br>6.85(1H, d, J=8.4 Hz),<br>6.30(1H, d, J=16 Hz),<br>3.88(3H, s),<br>3.08(4H, t, J=7.7 Hz),<br>1.37–1.54(4H, m),<br>0.25–1.36(8H, m),<br>0.87(6H, t, J=6.9 Hz). | FAB+<br>334[M+H+]<br>(100),<br>276(30). |
| 99 | MeO, N(Me)Pen, CO₂H (Pale-yellow oil) | CDCl3, 300 MHz<br>7.77(1H, dd, J=8.5, 2.1 Hz),<br>7.66(1H, d, J=2.0 Hz),<br>6.88(1H, d, J=8.5 Hz),<br>3.94(3H, s),<br>3.04(2H, t, J=7.8 Hz),<br>2.82(3H, s),<br>1.45–1.60(2H, m),<br>1.2–1.4(4H, m),<br>0.89(3H, t, J=6.9 Hz). | FAB+<br>252[M+H+]<br>(100),<br>194(50). |

TABLE 4

| Prep. Ex. | Structural formula | 1H NMR (δ) ppm | MS |
|---|---|---|---|
| 100 | PenO, NHPen, CO₂H (Colorless crystals) | CDCl3, 300 MHz<br>7.72(1H, d, J=16 Hz),<br>6.84(1H, dd, J=8.1, 1.8 Hz),<br>6.77(1H, d, J=2.4 Hz),<br>6.72(1H, d, J=8.1 Hz),<br>6.30(1H, d, J=16 Hz),<br>4.03(2H, t, J=6.3 Hz),<br>3.15(2H, t, J=7.1 Hz),<br>1.75–1.90(2H, m),<br>1.60–1.73(2H, m),<br>1.30–1.50(8H, m),<br>0.94(6H, t, J=6.9 Hz). | FAB+<br>320[M+H+]<br>(70),<br>262(20). |
| 101 | PenHN, OPen, CO₂H (Colorless crystals) | CDCl3, 300 MHz<br>7.69(1H, dd, J=8.1, 1.5 Hz),<br>7.41(1H, d, J=1.8 Hz),<br>6.54(1H, d, J=8.1 Hz),<br>4.05(2H, t, J=6.5 Hz),<br>3.20(2H, t, J=7.1 Hz),<br>1.75–1.90(2H, m),<br>1.60–1.75(2H, m),<br>1.30–1.50(8H, m),<br>0.85–1.2(6H, m). | FAB-30<br>294[M+H+]<br>(50),<br>293(100),<br>236(20). |

TABLE 4-continued

| Prep. Ex. | Structural formula | 1H NMR (δ) ppm | MS |
|---|---|---|---|
| 102 | MeO, NPen substituted cinnamic acid (CO2H); Pale-yellow crystals | CDCl3, 300 MHz 7.72(1H, d, J=16 Hz), 7.17(1H, bs), 6.88(1H, bs), 6.33(1H, s, J=16 Hz), 3.92(3H, s), 3.07(2H, bs), 2.82(3H, bs), 1.4–1.6(2H, m), 1.2–1.4(4H, m), 0.88(3H, t, J=6.8 Hz). | FAB+ 278[M+H+] (100), 220(30). |

TABLE 5

| Prep. Ex. | Structural formula | 1H NMR (δ) ppm | MS |
|---|---|---|---|
| 103 | MeO, S-pentyl substituted cinnamic acid (CO2H); Colorless crystals | CDCl3, 300 MHz 7.72(1H, d, J=16 Hz), 7.42(1H, d, J=2.1 Hz), 7.36(1H, dd, J=8.5, 2.1 Hz), 6.85(1H, d, J=8.5 Hz), 6.33(1H, d, J=16 Hz), 3.93(3H, s), 2.91(2H, t, J=7.4 Hz), 1.60–1.75(2H, m), 1.30–1.50(4H, m), 0.91(3H, t, J=7.1 Hz). | FAB+ 281[M+H+] (60), 280(100). |
| 104 | MeN, O-pentyl substituted benzoic acid (CO2H); Colorless crystals | CDCl3, 300 MHz 7.73(1H, d, J=8.4 Hz), 7.43(1H, s), 6.54(1H, d, J=8.4 Hz), 4.05(2H, t, J=6.3 Hz), 2.94(3H, s), 1.73–1.90(2H, m), 1.30–1.55(4H, m), 0.94(3H, t, J=6.9 Hz). | FAB+ 238[M+H+] (80), 220(60), 169(100). |
| 105 | PenHN, HN-pentyl substituted benzoic acid (CO2H); Colorless crystals | CDCl3, 300 MHz 7.67(1H, dd, J=8.4, 1.8 Hz), 7.41(1H, d, J=1.8 Hz), 6.61(1H, d, J=8.4 Hz), 3.18(2H, t, J=8.3 Hz), 3.12(2H, t, J=8.3 Hz), 1.6–1.8(4H, m), 1.30–1.50(8H, m), 0.94(6H, t, J=6.9 Hz). | 293[M+H+] (40), 292(100). |

TABLE 6

| Prep. Ex. | Structural formula | 1H NMR (δ) ppm | MS |
|---|---|---|---|
| 106 | (benzene ring with CO₂H, PenO, and N(CH₃)(pentyl) substituents)<br>Colorless crystals | CDCl3, 300 MHz<br>7.71(1H, dd, J=8.4, 2.1 Hz),<br>7.62(1H, d, J=2.1 Hz),<br>6.86(1H, d, J=8.4 Hz),<br>4.06(2H, t, J=6.6 Hz),<br>3.05(2H, t, J=7.7 Hz),<br>2.83(3H, s),<br>180–1.95(2H, m),<br>1.20–1.65(10H, m),<br>0.94(6H, t, J=7.0 Hz),<br>0.89(6H, t, J=7.0 Hz). | FAB+<br>308[M+H+]<br>(20),<br>185(100). |
| 107 | (benzene ring with CHO, PenO, and S-pentyl substituents)<br>Pale-yellow oil | CDCl3, 300 MHz<br>9.85(1H, s),<br>7.72(1H, d, J=2.1 Hz),<br>7.63(1H, dd, J=8.4, 1.8 Hz),<br>6.91(1H, d, J=8.4 Hz),<br>2.94(2H, t, J=7.4 Hz),<br>1.80–1.93(2H, m),<br>1.6–1.78(2H, m),<br>1.20–1.60(8H, m),<br>0.94(3H, t, J=7.2 Hz),<br>0.92(3H, t, J=7.2 Hz) | FAB+<br>295[M+H+]<br>(80),<br>294(100),<br>225(40). |
| 108 | (benzene ring with CO₂H, PenO, and Br substituents)<br>Colorless crystals | CDCl3, 300 MHz<br>8.29(1H, d, J=2.1 Hz),<br>8.02(1H, dd, J=9.0, 2.4 Hz),<br>6.91(1H, d, J=9.0 Hz),<br>4.10(2H, t, J=6.5 Hz),<br>1.80–1.95(2H, m),<br>1.30–1.60(4H, m),<br>0.95(3H, t, J=7.2 Hz). | FAB+<br>288[M+H+]<br>(30),<br>218(30). |

TABLE 7

| Prep. Ex. | Structural formula | 1H NMR (δ) ppm | MS |
|---|---|---|---|
| 109 | (benzene ring with CH=CH-CO₂H, PenO, and S-pentyl substituents)<br>Colorless crystals | CDCl3, 300 MHz<br>7.71(1H, d, J=16 Hz),<br>7.41(1H, d, J=2.4 Hz),<br>7.33(1H, dd, J=8.7, 1.8 Hz),<br>6.83(1H, d, J=8.7 Hz),<br>6.31(1H, d, J=16 Hz),<br>4.06(2H, t, J=6.5 Hz),<br>2.90(2H, t, J=7.4 Hz),<br>1.80–1.95(2H, m),<br>1.60–1.77(2H, m),<br>1.30–1.56(8H, m),<br>0.94(3H, t, J=8.0 Hz),<br>0.91(3H, t, J=8.0 Hz). | FAB+<br>337[M+H+]<br>(50),<br>266(50). |
| 111 | (benzene ring with CO₂H, MeO, and S-pentyl substituents)<br>Colorless crystals | CDCl3, 300 MHz<br>7.95(1H, s),<br>7.93(1H, d, J=8.4 Hz),<br>6.88(1H, d, J=8.4 Hz),<br>3.97(3H, s),<br>2.95(2H, t, J=7.4 Hz),<br>1.65–1.80(2H, m),<br>1.30–1.55(4H, m),<br>0.91(3H, t, J=7.2 Hz). | FAB+<br>255[M+H+]<br>(30),<br>254(40). |

TABLE 7-continued
| Prep. Ex. | Structural formula | 1H NMR (δ) ppm | MS |
|---|---|---|---|
| 112 | <br>Colorless crystals | CDCl3, 300 MHz<br>7.94(1H, d, J=2.0 Hz),<br>7.89(1H, dd, J=8.5, 2.0 Hz),<br>6.85(1H, d, J=2.0 Hz),<br>4.10(2H, t, J=6.6 Hz),<br>2.94(2H, t, J=7.4 Hz),<br>1.77–1.95(2H, m),<br>1.60–1.75(2H, m),<br>1.3–1.5(8H, m),<br>0.91(3H, t, J=7.1 Hz). | FAB+<br>311[M+H+]<br>(50),<br>310(100),<br>240(40). |
TABLE 8
| Prep. Ex. | Structural formula | 1H NMR (δ) ppm | MS |
|---|---|---|---|
| 113 | 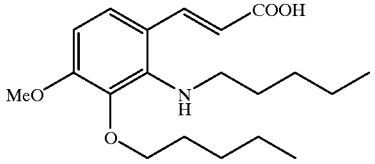<br>Colorless crystals | | |
| 114 | 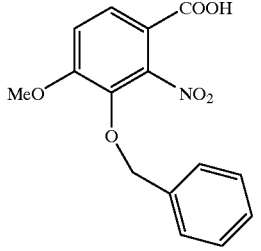<br>Colorless crystals | | |
| 115 | 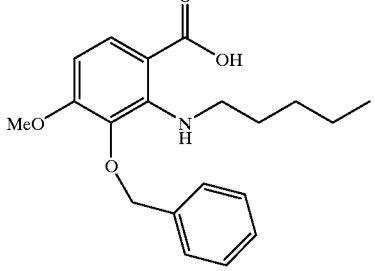<br>Colorless crystals | | |

TABLE 9

| Prep. Ex. | Structural formula | 1H NMR (δ) ppm | MS |
|---|---|---|---|
| 116 | (structure: 2-pentylamino-3-hydroxy-4-methoxybenzoic acid) Brown crystals | DMSO-d6, 300 MHz<br>7.39(1H, d, J=8.8 Hz)<br>6.48(1H, d, J=8.8 Hz)<br>3.80(3H, s)<br>3.32(2H, t, J=6.9 Hz)<br>1.35–1.50(2H, m)<br>1.20–1.33(4H, m)<br>0.85(3H, t, J=7.0 Hz) | |
| 117 | (structure: 2-amino-3-pentyloxy-4-methoxycinnamic acid) Pale-yellow crystals | CDCl3, 300 MHz<br>7.87(1H, d, J=15.6 Hz)<br>7.17(1H, d, J=8.7 Hz)<br>6.39(1H, d, J=8.7 Hz)<br>6.27(1H, d, J=15.6 Hz)<br>3.96(2H, t, J=6.8 Hz)<br>3.86(3H, s)<br>1.70–1.85(2H, m)<br>1.30–1.50(4H, m)<br>0.94(3H, t, J=7.1 Hz) | |
| 118 | (structure: 2-amino-4-methoxy-5-pentyloxybenzoic acid) Gray crystals | CDCl3, 300 MHz<br>7.37(1H, s)<br>6.13(1H, s)<br>3.94(2H, t, J=6.8 Hz)<br>3.86(3H, s)<br>1.75–1.85(2H, m)<br>1.35–1.50(4H, m)<br>0.93(3H, t, J=7.2 Hz) | |

TABLE 10

| Prep. Ex. | Structural formula | 1H NMR (δ) ppm | MS |
|---|---|---|---|
| 119 | (structure: 2-(methylthiomethyl)-3-pentyloxy-4-methoxybenzoic acid) Colorless crystals | CDCl3, 300 MHz<br>7.86(1H, d, J=8.8 Hz)<br>6.84(1H, d, J=8.8 Hz)<br>4.26(2H, s)<br>3.97(2H, t, J=6.7 Hz)<br>3.91(3H, s)<br>2.09(3H, s)<br>1.75–1.90(2H, m)<br>1.30–1.50(4H, m)<br>0.95(3H, t, J=7.1 Hz) | FAB+<br>299[M+H+]<br>(50)<br>289(60) |
| 120 | (structure: 4-bromo-3-pentyloxybenzoic acid) Colorless crystals | CDCl3, 300 MHz<br>8.29(1H, d, J=2.1 Hz)<br>8.02(1H, dd, J=9.0, 2.4 Hz)<br>6.91(1H, d, J=9.0 Hz)<br>4.10(2H, t, J=6.5 Hz)<br>1.80–1.95(2H, m)<br>1.30–1.60(4H, m)<br>0.95(3H, t, J=7.2 Hz) | 288[M+H+]<br>(30)<br>218(30) |

TABLE 10-continued

| Prep. Ex. | Structural formula | 1H NMR (δ) ppm | MS |
|---|---|---|---|
| 121 | (pentylthio, pentyloxy benzoic acid structure) <br> Colorless crystals | CDCl3, 300 MHz <br> 7.66(1H, d, J=9.0 Hz) <br> 7.47(1H, s) <br> 7.19(1H, d, J=9.0 Hz) <br> 4.09(2H, t, J=6.6 Hz) <br> 2.93(2H, t, J=7.4 Hz) <br> 1.30–1.90(12H, m) <br> 0.94(3H, t, J=7.5 Hz) <br> 0.92(3H, t, J=7.5 Hz) | FAB+ <br> 311[M+H+] <br> (50) <br> 310(100) <br> 240(40) |

TABLE 11

| Prep. Ex. | Structural formula | 1H NMR (δ) ppm | MS |
|---|---|---|---|
| 122 | (MeS, pentyloxy benzoic acid structure) <br> colorless crystals | CDCl3, 300 MHz <br> 7.71(1H, d, J=8.2Hz) <br> 7.48(1H, s) <br> 7.14(1H, d, J=8.2Hz) <br> 4.11(2H, t, J=6.5Hz) <br> 1.80–1.90(2H, m) <br> 1.30–1.55(4H, m) <br> 0.95(3H, t, J=7.2Hz) | FAB+ <br> 255[M+H+] <br> (30) <br> 254(50) |
| 123 | (pentylthio, pentyloxy cinnamic acid structure) <br> Colorless crystals | CDCl3, 300 MHz <br> 7.71(1H, d, J=16.2 Hz) <br> 7.08–7.19(2H, m) <br> 6.97(1H, s) <br> 6.38(1H, d, J=16.2 Hz) <br> 4.06(2H, t, J=6.5 Hz) <br> 2.912(2H, t, J=7.5 Hz) <br> 1.30–1.95(12H, m) <br> 0.87–0.98(6H, m) | FAB+ <br> 337[M+H+] <br> (40) <br> 336(100) |
| 124 | (MeS, pentyloxy cinnamic acid structure) <br> Colorless crystals | CDCl3, 300 MHz <br> 7.72(1H, d, J=15.9 Hz) <br> 7.08–7.15(2H, m) <br> 6.96(1H, s) <br> 6.39(1H, d, J=15.9 Hz) <br> 4.06(2H, t, J=6.5 Hz) <br> 2.45(3H, s) <br> 1.80–1.90(2H, m) <br> 1.35–1.60(4H, m) <br> 0.95(3H, t, J=7.4 Hz) | FAB+ <br> 281[M+H+] <br> (20) <br> 280(40) |

TABLE 12

| Prep. Ex. | Structural formula | 1H NMR (δ) ppm | MS |
|---|---|---|---|
| 125 | 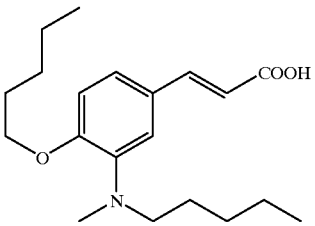<br>Colorless crystals | CDCl3, 300 MHz<br>7.72(1H, d, J=15.9 Hz)<br>7.11(1H, d, J=8.2 Hz)<br>7.10(1H, s)<br>6.82(1H, d, J=8.2 Hz)<br>6.30(1H, d, J=15.9 Hz)<br>4.05(2H, t, J=6.6 Hz)<br>3.05(2H, t, J=7.8 Hz)<br>2.81(3H, s)<br>1.80–195(2H, m)<br>1.20–1.65(10H, m)<br>0.94(3H, t, J=7.1 Hz)<br>0.89(3H, t, J=7.1 Hz) | |
| 126 | 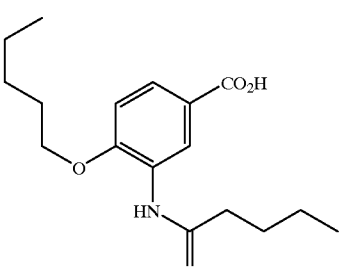<br>Colorless crystals | CDCl3, 300 MHz<br>9.04(1H, bs)<br>7.82(1H, d, J=8.7 Hz)<br>7.72(1H, bs)<br>6.90(1H, d, J=8.7 Hz)<br>4.11(2H, t, J=6.6 Hz)<br>2.42(2H, t, J=7.5 Hz)<br>1.63–1.94(4H, m)<br>1.33–1.53(6H, m)<br>0.96(6H, t, J=7.4 Hz) | |
| 127 | 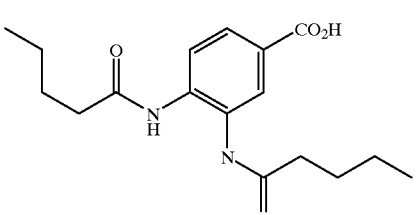<br>Colorless crystals | | FAB+<br>321[M+H+]<br>(60)<br>219(100) |

TABLE 13

| Prep. Ex. | Structural formula | 1H NMR (δ) ppm | MS |
|---|---|---|---|
| 128 | 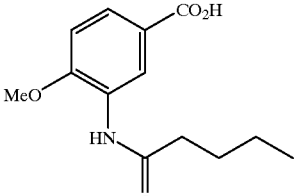<br>Colorless crystals | CDCl3, 300 MHz<br>9.05(1H, bs)<br>7.83(1H, d, J=8.7 Hz)<br>6.91(1H, d, J=8.7 Hz)<br>3.95(3H, s)<br>2.41(2H, t, J=7.5 Hz)<br>1.65–1.80(2H, m)<br>1.35–1.48(2H, m)<br>0.95(3H, t, J=7.3 Hz) | FAB+<br>252[M+H+]<br>(70)<br>185(100) |

TABLE 13-continued

| Prep. Ex. | Structural formula | 1H NMR (δ) ppm | MS |
|---|---|---|---|
| 129 | 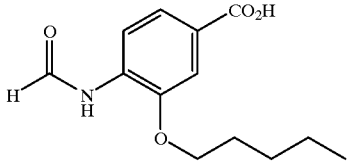<br>Colorless crystals | DMSO-d6, 300 MHz<br>12.8(1H, s)<br>9.71(1H, s)<br>8.40(1H, s)<br>8.32(1H, d, J=8.4 Hz)<br>7.52(1H, d, J=8.4 Hz)<br>7.59(1H, s)<br>4.07(2H, t, J=6.6 Hz)<br>1.75–1.83(2H, m)<br>1.30–1.50(4H, m)<br>0.90(3H, t, J=7.1 Hz) | FAB+<br>252[M+H+]<br>(100)<br>182(100) |
| 130 | 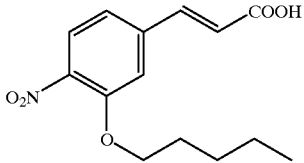<br>Pale-yellow crystals | | |

TABLE 14

| Prep. Ex. | Structural formula | 1H NMR (δ) ppm | MS |
|---|---|---|---|
| 131 | 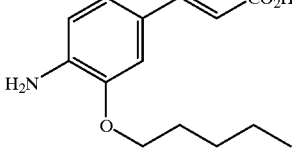<br>Pale-yellow crystals | DMSO-d6, 300 MHz<br>7.26(1H, d, J=15.7 Hz)<br>7.03(1H, s)<br>6.89(1H, d, J=8.2 Hz)<br>6.59(1H, d, J=8.2 Hz)<br>6.19(1H, d, J=15.7 Hz)<br>5.08(2H, bs)<br>3.98(2H, t, J=6.5 Hz)<br>1.68–1.80(2H, m)<br>1.27–1.50(4H, m)<br>0.90(3H, t, J=7.1 Hz) | FAB+<br>250[M+H+]<br>(60)<br>249(100) |

TABLE 15

| Ex. | Structural formula | m.p. | 1H NMR (δ) ppm | IRcm$^{-1}$ | MS | Elem. anal. |
|---|---|---|---|---|---|---|
| 1-1 | 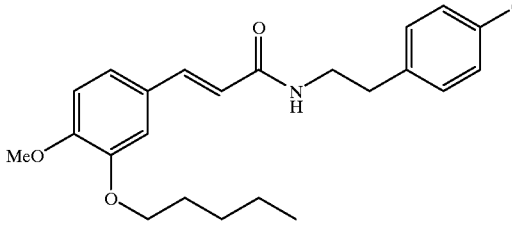 | 106.5~<br>107.3° C. | CDCl$_3$-300MHz<br>7.54(1H, d, J=15.5, 15.3Hz)<br>7.05(2H, d, J=8.4Hz)<br>7.05(1H, dd, J=8.2, 1.9Hz)<br>7.00(1H, d, J=1.9Hz)<br>6.83(1H, d, J=8.2Hz)<br>6.81(2H, d, J=8.4Hz)<br>6.18(1H, d, J=15.5Hz)<br>6.09(1H, bs)<br>5.6–5.7(1H, m)<br>4.00(2H, t, J=6.8Hz)<br>3.87(3H, s)<br>3.61(2H, q, J=6.8Hz)<br>2.80(2H, t, J=6.8Hz)<br>1.7–1.9(2H, m)<br>1.3–1.5(4H, m)<br>0.93(3H, t, J=7.0Hz) | KBr<br>3231<br>1646<br>1516 | FAB+<br>384<br>[M+H+]<br>(50)<br>136<br>(100) | C$_{10}$H$_{11}$N$_{12}$<br>Calcd.<br>C; 72.04%<br>H; 7.62%<br>N; 3.65%<br>Found<br>C; 72.04%<br>H; 7.81%<br>N; 3.64% |

TABLE 15-continued

| Ex. | Structural formula | m.p. | 1H NMR (δ) ppm | IRcm$^{-1}$ | MS | Elem. anal. |
|---|---|---|---|---|---|---|
| 1-2 | EtO-, pentyloxy substituted cinnamoyl-NH-CH2CH2-C6H4-OH; Colorless crystals | 126~127° C. | (DMSO-d6, 300MHz) 9.14(1H, s) 7.97(1H, t) 7.31(1H, d, J=15.8Hz] 6.93–7.12(5H, m) 6.67(2H, d, J=8.4Hz) 6.46(1H, d, J=15.8Hz) 4.04(2H, t, J=6.9Hz) 3.97(2H, t, J=6.6Hz) 3.26–3.37(2H, m) 2.63(2H, t, J=6.5Hz) 1.66–1.77(2H, m) 1.26–1.46(7H, m) 0.89(3H, t, J=7.2Hz) | | FAB+ 398 [M$^+$H$^+$] (52) 276(23) 261 (100) 190(85) 162(86) | |
| 1-3 | 3,4-bis(pentyloxy) cinnamoyl-NH-CH2CH2-C6H4-OH; Colorless crystals | 126~127° C. | (DMSO-d6, 300MHz) 9.15(1H, s) 7.97(1H, t) 7.32(1H, d, J=15.7Hz) 6.94–7.13(5H, m) 6.68(2H, d, J=8.4Hz) 6.47(1H, d, J=15.7Hz) 3.95–4.00(4H, m) 3.25–3.38(2H, m) 2.65(2H, t, J=7.5Hz) 1.64–1.78(4H, m) 1.27–1.47(8H, m) 0.81–0.94(6H, m) | | FAB+ 440 [M$^+$H$^+$] (50) 318(14) 303(44) 232(32) 162 (100) | |

TABLE 16

| Ex. | Structural formula | m.p. | 1H NMR (δ) ppm | IRcm$^{-1}$ | MS | Elem. anal. |
|---|---|---|---|---|---|---|
| 1-4 | MeO-, butyloxy substituted cinnamoyl-NH-CH2CH2-C6H4-OH; Colorless crystals | 123~125° C. | (DMSO-d6, 300MHz) 9.15(1H, s) 7.98(1H, t, J=5.5Hz] 7.33(1H, d, J=15.7Hz) 7.13(1H, d, J=2.0Hz) 7.09(1H, dd, 8.4, 2.0Hz) 7.01(2H, d, J=8.4Hz) 6.97(1H, d, J=8.3Hz) 6.68(2H, d, J=8.4Hz) 6.48(1H, d, J=15.8Hz) 3.98(2H, d, J=6.5Hz) 3.78(3H, s) 3.78(3H, s) 3.33(2H, m) 2.64(2H, t, J=7.5) 1.71(2H, m) 1.44(2H, m) 0.94(3H, t, J=7.4Hz) | KBr 3484 3305 1644 1589 1549 1516 1260 1241 1140 1018 | FAB+ 370 [M$^+$H$^+$] (100) 248(31) 233(58) 176(76) | |
| 1-5 | MeO-, hexyloxy substituted cinnamoyl-NH-CH2CH2-C6H4-OH; Colorless crystals | 117~118° C. | (DMSO-d6, 300MHz) 9.14(1H, s) 7.97(1H, t, J=5.6Hz) 7.32(1H, d, J=15.7Hz) 7.12(1H, d, J=2.0Hz) 7.09(1H, dd, 8.3, 2.0Hz) 7.01(2H, d, J=8.4Hz) 6.96(1H, d, J=8.3Hz) 6.68(2H, d, J=8.3Hz) 6.47(1H, d, J=15.8Hz) 3.97(2H, t, J=6.6Hz) 3.78(3H, s) 3.33(2H, m) 2.64(2H, t, J=7.5Hz) 1.72(2H, m) 1.41(2H, m) 1.37–1.25(4H, m) 0.88(3H, t, J=6.9Hz) | KBr 3456 2952 1652 1614 1594 1548 1514 1342 1259 1243 | FAB+ 398 [M$^+$H$^+$] (33) 397[M] (32) 276(25) 216(36) 176(69) 153 (100) | |

TABLE 16-continued

| Ex. | Structural formula | m.p. | 1H NMR (δ) ppm | IRcm⁻¹ | MS | Elem. anal. |
|---|---|---|---|---|---|---|
| 1-6 | (Colorless crystals) | 123~124° C. | (DMSO-d6, 300MHz)<br>9.14(1H, s)<br>7.97(1H, t, J=5.6Hz)<br>7.32(1H, d, J=15.9Hz)<br>7.12(1H, d, J=2.0Hz)<br>7.08(1H, dd, 8.3, 2.0Hz)<br>7.00(2H, d, J=8.4Hz)<br>6.95(1H, d, J=8.3Hz)<br>6.68(2H, d, J=8.3Hz)<br>6.47(1H, d, J=15.8Hz)<br>3.96(2H, t, J=6.6Hz)<br>3.78(3H, s)<br>3.33(2H, m]<br>2.64(2H, t, J=7.5Hz)<br>1.70(2H, m)<br>1.40(2H, m)<br>1.37–1.22(6H, m)<br>0.84(3H, t, J=6.9Hz) | KBr<br>3280<br>2933<br>1650<br>1614<br>1598<br>1538<br>1516<br>1259<br>1237<br>1138 | FAB+<br>412<br>[M⁺H⁺]<br>(66)<br>290(22)<br>275(28)<br>176(52)<br>168<br>(100) | C₂₅H₃₃NO₄<br>Calcd.<br>C; 72.96%<br>H; 8.08%<br>N; 3.40%<br>Found<br>C; 72.96%<br>H; 8.23%<br>N; 3.37% |

TABLE 17

| Ex. | Structural formula | m.p. | 1H NMR (δ) ppm | IRcm⁻¹ | MS | Elem. anal. |
|---|---|---|---|---|---|---|
| 1-7 | | 176.6~177.2° C. | (DMSO-d6, 300MHz)<br>9.8(1H, s)<br>9.2(1H, s)<br>7.5(2H, d, J=9Hz)<br>7.4(1H, d, J=18Hz)<br>7.2(1H, s)<br>7.1(1H, d, J=6Hz)<br>7.0(1H, d, J=6Hz)<br>6.7(2H, d, J=9Hz)<br>6.6(1H, d, J=18Hz)<br>4.0(2H, t, J=7.5Hz)<br>3.8(3H, s]<br>1.7–1.8(2H, m)<br>1.3–1.5(4H, m)<br>0.9(3H, t, J=7.5Hz) | KBr<br>3280<br>2934<br>1654<br>1619<br>1511 | FAB+<br>356<br>[M⁺H⁺]<br>(20)<br>169<br>(100) | C₂₁H₂₅NO₄<br>Calcd.<br>C; 70.96%<br>H; 7.09%<br>N; 3.94%<br>Found<br>C; 70.66%<br>H; 7.23%<br>N; 4.08% |
| 1-8 | | | (CDCl₃, 300MHz)<br>7.6(1H, d, J=15Hz)<br>7.1(2H, d, J=9Hz)<br>7.0(1H, d, J=9Hz)<br>7.0(1H, s)<br>6.8(2H, d, J=9Hz)<br>6.6[1H, bs)<br>6.3(1H, d, J=15Hz)<br>6.0(1H, bs)<br>4.5(2H, d, J=3Hz)<br>4.0(2H, t, J=7.5Hz)<br>3.9(3H, s)<br>1.8–1.9(2H, m)<br>1.3–1.5(4H, m)<br>0.9(3H, t, J=7.5 Hz) | KBr<br>3221<br>1513<br>1264 | FAB+<br>370<br>[M⁺H⁺]<br>(40) | C₂₂H₂₇NO₄<br>Calcd.<br>C; 71.52%<br>H; 7.37%<br>N; 3.79%<br>Found<br>C; 71.64%<br>H; 7.48%<br>N; 3.82% |

TABLE 17-continued

| Ex. | Structural formula | m.p. | 1H NMR (δ) ppm | IRcm$^{-1}$ | MS | Elem. anal. |
|---|---|---|---|---|---|---|
| 1-9 | | | CDCl$_3$, 300MHz<br>7.51(1H, d, J=15.5Hz)<br>7.04(1H, dd, J=8.4, 2.4Hz)<br>7.00(1H, d, J=2.4Hz)<br>7.00(2H, d, J=8.3Hz)<br>6.82(1H, d, J=8.4Hz)<br>6.78(2H, d, J=8.3Hz)<br>6.51(1H, bs)<br>6.21(1H, d, J=15.5Hz)<br>5.73(1H, bs)<br>4.00(2H, t, J=6.8Hz)<br>3.86(3H, s)<br>3.38(2H, q, J=6.7Hz)<br>2.59(2H, t, J=7.4Hz)<br>1.7–1.9(2H, m)<br>1.3–1.5(4H, m)<br>0.92(3H, t, J=7.0Hz) | Neat<br>3300<br>2932<br>1652<br>1594<br>1514<br>1260 | FAB+<br>398<br>[M$^+$H$^+$]<br>(95)<br>247(50)<br>177<br>(100) | |

TABLE 18

| Ex. | Structural formula | m.p. | 1H NMR (δ) ppm | IRcm$^{-1}$ | MS | Elem. anal. |
|---|---|---|---|---|---|---|
| 1-10 | | | CDCl$_3$, 300MHz<br>7.52(1H, d, J=15.5Hz)<br>7.27(1H, bs)<br>7.16(1H, t, J=7.6Hz)<br>7.01(1H, dd, J=8.3, 1.8Hz)<br>6.97(1H, d, J=1.8Hz)<br>6.80(1H, d, J=8.3Hz)<br>6.77(1H, d, J=7.6Hz)<br>6.76(1H, s)<br>6.71(1H, t, J=7.6Hz)<br>6.19(1H, d, J=15.5Hz)<br>5.82(1H, bs)<br>3.97(2H, t, J=6.8Hz)<br>3.85(3H, s)<br>3.61(2H, q, J=6.8Hz)<br>2.79(2H, t, J=6.8Hz)<br>1.7–1.9(2H, m)<br>1.3–1.9(4H, m)<br>0.91(3H, t, J=7.1Hz) | Neat<br>3280<br>2933<br>1656<br>1586<br>1573<br>1260 | FAB+<br>[M$^+$H$^+$](40)<br>HRFAB<br>(m/z)<br>Calcd.<br>C$_{23}$H$_{30}$NO$_4$<br>384.5006<br>Found<br>384.2166 | C$_{23}$H$_{30}$NO$_4$ |
| 1-11 | | | CDCl$_3$, 300MHz<br>7.82(1H, bs)<br>7.60(1H, d, J=15.5Hz)<br>7.14(1H, t, J=7.9Hz)<br>7.06(1H, d, J=8.5Hz)<br>7.06(1H, d, J=7.9Hz)<br>7.01(1H, s)<br>6.92(1H, d, J=7.9Hz)<br>6.83(1H, d, J=8.5Hz)<br>6.81(1H, d, J=7.9Hz)<br>6.24(1H, d, J=15.5Hz)<br>6.17(1H, bs)<br>4.01(2H, t, J=6.8Hz)<br>3.88(3H, s)<br>3.52(2H, q, J=7.0Hz)<br>2.93(2H, t, J=7.0Hz)<br>1.8–1.9(2H, m)<br>1.2–1.5(4H, m)<br>0.94(3H, t, J=7.0Hz) | Neat<br>3280<br>1655<br>1594<br>1513<br>1260 | FAB+<br>384<br>[M$^+$H$^+$](100) | |

TABLE 18-continued

| Ex. | Structural formula | m.p. | 1H NMR (δ) ppm | IRcm⁻¹ | MS | Elem. anal. |
|---|---|---|---|---|---|---|
| 1-12 | | | CDCl₃, 300MHz<br>7.54(1H, d, J=15.5Hz)<br>7.07(1H, dd, J= 8.3, 1.9Hz)<br>7.02(1H, d, J=1.9Hz)<br>6.85(1H, d, J=8.3Hz)<br>6.23(1H, d, J=15.5Hz)<br>5.52(1H, bt)<br>4.02(2H, t, J=6.9Hz)<br>3.88(3H, s)<br>3.9–4.1(0.5H, m)<br>3.5–3.7(0.5H, m)<br>3.3–3.5(2H, m)<br>1.9–2.1(2H, m)<br>1.8–1.9(4H, m)<br>1.2–1.8(10H, m)<br>1.0–1.1(2H, m)<br>0.94(3H, t, J=7.1Hz) | Neat<br>3288<br>2927<br>1513<br>1260 | FAB+<br>[M⁺H⁺](40)<br>247(35)<br>HRFAB<br>(m/z)<br>Calcd.<br>C₂₃H₃₆NO₄<br>390.5486<br>Found<br>390.2638 | |

TABLE 19

| Ex. | Structural formula | m.p. | 1H NMR (δ) ppm | IRcm⁻¹ | MS | Elem. anal. |
|---|---|---|---|---|---|---|
| 1-13 | Colorless crystals | 125~ 126° C. | CDCl₃, 300MHz<br>8.53–8.55(2H, m)<br>7.56(1H, d, J=15.7Hz)<br>7.16–7.18(2H, m)<br>7.06(1H, dd, J= 8.0, 2.1Hz)<br>7.01(1H, d, J=2.1Hz)<br>6.85(1H, d, J=8.0Hz)<br>6.19(1H, d, J=15.7Hz)<br>5.01(1H, t)<br>4.06(2H, t, J=7.2Hz)<br>3.88(3H, s)<br>3.68(2H, q, J=6.9Hz)<br>2.91(2H, t, J=6.9Hz)<br>1.80–1.90(2H, m)<br>1.32–1.51(4H, m)<br>0.93(3H, t, J=6.9Hz) | Neat<br>3301<br>2949<br>1615<br>1263 | FAB+<br>369<br>[M⁺H⁺](100) | C₂₂H₂₈N₂O₃<br>Calcd.<br>C; 71.71%<br>H; 7.66%<br>N; 7.60%<br>Found<br>C; 71.63%<br>H; 7.82%<br>N; 7.59% |
| 1-14 | Colorless crystals | 91~ 93° C. | CDCl₃, 300MHz<br>8.53–8.60(1H, m)<br>7.63(1H, td, J=7.7, 1.8Hz)<br>7.53(1H, d, J=15.6Hz)<br>7.03–7.22(4H, m)<br>6.84(1H, d, J=8.3Hz)<br>6.63(1H, br s)<br>6.25(1H, d, J=15.6Hz)<br>4.03(2H, t, J=6.9Hz)<br>3.88(3H, s)<br>3.81(2H, q, J=6.2Hz)<br>3.07(2H, t, J=6.2Hz)<br>1.81–1.89(2H, m)<br>1.36–1.49(4H, m)<br>0.94(3H, t, J=7.0Hz) | Neat<br>3249<br>2951<br>1654<br>1592<br>1513<br>1258<br>1134 | FAB+<br>369<br>[M⁺H⁺](100)<br>289(23)<br>247(59)<br>177(72) | C₂₂H₂₈N₂O₃<br>Calcd.<br>C; 71.71%<br>H; 7.66%<br>N; 7.60%<br>Found<br>C; 71.76%<br>H; 7.85%<br>N; 7.56% |

TABLE 19-continued

| Ex. | Structural formula | m.p. | 1H NMR (δ) ppm | IRcm⁻¹ | MS | Elem. anal. |
|---|---|---|---|---|---|---|
| 1-15 | Pale-yellow oil | | CDCl$_3$, 300MHz<br>8.43–8.59(2H, m)<br>7.50–7.64(2H, m)<br>7.50(1H, d, J=15.3Hz)<br>7.02–7.16(5H, m)<br>7.01(1H, d, J=1.9Hz)<br>6.84(1H, d, J=8.3Hz)<br>6.61(1H, d, J=15.3Hz)<br>4.05(2H, t, J=6.8Hz)<br>3.89(3H, s)<br>3.73–3.86(4H, m)<br>2.98–3.20(4H, m)<br>1.77–1.95(2H, m)<br>1.31–1.53(4H, m)<br>0.93(3H, t, J=7.1Hz) | Neat<br>1645<br>1592<br>1434<br>1261<br>1139 | FAB+<br>474<br>[M⁺H⁺](100)<br>247(81)<br>177(99) | |

TABLE 20

| Ex. | Structural formula | m.p. | 1H NMR (δ) ppm | IRcm⁻¹ | MS | Elem. anal. |
|---|---|---|---|---|---|---|
| 1-16 | Colorless crystals | 114~<br>116° C. | CDCl$_3$, 300MHz<br>8.52–8.54(4H, m)<br>7.61(1H, d, J=15.0Hz)<br>7.05–7.20(4H, m)<br>7.05(1H, dd, J=8.8, 1.9Hz)<br>6.95(1H, d, J=1.9Hz)<br>6.87(1H, d, J=8.8Hz)<br>6.47(1H, d, J=1.5Hz)<br>4.03(2H, t, J=6.7Hz)<br>3.90(3H, s)<br>3.50–3.67(4H, m)<br>2.80–2.99(4H, m)<br>1.83–1.94(2H, m)<br>1.34–1.54(4H, m)<br>0.94(3H, t, J=7.3Hz) | Neat<br>2953<br>1642<br>1596<br>1510<br>1260 | FAB+<br>474<br>[M⁺H⁺]<br>(36)<br>369(23)<br>247(50)<br>177(73)<br>106<br>(100) | C$_{29}$H$_{25}$N$_3$O$_3$<br>Calcd.<br>C; 73.54%<br>H; 7.45%<br>N; 8.87%<br>Found<br>C; 73.65%<br>H; 7.62%<br>N; 8.88% |
| 1-17 | | | CDCl$_3$, 300MHz<br>7.44(1H, d, J=15.4Hz)<br>7.00(2H, d, J=8.3Hz)<br>6.7–7.1(4H, m)<br>6.77(2H, d, J=8.3Hz)<br>6.31(1H, d, J=15.4Hz)<br>4.02(2H, t, J=6.7Hz)<br>3.87(3H, s)<br>3.6–3.7(2H, m)<br>2.99(3H, s)<br>**2.8–2.9(2H, ]<br>1.8–1.9(2H, m)<br>1.3–1.5(4H, m)<br>0.93(3H, t, J=7.1Hz) | Neat<br>3220<br>2931<br>1643<br>1584<br>1514 | FAB+<br>398<br>[M⁺H⁺]<br>(70)<br>247<br>(100)<br>177(80) | |
| 1-18 | Colorless crystals | 91~<br>92° C. | DMSO-d6, 300MHz<br>9.14(1H, s)<br>7.98(1H, t)<br>7.32(1H, d, 15.8Hz)<br>6.94–7.15(5H, m)<br>6.67(2H, d, J=8.4Hz)<br>6.47(1H, d, J=15.8Hz)<br>3.99(2H, t, J=6.7Hz)<br>3.77(3H, s)<br>3.29–3.36(2H, m)<br>2.64(2H, t, J=7.5Hz)<br>1.70–1.85(1H, m)<br>1.61(2H, q, J=6.7Hz)<br>0.92(6H, t, J=6.6Hz) | | FAB+<br>384<br>[M⁺H⁺]<br>(70)<br>247(44)<br>176<br>(100) | |

TABLE 21

| Ex. | Structural formula | m.p. | 1H NMR (δ) ppm | IRcm$^{-1}$ | MS | Elem. anal. |
|---|---|---|---|---|---|---|
| 1-19 | Pale-yellow oil | | DMSO-d6, 300MHz<br>9.15(1H, s)<br>7.98(1H, t)<br>7.31(1H, d, J=15.8Hz)<br>6.94–7.15(5H, m)<br>6.68(2H, d, J=8.4Hz)<br>6.47(1H, d, J=15.8Hz)<br>3.86(2H, d, J=5.8Hz)<br>3.78(3H, s)<br>3.27–3.39(2H, m)<br>2.64(2H, t, J=7.2Hz)<br>1.57–1.68(1H, m)<br>1.33–1.53(4H, m)<br>0.90(6H, t, J=7.4Hz) | | FAB+<br>398<br>[M$^+$H$^+$]<br>(24)<br>261(14)<br>176<br>(100) | |
| 1-20 | Colorless crystals | 135~136° C. | DMSO-d6, 300MHz<br>9.14(1H, s)<br>7.97(1H, t, J=5.7Hz)<br>7.30(1H, d, J=15.6Hz)<br>6.94–7.09(5H, m)<br>6.67(2H, d, J=8.4Hz)<br>6.46(1H, d, J=15.6Hz)<br>3.81(2H, d, J=6.9Hz)<br>3.78(3H, s)<br>3.29–3.35(2H, m)<br>2.63(2H, t, J=7.5Hz)<br>1.14–1.29(1H, m)<br>0.53–0.60(2H, m)<br>0.28–0.32(2H, m) | | FAB+<br>368<br>[M$^+$H$^+$]<br>(37)<br>231(36)<br>176<br>(100) | |
| 1-21 | | | CDCl$_3$, 300MHz<br>7.56(1H, d, J=15.6Hz)<br>7.17(2H, d, J=8.51Hz)<br>7.07(1H, d, J=8.27Hz)<br>7.03(1H, s)<br>6.85(1H, d, J=8.27Hz)<br>6.79(2H, d, J=8.51Hz)<br>6.25(1H, d, J=15.6Hz)<br>6.17(1H, d, J=7.58Hz)<br>5.68(1H, bs)<br>5.28(1H, bs)<br>4.70–4.80(2H, m)<br>4.03(2H, t, J=6.89Hz)<br>3.89(1H, s)<br>3.15(1H, dd, J=13.8, 5.65Hz)<br>3.03(1H, dd, J=13.8, 7.96Hz)<br>1.80–1.4(2H, m)<br>1.34–1.53(4H, m)<br>0.95(3H, t, J=7.08Hz) | KBr<br>3600–3000<br>1652<br>1612 | FAB+<br>427<br>[M$^+$H$^+$]<br>(20)<br>247(50)<br>136(70) | $C_{24}H_{30}N_2O_5$<br>Calcd.<br>C; 67.59%<br>H; 7.09%<br>N; 6.57%<br>Found<br>C; 67.30%<br>H; 7.17%<br>N; 6.55% |

TABLE 22

| Ex. | Structural formula | m.p. | 1H NMR (δ) ppm | IR cm$^{-1}$ | MS | Elem. anal. |
|---|---|---|---|---|---|---|
| 1-22 | (structure: MeO, pentyloxy-phenyl-CH=CH-C(O)-NH-CH(COOMe)-CH2-C6H4-OH) | | CDCl$_3$, 300MHz<br>7.55(1H, d, J=15.6Hz)<br>7.04(1H, d, J=8.3Hz)<br>7.01(1H, s)<br>6.96(2H, d, J=8.4Hz)<br>6.83(1H, d, J=8.3Hz)<br>6.75(2H, d, J=8.4Hz)<br>6.26(1H, d, J=15.6Hz)<br>6.20(1H, bs)<br>6.13(1H, bd)<br>4.9–5.1(1H, m)<br>4.01(2H, t, J=6.8Hz)<br>3.88(3H, s)<br>3.74(3H, s)<br>3.0–3.2(2H, m)<br>1.8–1.9(2H, m)<br>1.3–1.5(4H, m)<br>0.93(3H, t, J=7.0Hz) | Neat<br>3283<br>1747<br>1658<br>1514<br>1261 | 422<br>[M$^+$H$^+$]<br>(60)<br>247<br>(100)<br>HRFAB<br>(m/z)<br>C$_{25}$H$_{32}$NO$_6$<br>422.5370<br>Found<br>442.2238 | |
| 1-23 | (structure: MeO, pentyloxy-phenyl-CH=CH-C(O)-NH- tetrahydronaphthalenediol) | 188–190° C. | DMSO-d6, 300MHz<br>8.55(2H, s)<br>7.95(1H, d, J=8.0Hz)<br>7.34(1H, d, J=16.0Hz)<br>7.14(1H, d, J=2.0Hz]<br>7.09(1H, dd, 8.2, 2.0Hz)<br>6.97(1H, d, J=8.2Hz)<br>6.54(1H, d, J=16.0Hz)<br>6.44(1H, s)<br>6.41(1H, s)<br>3.93–4.05(3H, m)<br>3.78(3H, s)<br>2.80(1H, dd, J=16.3, 5.2Hz)<br>2.65(2H, t)<br>2.46(1H, dd, J=13.6, 9.4Hz)<br>1.28–1.96(8H, m)<br>0.90(3H, t, J=6.9Hz) | Neat<br>3347<br>2941<br>1518<br>1257 | FAB+<br>426<br>[M$^+$H$^+$](34)<br>154(100) | C$_{25}$H$_{31}$NO$_5$<br>Calcd.<br>C; 70.57%<br>H; 7.34%<br>N; 3.29%<br>Found<br>C; 70.17%<br>H; 7.43%<br>N; 3.23% |
| 1-24 | (structure: MeO, pentyloxy-phenyl-CH=CH-C(O)-NH-CH2CH2-C6H3(OH)(OMe))<br>Pale-yellow column | 114–116° C. | CDCl$_3$, 300MHz<br>7.45(1H, d, J=15.7Hz)<br>7.05(1H, dd, J=8.5, 2.2Hz)<br>7.01(1H, d, J=2.2Hz)<br>6.87(1H, d, J=8.5Hz)<br>6.84(1H, d, J=8.5Hz)<br>6.70–6.73(2H, m)<br>6.18(1H, d, J=15.7Hz)<br>5.54–5.61(2H, m)<br>4.01(2H, t, J=6.7Hz)<br>3.88(3H, s)<br>3.87(3H, s)<br>3.63(2H, q, J=6.7Hz)<br>2.82(2H, t, J=6.7Hz)<br>1.80–1.90(2H, m)<br>1.33–1.5(4H, m)<br>0.93(3H, t, J=6.7Hz) | Neat<br>3244<br>2930<br>1516<br>1258 | FAB+<br>414<br>[M$^+$H$^+$](69)<br>263(58)<br>247(80)<br>177(100) | C$_{24}$H$_{31}$NO$_5$<br>Calcd.<br>C; 69.71%<br>H; 7.56%<br>N; 3.39%<br>Found<br>C; 69.73%<br>H; 7.71%<br>N; 3.36% |

TABLE 23

| Ex. | Structural formula | m.p. | 1H NMR (δ) ppm | IRcm⁻¹ | MS | Elem. anal. |
|---|---|---|---|---|---|---|
| 1-25 | | (dec.) 92.5~ 95.3° C. | DMSO-d6, 300MHz 9.54(1H, s) 9.36(1H, s) 8.30(H, bt) 7.23(1H, d, J=15.8Hz) 7.00(2H, d, J=8.4Hz) 6.67(2H, d, J=8.4Hz) 6.50(1H, d, J=15.8Hz) 6.50(2H, s) 6.31(1H, s) 3.8–4.0(2H, m) 3.2–3.3(4H, m) 2.5–2.7(2H, m) 1.2–1.4(4H, m) 0.88(3H, t, J=7.0Hz) | KBr 3377 2954 1655 1586 | FAB+ 370 [M⁺H⁺] (40) 163(40) | |
| 1-26 | | | DMSO-d6, 300MHz 9.5(1H, s) 9.2(1H, bs) 7.3(1H, d, J=15Hz) 7.0(1H, d, J=9Hz) 6.6(1H, d, J=9Hz) 6.2–6.9(3H, s) 6.0(1H, d, J=15Hz) 3.9(3H, t, J=7.5Hz) 3.8–3.9(1H, m) 3.6–3.7(1H, m) 3.4–3.5(1H, m) 3.2–3.4(1H, m) 2.8–3.6(3H, m) 2.6–2.8(2H, m) 1.6–1.8(2H, m) 1.2–1.5(4H, m) 0.89(3H, t, J=7.5Hz) | Neat 3330 2933 2360 2341 1590 | FAB+ 384 [M⁺H⁺](30) | $C_{23}H_{29}NO_4$ Calcd. C; 72.04% H; 7.62% N; 3.65% Found C; 71.64% H; 7.74% N; 3.54% |
| 1-27 | | | CDCl₃, 300MHz 7.89(1H, d, J=16Hz) 6.97–7.10(4H, m) 6.89(1H, dd, J=8.1, 1.8Hz) 6.80(2H, dd, J=6.6, 1.8Hz) 6.39(1H, d, J=16Hz) 5.09–5.15(1H, m) 5.53(1H, s) 3.94(2H, t, J=6.8Hz) 3.85(3H, s) 3.61(2H, q, J=6.6Hz) 2.81(2H, t, J=6.9Hz) 1.70–1.85(2H, m) 1.30–1.50(4H, m) 0.91(3H, t, J=6.9Hz) | | FAB+ 384 [M+H+] (100) 177(90) | |

TABLE 24

| Ex. | Structural formula | m.p. | 1H NMR (δ) ppm | IRcm⁻¹ | MS | Elem. anal. |
|---|---|---|---|---|---|---|
| 1-28 | | | CDCl₃, 300MHz<br>9.12(1H, s)<br>8.99(1H, s)<br>8.00(1H, t, J=4.1Hz)<br>7.25(1H, d, J=1.8Hz)<br>7.01(2H, d, J=6.2Hz)<br>6.97(1H, s)<br>6.91(1H, d, J=6.2Hz)<br>6.91(1H, d, J=6.2Hz)<br>6.68(2H, d, J=6.2Hz)<br>6.37(1H, d, J=11.8Hz)<br>3.97(2H, t, J=4.9Hz)<br>3.3–3.4(2H, m)<br>2.66(1H, d, J=5.5Hz)<br>1.6–1.8(2H, m)<br>1.3–1.5(4H, m)<br>0.90(3H, t, J=5.3Hz) | KBr<br>3340<br>2932<br>1646<br>1583 | FAB+<br>370<br>[M⁺H⁺]<br>(40)<br>233(35) | C₂₂H₂₇NO₄<br>Calcd.<br>C; 71.52%<br>H; 7.37%<br>N; 3.79%<br>Found<br>C; 71.06%<br>H; 7.50%<br>N; 3.74% |
| 1-29 | | | CDCl₃, 300MHz<br>7.57(1H, d, J=15.3Hz)<br>7.34(1H, s)<br>7.32(1H, dd, J=8.2Hz)<br>7.06(2H, d, J=8.2Hz)<br>6.82(3H, d, J=8.2Hz)<br>6.19(1H, bs)<br>6.18(1H, d, J=15.3Hz)<br>3.83(2H, t, J=6.9Hz)<br>3.61(2H, q, J=6.6Hz)<br>2.80(2H, t, J=7.0Hz)<br>1.72–1.82(2H, m)<br>1.32(6H, s)<br>1.11–1.25(6H, m)<br>0.84–0.99(2H, m)<br>0.83(3H, t, J=6.7Hz) | KBr<br>3389<br>3162<br>1654<br>1611 | FAB+<br>424<br>[M⁺H⁺]<br>(100)<br>287(57)<br>161(53) | C₂₇H₃₇NO₃<br>Calcd.<br>C; 76.56%<br>H; 8.80%<br>N; 3.31%<br>Found<br>C; 76.80%<br>H; 9.18%<br>N; 3.48% |
| 1-30 | | | CDCl₃, 300MHz<br>8.50(1H, d, J=8.35Hz)<br>7.59(1H, d, J=15.6Hz)<br>7.36(1H, bs)<br>7.32(1H, d, J=5.85Hz)<br>7.16(1H, d, J=5.85Hz)<br>6.83(1H, d, J=5.85Hz)<br>6.23(1H, d, J=15.6Hz)<br>5.89(1H, bs)<br>3.84(3H, s)<br>3.68(2H, q, J=6.56Hz)<br>2.91(2H, t, J=7.02Hz)<br>1.72–1.83(2H, m)<br>1.33(6H, s)<br>1.08–1.28(6H, m]<br>0.85–1.02(2H, m)<br>0.84(3H, t, J=6.72Hz) | Neat<br>3270<br>1655<br>1618<br>1600 | FAB+<br>409<br>[M⁺H⁺]<br>(30)<br>106<br>(100) | |

TABLE 25

| Ex. | Structural formula | m.p. | 1H NMR (δ) ppm | IRcm⁻¹ | MS | Elem. anal. |
|---|---|---|---|---|---|---|
| 1-31 | (structure: MeO-phenyl with C(CH₃)₂-hexyl substituent, cinnamamide linked to ethyl-3,4-dihydroxyphenyl) | | CDCl₃, 300MHz<br>7.50–7.88(1H, bs)<br>7.55(1H, d, J=15.5Hz)<br>7.25–7.34(2H, m)<br>6.55–6.60(1H, m)<br>6.21(1H, d, J=15.5Hz)<br>5.90(1H, bs)<br>3.81(3H, s)<br>3.72(2H, t, J=6.9Hz)<br>3.50–3.62(2H, m)<br>1.72–1.80(2H, m)<br>1.31(6H, s)<br>1.08–1.25(6H, m)<br>0.83–0.99(2H, m)<br>0.82(3H, t, J=6.7Hz) | KBr<br>3650–<br>3000<br>1651<br>1598 | FAB+<br>440<br>[M⁺H⁺](90)<br>287(100)<br>161(77) | |
| 1-32 | (structure: MeO-phenyl with hexyl substituent, cinnamamide linked to ethyl-4-hydroxyphenyl) | | CDCl₃, 300MHz<br>7.55(1H, d, J=16Hz)<br>7.28(1H, d, J=9.6Hz)<br>7.27(1H, s)<br>7.07(2H, d, J=8.4Hz)<br>6.81(2H, d, J=8.4Hz)<br>6.80(1H, d, J=9.6Hz)<br>6.18(1H, d, J=16Hz)<br>5.50–5.60(2H, m, involving a singlet at 5.55)<br>3.83(3H, s)<br>3.61(2H, q, J=6.6Hz)<br>2.81(2H, t, J=6.8Hz)<br>2.58(2H, t, J=7.7Hz)<br>1.48–1.64(2H, m)<br>1.20–1.40(6H, m)<br>0.88(3H, t, J=6.9Hz) | | FAB+<br>382<br>[M⁺H⁺](80)<br>260(20)<br>245(50) | |
| 1-33 | (structure: MeO-phenyl with hexyl substituent, cinnamamide linked to ethyl-4-pyridyl) | | CDCl₃, 300MHz<br>8.54(2H, d, J=6.0Hz)<br>7.57(1H, d, J=15Hz)<br>7.29(1H, d, J=8.7Hz)<br>7.28(1H, s)<br>7.16(2H, d, J=6.0Hz)<br>6.81(1H, d, J=8.7Hz)<br>6.19(1H, d, J=15Hz)<br>5.53–5.61(1H, m)<br>3.84(3H, s)<br>3.67(2H, q, J=6.5Hz)<br>2.91(2H, t, J=6.9Hz)<br>2.58(2H, t, J=7.7Hz)<br>1.47–1.70(3H, m)<br>1.23–1.40(6H, m)<br>0.89(3H, t, J=6.9Hz) | | FAB+<br>367<br>[M⁺H⁺](90)<br>245(20) | |

TABLE 26

| Ex. | Structural formula | m.p. | 1H NMR (δ) ppm | IR cm⁻¹ | MS | Elem. anal. |
|---|---|---|---|---|---|---|
| 1-34 | (structure: MeO-phenyl with S-pentyl substituent, cinnamamide linked to ethyl-4-hydroxyphenyl) | 107.3~<br>108.5° C. | CDCl₃, 300MHz<br>7.55(1H, d, J=15.4Hz)<br>7.36(1H, d, J=1.8Hz)<br>7.29(1H, dd, J=1.8, 8.4Hz)<br>7.08(1H, d, J=8.4Hz)<br>6.78–6.84(3H, m)<br>6.19(1H, d, J=15.4Hz)<br>3.91(3H, s)<br>3.62(2H, q, J=6.5Hz)<br>2.89(2H, t, J=7.2Hz)<br>2.81(2H, t, J=6.8Hz)<br>1.58–1.73(2H, m)<br>1.25–1.50(4H, m)<br>0.90(3H, t, J=7.1Hz) | | FAB+<br>400<br>[M+H+]<br>(100) | $C_{23}H_{29}NO_3S$ |

TABLE 26-continued

| Ex. | Structural formula | m.p. | 1H NMR (δ) ppm | IR cm$^{-1}$ | MS | Elem. anal. |
|---|---|---|---|---|---|---|
| 1-35 | (structure: MeO, HN-pentyl substituted cinnamamide-N-ethyl-phenyl-NH₂) | 143.1~ 144.9° C. | CDCl₃, 300MHz<br>7.52(1H, d, J=15Hz)<br>7.02(2H, d, J=8.1Hz)<br>6.79(1H, d, J=8.1Hz)<br>6.71(1H, d, J=8.1Hz)<br>6.70(1H, s)<br>6.66(2H, d, J=8.1Hz)<br>6.16(1H, d, J=1.5Hz)<br>5.50(1H, bt)<br>4.18(1H, bs)<br>3.86(3H, s)<br>3.61(2H, bs)<br>3.60(2H, q, J=6.5Hz)<br>3.12(2H, bs)<br>2.77(2H, t, J=6.6Hz)<br>1.6–1.75(2H, m)<br>1.3–1.5(4H, m)<br>0.93(3H, t, J=6.9Hz) | | FAB+<br>382<br>[M⁺H⁺]<br>(50)<br>246<br>(20) | |
| 1-36 | (structure: pentyloxy-phenyl cinnamamide-N-ethyl-phenyl-O-pentyl) | | DMSO-d6, 300MHz<br>8.0(1H, bt)<br>7.5(2H, d, J=9Hz)<br>7.3(1H, d, J=15Hz)<br>7.1(2H, d, J=9Hz)<br>6.9(2H, d, J=9Hz)<br>6.8(2H, d, J=9Hz)<br>6.4(1H, d, J=15Hz)<br>4.0(2H, t, J=4Hz)<br>3.9(2H, t, J=4Hz)<br>3.3(2H, t, J=4Hz)<br>2.7(2H, t, J=4Hz)<br>1.6–1.8(4H, m)<br>1.3–1.4(8H, m)<br>0.8–0.9(6H, m) | Neat<br>3298<br>2932<br>1651<br>1606<br>1543<br>1513<br>1256 | FAB+<br>424<br>[M+H+]<br>(100) | |

TABLE 27

| Ex. | Structural formula | m.p. | 1H NMR (δ) ppm | IR cm$^{-1}$ | MS | Elem. anal. |
|---|---|---|---|---|---|---|
| 1-37 | (structure: MeO, O-pentyl-phenyl cinnamamide-N-ethyl-phenyl-O-pentyl) | | DMSO-d6, 300MHz<br>8.0(1H, bt)<br>7.3(1H, d, J=15Hz)<br>7.1(1H, s)<br>7.1(2H, d, J=9Hz)<br>7.1(1H, d, J=9Hz)<br>6.9(1H, d, J=9Hz)<br>6.8(2H, d, J=9Hz)<br>6.5(1H, d, J=15Hz)<br>3.8–4.0(4H, m)<br>3.8(3H, s)<br>3.2–3.3(2H, m)<br>2.7(2H, t, J=4Hz)<br>1.6–1.8(4H, m)<br>1.3–1.5(8H, m)<br>0.8–1.0(6H, m) | Neat<br>3303<br>2955<br>2870<br>1652<br>1619<br>1515<br>1258 | FAB+<br>454<br>[M+H+]<br>(100) | |
| 1-38 | (structure: pentyloxy-phenyl cinnamamide-N-ethyl-phenyl-OH) | | DMSO-d6, 300MHz<br>9.2(1H, s)<br>8.0(1H, bt)<br>7.5(2H, d, J=9Hz)<br>7.3(1H, d, J=15Hz)<br>7.0(2H, d, J=9Hz)<br>6.9(2H, d, J=9Hz)<br>6.7(2H, d, J=9Hz)<br>6.4(1H, d, J=15Hz)<br>4.0(2H, t, J=4Hz)<br>3.3(2H, t, J=4Hz)<br>2.6(2H, t, J=4Hz)<br>1.6–1.8(2H, m)<br>1.3–1.4(4H, m)<br>0.9(3H, t, J=4Hz) | Neat<br>3300<br>2933<br>2359<br>1652<br>1602<br>1513<br>1227 | FAB+<br>354<br>[M+H+]<br>(100) | C₂₂H₂₇NO₃<br>Calcd.<br>C; 74.46%<br>H; 7.70%<br>N; 3.96%<br>Found<br>C; 74.68%<br>H; 7.88%<br>N; 3.98% |

TABLE 27-continued

| Ex. | Structural formula | m.p. | 1H NMR (δ) ppm | IRcm$^{-1}$ | MS | Elem. anal. |
|---|---|---|---|---|---|---|
| 1-39 | (structure) | | DMSO-d6, 300MHz<br>8.0(1H, bt)<br>7.3(1H, d, J=15Hz)<br>7.1(2H, d, J=9Hz)<br>7.0–7.1(2H, m)<br>7.0(1H, d, J=6Hz)<br>6.8(2H, d, J=9Hz)<br>6.5(1H, d, J=15Hz)<br>3.8–4.0(4H, m)<br>3.8(3H, s)<br>3.3–3.5(2H, m)<br>2.7(2H, t, J=4Hz)<br>1.6–1.8(4H, m)<br>1.3–1.5(8H, m)<br>0.8–0.9(6H, m) | NaCl<br>3305<br>2933<br>1652<br>1619<br>1514<br>1257 | FAB+<br>454<br>[M+H+]<br>(50) | $C_{28}H_{39}NO_4$<br>Calcd.<br>C; 74.14%<br>H; 8.67%<br>N; 3.09%<br>Found<br>C; 74.29%<br>H; 8.84%<br>N; 3.16% |

TABLE 28

| Ex. | Structural formula | m.p. | 1H NMR (δ) ppm | IR cm$^{-1}$ | MS | Elem. anal. |
|---|---|---|---|---|---|---|
| 1-40 | (structure) | | DMSO-d6, 300MHz<br>9.1(1H, s)<br>7.9(1H, bs)<br>7.3(1H, d, J=15Hz)<br>7.1(1H, s)<br>7.1(1H, d, J=6Hz)<br>7.0(2H, d, J=4Hz)<br>7.0(1H, d, J=6Hz)<br>6.7(2H, d, J=4Hz)<br>6.5(1H, d, J=15Hz)<br>4.0(2H, t, J=6Hz)<br>3.8(3H, s)<br>3.3(2H, m)<br>2.7(2H, t, J=4Hz)<br>1.8–1.9(2H, m)<br>1.3–1.5(4H, m)<br>0.9(3H, t, J=9Hz) | Neat<br>3462<br>3312<br>2938<br>1648<br>1600<br>1540<br>1512<br>1263<br>1138 | FAB+<br>384<br>[M+H+]<br>(30) | $C_{23}H_{29}NO_4$<br>Calcd.<br>C; 72.04%<br>H; 7.62%<br>N; 3.65%<br>Found<br>C; 72.16%<br>H; 7.80%<br>N; 3.65% |
| 1-41 | (structure) | 73.8~<br>74.1° C. | CDCl$_3$, 300MHz<br>6.92(2H, d, J=8.5Hz)<br>6.77(1H, d, J=8.1Hz)<br>6.76(2H, d, J=8.5Hz)<br>6.71(1H, d, J=1.9Hz)<br>6.68(2H, dd, J=8.0, 1.9Hz)<br>6.50(1H, s)<br>5.43(1H, bs)<br>3.95(2H, t, J=6.9Hz)<br>3.82(3H, s)<br>3.43(2H, q, J=6.9Hz)<br>2.86(2H, t, J=7.5Hz)<br>2.65(2H, t, J=6.9Hz)<br>2.40(2H, t, J=7.5Hz)<br>1.7–1.8(2H, m)<br>1.3–1.5(4H, m)<br>0.91(3H, t, J=7.1Hz) | Neat<br>3354<br>2933<br>1644<br>1515 | FAB+<br>386<br>[M+H+]<br>(95)<br>137<br>(100) | $C_{23}H_{31}NO_4$<br>Calcd.<br>C; 71.66%<br>H; 8.11%<br>N; 3.63%<br>Found<br>C; 71.64%<br>H; 8.28%<br>N; 3.63% |

TABLE 28-continued

| Ex. | Structural formula | m.p. | 1H NMR (δ) ppm | IR cm$^{-1}$ | MS | Elem. anal. |
|---|---|---|---|---|---|---|
| 1-42 | (structure: MeO, pentyloxy-substituted phenyl cinnamide with 4-methoxyphenethylamine) | 116.2~117.2° C. | CDCl3, 300MHz<br>7.8(1H, d, J=15Hz)<br>7.2(2H, d, J=9Hz)<br>7.1(1H, dd, J=9, 1Hz)<br>7.0(1H, d, J=1Hz)<br>6.9(2H, d, J=9Hz)<br>6.8(1H, d, J=9Hz)<br>6.2(1H, d, J=15Hz)<br>5.6(1H, bs)<br>4.0(2H, t, J=4Hz)<br>3.9(3H, s)<br>3.6(2H, q, J=7Hz)<br>2.8(2H, t, J=7Hz)<br>1.8–2.0(2H, m)<br>1.2–1.5(4H, m)<br>0.93(3H, t, J=7Hz) | KBr<br>3293<br>2934<br>1650<br>1614<br>1511 | FAB+<br>398<br>[M+H]<br>(70)<br>262(60)<br>177<br>(100) | $C_{24}H_{31}NO_4$<br>Calcd.<br>C; 72.52%<br>H; 7.86%<br>N; 3.52%<br>Found<br>C; 72.07%<br>H; 7.99%<br>N; 3.56% |

TABLE 29

| Ex. | Structural formula | m.p. | 1H NMR (δ) ppm | IRcm$^{-1}$ | MS | Elem. anal. |
|---|---|---|---|---|---|---|
| 1-43 | (structure: MeO, pentyloxy-substituted phenyl cinnamide with 4-hydroxyphenethylamine) | | CDCl3, 300MHz<br>7.8(1H, d, J=15Hz)<br>7.4(1H, d, J=6Hz)<br>7.4(1H, d, J=6Hz)<br>7.1(1H, d, J=8Hz)<br>6.8(1H, d, J=8Hz)<br>6.5(1H, d, J=6Hz)<br>6.4(1H, s)<br>6.4(1H, d, J=15Hz)<br>5.5(1H, bt)<br>5.2(1H, bs)<br>4.0(2H, t, 6Hz)<br>3.8(3H, s)<br>3.6(2H, q, 6Hz)<br>2.8(2H, t, 6Hz)<br>1.8–1.9(2H, m)<br>1.2–1.5(4H, m)<br>0.9(3H, t, 8Hz) | Neat<br>3278<br>2933<br>1649<br>1602<br>1602<br>1514 | FAB+<br>384<br>[M+H]<br>(60)<br>177<br>(100) | $C_{23}H_{29}NO_4$<br>Calcd.<br>C; 72.04%<br>H; 7.62%<br>N; 3.65%<br>Found<br>C; 72.25%<br>H; 7.81%<br>N; 3.60% |
| 1-44 | (structure: MeO, pentyloxy-substituted phenyl cinnamide with 4-pentyloxyphenethylamine) | | | | | |
| 1-45 | (structure: pentyloxy, hydroxy-substituted phenyl propanamide with 4-hydroxyphenethylamine) | | | | | |

TABLE 30

| Ex. | Structural formula | m.p. | 1H NMR (δ) ppm | IR cm$^{-1}$ | MS | Elem. anal. |
|---|---|---|---|---|---|---|
| 1-46 | (structure: MeO, O-pentyl phenyl, CH=CH-C(O)-NH-CH2CH2-morpholine) | 170.1~171.2° C. | CDCl3,300MHz<br>8.3(1H, bt)<br>7.5(1H, d, J=18Hz)<br>7.0(2H, d, J=9Hz)<br>7.0(1H, s)<br>6.8(1H, d, J=9Hz)<br>6.4(1H, d, J=18 Hz)<br>4.0–4.2(4H, m)<br>4.0(2H, t, J=7.5Hz)<br>3.9–4.0(2H, m)<br>3.9(3H, s)<br>3.5–3.8(2H, m)<br>3.3–3.4(2H, m)<br>3.0–3.2(2H, m)<br>1.8–1.9(2H, m)<br>1.3–1.5(4H, m)<br>0.9(3H, t, J=7.5Hz) | KBr<br>3276<br>2956<br>1666<br>1627<br>1514 | FAB+<br>377<br>[M+H+]<br>(100) | C$_{21}$H$_{32}$N$_2$O$_4$<br>Calcd.<br>C; 66.99%<br>H; 8.57%<br>N; 7.44%<br>Found<br>C; 66.94%<br>H; 8.80%<br>N; 7.43% |
| 1-47 | (structure: MeO, O-pentyl phenyl, CH=CH-C(O)-NH-CH2-C6H4-OMe) | | | | | |
| 1-48 | (structure: MeO, O-pentyl phenyl, CH=CH-C(O)-NH-CH2CH2-C6H3(OH)2)<br>Colorless crystals | 150~153° C. | DMSO-d6,300MHz<br>8.73(1H, s)<br>8.62(1H, s)<br>7.97(1H, t, J=5.9Hz)<br>7.33(1H, d, J=16.5Hz)<br>7.13(1H, d, J=2.0Hz)<br>7.09(1H, dd, J=9.0, 2.0Hz)<br>6.97(1H, d, J=9.0Hz)<br>6.63(1H, d, J=9.0Hz)<br>6.60(1H, d, J=2.0Hz)<br>6.48(1H, d, J=9.0Hz)<br>6.46(1H, dd, J=9.0, 2.0Hz)<br>3.97(2H, t, J=7.5Hz)<br>3.78(1H, s)<br>3.26–3.36(2H, m)<br>2.58(2H, t, J=7.5Hz)<br>1.67–1.78(1H, m)<br>0.90(3H, t, J=6.0Hz) | 3340<br>1515<br>1259<br>1140 | FAB+<br>400<br>[M+H+]<br>(92)<br>307(14)<br>247(71)<br>177(80)<br>154(100) | |

TABLE 31

| Ex. | Structural formula | m.p. | 1H NMR (δ) ppm | IR cm⁻¹ | MS | Elem. anal. |
|---|---|---|---|---|---|---|
| 1-49 | Pale-yellow amorphous | | CDCl3,300MHz<br>8.79(2H, d, J=6.9Hz)<br>8.16(1H, brt)<br>7.88(2H, d, J=6.9Hz)<br>7.32(1H, d, J=15.8Hz)<br>7.07–7.12(2H, m)<br>6.97(1H, d, J=8.3Hz)<br>6.44(1H, d, J=15.8Hz)<br>3.96(2H, t, J=6.6Hz)<br>3.788(3H, s)<br>3.56(2H, q, J=6.5Hz)<br>3.06(2H, t, J=6.5Hz)<br>1.66–1.779(2H, m)<br>1.27–1.45(4H, m)<br>0.90(3H, t, J=7.3Hz) | 3250<br>2933<br>2528<br>1261<br>1136<br>1023 | | |
| 1-50 | Colorless crystals | 108~<br>110° C. | CDCl3,300MHz<br>8.28(1H, d, J=6.3Hz)<br>7.72–7.79(1H, m)<br>7.50(1H, d, J=15.4Hz)<br>7.19–7.38(3H, m)<br>7.02–7.09(2H, m)<br>6.84(1H, d, J=8.1Hz)<br>6.26(1H, d, J=15.4Hz)<br>4.03(2H, t, J=6.8Hz)<br>3.88(3H, s)<br>3.72–3.82(1H, m)<br>3.28(2H, t, J=6.3Hz)<br>1.80–1.92(2H, m)<br>1.33–1.52(4H, m)<br>0.94(3H, t, J=7.0Hz) | 1512<br>1262 | 384[M+H+]<br>(100)<br>247(89)<br>177(75) | |
| 1-51 | Colorless crystals | 130~<br>132° C. | CDCl3,300MHz<br>8.47–8.54(2H, m)<br>7.51–7.62(2H, m)<br>7.24–7.28(1H, m)<br>6.59–7.09(1H, m)<br>6.85(1H, d, J=8.5Hz)<br>6.19(1H, d, J=18.2Hz)<br>5.51–5.70(1H, m)<br>4.02(2H, t, J=7.3Hz)<br>3.89*1H, s)<br>3.66(2H, q, J=6.9Hz)<br>2.91(2H, t, J=6.9Hz)<br>1.80–1.92(2H, m)<br>1.33–1.52(4H, m)<br>0.93(3H, t, J=6.9Hz) | 3245<br>1596<br>1263<br>1140 | FAB+<br>369[M+H+]<br>(100)<br>311(21)<br>247(14)<br>177(29) | |

TABLE 32

| Ex. | Structural formula | m.p. | 1H NMR (δ) ppm | IR cm⁻¹ | MS | Elem. anal. |
|---|---|---|---|---|---|---|
| 1-52 | | | | | | |

TABLE 32-continued

| Ex. | Structural formula | m.p. | 1H NMR (δ) ppm | IR cm⁻¹ MS | Elem. anal. |
|---|---|---|---|---|---|
| 1-53 | (MeO, pentyloxy-phenyl)-CH=CH-C(=O)-NH-CH₂CH₂-(3-pyridyl) ·HCl | | | | |
| 1-54 | (MeO, pentylamino-phenyl)-CH=CH-C(=O)-NH-CH₂CH₂-(4-hydroxyphenyl)<br>Yellow crystals | 162.7~163.5° C. | CDCl₃, 300MHz<br>7.53(1H, d, J=15Hz)<br>7.31(2H, d, J=8.7Hz)<br>6.75–6.85(3H, m)<br>6.71(1H, d, J=8.1Hz)<br>6.70(1H, s)<br>6.17(1H, d, J=15Hz)<br>5.58(1H, bs)<br>5.58(1H, bt)<br>4.2(1H, bs)<br>3.86(3H, s)<br>3.61(2H, q, J=6.4Hz)<br>3.12(2H, t, J=7.2Hz)<br>2.81(2H, t, J=6.8Hz)<br>1.6–1.75(2H, m)<br>1.3–1.5(4H, m)<br>0.93(3H, t, J=7.1Hz) | FAB+<br>383<br>[M⁺H⁺](50)<br>246(60) | |

TABLE 33

| Ex. | Structural formula | m.p. | 1H NMR (δ) ppm | IR cm⁻¹ MS | Elem. anal. |
|---|---|---|---|---|---|
| 1-55 | (MeO, dipentylamino-phenyl)-CH=CH-C(=O)-NH-CH₂CH₂-(4-hydroxyphenyl) | | CDCl₃, 300MHz<br>7.54(1H, d, J=16Hz)<br>7.03–7.12(4H, m)<br>6.81(1H, d, J=8.4Hz)<br>6.80(2H, d, J=8.1Hz)<br>6.17(1H, d, J=16Hz)<br>5.56(1H, bt)<br>3.86(3H, s)<br>3.61(2H, q, J=6.3Hz)<br>3.06(4H, t, J=7.7Hz)<br>2.81(2H, t, J=6.8Hz)<br>1.38–1.5(4H, m)<br>1.07–1.35(8H, m)<br>0.86(6H, t, J=7.1Hz) | FAB+<br>453<br>[M⁺H⁺](100)<br>395(80) | |
| 1-56 | (tri-pentyloxy-phenyl)-CH=CH-C(=O)-NH-CH₂CH₂-(4-hydroxyphenyl)<br>Colorless crystals | 144.9~145.5° C. | CDCl₃, 300MHz<br>7.50(1H, d, J=15Hz)<br>7.08(2H, d, J=8.4Hz)<br>6.80(2H, d, J=8.4Hz)<br>6.67(2H, s)<br>6.19(1H, d, J=15Hz)<br>5.58(1H, bt)<br>5.49(1H, s)<br>3.97(6H, t, J=6.5Hz)<br>3.62(2H, q, J=6.5Hz)<br>2.81(2H, t, J=6.8Hz)<br>1.7–1.85(6H, m)<br>1.3–1.5(12H, m)<br>0.86–0.97(9H, m) | FAB+<br>526<br>[M⁺H⁺](30)<br>389(40) | |

TABLE 33-continued

| Ex. | Structural formula | m.p. | 1H NMR (δ) ppm | IR cm$^{-1}$ | MS | Elem. anal. |
|---|---|---|---|---|---|---|
| 1-57 | 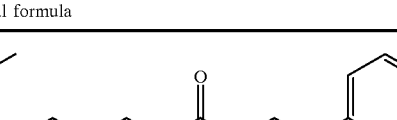<br>Colorless crystals | 119.9~<br>121.3° C. | CDCl$_3$,300MHz<br>7.54(1H, d, J=16Hz)<br>7.07(2H, d, J=8.4Hz)<br>6.80(2H, d, J=8.4Hz)<br>6.77(1H, dd, J=8.7, 2.1Hz)<br>6.70(1H, s)<br>6.69(1H, d, J=8.7Hz)<br>6.17(1H, dd, J=16Hz)<br>5.8(1H, bs)<br>5.58(1H, bt)<br>4.00(2H, t, J=6.6Hz)<br>3.61(2H, q, J=6.6Hz)<br>3.12(2H, t, J=7.1Hz)<br>2.80(2H, t, J=6.8Hz)<br>1.75–1.85(2H, m)<br>1.6–1.7(2H, m)<br>1.3–1.5(8H, m)<br>0.9–0.97(6H, m) | | FAB+<br>439<br>[M$^+$H$^+$](50)<br>302(100) | |

TABLE 34

| Ex. | Structural formula | m.p. | 1H NMR (δ) ppm | IR cm$^{-1}$ | MS | Elem. anal. |
|---|---|---|---|---|---|---|
| 1-58 | Colorless crystals | 104.8–<br>106.4° C. | CDCl$_3$,300MHz<br>7.55(1H, d, J=16Hz)<br>7.02–7.12(4H, m)<br>6.77–6.85(3H, m)<br>6.17(1H, d, J=16Hz),<br>5.58(1H, bt)<br>3.88(3H, s)<br>3.61(2H, q, J=6.5Hz)<br>3.02(2H, t, J=8.0Hz)<br>2.881(2H, t, J=6.9Hz)<br>2.78(3H, s)<br>1.5–1.65(2H, m)<br>1.22–1.48(4H, m)<br>0.88(3H, t, J=6.9Hz) | | FAB+<br>397<br>[M$^+$H$^+$]<br>(100)<br>39(80) | |
| 1-59 | Colorless crystals | | CDCl3,300MHz<br>7.67(1H, d, J=15.4Hz)<br>7.62(1H, d, J=2.2Hz)<br>7.30(1H, d, J=1.5Hz)<br>7.06–7.09(2H, m)<br>6.92(1H, d, J=1.5Hz)<br>6.81–6.844(2H, m)<br>6.73(1H, d, J=2.2Hz)<br>6.27(1H, d, J=15.4Hz)<br>5.95(1H, s)<br>5.67(1H, brt)<br>4.17(2H, t, J=6.6Hz)<br>3.63(2H, q, J=6.6Hz)<br>2.81(2H, t, J=6.6Hz)<br>1.84–1.93(2H, m)<br>1.35–1.54(4H, m)<br>0.94(3H, t, J=7.2Hz) | 2953<br>1656<br>1606<br>1516<br>1339<br>1150 | FAB+<br>394<br>[M+H+]<br>(73)<br>187(100) | C$_{24}$H$_{27}$NO$_4$<br>Calcd.<br>C; 73.2%<br>H; 6.92%<br>N; 3.56%<br>Found<br>C; 73.25%<br>6.96%<br>N; 3.56% |

TABLE 34-continued

| Ex. | Structural formula | m.p. | 1H NMR (δ) ppm | IR cm⁻¹ MS | Elem. anal. |
|---|---|---|---|---|---|
| 1-60 | (structure: MeO, OBn-substituted cinnamamide-N-ethyl-4-hydroxyphenyl) Colorless crystals | 161~162° C. | CDCl3,300MHz<br>7.26–7.52(6H, m)<br>7.03–7.08(4H, m)<br>6.79–6.88(3H, m)<br>6.10(1H, d, J=15.4)<br>5.49–5.60(2H, m)<br>5.14(2H, s)<br>3.90(3H, s)<br>3.60(2H, q, J=6.6Hz)<br>2.80(2H, t, J=6.8Hz) | FAB+<br>404<br>[M+H+]<br>(32)<br>154(100) | |

TABLE 35

| Ex. | Structural formula | m.p. | 1H NMR (δ) ppm | IR cm⁻¹ MS | Elem. anal. |
|---|---|---|---|---|---|
| 1-61 | (structure: MeO, O-pentenyl-substituted cinnamamide-N-ethyl-4-hydroxyphenyl) | | | | |
| 1-62 | (structure: MeO, O-pentynyl-substituted cinnamamide-N-ethyl-4-hydroxyphenyl) | | | | |
| 1-63 | (structure: allyloxy, pentyloxy-substituted cinnamamide-N-ethyl-4-hydroxyphenyl) Colorless crystals | 132~133° C. | CDCl3,300MHz<br>7.53(1H, d, J=15.5Hz)<br>6.99–7.06(4H, m)<br>6.79+144 6.84(3H, m)<br>6.31(1H, s)<br>6.18(1H, d, J=15.5Hz)<br>5.99–6.11(1H, m)<br>5.68(1H, brt)<br>5.25–5.44(2H, m)<br>4.59(2H, m)<br>3.99(2H, t, J=6.7Hz)<br>3.60(2H, q, J=6.7Hz)<br>2.79(2H, t, J=6.7Hz)<br>1.80–1.87(2H, m)<br>1.39–1.49(4H, m)<br>0.92(3H, t, J=7.1Hz) | FAB+<br>410[M+H+]<br>(100)<br>288(25)<br>273(55) | |

TABLE 36

| Ex. | Structural formula | m.p. | 1H NMR (δ) ppm | IR cm⁻¹ | MS | Elem. anal. |
|---|---|---|---|---|---|---|
| 1-64 | Colorless crystals | 119~120° C. | CDCl3,300MHz<br>7.52–(1H, d, J=15.4Hz)<br>7.02–7.09(4H, m)<br>6.79–6.86(3H, m)<br>6.15(1H, d, J=15.4Hz)<br>6.01–6.12(1H, m)<br>5.55(1H, brt)<br>5.34(1H, s)<br>5.26–5.45(2H, m)<br>4.58–4.61(2H, m)<br>4.02(2H, t, J=6.9Hz)<br>3.61(2H, q, J=6.7Hz)<br>2.81(1H, t, J=6.7Hz)<br>1.79–1.86(2H, m)<br>1.38–1.48(4H, m)<br>0.93(3H, t, J=7.0Hz) | | FAB+<br>410<br>[M+H+]<br>(77)<br>273(36)<br>154<br>(100) | |
| 1-65 | Colorless crystals | 109.5~110.4° C. | CDCl3,300MHz<br>7.53(1H, d, J=15.5Hz)<br>7.36(1H, d, J=2.1Hz)<br>7.26(1H, dd, J=2.1, 8.4Hz)<br>7.08(2H, d, J=8.5Hz)<br>6.80(2H, d, J=8.5Hz)<br>6.79(1H, d, J=8.4Hz)<br>6.17(1H, d, J=15.5Hz)<br>5.54(1H, bt)<br>5.14(1H, s)<br>4.03(2H, t, J=6.6Hz)<br>3.61(2H, t, J=6.6Hz)<br>2.88(2H, t, J=7.4Hz)<br>2.81(2H, t, J=6.9Hz)<br>1.80–1.90(2H, m)<br>1.60–1.70(2H, m)<br>1.25–1.55(8H, m)<br>0.93(3H, t, J=7.1Hz)<br>0.90(3H, t, J=7.1Hz) | | FAB+<br>456<br>[M+H+]<br>(100)<br>319(50) | $C_{27}H_{37}NO_3S$ |
| 1-66 | Yellow crystals | 221~222° C. | DMSO-d6,300MHz<br>8.97(2H, bs)<br>8.63(1H, bs)<br>8.05(1H, t, J=5.7Hz)<br>7.31(1H, d, J=15.6Hz)<br>7.15(1H, d, J=1.8Hz)<br>7.12(1H, dd, J=8.4, 1.8Hz)<br>6.99(2H, d, J=8.4Hz)<br>6.99(1H, d, J=8.4Hz)<br>6.67(2H, d, J=8.4Hz)<br>6.52(1H, d, J=15.6Hz)<br>4.08(2H, t, J=6.6Hz)<br>3.78(3H, s)<br>3.31(2H, q, J=6.6Hz)<br>2.9–3.1(2H, m)<br>2.63(2H, t, J=7.5Hz)<br>2.55(3H, t, J=6.0Hz)<br>2.0–2.2(2H, m) | KBr<br>3215<br>1653<br>1617<br>1516 | FAB+<br>385<br>[M+H+]<br>(80),<br>154<br>(100),<br>136<br>(80). | $C_{22}H_{28}N_2O_4$<br>.HCl<br>Calcd.<br>C; 62.77%<br>H; 6.70%<br>N; 6.65%<br>Found<br>C; 57.75%<br>H; 6.75%<br>N; 6.05% |

TABLE 37

| Ex. | Structural formula | m.p. | 1H NMR (δ) ppm | IR cm⁻¹ | MS | Elem. anal. |
|---|---|---|---|---|---|---|
| 1-68 | (structure: MeO, O-pentyl substituted cinnamamide with 4-aminophenethyl) Colorless crystals | 139.7~ 142.3° C. | CDCl₃,300MHz<br>7.53(1H, d, J=16Hz)<br>7.05(1H, d, J=8.4Hz)<br>7.02(2H, d, J=8.4Hz)<br>7.00(1H, s)<br>6.84(1H, d, J=8.4Hz)<br>6.66(2H, d, J=8.4Hz)<br>6.16(1H, d, J=16Hz)<br>5.50(1H, bt)<br>4.02(2H, t, J=6.8Hz)<br>3.88(3H, s)<br>3.60(2H, bs)<br>3.60(2H, q, J=6.5Hz)<br>2.77(2H, t, J=6.8Hz)<br>1.8–1.93(2H, m)<br>1.3–1.55(4H, m)<br>0.94(3H, t, J=7.2Hz) | | FAB+<br>383<br>[M⁺H⁺](40)<br>247(80) | |
| 1-69 | (structure: MeO, S-pentyl substituted cinnamamide with 4-aminophenethyl) Colorless crystals | 115.2~ 116.3° C. | CDCl₃,300MHz<br>7.53(1H, d, J=16Hz)<br>7.37(1H, d, J=2.1Hz)<br>7.27(1H, d, J=8.5Hz)<br>7.01(2H, d, J=8.3Hz)<br>6.81(1H, d, J=8.5Hz)<br>6.66(2H, d, J=8.3Hz)<br>6.17(1H, d, J=16Hz)<br>5.53(1H, bt)<br>3.91(3H, s)<br>3.61(2H, bs)<br>3.60(2H, q, J=6.5Hz)<br>2.89(2H, t, J=7.4Hz)<br>2.77(2H, t, J=6.8Hz)<br>1.6–1.73(2H, m)<br>1.3–1.5(4H, m)<br>0.90(3H, t, J=7.2Hz) | | FAB+<br>399<br>[M⁺H⁺](50)<br>263(40) | |

TABLE 38

| Ex. | Structural formula | m.p. | 1H NMR (δ) ppm | IR cm⁻¹ | MS | Elem. anal. |
|---|---|---|---|---|---|---|
| 1-70 | (structure: MeO, S-pentyl substituted cinnamamide with 4-nitrophenethyl) Pale-yellow crystals | 114.1~ 114.6° C. | CDCl₃,300MHz<br>8.20(2H, d, J=8.7Hz)<br>7.58(1H, d, J=16Hz)<br>7.41(2H, d, J=8.7Hz)<br>7.39(1H, d, J=2.4Hz)<br>7.31(1H, dd, J=2.1, 8.4Hz)<br>6.84(1H, d, J=16Hz)<br>5.64(1H, bt)<br>3.93(3H, s)<br>3.70(2H, q, J=6.9Hz)<br>3.04(2H, t, J=7.0Hz)<br>2.90(2H, t, J=7.4Hz)<br>1.58–1.75(2H, m)<br>1.25–1.50(4H, m)<br>0.91(3H, t, J=7.1Hz) | | FAB+<br>429<br>[M⁺H⁺](20)<br>307(20) | |
| 1-71 | (structure: MeO, S-pentyl substituted cinnamamide with imidazolylethyl) Colorless crystals | 119.2~ 120.4° C. | CDCl₃,300MHz<br>7.60(1H, s)<br>7.54(1H, d, J=16Hz)<br>7.38(1H, d, J=2.1Hz)<br>7.30(1H, dd, J=2.1, 8.5Hz)<br>6.85(1H, s)<br>6.82(1H, d, J=8.5Hz)<br>6.56(1H, bt)<br>6.28(1H, d, J=16Hz)<br>3.91(3H, s)<br>3.69(2H, q, J=6.9Hz)<br>2.83–2.92(4H, m)<br>1.6–1.73(2H, m)<br>1.3–1.5(4H, m)<br>0.90(3H, t, J=7.1Hz) | | FAB+<br>374<br>[M⁺H⁺](100)<br>263(30) | |

TABLE 38-continued

| Ex. | Structural formula | m.p. | 1H NMR (δ) ppm | IR cm⁻¹ MS | Elem. anal. |
|---|---|---|---|---|---|
| 1-72 | 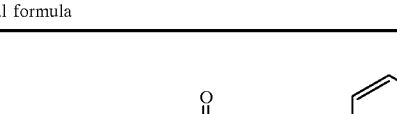 Colorless crystals | 122.1~ 122.7° C. | CDCl₃,300MHz 8.18(2H, d, J=8.6Hz) 7.54(1H, d, J=15Hz) 7.39(2H, d, J=8.6Hz) 6.80(1H, d, J=8.2Hz) 6.71(1H, d, J=8.2Hz) 6.70(1H, s) 6.17(1H, d, J=15Hz) 5.35(1H, bt) 4.20(1H, bt) 3.87(3H, s) 3.68(2H, q, J=6.7Hz) 3.12(2H, q, J=5.7Hz) 3.02(2H, t, J=6.9Hz) 1.6–1.73(2H, m) 1.3–1.5(4H, m) 0.93(3H, t, J=7.1Hz) | FAB+ 412 [M⁺H⁺](30) 246(30) | |

TABLE 39

| Ex. | Structural formula | m.p. | 1H NMR (δ) ppm | IR cm⁻¹ MS | Elem. anal. |
|---|---|---|---|---|---|
| 1-73 | 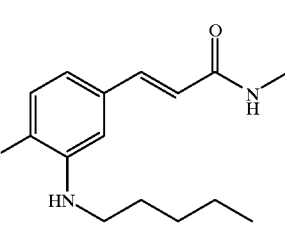 Colorless crystals | 150.7~ 151.6° C. | CDCl₃,300MHz 7.55(1H, s) 7.48(1H, d, J=15Hz) 6.80(1H, s) 6.67(1H, s) 6.66(1H, d, J=8.0Hz) 6.32(1H, s) 6.19(1H, d, J=15Hz) 4.12(1H, bs) 3.81(3H, s) 3.63(2H, q, J=6.1Hz) 3.08(2H, bt) 2.83(2H, t, J=6.3Hz) 1.55–1.70(2H, m) 1.3–1.43(4H, m) 0.88(3H, t, J=7.1Hz) | FAB+ 3577 [M⁺H⁺](50) 246(30) | |
| 1-74 | 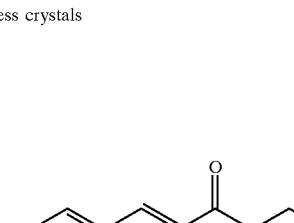 Colorless crystals | 100.6~ 101.2° C. | CDCl3,3000MHz 7.55(1H, d, J=16.0Hz) 7.18(1H, dd, J=5.1, 1.1Hz) 7.06(1H, dd, J=8.2, 1.9Hz) 7.01(1H, d, J=1.9Hz) 6.96(1H, dd, J=5.1, 3.5Hz) 6.86(1H, dd, J=3.5, 1.5Hz) 6.84(1H, d, J=8.3Hz) 6.20(1H, d, J=16.0Hz) 5.70(1H, bt) 4.01(2H, t, J=6.9Hz) 3.88(3H, s) 3.67(2H, q, J=6.4Hz) 3.11(2H, t, J=6.4Hz) 1.8–1.9(2H, m) 1.3–1.5(4H, m) 0.93(3H, t, J=7.0Hz) | FAB+ 374[M+H+] (100) | C₂₁H₂₇NO₃S Calcd. C; 67.53% H; 7.29% N; 3.75% Found C; 67.51% H; 7.47% N; 3.77% |

TABLE 39-continued

| Ex. | Structural formula | m.p. | 1H NMR (δ) ppm | IR cm⁻¹ | MS | Elem. anal. |
|---|---|---|---|---|---|---|
| 1-75 | 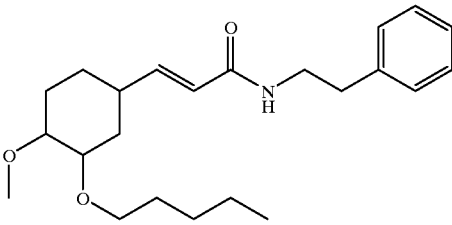<br>Pale-yellow flakes | 69.8~<br>70.2° C. | CDCl3,300MHz<br>7.60(2H, d, J=8.4Hz)<br>7.55(1H, d, J=15.6Hz)<br>7.34(2H, d, J=8.4Hz)<br>7.06(1H, dd,<br>J=8.1, 2.1Hz)<br>7.00(1H, d, J=2.1Hz)<br>6.84(1H, d, J=8.1Hz)<br>6.19(1H, d, J=15.6Hz)<br>5.64(1H, bt)<br>4.00(2H, t, J=6.6Hz)<br>3.88(3H, s)<br>3.65(2H, q, J=6.9Hz)<br>2.96(2H, t, J=6.9Hz)<br>1.8–2.0(2H, m)<br>1.3–1.5(4H, m)<br>0.93(3H, t, J=6.9Hz) | KBr<br>3280<br>2936<br>2856<br>2229<br>1651<br>1609<br>1518<br>1262 | FAB+<br>393[M+H+]<br>(100) | |

TABLE 40

| Ex. | Structural formula | m.p. | 1H NMR (δ) ppm | IR cm⁻¹ | MS | Elem. anal. |
|---|---|---|---|---|---|---|
| 1-76 | 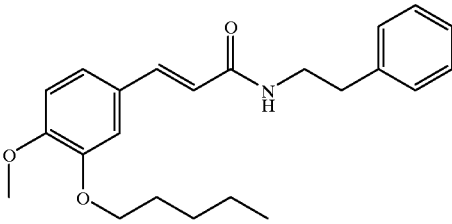<br>Colorless crystals | 174.2~<br>175.1° C. | DMSO-d6,300MHz<br>9.0(1H, bs)<br>8.04(1H, bt)<br>7.87(2H, d, J=8.1Hz)<br>7.36(2H, d, J=8.1Hz)<br>7.30(1H, d, J=15.7Hz)<br>7.13(1H, d, J=1.7Hz)<br>7.08(1H, dd,<br>J=8.3, 1.7Hz)<br>6.46(1H, d, J=15.7Hz)<br>3.97(2H, t, J=6.6Hz)<br>3.78(3H, s)<br>3.44(2H, q, J=6.9Hz)<br>2.85(2H, t, J=6.9Hz)<br>1.6–1.8(2H, m)<br>1.3–1.5(4H, m)<br>0.90(3H, t, J=7.1Hz) | KBr<br>3422<br>2938<br>1610<br>1518<br>1262 | FAB+<br>412<br>[M+H+]<br>(100) | |
| 1-77 | 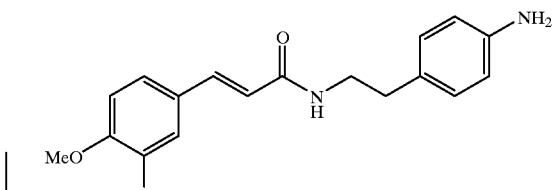<br>Colorless oil | | CDCl3,300MHz<br>7.89(1H, d, J=15.3Hz)<br>7.13(2H, d, J=8.4Hz)<br>7.00(1H, dd,<br>J=2.1, 7.2Hz)<br>6.75–6.885(2H, m)<br>6.66(2H, d, J=8.4Hz)<br>6.28(1H, d, J=15.3Hz)<br>5.71(1H, bt)<br>4.45(2H, d, J=5.4Hz)<br>3.84(3H, s)<br>3.65(1H, bs)<br>3.08(2H, t, J=6.9Hz)<br>1.45–1.60(2H, m)<br>1.20–1.40(4H, m)<br>0.88(3H, t, J=7.1Hz) | | | $C_{22}H_{29}N_3O_2$ |
| 1-78 | 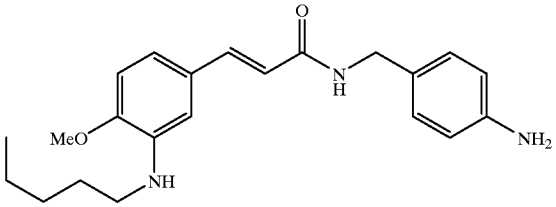<br>Colorless oil | | CDCl3,300MHz<br>7.84(1H, d, J=15.3Hz)<br>6.97–7.04(3H, m)<br>6.75–6.85(2H, m)<br>6.66(2H, d, J=8.4Hz)<br>6.22(1H, d, J=15.3Hz)<br>5.56(1H, bt)<br>3.84(3H, s)<br>3.63(1H, bs)<br>3.60(2H, q, J=6.6Hz)<br>3.07(2H, t, J=7.1Hz)<br>2.77(2H, t, J=6.8Hz)<br>1.45–1.60(2H, m)<br>1.20–1.38(4H, m)<br>0.88(3H, t, J=7.1Hz) | | | $C_{23}H_{31}N_3O_2$ |

TABLE 41

| Ex. | Structural formula | m.p. | 1H NMR (δ) ppm | IR cm⁻¹ | MS | Elem. anal. |
|---|---|---|---|---|---|---|
| 1-79 | (Colorless crystals) | 125.5~ 126.2° C. | CDCl3,300MHz<br>8.04(1H, bt)<br>7.91(1H, d, J=15.9Hz)<br>7.75(2H, d, J=8.4Hz)<br>7.34(1H, s)<br>7.28(2H, d, J=8.4Hz)<br>7.06(1H, d, J=8.4Hz)<br>6.95(1H, d, J=8.4Hz)<br>6.46(1H, d, J=15.9Hz)<br>6.00(2H, bs)<br>3.96(2H, t, J=6.9Hz)<br>3.98(3H, s)<br>3.4–3.5(2H, m)<br>2.81(2H, bt)<br>1.7–1.8(2H, m)<br>1.3–1.5(4H, m)<br>0.89(3H, t, J=6.9Hz) | KBr<br>3440<br>1684<br>1214<br>1138 | FAB+<br>411<br>[M+H+]<br>(100) | |
| 1-80 | (Pale-yellow crystals) | 130.0~ 131.6° C. | CDCl3,300MHz<br>7.69(1H, d, J=15.3Hz)<br>7.06(1H, d, J=8.8Hz)<br>7.01(2H, d, J=8.4Hz)<br>6.66(2H, d, J=8.4Hz)<br>6.35(1H, d, J=8.8Hz)<br>6.13(1H, d, J=15.3Hz)<br>5.49(1H, bt)<br>4.21(2H, bs)<br>3.94(2H, t, J=6.8Hz)<br>3.84(3H, s)<br>3.61(2H, bs)<br>3.59(2H, q, J=6.5Hz)<br>2.77(2H, t, J=6.8Hz)<br>1.70–1.90(2H, m)<br>1.30–1.50(4H, m)<br>0.93(3H, t, J=7.1Hz) | KBr<br>3292<br>2931<br>1649<br>1611<br>1516<br>1293<br>1235<br>1097 | FAB+<br>398<br>[M+H+]<br>(35)<br>262(40) | C₂₃H₃₁N₃O₃ |
| 1-81 | (Pale-yellow crystals) | 105.8~ 106.9° C. | CDCl3,300MHz<br>8.53(2H, d, J=6.0Hz)<br>7.70(1H, d, J=15.3Hz)<br>7.16(2H, d, J=6.0Hz)<br>7.07(1H, d, J=8.8Hz)<br>6.35(1H, d, J=8.8Hz)<br>6.16(1H, d, J=15.3Hz)<br>5.60(1H, bt)<br>4.20(2H, bs)<br>3.94(2H, t, J=6.8Hz)<br>3.84(3H, s)<br>3.67(2H, q, J=6.6Hz)<br>2.90(2H, t, J=6.9Hz)<br>1.70–1.85(2H, m)<br>1.30–1.50(4H, m)<br>0.93(3H, t, J=7.0Hz) | KBr<br>3337<br>2952<br>1657<br>1608<br>1519<br>1458<br>1096 | FAB+<br>384<br>[M+H+]<br>(100) | C₂₂H₂₉N₃O₃ |

TABLE 42

| Ex. | Structural formula | m.p. | 1H NMR (δ) ppm | IR cm-1 | MS | Elem. anal. |
|---|---|---|---|---|---|---|
| 1-82 | Pale-yellow amorphous | | CDCl3,300MHz<br>7.75(1H, d, J=15.5Hz)<br>7.09(1H, d, J=8.8Hz)<br>7.01(2H, d, J=8.3Hz)<br>6.66(2H, d, J=8.3Hz)<br>6.45(1H, d, J=8.8Hz)<br>6.14(1H, d, J=15.5Hz)<br>5.51(1H, bs)<br>3.92(2H, t, J=6.7Hz)<br>3.84(3H, s)<br>3.62(2H, bs)<br>3.59(2H, q, J=6.5Hz)<br>3.08(2H, t, J=7.1Hz)<br>2.76(2H, t, J=6.8Hz)<br>1.70–1.85(2H, m)<br>1.25–1.65(10H, m)<br>0.94(3H, t, J=7.1Hz)<br>0.88(3H, t, J=7.0Hz) | KBr<br>3290<br>2992<br>1645<br>1602<br>1515<br>1292<br>1231 | FAB+<br>468<br>[M+H+]<br>(20)<br>332(20)<br>262(60) | $C_{28}H_{41}N_3O_3$ |
| 1-83 | Pale-yellow crystals | 68.4~<br>69.6° C. | CDCl3,300MHz<br>8.53(2H, d, J=5.7Hz)<br>7.78(1H, d, J=15.9Hz)<br>7.16(2H, d, J=5.7Hz)<br>7.09(1H, d, J=8.7Hz)<br>6.46(1H, d, J=8.7Hz)<br>6,16(1H, d, J=15.9Hz)<br>5.60(1H, bt)<br>3.92(2H, t, J=6.8Hz)<br>3.84(3H, s)<br>3.66(2H, q, J=6.7Hz)<br>3.08(2H, t, J=7.1Hz)<br>2.90(2H, t, J=7.1Hz)<br>1.70–1.85(2H, m)<br>1.20–1.60(10H, m)<br>0.8–1.0(6H, m) | KBr<br>3294<br>2936<br>1648<br>1604<br>1550<br>1292<br>1232<br>1106 | FAB+<br>454<br>[M+H+]<br>(100) | $C_{27}H_{39}N_3O_3$ |
| 1-84 | Colorless crystals | 107.3~<br>109.5° C. | CDCl$_3$,300MHz<br>7.54(1H, d, J=15Hz)<br>7.14(1H, d, J=8.1Hz)<br>7.08(2H, d, J=8.3Hz)<br>7.03(1H, d, J=8.1Hz)<br>6.90(1H, s)<br>6.80(2H, d, J=8.3Hz)<br>6.24(1H, d, J=15Hz)<br>5.55(1H, bt)<br>5.00(1H, bs)<br>4.02(2H, t, J=6.6Hz)<br>3.62(2H, q, J=6.1Hz)<br>2.89(2H, t, J=7.4Hz)<br>2.81(2H, t, J=6.9Hz)<br>1.78–1.90(2H, m)<br>1.6–1.74(2H, m)<br>1.28–1.55(8H, m)<br>0.94(3H, t, J=7.1Hz)<br>0.90(3H, t, J=7.2Hz) | | FAB+<br>456<br>[M+H+]<br>(100)<br>319(60) | |

TABLE 43

| Ex. | Structural formula | m.p. | 1H NMR (δ) ppm | IR cm$^{-1}$ | MS | Elem. anal. |
|---|---|---|---|---|---|---|
| 1-85 | 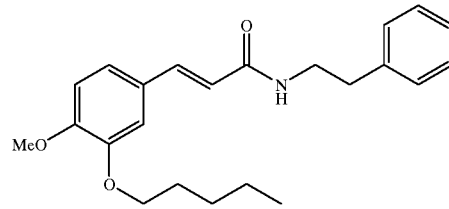<br>Colorless crystals | 140.3~<br>140.9° C. | CDCl$_3$, 300MHz<br>7.55(1H, d, J=16Hz)<br>7.06–7.13(4H, m)<br>6.90(1H, s)<br>6.80(2H, d, J=8.5Hz)<br>6.24(1H, d, J=16Hz)<br>5.54(1H, bt)<br>4.977(1H, bs)<br>4.03(2H, t, J=6.5Hz)<br>3.62(2H, q, J=6.1Hz)<br>2.81(2H, t, J=6.9Hz)<br>2.43(3H, s)<br>1.8–1.9(2H, m)<br>1.35–1.57(4H, m)<br>0.94(3H, t, J=7.1Hz) | | FAB+<br>400<br>[M$^+$H$^+$](40)<br>307(100) | |
| 1-86 | 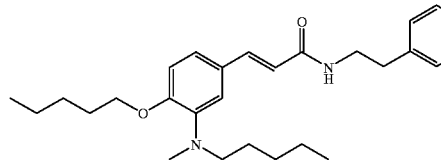<br>Colorless crystals | 113.9~114.5 | CDCl3, 300MHz<br>7.54(1H, d, J=15.5Hz)<br>7.08(2H, d, J=8.5Hz)<br>7.07(1H, d, J=8.45Hz)<br>7.03(1H, s)<br>6.80(2H, d, J=8.5Hz)<br>6.79(1H, d, J=8.4Hz)<br>6.17(1H, d, J=15.5H)<br>5.53(1H, bt)<br>5.17(1H, s)<br>4.01(2H, t, J=6.6Hz)<br>3.61(2H, q, J=6.6Hz)<br>3.04(2H, t, J=7.8Hz)<br>2.81(2H, t, J=6.8Hz)<br>2.79(3H, s)<br>1.8–1.91(2H, m)<br>1.2–1.6(10H, m)<br>0.94(3H, t, J=7.1Hz)<br>0.89(3H, t, J=7.1Hz) | | FAB+<br>453[M+H+]<br>(100)<br>395(90)<br>316(50) | C$_{28}$H$_{40}$N$_2$O$_3$ |
| 1-87 | 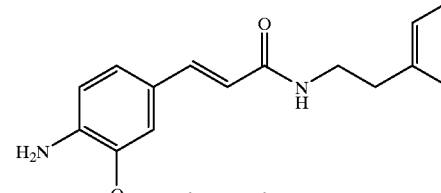<br>Colorless crystals | | DMSO-d6, 300MHz<br>9.14(1H, s)<br>7.84(1H, t, J=5.7Hz)<br>7.23(1H, d, J=15.6Hz)<br>6.99(1H, d, J=8.4Hz)<br>6.94(1H, s)<br>6.87(1H, d, J=8.1Hz)<br>6.66(2H, d, J=8.4Hz)<br>6.60(1H, d, J=8.1Hz)<br>6.19(1H, d, J=15.6Hz)<br>5.11(2H, bs)<br>3.95(2H, t, J=6.6Hz)<br>3.25–3.34(5H, m)<br>2.62(2H, t, J=7.4Hz)<br>1.60–1.80(2H, m)<br>1.15+144 1.50(4H, m)<br>0.90(3H, t, J=6.9Hz) | | FAB+<br>369<br>[M+H+](80)<br>368(80) | |

TABLE 44

| Ex. | Structural formula | m.p. | 1H NMR (δ) ppm | IR cm⁻¹ | MS | Elem. anal. |
|---|---|---|---|---|---|---|
| 1-88 | Pale-yellow crystals | 213.7~214.7° C. | CDCl3,300MHz<br>7.52(1H, d, J=15Hz)<br>7.09(2H, d, J=8.5Hz)<br>7.03(1H, d, J=8.1Hz)<br>6.87(1H, s)<br>6.79(2H, d, J=8.5Hz)<br>6.51(1H, d, J=8.1Hz)<br>6.08(1H, d, J=15Hz)<br>5.47(1H, bt)<br>4.98(1H, s)<br>4.51(1H, bs)<br>3.99(2H, t, J=6.5Hz)<br>3.61(2H, q, J=6.2Hz)<br>2.89(3H, bs)<br>2.81(2H, t, J=6.9Hz)<br>1.76–1.9(2H, m)<br>1.33–1.5(4H, m)<br>0.94(3H, t, J=7.1Hz) | | FAB+<br>357<br>[M+H+](50)<br>246(30)<br>$C_{23}H_{30}N_2O_3$ | |
| 1-89 | Colorless crystals | | CDCl3,300MHz<br>7.51(1H, d, J=15,4Hz)<br>7.08(2H, d, J=8.4Hz)<br>7.01(1H, d, J=8.2Hz)<br>6.87(1H, s)<br>6.79(2H, d, J=8.4Hz)<br>6.51(1H, d, J=8.2Hz)<br>6.06(1H, d, J=15.4Hz)<br>5.45(1H, bt)<br>4.99(1H, s)<br>4.49(1H, bs)<br>3.99(2H, t, J=6.5Hz)<br>3.60(2H, q, J=6.5Hz)<br>3.15(2H, bs)<br>2.80(2H, t, J=6.9Hz)<br>1.75–1.90(2H, m)<br>1.3–1.72(10H, m)<br>0.85–1.0(6H, m) | | FAB+<br>438<br>[M+H+](30)<br>302(30)<br>$C_{27}H_{28}N_2O_3$ | |
| 1-90 | Pale-yellow crystals | | CDCl3,300MHz<br>7.52(1H, d, J=15.5Hz)<br>7.02(2H, d, J=8.3Hz)<br>6.63–6.81(5H, m)<br>6.61(1H, d, J=15.5Hz)<br>5.53(1H, bt)<br>3.66–3.75(2H, m)<br>3.59(2H, q, J=6.5Hz)<br>3.13(2H, bs)<br>2.77(2H, t, J=6.8Hz)<br>1.60–1.75(2H, m)<br>1.30–1.50(4H, m)<br>0.93(3H, t, J=7.1Hz) | | | |

TABLE 45

| Ex. | Structural formula | m.p. | 1H NMR (δ) ppm | IR cm-1 | MS | Elem. anal. |
|---|---|---|---|---|---|---|
| 1-91 | Pale-orange crystals | 136.5~137.0° C. | CDCl3,300MHz 8.17(2H, d, J=8.7Hz) 7.52(1H, d, J=15Hz) 7.38(2H, d, J=8.7Hz) 7.03(1H, d, J=8.2Hz) 6.86(1H, s) 6.50(1H, d, J=8.2Hz) 6.07(1H, d, J=15Hz) 5.47(1H, bt) 4.55(1H, bs) 3.98(2H, t, J=6.5Hz) 3.66(2H, q, J=.6.6Hz) 3.00(2H, t, J=6.9Hz) 2.89(3H, d, J=5.0Hz) 1.75–1.87(2H, m) 1.3–1.5(4H, m) 0.93(3H, t, J=7.1Hz) | | FAB+ 412 [M+H+] (20) 246(50) | $C_{23}H_{29}N_3O_4$ |
| 1-92 | Yellow oil | | CDCl3,300MHz 7.10(2H, d, J=8.5Hz) 7.00(2H, d, J=8.5Hz) 6.93(2H, t, J=7.9Hz) 6.77(1H, d, J=7.9Hz) 6.63(1H, d, J=7.9Hz) 5.80(1H, bs) 3.91(2H, t, J=6.7Hz) 3.84(3H, s) 3.47(2H, s) 3.45(2H, q, J=6.2Hz) 2.78(2H, t, J=6.2Hz) 2.29(3H, s) 1.7–1.8(2H, m) 1.4–1.5(4H, m) 0.92(3H, t, J=7.0Hz) | | FAB+ 414 [M+H+] (100) | |

TABLE 46

| Ex. | Structural formula | m.p. | 1H NMR (δ) ppm | IRcm$^{-1}$ | MS | Elem. anal. |
|---|---|---|---|---|---|---|
| 2-1 | | 114.3~115.6° C. | CDCl$^3$, 300 MHz 7.35(1H, d, J=2.0 Hz) 7.15(1H, dd, J=8.3, 2.0 Hz) 7.03(2H, d, J=8.4 Hz) 6.80(2H, d, J=8.4 Hz) 6.80(1H, d, J=8.3 Hz) 6.62(1H, bs) 6.19(1H, bt) 3.98(2H, t, J=6.9 Hz) 3.86(3H, s) 3.64(2H, q, J=6.9 Hz) 2.82(2H, t, J=6.9 Hz) 1.7–1.9(2H, m) 1.3–1.5(4H, m) 0.90(3H, t, J=7.0 Hz) | KBr 3322 1633 | FAB+ 358 [M+H+] (100) 221(100) | $C_{21}H_{27}NO_4$ Calcd. C; 70.56% H; 7.61% N; 3.92% Found C; 70.58% H; 7.79% N; 3.89% |
| 2-2 | Colorless crystals | 116~117° C. | DMSO-d6, 300 MHz 9.14(1H, s) 8.33(1H, t) 7.39–7.41(2H, m) 6.96–7.02(3H, m) 6.66(2H, d, J=8.4 Hz) 4.05(2H, q, J=6.9 Hz) 3.97(2H, t, J=6.6 Hz) 3.32–3.43(2H, m) 2.69(2H, t, J=7.5 Hz) 1.66–1.78(2H, m) 1.28–1.47(7H, m) 0.89(3H, t, J=7.2 Hz) | | FAB+ 372 [M+H+] (55) 235(100) 206(24) 164(23) | |

TABLE 46-continued

| Ex. | Structural formula | m.p. | 1H NMR (δ) ppm | IRcm$^{-1}$ | MS | Elem. anal. |
|---|---|---|---|---|---|---|
| 2-3 | (Colorless crystals) | 134~136° C. | DMSO-d6, 300 MHz<br>9.14(1H, s)<br>8.33(1H, t, J=5.4 Hz)<br>7.40–7.42(2H, m)<br>6.97–7.03(3H, m)<br>6.68(2H, d, J=8.4 Hz)<br>3.96–4.01(4H, m)<br>3.32–3.45(2H, m)<br>2.70(2H, t, J=7.4 Hz)<br>1.64–1.78(4H, m)<br>1.26–1.49(8H, m)<br>0.83–0.94(6H, m) | | FAB+<br>414<br>[M$^+$H$^+$] (100)<br>277(58)<br>207(59)<br>170(75)<br>136(85) | |

TABLE 47

| Ex. | Structural formula | m.p. | 1H NMR (δ) ppm | IR cm$^{-1}$ | MS | Elem. anal. |
|---|---|---|---|---|---|---|
| 2-4 | (Colorless crystals) | 93.6~94.2° C. | CDCl$_3$, 300 MHz<br>7.09(2H, d, J=8.4 Hz)<br>6.86(2H, s)<br>6.79(2H, dd, J=8.4, 2.1 Hz)<br>6.0(1H, bt)<br>3.92–4.03(6H, m)<br>3.64(2H, q. J=6.6 Hz)<br>2.84(2H, t, J=7.1 Hz)<br>1.7–1.88(6H, m)<br>1.3–1.5(12H, m)<br>0.88–1.0(12H, m) | | FAB+<br>500<br>[M$^+$H$^+$] (70)<br>293(65) | |
| 2-5 | (Colorless crystals) | 95.3~96.4° C. | CDCl$_3$, 300 MHz<br>7.33(1H, s)<br>7.09(2H, d, J=8.4 Hz)<br>7.08(1H, d, J=8.1 Hz)<br>6.8(1H, d, J=8.1 Hz)<br>6.79(2H, d, J=8.4 Hz)<br>6.05(1H, bt)<br>5.33(1H, bs)<br>4.03(2H, t, J=6.6 Hz)<br>3.65(2H, q, J=6.6 Hz)<br>2.86(6H, s)<br>2.85(2H, t, J=6.9 Hz)<br>1.8–1.9(2H, m)<br>1.3–1.6(4H, m)<br>0.93(3H, t, J=7.2 Hz) | | FAB+<br>371<br>[M$^+$H$^+$](100)<br>234(50) | |
| 2-6 | (Colorless crystals) | 145.9~146.5° C. | CDCl$_3$, 300 MHz<br>7.09(2H, d, J=8.4 Hz)<br>6.98(1H, d, J=1.8 Hz)<br>6.91(1H, dd, J=7.8, 2.1 Hz)<br>6.79(2H, d, J=8.4 Hz)<br>6.70(1H, d, J=7.8 Hz)<br>6.04(1H, bt)<br>5.30(1H, bs)<br>4.11(1H, bs)<br>3.87(3H, s)<br>3.65(2H, q, J=6.6 Hz)<br>3.13(2H, t, J=7.1 Hz)<br>2.85(2H, t, J=6.9 Hz)<br>1.6–1.75(2H, m)<br>1.33–1.5(4H, m)<br>0.92(3H, t, J=7.2 Hz) | | FAB+<br>357<br>[M$^+$H$^+$] (100)<br>220(80) | |

TABLE 48

| Ex. | Structural formula | m.p. | 1H NMR (δ) ppm | IRcm$^{-1}$ | MS | Elem. anal. |
|---|---|---|---|---|---|---|
| 2-7 | (MeO, O-butyl substituted benzamide of 4-hydroxyphenethylamine)<br>Colorless crystals | 116~117° C. | DMSO-d6, 300 MHz<br>9.14(1H, s)<br>8.34(1H, t, J=5.5 Hz)<br>7.43(1H, dd, J=8.4, 1.8 Hz)<br>7.40(1H, d, J=1.8 Hz)<br>7.02(2H, d, J=8.3 Hz)<br>7.00(1H, d, J=8.2 Hz)<br>6.67(2H, d, J=8.3 Hz)<br>3.98(2H, t, J=6.5 Hz)<br>3.80(3H, s)<br>3.36(2H, m)<br>2.70(2H, t, J=7.5 Hz)<br>1.72(2H, m)<br>1.45(2H, m)<br>0.94(3H, t, J=7.4 Hz) | KBr<br>3310<br>1613<br>1549<br>1514<br>1272<br>1238<br>1135 | FAB+<br>344<br>[M$^+$H$^+$] (100)<br>237(27)<br>223(35)<br>207(61)<br>168(60)<br>153(86) | |
| 2-8 | (MeO, O-hexyl substituted benzamide of 4-hydroxyphenethylamine)<br>Colorless crystals | 134~135° C. | DMSO-d6, 300 MHz<br>9.14(1H, s)<br>8.34(1H, t, J=5.5 Hz)<br>7.41(1H, br d, J=8.4 Hz)<br>7.39(1H, br s)<br>7.00(2H, d, J=8.3 Hz)<br>6.98(1H, d, J=8.2 Hz)<br>6.66(2H, d, J=8.3 Hz)<br>3.96(2H, t, J=6.5 Hz)<br>3.79(3H, s)<br>3.36(2H, m)<br>2.69(2H, t, J=7.5 Hz)<br>1.71(2H, m)<br>1.41(2H, m)<br>1.23–1.35(4H, m)<br>0.87(3H, t, J=7.4 Hz) | KBr<br>3445<br>3256<br>2940<br>1641<br>1556<br>1509<br>1267<br>1224<br>1188 | FAB+<br>372<br>[M$^+$H$^+$] (100)<br>251(30)<br>235(61) | $C_{22}H_{29}NO_4$<br>Calcd.<br>C; 71.13%<br>H; 7.87%<br>N; 3.77%<br>Found<br>C; 71.02%<br>H; 7.99%<br>N; 3.74% |
| 2-9 | (MeO, O-heptyl substituted benzamide of 4-hydroxyphenethylamine)<br>Colorless crystals | 125~126° C. | DMSO-d6, 300 MHz<br>9.13(1H, s)<br>8.33(1H, t, J=5.5 Hz)<br>7.40(1H, dd, J=8.4, 1.9 Hz)<br>7.37(1H, d, J=1.9 Hz)<br>7.69(2H, d, J=8.3 Hz)<br>6.97(1H, d, J=8.2 Hz)<br>6.65(2H, d, J=8.3 Hz)<br>3.95(2H, t, J=6.5 Hz)<br>3.78(3H, s)<br>3.36(2H, m)<br>2.68(2H, t, J=7.5 Hz)<br>1.70(2H, m)<br>1.23–1.42(8H, m)<br>0.85(3H, t, J=7.4 Hz) | KBr<br>3452<br>3263<br>2921<br>1642<br>1615<br>1549<br>1510<br>1442<br>1318<br>1269 | FAB+<br>386<br>[M$^+$H$^+$] (100)<br>265(15)<br>249(73)<br>170(32)<br>151(40) | $C_{23}H_{31}NO_4$<br>Calcd.<br>C; 71.66%<br>H; 8.11%<br>N; 3.63%<br>Found<br>C; 71.57%<br>H; 8.24%<br>N; 3.53% |

TABLE 49

| Ex. | Structural formula | m.p. | 1H NMR (δ) ppm | IRcm⁻¹ | MS | Elem. anal. |
|---|---|---|---|---|---|---|
| 2-10 | 4-methoxy-3-pentyloxy-N-(4-hydroxyphenyl)benzamide | 162.7~163.2° C. | ((CD$_3$)$_2$NCDO, 300 MHz) 9.80(1H, s) 9.19(1H, s) 7.57(1H, dd, J=8.4, 1.8 Hz) 7.51(1H, d, J=1.8 Hz) 7.48(2H, d, J=8.8 Hz) 7.05(1H, d, J=8.4 Hz) 6.73(2H, d, J=8.8 Hz) 4.02(2H, t, J=6.5 Hz) 3.83(3H, s) 1.7–1.8(2H, m) 1.3–1.5(4H, m) 0.91(3H, t, J=7.9 Hz), | KBr 3295 1642 1514 | FAB+ 330 [M⁺H⁺] (100) 221(70) 154(75) | C$_{19}$H$_{23}$NO$_4$ Calcd. C; 69.28% H; 7.04% N; 4.25% Found C; 68.84% H; 7.24% N; 4.25% |
| 2-11 | 4-methoxy-3-pentyloxy-N-(4-hydroxybenzyl)benzamide | | CDCl$_3$, 300 MHz 7.43(1H, d, J=2.1 Hz) 7.26(1H, dd, J=8.3, 2.1 Hz) 7.20(2H, d, J=8.5 Hz) 6.84(1H, d, J=8.3 Hz) 6.81(1H, d, J=8.5 Hz) 6.32(1H, bt) 5.80(1H, bs) 4.55(2H, d, J=5.6 Hz) 4.04(2H, t, J=6.9 Hz) 3.89(3H, s) 1.7–1.9(2H, m) 1.3–1.5(4H, m) 0.92(3H, t, J=7.1 Hz) | KBr 3320 2955 1510 | FAB+ 344 [M⁺H⁺] (100) 238(45) 221(70) | C$_{20}$H$_{25}$NO$_4$ Calcd. C; 69.95% H; 7.34% N; 4.08% Found C; 70.05% H; 7.42% N; 4.14% |
| 2-12 | 4-methoxy-3-pentyloxy-N-[3-(4-hydroxyphenyl)propyl]benzamide | | CDCl$_3$, 300 MHz 7.37(1H, d, J=2.0 Hz) 7.12(1H, dd, J=8.4, 2.0 Hz) 7.06(2H, d, J=8.4 Hz) 6.83(1H, d, J=8.4 Hz) 6.77(2H, d, J=8.4 Hz) 6.02(1H, bt) 5.60(1H, bs) 4.04(2H, t, J=6.9 Hz) 3.89(3H, s) 3.47(2H, q, J=6.2 Hz) 2.65(2H, t. J=6.2 Hz) 1.8–1.9(2H, m) 1.8–1.9(2H, m) 1.3–1.5(4H, m) 0.92(3H, t, J=7.0 Hz) | KBr 3319 2933 1513 1267 | FAB+ 372 [M⁺H⁺](42) 221(35) | |

TABLE 50

| Ex. | Structural formula | m.p. | 1H NMR (δ) ppm | IRcm⁻¹ | MS | Elem. anal. |
|---|---|---|---|---|---|---|
| 2-13 | 4-methoxy-3-pentyloxy-N-[2-(3-hydroxyphenyl)ethyl]benzamide | | CDCl$_3$, 300 MHz 7.34(1H, d, J=2.0 Hz) 7.17(1H, dd, J=8.3, 2.0 Hz) 7.1–7.2(1H, m) 7.00(1H, bs) 6.80(1H, d, J=8.3 Hz) 6.7–6.8(3H, m) 6.22(1H, bs) 3.99(2H, t, J=6.9 Hz) 3.86(3H, s) 3.65(2H, q, J=6.8 Hz) 2.83(2H, t, J=6.8 Hz) 1.8.1.9(2H, m) 1.3–1.5(4H, m) 0.91(3H, t, J=7.0 Hz) | KBr 3319 2954 1581 1505 1268 | FAB+ 358 [M⁺H⁺] (40) 221(50) HRFAB(m/z) Calcd. C$_{21}$H$_{28}$NO$_4$ 358.4622 Found 358.2008 | |

TABLE 50-continued

| Ex. | Structural formula | m.p. | 1H NMR (δ) ppm | IRcm⁻¹ | MS | Elem. anal. |
|---|---|---|---|---|---|---|
| 2-14 | (structure) | | CDCl$_3$, 300 MHz<br>7.96(1H, bs)<br>7.41(1H, d, J=1.9 Hz)<br>7.26(1H, dd, J=8.3, 1.9 Hz)<br>7.10(1H, t, J=8.0 Hz)<br>7.08(2H, d, J=8.0 Hz)<br>6.92(1H, d, J=8.0 Hz)<br>6.7–6.9(3H, m)<br>4.00(2H, t, J=6.8 Hz)<br>3.86(3H, s)<br>3.59(2H, q, J=7.0 Hz)<br>2.96(2H, t, J=7.0 Hz)<br>1.8–1.9(2H, m)<br>1.3–1.5(4H, m)<br>0.91(3H, t, J=7.0 Hz) | Neat<br>3347<br>2951<br>1620<br>1578<br>1514 | FAB+<br>358<br>[M⁺H⁺] (90)<br>221(100) | C$_{21}$H$_{27}$NO$_4$<br>Calcd.<br>C; 70.56%<br>H; 7.61%<br>N; 3.92%<br>Found<br>C; 70.59%<br>H; 7.77%<br>N; 3.87% |
| 2-15 | (structure) | | CDCl$_3$, 300 MHz<br>7.39(1H, d, J=1.9 Hz)<br>7.21(1H, dd, J=8.3, 1.9 Hz)<br>6.83(1H, d, J=8.3 Hz)<br>6.03(1H, bs)<br>4.04(2H, t, J=6.9 Hz)<br>3.9–4.0(2H, m)<br>3.88(3H, s)<br>3.2–3.6(4H, m)<br>1.0–2.1(15H, m)<br>0.91(3H, t, J=7.1 Hz) | Neat<br>3316<br>2927<br>1633<br>1504<br>1267 | FAB+<br>364<br>[M⁺H⁺] (50)<br>221(100)<br>HRFAB(m/z)<br>Calcd.<br>C$_{21}$H$_{34}$NO$_4$<br>364.5102<br>Found<br>364.2481 | |

TABLE 51

| Ex. | Structural formula | m.p. | 1H NMR (δ) ppm | IRcm⁻¹ | MS | Elem. anal. |
|---|---|---|---|---|---|---|
| 2-16 | (structure) | 96~98° C. | CDCl$_3$, 300 MHz<br>8.52–8.54(2H, m)<br>7.38(1H, d, J=2.0 Hz)<br>7.16–7.18(2H, m)<br>7.15(1H, dd, J=8.5, 2.1 Hz)<br>6.84(1H, d, J=8.5 Hz)<br>6.12(1H, br t)<br>4.05(2H, t, J=7.0 Hz)<br>3.89(3H, s)<br>3.72(2H, q, J=7.0 Hz)<br>2.95(2H, t, J=7.0 Hz)<br>1.81–1.90(2H, m)<br>1.35–1.47(4H, m)<br>0.93(3H, t, J=7.2 Hz) | Neat<br>3309<br>2947<br>1634<br>1513<br>1269 | FAB+<br>343<br>[M⁺H⁺] (100)<br>285(27)<br>221(48) | C$_{20}$H$_{26}$N$_2$O$_3$<br>Calcd.<br>C; 70.15%<br>H; 7.65%<br>N; 8.18%<br>Found<br>C; 70.14%<br>H; 7.81%<br>N; 8.12% |
| | Colorless crystals | | | | | |
| 2-17 | (structure) | 82~83° C. | CDCl$_3$, 300 MHz<br>8.55–8.57(1H, m)<br>7.63(1H, td, J=7.6, 1.8 Hz)<br>7.42(1H, d, J=2.0 Hz)<br>7.27(1H, dd, J=8.3, 2.0 Hz)<br>7.15–7.22(2H, m)<br>6.85(1H, d, J=8.3 Hz)<br>4.07(2H, t, J=6.9 Hz)<br>3.90(3H, s)<br>3.84(2H, q, J=6.0 Hz)<br>3.10(2H, t, J=6.0 Hz)<br>1.80–1.90(2H, m)<br>1.30–1.50(4H, m)<br>0.93(3H, t, J=7.0 Hz) | Neat<br>3242<br>1630<br>1508<br>1272 | FAB+<br>343<br>[M⁺H⁺] (100)<br>221(52)<br>154(74) | C$_{20}$H$_{26}$N$_2$O$_3$<br>Calcd.<br>C; 70.15%<br>H; 7.65%<br>N; 8.18%<br>Found<br>C; 70.22%<br>H; 7.86%<br>N; 8.15% |
| | Colorless crystals | | | | | |

TABLE 51-continued

| Ex. | Structural formula | m.p. | 1H NMR (δ) ppm | IRcm⁻¹ | MS | Elem. anal. |
|---|---|---|---|---|---|---|
| 2-18 | (Pale-yellow oil) | | CDCl₃, 300 MHz<br>8.38–8.58(2H, m)<br>7.49–7.64(2H, m)<br>7.27(1H, d)<br>7.02–7.19(3H, m)<br>6.70–6.32(3H, m)<br>3.95(2H, t, J=6.9 Hz)<br>3.86(3H, s)<br>3.55–3.90(4H, m)<br>2.81–3.33(4H, m)<br>1.78–1.91(2H, m)<br>1.30–1.50(4H, m)<br>0.93(3H, t, J=7.0 Hz) | Neat<br>2953<br>1628<br>1433<br>1261 | FAB+<br>448<br>[M⁺H⁺] (83)<br>354(29)<br>434(33)<br>221(100) | $C_{27}H_{33}N_3O_3$<br>Calcd.<br>C; 72.46%<br>H; 7.43%<br>N; 9.39%<br>Found<br>C; 71.57%<br>H; 7.66%<br>N; 9.12% |

TABLE 52

| Ex. | Structural formula | m.p. | 1H NMR (δ) ppm | IRcm⁻¹ | MS | Elem. anal. |
|---|---|---|---|---|---|---|
| 2-19 | (Yellow oil) | | CDCl₃, 300 MHz<br>8.50(4H, br s)<br>7.03(4H, br s)<br>6.81(1H, d, J=9.0 Hz)<br>6.66–6.70(2H, m)<br>3.94(2H, t, J=6.5 Hz)<br>3.88(3H, s)<br>3.44–3.73(4H, m)<br>2.70–3.00(4H, m)<br>1.79–1.90(2H, m)<br>1.31–1.50(4H, m)<br>0.93(3H, t, J=7.3 Hz). | Neat<br>2933<br>1628<br>1601<br>1261 | FAB+<br>448<br>[M+H+] (55)<br>390(14)<br>343(29)<br>221(100) | |
| 2-20 | | 83.4~<br>85.2° C. | CDCl₃, 300 MHz<br>7.1(1H, bs)<br>6.8–7.0(6H, m)<br>6.3(1H, bs)<br>3.9(2H, d, J=7.5 Hz)<br>3.9(3H, s)<br>3.6–3.8(2H, m)<br>2.6–3.0(2H, m)<br>2.8(3H, bs)<br>1.7–1.9(2H, m)<br>1.3–1.5(4H, m)<br>0.9(3H, t, J=7.5 Hz) | KBr<br>3300<br>2932<br>2362<br>1606<br>1516 | FAB+<br>372<br>[M⁺H⁺] (35)<br>221(40) | $C_{22}H_{29}NO_4$<br>Calcd.<br>C; 71.13%<br>H; 7.87%<br>N; 3.77%<br>Found<br>C; 71.41%<br>H; 8.07%<br>N; 3.88% |
| 2-21 | (Colorless crystals) | 128~<br>129° C. | DMSO-d6, 300 MHz<br>9.14(1H, s)<br>8.34(1H, t)<br>7.41–7.43(2H, m)<br>6.97–7.02(3H, m)<br>6.67(2H, d, J=8.4 Hz)<br>4.00(2H, t, J=6.8 Hz)<br>3.79(3H, s)<br>3.33–3.43(2H, m)<br>2.70(2H, t, J=7.5 Hz)<br>1.72–1.86(1H, m)<br>1.62(2H, q, J=6.8 Hz)<br>0.93(6H, d, J=6.6 Hz) | | FAB+<br>358<br>[M⁺H⁺] (65)<br>221(99)<br>150(100) | |

TABLE 53

| Ex. | Structural formula | m.p. | 1H NMR (δ) ppm | IRcm⁻¹ | MS | Elem. anal. |
|---|---|---|---|---|---|---|
| 2-22 | (structure: 4-MeO-3-(2-ethylbutoxy)benzamide linked to N-CH2CH2-(4-hydroxyphenyl)) Colorless crystals | 97~98° C. | DMSO-d6, 300 MHz<br>9.14(1H, s)<br>8.34(1H, t)<br>7.41–7.44(2H, m)<br>6.98–7.03(2H, m)<br>6.67(2H, d, J=8.4 Hz)<br>3.86(2H, d, J=5.8 Hz)<br>3.80(3H, s)<br>3.27–3.94(2H, m)<br>2.70(2H, t, J=7.3 Hz)<br>1.58–1.70(1H, m)<br>1.33–1.54(4H, m)<br>0.90(6H, 1, J=7.4 Hz) | | FAB+<br>372<br>[M⁺H⁺] (55)<br>235(71)<br>150(100) | |
| 2-23 | (structure: 4-MeO-3-(cyclopropylmethoxy)benzamide linked to N-CH2CH2-(4-hydroxyphenyl)) Colorless crystals | 168~169° C. | DMSO-d6, 300 MHz<br>9.14(1H, s)<br>8.33(1H, t, J=5.4 Hz)<br>7.37–7.45(2H, m)<br>6.97–7.02(3H, m)<br>6.67(2H, d, J=8.3 Hz)<br>3.80–3.82(5H, m)<br>3.24–3.44(2H, m)<br>2.70(2H, t, J=7.4 Hz)<br>1.13–1.30(1H, m)<br>0.50–0.63(2H, m)<br>0.26–9.37(2H, m) | | FAB+<br>342<br>[M⁺H⁺] (100)<br>205(42)<br>185(38)<br>150(50) | |
| 2-24 | (structure: 4-MeO-3-pentyloxybenzamide linked to N-CH(CONH2)-CH2-(4-hydroxyphenyl)) | 199.3~200.9° C. | DMSO-d6, 300 MHz<br>9.10(1H, s)<br>8.22(1H, d, J=8.5 Hz)<br>7.42(1H, bs)<br>7.40(1H, d, J=8.48 Hz)<br>7.35(1H, s)<br>7.10(2H, d, J=8.41 Hz)<br>7.01(2H, bs)<br>6.78(1H, d, J=8.48 Hz)<br>6.60(2H, d, J=8.41 Hz)<br>4.45–4.57(1H, m)<br>3.92–4.00(2H, m)<br>3.79(3H, s)<br>2.97(1H, dd, J=13.6, 4.7 Hz)<br>2.85(1H, dd, J=13.6, 10.9 Hz)<br>1.65–1.79(2H, m)<br>1.28–1.48(4H, m)<br>0.91(3H, t, J=7.01 Hz) | KBr<br>3600–<br>3000<br>1652<br>1612 | FAB+<br>401<br>[M⁺H⁺] (35)<br>384(40)<br>221(100) | C₂₂H₂₈N₂O₅<br>Calcd.<br>C; 65.98%<br>H; 7.05%<br>N; 6.99%<br>Found<br>C; 66.02%<br>H; 7.10%<br>N; 6.91% |

TABLE 54

| Ex. | Structural formula | m.p. | 1H NMR (δ) ppm | IRcm⁻¹ | MS | Elem. anal. |
|---|---|---|---|---|---|---|
| 2-25 | (structure: 4-MeO-3-pentyloxybenzamide linked to N-CH(COOMe)-CH2-(4-hydroxyphenyl)) | | CDCl₃, 300 MHz<br>7.4(1H, d, J=3 Hz)<br>7.2(1H, dd, J=9.3 Hz)<br>7.0(2H, d, J=9 Hz)<br>6.8(1H, d, J=9 Hz)<br>6.7(2H, d, J=9 Hz)<br>6.5(1H, m)<br>5.9(1H, bs)<br>5.0(1H, m)<br>4.0(2H, t, J=9 Hz)<br>3.9(3H, s)<br>3.8(3H, s)<br>3.2(2H, m)<br>1.7–1.8(2H, m)<br>1.3–1.5(4H, m)<br>0.9(3H, t, J=4 Hz) | Neat<br>3331<br>1743<br>1506 | FAB+<br>416<br>[M⁺H⁺] (30)<br>237(30)<br>221(100) | |

TABLE 54-continued

| Ex. | Structural formula | m.p. | 1H NMR (δ) ppm | IRcm⁻¹ | MS | Elem. anal. |
|---|---|---|---|---|---|---|
| 2-26 | | 160~161° C. | CDCl₃, 300 MHz<br>7.39(1H, d, J=2.0 Hz)<br>7.21(1H, dd, J=8.1, 2.0 Hz)<br>6.84(1H, d, J=8.1 Hz)<br>6.62(1H, s)<br>6.57(1H, s)<br>6.17(1H, d, J=7.7 Hz)<br>4.29–4.42(1H, m)<br>4.04(2H, t, J=7.2 Hz)<br>3.89(3H, s)<br>3.05(1H, dd, J=16.1, 5.2 Hz)<br>2.75(2H, t, J=6.9 Hz)<br>2.60(1H, dd, J=16.1, 8.5 Hz)<br>1.30–2.12(10H, m)<br>0.92(3H, t, J=7.0 Hz) | Neat<br>3456<br>1503<br>1270 | FAB+<br>400<br>[M⁺H⁺] (83)<br>238(66)<br>221(100) | C₂₃H₂₉NO₅<br>Calcd.<br>C; 69.15%<br>H; 7.32%<br>N; 3.51%<br>Found<br>C; 68.57%<br>H; 7.39%<br>N; 3.43% |
| 2-27<br>Colorless crystals | | 152~154° C. | CDCl₃, 300 MHz<br>7.36(1H, d, J=2.0 Hz)<br>7.13(dd, J=8.3, 2.0 Hz)<br>6.50–5.91(4H, m)<br>5.99–6.08(1H, m)<br>5.52(1H, s)<br>4.04(2H, t, J=6.9 Hz)<br>3.89(3H, s)<br>3.85(3H, s)<br>3.66(2H, q, J=6.9 Hz)<br>2.86(2H, t, J=6.9 Hz)<br>1.80–1.91(2H, m)<br>1.33–1.50(4H, m)<br>0.93(3H, t, J=7.0 Hz) | Neat<br>3280<br>1508<br>1274 | FAB+<br>388<br>[M⁺H⁺] (72)<br>221(100) | C₂₂H₂₉NO₃<br>Calcd.<br>C; 68.20%<br>H; 7.54%<br>N; 3.61%<br>Found<br>C; 78.23%<br>H; 7.69%<br>N; 3.60% |

TABLE 55

| Ex. | Structural formula | m.p. | 1H NMR (δ) ppm | IRcm⁻¹ | MS | Elem. anal. |
|---|---|---|---|---|---|---|
| 2-28 | | 73.1~73.5° C. | CDCl₃, 300 MHz<br>8.16–8.26(1H, m)<br>7.70(1H, d, J=8.0 Hz)<br>7.04–7.16(3H, m)<br>7.01(1H, d, J=8.0 Hz)<br>6.79(2H, d, J=8.5 Hz)<br>6.00(1H, s)<br>3.85(3H, s)<br>3.91(2H, t, J=6.9 Hz)<br>3.85(3H, s)<br>3.69(2H, q, J=6.68 Hz)<br>2.85(2H, t, J=7.2 Hz)<br>1.50–1.65(2H, m)<br>1.22–1.40(4H, m)<br>0.91(3H, t, J=6.8 Hz) | | FAB+<br>358<br>[M⁺H⁺] (100)<br>221(40)<br>150.9(70) | |
| 2-29 | | 76.2~77.0° C. | DMSO-d6, 300 MHz<br>9.76(1H, d, J=4.4 Hz)<br>9.13(1H, s)<br>8.39(1H, d, bs)<br>7.59(1H, d, J=1.8 Hz)<br>7.45(1H, d, J=1.8 Hz)<br>7.36(1H, dd, J=8.8, 1.8 Hz)<br>6.99(2H, d, J=5.4 Hz)<br>6.65(2H, d, J=8.4 Hz)<br>4.02(2H, t, J=6.6 Hz)<br>3.2–3.4(2H, m)<br>2.67(2H, t, J=7.5 Hz)<br>1.7–1.8(2H, m)<br>1.3–1.5(4H, m)<br>0.88(3H, t, J=7.2 Hz) | KBr<br>3242<br>2931<br>1637<br>1515<br>1496 | | |

TABLE 55-continued

| Ex. | Structural formula | m.p. | 1H NMR (δ) ppm | IRcm$^{-1}$ | MS | Elem. anal. |
|---|---|---|---|---|---|---|
| 2-30 | (structure: 4-hydroxy-3-pentyloxy-N-methyl-N-[2-(4-hydroxyphenyl)ethyl]benzamide) | | DMSO-d6, 300 MHz<br>9.48(1H, bs)<br>9.20(1H, s)<br>6.5–7.2(7H, m)<br>3.9–4.0(2H, m)<br>3.3–3.5(2H, m)<br>2.7–3.0(3H, m)<br>2.6–2.7(2H, m)<br>1.6–1.8(2H, m)<br>1.3–1.5(4H, m)<br>0.87(3H, t, J=7.0 Hz) | | FAB+<br>358<br>[M$^+$H$^{+1}$] (20) | |

TABLE 56

| Ex. | Structural formula | m.p. | 1H NMR (δ) ppm | IRcm$^{-1}$ | MS | Elem. anal. |
|---|---|---|---|---|---|---|
| 2-31 | (structure) | 77.5~<br>77.8° C. | DMSO-d6, 300 MHz<br>9.84(1H, s)<br>9.80(1H, d, J=8.1 Hz)<br>9.22(1H, s)<br>7.76(1H, dd, J=8.1, 2.0 Hz)<br>7.49(1H, s)<br>7.47(2H, d, J=8.8 Hz)<br>7.42(1H, d, J=8.1 Hz)<br>6.72(2H, d, J=8.8 Hz)<br>4.07(2H, t, J=6.6 Hz)<br>1.7–1.8(2H, m)<br>1.3–1.4(4H, m)<br>0.90(3H, t, J=7.2 Hz) | Neat<br>3383<br>2955<br>1646<br>1602<br>1513 | FAB+<br>316<br>[M+H+] (25) | |
| 2-32 | (structure) | | CDCl$_3$, 300MHz<br>7.58(1H, s)<br>7.49(1H, d, J=8.44 Hz)<br>7.09(2H, d, J=8.36 Hz)<br>6.81(1H, d, J=8.44 Hz)<br>6.78(2H, d, J=8.36 Hz)<br>5.96–6.03(1H, m)<br>5.18(1H, s)<br>3.83(3H, s)<br>3.65(2H, q, J=6.53 Hz)<br>2.82–2.86 (2H, m)<br>1.73–1.78(2H, m)<br>1.32(6H, s)<br>1.10–1.26(6H, m)<br>0.85–0.95(2H, m)<br>0.82(3H, t, J=6.82 Hz) | Neat<br>3500–<br>2970<br>1634 | FAB+<br>398<br>[M+H+] (90)<br>261(100)<br>121(42) | |
| 2-33 | (structure) | | CDCl$_3$, 300 MHz<br>8.52(2H, d, J=5.99 Hz)<br>7.60(1H, s)<br>7.49(1H, d, J=8.49 Hz)<br>7.17(2H, d, J=5.99 Hz)<br>6.84(1H, d, J=8.49 Hz)<br>6.0–6.10(1H, m)<br>3.85(3H, s)<br>3.71(2H, q, J=6.66 Hz)<br>2.95(2H, t, J=6.96 Hz)<br>1.73–1.83(2H, m)<br>1.33(6H, s)<br>1.10–1.27(6H, m)<br>0.84–1.00(2H, m)<br>0.83(3H, d, J=6.7 Hz) | Neat<br>3300<br>1633 | FAB+<br>383<br>[M$^+$H$^+$] (70)<br>261(60) | |

TABLE 57

| Ex. | Structural formula | m.p. | 1H NMR (δ) ppm | IRcm$^{-1}$ | MS | Elem. anal. |
|---|---|---|---|---|---|---|
| 2-34 | | | CDCl$_3$, 300 MHz<br>8.56(1H, d, J=4.90 Hz)<br>7.58–7.68(3H, m)<br>7.38–7.46(1H, m)<br>7.14–7.24(2H, m)<br>6.85(1H, d, J=8.44 Hz)<br>3.79–3.80(5H, m, involving a singlet at 3.85<br>3.10(2H, t, J=6.21 Hz)<br>1.74–1.82(2H, m)<br>1.35(6H, s)<br>1.11–1.24(6H, s)<br>0.86–0.98(2H, m)<br>0.82(3H, t, J=6.67 Hz) | Neat<br>3316<br>1634 | FAB+383<br>[M$^+$H$^{+1}$] (100)<br>261(70) | |
| 2-35 | | | CDCl$_3$, 300 MHz<br>7.49(1H, bs)<br>7.58(1H, d, J=2.25 Hz)<br>7.50(1H, dd, J=8.0, 2.25 Hz)<br>6.82(2H, d, J=8.18 Hz)<br>6.76(1H, d, J=1.88 Hz)<br>6.61(1H, dd, J=8.0, 1.88 Hz)<br>6.16(1H, d, J=5.56 Hz)<br>5.95(1H, bs)<br>3.83(3H, s)<br>3.61(2H, q, J=6.59 Hz)<br>2.77(2H, t, J=6.98 Hz)<br>1.72–1.78(2H, m)<br>1.31(6H, s)<br>1.21–1.22(6H, m)<br>0.84–0.94(2H, m)<br>0.82(3H, d, J=6.90 Hz) | Neat<br>3600–<br>3000<br>1602 | FAB+<br>414<br>[M$^+$H$^+$] (60)<br>278(25)<br>261(100) | C$_{25}$H$_{35}$NO$_4$<br>Calcd.<br>C; 72.01%<br>H; 8.53%<br>N; 3.39%<br>Found<br>C; 72.12%<br>H; 8.92%<br>N; 3.42% |
| 2-36 | | | CDCl$_3$, 300 MHz<br>7.60(1H, s)<br>7.47–7.59(1H, m)<br>6.80–6.89(2H, m)<br>6.71–6.74(2H, m)<br>6.00–6.10(1H, m)<br>5.56(1H, bs)<br>3.84(3H, s)<br>3.72(2H, q, J=7.15 Hz)<br>2.86(2H, t, J=6.7 Hz)<br>1.73–1.80(2H, m)<br>1.73–1.80(2H, m)<br>1.32(6H, s)<br>1.10–1.23(6H, m)<br>0.84–1.0(2H, m)<br>0.83(3H, t, J=6.6 Hz) | KBr<br>3600–<br>3050<br>1625<br>1602 | FAB+<br>428<br>[M$^+$H$^+$] (50)<br>261(100)<br>150(43) | C$_{26}$H$_{37}$NO$_4$<br>Calcd.<br>C; 73.04%<br>H; 8.72%<br>N; 3.28%<br>Found<br>C; 73.06%<br>H; 8.82%<br>N; 3.27% |

TABLE 58

| Ex. | Structural formula | m.p. | 1H NMR (δ) ppm | IRcm$^{-1}$ | MS | Elem. anal. |
|---|---|---|---|---|---|---|
| 2-37 | | 188.9~189.5° C. | DMSO-d6, 300 MHz<br>8.53(2H, bs)<br>8.15(1H, d, J=7.63 Hz)<br>7.74(1H, d, J=8.61 Hz)<br>7.66(1H, s)<br>7.00(1H, d, J=8.61 Hz)<br>6.65(1H, s)<br>6.43(1H, s)<br>3.95–4.12(1H, m)<br>3.84(3H, s)<br>2.59–2.85(4H, m)<br>1.90–2.03(1H, m)<br>1.60–1.83(3H, m)<br>1.32(6H, s)<br>1.08–1.23(6H, m)<br>0.82–0.96(2H, m)<br>0.81(3H, t, J=6.67 Hz) | KBr<br>3282<br>2416<br>1599<br>1531 | FAB+<br>440<br>[M$^+$H$^+$] (100)<br>278(60)<br>261(90) | C$_{27}$H$_{37}$NO$_4$<br>Calcd.<br>C; 73.77%<br>H; 8.48%<br>N; 3.19%<br>Found<br>C; 73.61%<br>H; 8.72%<br>N; 3.22% |
| 2-38 | | 149.7~150.2° C. | DMSO-d6, 300 MHz<br>9.76(1H, s)<br>9.13(1H, s)<br>8.20(1H, t, J=5.49 Hz)<br>7.58(1H, s)<br>7.50(1H, d, J=8.36 Hz)<br>7.01(2H, d, J=8.42 Hz)<br>6.76(1H, d, J=8.36 Hz)<br>6.67(2H, d, J=8.42 Hz)<br>3.27–3.40(5H, m, involving a singlet at 3.06)<br>2.69(2H, t, J=7.5 Hz)<br>1.73–1.87(2H, m)<br>1.31(6H, s)<br>1.06–1.23(6H, m)<br>0.83–1.00(2H, m)<br>0.81(3H, t, J=6.6 Hz) | KBr<br>3450–3000<br>1698<br>1622<br>1574 | FAB+<br>384<br>[M$^+$H$^+$] (100)<br>264(30)<br>247(60) | C$_{24}$H$_{33}$NO$_3$<br>Calcd.<br>C; 75.16%<br>H; 8.67%<br>N; 3.65%<br>Found<br>C; 74.91%<br>H; 8.85%<br>N; 3.62% |
| 2-39 | | 159.3~160.0° C. | DMSO-d6, 300 MHz<br>8.77(1H, s)<br>8.71(1H, s)<br>8.60(1H, s)<br>8.17–8.23(1H, m)<br>7.58(1H, s)<br>7.48–7.52(1H, m)<br>6.75(1H, d, J=8.3 Hz)<br>6.63(1H, d, J=8.3 Hz)<br>6.61(1H, s)<br>6.42–6.47(1H, m)<br>3.22–3.38(5H, m, involving a singlet at 3.31)<br>2.56–2.68(2H, m)<br>1.74–1.86(2H, m)<br>1.31(6H, s)<br>1.10–1.27(6H, m)<br>0.85–1.00(2H, m)<br>0.81(3H, t, J=6.6 Hz) | KBr<br>3700–3050<br>1629<br>1602 | FAB+<br>400<br>[M$^+$H$^+$] (55)<br>264(35)<br>247(100) | C$_{24}$H$_{33}$NO$_4$<br>Calcd.<br>C; 72.15%<br>H; 8.33%<br>N; 3.66%<br>Found<br>C; 71.95%<br>H; 8.56%<br>N; 3.52% |

TABLE 59

| Ex. | Structural formula | m.p. | 1H NMR (δ) ppm | IRcm⁻¹ | MS | Elem. anal. |
|---|---|---|---|---|---|---|
| 2-40 | | 179.9~180.5° C. | CDCl₃, 300 MHz<br>9.78(1H, s)<br>8.45(2H, d, J=5.68 Hz)<br>8.23–8.29(1H, m)<br>7.56(1H, s)<br>7.25(2H, d, J=5.68 Hz)<br>6.75(1H, d, J=8.3 Hz)<br>3.42–3.51(2H, m)<br>3.30(3H, s)<br>2.80–2.88(2H, m)<br>1.74–1.83(2H, m)<br>1.30(6H, s)<br>1.08–1.20(6H, s)<br>0.84–0.98(2H, m)<br>0.80(3H, t, J=6.57 Hz) | KBr<br>3450<br>2950<br>1632<br>1602<br>1575 | FAB+<br>369<br>[M⁺H⁺]<br>(100)<br>247(20)<br>169(40) | $C_{23}H_{32}N_2O_2$<br>Calcd.<br>C; 74.96%<br>H; 8.75%<br>N; 7.60%<br>Found<br>C; 74.46%<br>H; 8.90%<br>N; 7.69% |
| 2-41 | | | CDCl₃, 300 MHz<br>7.72(1H, s)<br>7.45(1H, d, J=7.6 Hz)<br>7.42(2H, d, J=7.6 Hz)<br>7.31(1H, t, J=7.6 Hz)<br>7.06(2H, d, J=8.2 Hz)<br>7.07(1H, s)<br>7.01(2H, d, J=8.2 Hz)<br>6.27(1H, t, J=5.5 Hz)<br>3.67(2H, q, J=6.7 Hz)<br>2.84(2H, t, J=6.9 Hz)<br>1.5–1.6(2H, m)<br>1.28(3H, s)<br>1.28(3H, s)<br>1.0–1.3(6H, m)<br>0.9–1.0(2H, m)<br>0.83(3H, t, J=6.7 Hz) | | FAB+<br>368<br>[M⁺H⁺]<br>(100)<br>231(80) | |
| 2-42 | | 101.8~102.4° C. | CDCl₃, 300 MHz<br>7.52(1H, d, J=10.3 Hz)<br>7.49(1H, s)<br>7.09(2H, d, J=8.46 Hz)<br>6.81(1H, d, J=10.3 Hz)<br>6.80(2H, d, J=8.46 Hz)<br>5.98–6.10(1H, m)<br>5.32(1H, s)<br>3.84(3H, s)<br>3.65(2H, q, J=6.56 Hz)<br>2.85(2H, t, J=6.92 Hz)<br>2.59(2H, t, J=7.73 Hz)<br>1.48–1.60(2H, m)<br>1.22–1.40(4H, m)<br>0.88(3H, t, J=6.68 Hz) | | FAB+<br>356.1<br>[M⁺H⁺]<br>(100)<br>236(30)<br>219(80) | |

TABLE 60

| Ex. | Structural formula | m.p. | 1H NMR (δ) ppm | IRcm⁻¹ | MS | Elem. anal. |
|---|---|---|---|---|---|---|
| 2-43 | 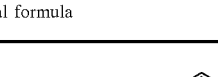 | 88.6~89.4° C. | 8.53(1H, d, J=5.97 Hz)<br>7.52(1H, d, J=8.7 Hz)<br>7.50(1H, s)<br>7.18(2H, d, J=5.97 Hz)<br>6.82(1H, d, J=8.7 Hz)<br>6.00–6.13(1H, m)<br>3.85(3H, s)<br>3.72(2H, q, J=6.67 Hz)<br>2.95(2H, t, J=6.96 Hz)<br>2.60(2H, t, J=7.74 Hz)<br>1.49–1.60(2H, m)<br>1.25–1.40(4H, m)<br>0.88(3H, t, J=6.86 Hz) | | FAB+<br>341<br>[M⁺H⁺] (100)<br>219(40)<br>105.9(87) | |

TABLE 60-continued

| Ex. | Structural formula | m.p. | 1H NMR (δ) ppm | IRcm$^{-1}$ | MS | Elem. anal. |
|---|---|---|---|---|---|---|
| 2-44 | | 116.6~116.9° C. | CDCl$_3$, 300 MHz<br>7.34(1H, d, J=2.1 Hz)<br>7.12(1H, dd, J=8.4, 2.1 Hz)<br>7.02(2H, d, J=8,3 Hz)<br>6.83(1H, d, J=8.4 Hz)<br>6.65(2H, d, J=8.3 Hz)<br>6.01(1H, bt)<br>4.02(2H, I, J=6.6 Hz)<br>4.01(2H, t, J=6.6 Hz)<br>3.63(2H, q, J=6.8 Hz)<br>3.60(2H, bs)<br>2.80(2H, t, J=6.8 Hz)<br>1.8–1.9(4H, m)<br>1.3–1.5(8H, m)<br>0.93(3H, t, J=7.0 Hz)<br>0.93(3H, t, J=7.0 Hz) | KBr<br>3327<br>2934<br>1626<br>1513<br>1270<br>1226 | FAB+<br>413<br>[M$^+$H$^+$] (40)<br>277(80)<br>137(100) | C$_{25}$H$_{36}$N$_2$O$_3$<br>Calcd.<br>C; 72.78%<br>H; 8.80%<br>N; 6.79%<br>Found<br>C; 72.91%<br>H; 9.05%<br>N; 6.74% |
| 2-45 | | 127~128° C. | CDCl3, 300 MHz<br>7.34(1H, d, J=2.0 Hz)<br>7.08–7.26(3H, m)<br>6.78–6.83(3H, m)<br>6.04(1H, m)<br>5.21(1H, s)<br>3.99–4.04(4H, m)<br>3.65(2H, q, J=7.0 Hz)<br>2.85(2H, t, J=7.0 Hz)<br>1.77–1.86(4H, m)<br>1.31–1.57(12H, m)<br>0.88–0.92(6H, m) | | FAB+<br>442<br>[M$^+$H$^+$] (100) | |

TABLE 61

| Ex. | Structural formula | m.p. | 1H NMR (δ) ppm | IR cm$^{-1}$ | MS | Elem. anal. |
|---|---|---|---|---|---|---|
| 2-46 | | | CDCl3,300MHz<br>8.18(2H, d, J=8.4Hz)<br>7.40(2H, d, J=8.4Hz)<br>6.91(1H, d, J=8.9Hz)<br>6.20(1H, d, J=8.9Hz)<br>5.97(1H, bt)<br>5.78(1H, bs)<br>3.93(2H, t, J=6.7Hz)<br>3.84(3H, s)<br>3.69(2H, q, J=6.6Hz)<br>3.04(2H, t, J=6.9Hz)<br>1.70–1.83(2H, m)<br>1.30–1.50(4H, m)<br>0.93(3H, t, J=7.1Hz) | | | |
| 2-47 | | | CDCl3,300MHz<br>8.15(2H, d, J=8.1Hz)<br>7.39(2H, d, J=8.1Hz)<br>7.18(1H, d, J=8.7Hz)<br>6.94(1H, d, J=8.7Hz)<br>6.11(1H, bt)<br>4.08(2H, t, J=6.6Hz)<br>3.91(3H, s)<br>3.64(2H, q, J=6.6Hz)<br>3.00(2H, t, J=7.1Hz)<br>1.65–1.77(2H, m)<br>1.30–1.50(4H, m)<br>0.94(3H, t, J=7.1Hz) | | | |

TABLE 61-continued

| Ex. | Structural formula | m.p. | 1H NMR (δ) ppm | IR cm$^{-1}$ | MS | Elem. anal. |
|---|---|---|---|---|---|---|
| 2-48 | | | CDCl3,300MHz<br>8.19(2H, d, J=8.5Hz)<br>7.47(2H, d, J=8.5Hz)<br>7.23(1H, d, J=8.4Hz)<br>7.00(1H, d, J=8.4Hz)<br>4.13–4.40(6H, m)<br>3.92(3H, s)<br>3.73(2H, bt)<br>3.08(2H, bt)<br>1.70–1.83(2H, m)<br>1.20–1.45(7H, m)<br>0.93(3H, t, J=7.0Hz) | | | |

TABLE 62

| Ex. | Structural formula | m.p. | 1H NMR (δ) ppm | IR cm$^{-1}$ | MS | Elem. anal. |
|---|---|---|---|---|---|---|
| 2-49 | | 93.2~<br>94.1° C. | CDCl$_3$,300MHz<br>7.12(2H, d, J=8.5Hz)<br>6.98(1H, d, J=8.3Hz)<br>6.77(2H, d, J=8.5Hz)<br>6.71(1H, d, J=8.3Hz)<br>6.35(1H, bt)<br>4.90(1H, bs)<br>3.94(2H, s)<br>3.83(3H, s)<br>3.66(2H, q, J=6.6Hz)<br>3.11(2H, t, J=7.1Hz)<br>2.87(2H, t, J=7.0Hz)<br>2.05(3H, s)<br>1.5–1.6(2H, m)<br>1.3–1.4(4H, m)<br>0.91(3H, t, J=6.9Hz) | | FAB+<br>417<br>[M$^+$H$^+$](10)<br>369(100) | |
| 2-50 | | | CDCl$_3$,300MHz<br>7.57(1H, d, J=9.0Hz)<br>7.52(1H, bt)<br>7.12(2H, d, J=8.4Hz)<br>6.87(1H, d, J=9.0Hz)<br>6.78(2H, d, J=8.4Hz)<br>5.35(1H, bs)<br>3.96(2H, t, J=6.8Hz)<br>3.86(3H, s)<br>3.71(2H, q, J=6.6Hz)<br>2.88(2H, t, J=7.1Hz)<br>2.30(3H, s)<br>1.76–1.90(2H, m)<br>1.3–1.55(4H, m)<br>0.94(3H, t, J=7.2Hz) | | FAB+<br>404<br>[M$^+$H$^+$](50)<br>267(100) | |
| 2-51 | | | | | | |

TABLE 63

| Ex. | Structural formula | m.p. | 1H NMR (δ) ppm | IR cm⁻¹ MS | Elem. anal. |
|---|---|---|---|---|---|
| 2-52 | (structure with pentyloxy, pentylthio benzamide linked via NH to 4-aminophenethyl) | 101.1~102.6° C. | CDCl₃,300MHz<br>7.62(1H, d, J=3.0Hz)<br>7.40(1H, dd, J=2.1, 8.4Hz)<br>7.02(2H, d, J=8.4Hz)<br>6.78(1H, d, J=8.4Hz)<br>6.66(2H, d, J=8.4Hz)<br>5.99(1H, bt)<br>4.04(2H, t, J=6.6Hz)<br>3.64(2H, q, J=6.5Hz)<br>3.63(2H, bs)<br>2.91(2H, t, J=7.5Hz)<br>2.81(2H, t, J=6.8Hz)<br>1.7–1.8(2H, m)<br>1.62–1.73(2H, m)<br>1.28–1.54(8H, m)<br>0.94(3H, t, J=7.2Hz)<br>0.90(3H, t, J=7.1Hz) | FAB+<br>429<br>[M⁺H⁺](50)<br>293(100) | |
| 2-53 | (structure with MeO, NH₂, pentyloxy benzamide linked via NH to 4-hydroxyphenethyl)<br>Pale-yellow crystals | | CDCl3,300MHz<br>7.04(2H, d, J=8.4Hz)<br>6.92(1H, d, J=8.7Hz)<br>6.78(2H, d, J=8.4Hz)<br>6.20(1H, d, J=8.7Hz)<br>6.04(1H, bt)<br>5.71(2H, bs)<br>3.92(2H, t, J=6.8Hz)<br>3.82(3H, s)<br>3.59(2H, q, J=6.6Hz)<br>2.80(2H, t, J=6.9Hz)<br>1.70–1.85(2H, m)<br>1.30–1.50(4H, m)<br>0.92(3H, t, J=7.1Hz) | | |
| 2-54 | (structure with Br, pentyloxy benzamide linked via NH to 4-hydroxyphenethyl)<br>Colorless crystals | 139.8~140.3° C. | CDCl₃,300MHz<br>7.53(1H, d, J=8.1Hz)<br>7.34(1H, d, J=1.9Hz)<br>7.09(2H, d, J=8.5Hz)<br>6.96(1H, dd, J=1.9, 8.1Hz)<br>6.70(2H, d, J=8.5Hz)<br>6.08(1H, bt)<br>5.00(1H, bs)<br>4.06(2H, t, J=6.5Hz)<br>3.65(2H, q, J=6.6Hz)<br>3.13(2H, t, J=7.1Hz)<br>2.85(2H, t, J=6.9Hz)<br>1.6–1.75(2H, m)<br>1.33–1.5(4H, m)<br>0.92(3H, t, J=7.2Hz) | FAB+<br>407<br>[M⁺H⁺](20)<br>271(20) | |

TABLE 64

| Ex. | Structural formula | m.p. | 1H NMR (δ) ppm | IR cm⁻¹ MS | Elem. anal. |
|---|---|---|---|---|---|
| 2-55 | (structure with MeS, pentyloxy benzamide linked via NH to 4-hydroxyphenethyl)<br>Colorless crystals | 148.2~149.3° C. | CDCl₃,300MHz<br>7.27(1H, d, J=1.5Hz)<br>7.04–7.13(4H, m)<br>6.80(2H, d, J=8.4Hz)<br>6.06(1H, bt)<br>4.95(1H, s)<br>4.07(2H, t, J=6.5Hz)<br>3.67(2H, q, J=6.5Hz)<br>2.86(2H, t, J=7.7Hz)<br>2.43(3H, s)<br>1.78–1.92(2H, m)<br>1.37–1.6(4H, m)<br>0.94(3H, t, J=7.1Hz) | FAB+<br>374<br>[M⁺H⁺](30)<br>307(20) | |

TABLE 64-continued

| Ex. | Structural formula | m.p. | 1H NMR (δ) ppm | IR cm$^{-1}$ MS | Elem. anal. |
|---|---|---|---|---|---|
| 2-56 | Pale-yellow crystals | 80.8~82.7° C. | CDCl$_3$, 300MHz<br>7.53(1H, d, J=8.7Hz)<br>7.35(1H, bt)<br>7.02(2H, d, J=8.3Hz)<br>6.87(1H, d, J=8.7Hz)<br>6.63(2H, d, J=8.3Hz)<br>3.95(2H, t, J=6.7Hz)<br>3.85(3H, s)<br>3.69(2H, q, J=5.7Hz)<br>3.57(2H, bs)<br>2.83(2H, t, J=6.9Hz)<br>2.31(3H, s)<br>1.75–1.88(2H, m)<br>1.3–1.52(4H, m)<br>0.93(3H, t, J=7.1Hz) | FAB+<br>403<br>[M$^+$H$^+$](50)<br>267(100) | |
| 2-57 | Colorless crystals | 98.6~99.3° C. | CDCl$_3$, 300MHz<br>7.62(1H, bt)<br>7.56(1H, s)<br>7.48(1H, d, J=8.7Hz)<br>6.87(1H, d, J=8.7Hz)<br>6.87(1H, s)<br>3.97(2H, t, J=6.6Hz)<br>3.86(3H, s)<br>3.78(2H, q, J=6.3Hz)<br>2.97(2H, t, J=6.5Hz)<br>2.36(3H, s)<br>1.75–1.88(2H, m)<br>1.3–1.55(4H, m)<br>0.94(3H, t, J=7.1Hz) | FAB+<br>378<br>[M$^+$H$^+$](100)<br>267(50) | |

TABLE 65

| Ex. | Structural formula | m.p. | 1H NMR (δ) ppm | IR cm$^{-1}$ MS | Elem. anal. |
|---|---|---|---|---|---|
| 2-58 | | | CDCl$_3$, 300MHz<br>7.20(1H, d, J=.5Hz)<br>7.12(2H, d, J=8.6Hz)<br>6.79(1H, d, J=8.5Hz)<br>6.78(2H, d, J=8.6Hz)<br>6.70(1H, bt)<br>5.06(1H, s)<br>3.95(2H, t, J=6.7Hz)<br>3.91 (2H, s)<br>3.85(3H, s)<br>3.67(2H, q, J=6.6Hz)<br>2.88(2H, t, J=7.0Hz)<br>1.75–1.87(2H, m)<br>1.3–1.53(4H, m)<br>0.94(3H, t, J=7.1Hz) | FAB+<br>418<br>[M$^+$H$^+$]<br>(30)<br>281(100) | |
| 2-59 | Colorless crystals | 99.3~100.1° C. | CDCl$_3$, 300MHz<br>8.18(2H, d, J=8.7Hz)<br>7.63(1H, bt)<br>7.60(1H, d, J=8.6Hz)<br>7.45(2H, d, J=8.7Hz)<br>6.90(1H, d, J=8.6Hz)<br>3.96(2H, t, J=6.7Hz)<br>3.87(3H, s)<br>3.78(2H, q, J=6.6Hz)<br>3.09(2H, t, J=7.0Hz)<br>2.39(3H, s)<br>1.75–1.9(2H, m)<br>1.32–1.54(4H, m) | FAB+<br>433<br>[M$^+$H$^+$]<br>(40)<br>267(100) | |

TABLE 65-continued

| Ex. | Structural formula | m.p. | 1H NMR (δ) ppm | IR cm$^{-1}$ | MS | Elem. anal. |
|---|---|---|---|---|---|---|
| 2-60 | 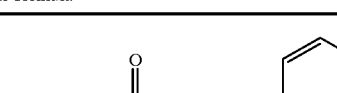<br>Colorless crystals | 97.4~<br>98.3° C. | CDCl3,300MHz<br>7.02(2H, d, J=7.8Hz)<br>6.91(1H, d, J=8.7Hz)<br>6.66(2H, d, J=7.8Hz)<br>6.19(1H, d, J=8.7Hz)<br>5.92(1H, bs)<br>5.77(2H, bs)<br>3.92(2H, t, J=6.8Hz)<br>3.83(3H, s)<br>3.61(2H, bs)<br>3.60(2H, q, J=6.5Hz)<br>2.79(2H, t, J=6.9Hz)<br>1.7–1.93(2H, m)<br>1.3–1.5(4H, m)<br>0.93(3H, t, J=7.2Hz) | KBr<br>3455<br>3311<br>2936<br>1621<br>1535<br>1287 | FAB+<br>372<br>[M$^+$H$^+$]<br>(20)<br>236(50) | C$_{21}$H$_{29}$N$_3$O$_3$ |

TABLE 66

| Ex. | Structural formula | m.p. | 1H NMR (δ) ppm | IR cm$^{-1}$ | MS | Elem. anal. |
|---|---|---|---|---|---|---|
| 2-61 | Colorless crystals | 86.5~<br>87.6° C. | CDCl3,300MHz<br>8.53(2H, d, J=6.0Hz)<br>7.16(2H, d, J=6.0Hz)<br>6.91(1H, d, J=8.9Hz)<br>6.19(1H, d, J=8.9Hz)<br>5.96(1H, bt)<br>5.78(1H, bs)<br>3.92(2H, t, J=6.8Hz)<br>3.83(3H, s)<br>3.66(2H, q, J=6.6Hz)<br>2.91(2H, t, J=6.9Hz)<br>1.70–1.83(2H, m)<br>1.30–1.50(4H, m)<br>0.92(3H, t, J=7.1Hz) | KBr<br>3345<br>1626<br>1530<br>1282 | FAB+<br>358<br>[M$^+$H$^+$](60)<br>236(70) | C$_{20}$H$_{27}$N$_3$O$_3$ |
| 2-62 | Pale-orange crystals | 116.8~<br>117.6° C. | CDCl3,300MHz<br>8.77(1H, bt)<br>8.52(2H, d, J=6.1Hz)<br>7.50(1H, d, J=8.8Hz)<br>7.23(2H, d, J=6.1Hz)<br>6.64(1H, d, J=8.8Hz)<br>3.91(3H, s)<br>3.73(2H, q, J=6.2Hz)<br>2.96(2H, t, J=7.1Hz)<br>2.87(2H, t, J=7.2Hz)<br>1.40–1.58(2H, m)<br>1.20–1.40(4H, m)<br>0.88(3H, t, J=6.8Hz) | KBr<br>3330<br>2955<br>1630<br>1529<br>1289 | FAB+<br>358<br>[M$^+$H$^+$](50)<br>307(20) | C$_{20}$H$_{27}$N$_3$O$_3$ |
| 2-63 | Colorless crystals | 128.7~<br>129.4° C. | CDCl3,300MHz<br>8.53(2H, d, J=6.0Hz)<br>7.18(2H, d, J=6.0Hz)<br>6.73(1H, s)<br>6.18(1H, s)<br>5.99(1H, bt)<br>5.35(2H, bs)<br>3.85(2H, t, J=6.6Hz)<br>3.83(3H, s)<br>3.67(2H, q, J=6.7Hz)<br>2.93(2H, t, J=7.1Hz)<br>1.70–1.80(2H, m)<br>1.30–1.50(4H, m)<br>0.92(3H, t, J=7.1Hz) | KBr<br>3332<br>2930<br>1632<br>1598<br>1542<br>1259<br>1214 | FAB+<br>358<br>[M+H+](40)<br>236(100) | C$_{20}$H$_{27}$N$_3$O$_3$ |

TABLE 67

| Ex. | Structural formula | m.p. | 1H NMR (δ) ppm | IR cm$^{-1}$ | MS | Elem. anal. |
|---|---|---|---|---|---|---|
| 2-64 | (structure: 2-amino-4-methoxy-5-pentyloxy-N-[2-(4-aminophenyl)ethyl]benzamide) Orange crystals | 125.7~127.2° C. | CDCl3,300MHz 7.59(1H, s) 7.03(2H, d, J=8.4Hz) 6.77(1H, s) 6.63(2H, d, J=8.4Hz) 5.64(1H, bt) 4.05(2H, t, J=6.8Hz) 3.93(3H, s) 3.68(2H, q, J=6.5Hz) 3.60(2H, bs) 2.85(2H, t, J=6.8Hz) 1.80–1.90(2H, m) 1.30–1.45(4H, m) 0.94(3H, t, J=7.1Hz) | KBr 3258 2934 1650 1514 1336 1272 1220 | FAB+ 402 [M+H+](20) 266(20) | $C_{21}H_{29}N_3O_3$ |
| 2-65 | (structure: 2-nitro-4-methoxy-5-pentyloxy-N-[2-(4-aminophenyl)ethyl]benzamide) Yellow oil | | CDCl3,300MHz 7.59(1H, s) 7.03(2H, d, J=8.4Hz) 6.77(1H, s) 6.63(2H, d, J=8.4Hz) 5.64(1H, bt) 4.05(2H, t, J=6.8Hz) 3.93(3H, s) 3.68(2H, q, J=6.5Hz) 3.60(2H, bs) 2.85(2H, t, J=6.8Hz) 1.80–1.90(2H, m) 1.30–1.45(4H, m) 0.94(3H, t, J=7.1Hz) | Neat 3258 2934 1650 1514 1336 1272 1221 | FAB+ 402 [M+H+](20) 266(20) | $C_{21}H_{27}N_3O_5$ |
| 2-66 | (structure: 4-methoxy-3-pentyloxy-N,N-bis[2-(4-pyridyl)ethyl]benzamide) Yellow oil | | CDCl$_3$,300MHz 8.50(4H, br s) 7.03(4H, br s) 6.81(1H, d, J=9.0Hz) 6.66–6.70(2H, m) 3.94(2H, t, J=6.5Hz) 3.88(3H, s) 3.44–3.73(4H, m) 2.70–3.00(4H, m) 1.79–1.90(2H, m) 1.31–1.50(4H, m) 0.93(3H, t, J=7.3Hz) | Neat 2933 1628 1601 1261 | FAB+ 448 [M+H+](55) 390(14) 343(29) 221(100) | |

TABLE 68

| Ex. | Structural formula | m.p. | 1H NMR (δ) ppm | IR cm$^{-1}$ | MS | Elem. anal. |
|---|---|---|---|---|---|---|
| 2-67 | (structure: 4-methoxy-3-[3-(N-methyl-N-Boc-amino)propoxy]-N-[2-(4-hydroxyphenyl)ethyl]benzamide) Yellow oil | | CDCl3,300MHz 7.1–7.5 (3H, m) 7.08(2H, d, J=8.4Hz) 6.86(2H, d, J=8.4Hz) 6.80(1H, bs) 5.91(1H, bs) 3.99(2H, bs) 3.87(3H, s) 3.64(2H, q, J=6.3Hz) 3.42(2H, t, J=6.6Hz) 2.87(3H, s) 2.84(2H, t, J=6.6Hz) 2.0–2.1(2H, m) 1.46(9H, s) | | FAB+ 459 [M+H+](50). | |

TABLE 68-continued

| Ex. | Structural formula | m.p. | 1H NMR (δ) ppm | IR cm⁻¹ | MS | Elem. anal. |
|---|---|---|---|---|---|---|
| 2-68 | Pale-yellow crystals | | CDCl3,300MHz<br>7.18(1H, d, J=4.8Hz)<br>7.18(1H, d, J=8.4Hz)<br>6.96(1H, dd, J=4.8, 3.3Hz)<br>6.88(1H, d, J=3.3Hz)<br>6.81(1H, d, J=8.4Hz)<br>6.35(1H, bs)<br>4.67(2H, d, J=6.9Hz)<br>4.14(1H, t, J=6.9Hz)<br>3.97(2H, t, J=6.6Hz)<br>3.86(3H, s)<br>3.72(2H, q, J=6.3Hz)<br>3.16(2H, t, J=6.3Hz)<br>1.7–1.9(2H, m)<br>1.3–1.5(4H, m)<br>0.93(3H, t, JJ=6.9Hz) | | FAB+<br>378<br>[M+H+](30),<br>360(100). | |
| 2-69 | Colorless crystals | | CDCl3,300MHz<br>7.11(4H, s)<br>7.10(1H, d, J=8.4Hz),<br>6.78(1H, d, J=8.4Hz),<br>6.20(1H, bs)<br>4.63(2H, d, J=6.9Hz),<br>4.20(1H, t, J=6.6Hz),<br>3.96(2H, t, J=6.6Hz),<br>3.84(3H, s),<br>3.67(2H, q, J=6.6Hz)<br>2.88(2H, t, J=6.6Hz)<br>2.32(3H, s)<br>1.7–1.9(4H, m)<br>1.3–1.5(4H, m)<br>0.91(3H, t, J=6.9Hz) | | FAB+<br>386<br>[M+H+](30)<br>368(100) | |

TABLE 69

| Ex. | Structural formula | m.p. | 1H NMR (δ) ppm | IR cm⁻¹ | MS | Elem. anal. |
|---|---|---|---|---|---|---|
| 2-70 | Pale-yellow solid | | CDCl3,300MHz<br>8.18(2H, d, J=8.4Hz),<br>7.42(2H, d, J=8.4Hz),<br>7.09(1H, d, J=8.4Hz),<br>6.78(1H, d, J=8.4Hz),<br>6.75(1H, bs)<br>3.94(2H, t, J=6.9Hz)<br>3.90(2H, q, J=5.4Hz)<br>3.85(3H, s)<br>3.72(2H, q, J=6.9Hz)<br>3.60(1H, t, J=4.8Hz)<br>3.06(2H, t, J=6.9Hz)<br>2.92(2H, t, J=5.7Hz),<br>1.7–1.8(2H, m)<br>1.3–1.5(4H, m)<br>0.92(3H, t, J=7.2Hz) | | FAB+<br>431[M+H+]<br>(100),<br>413(80). | |
| 2-71 | Colorless crystals | | CDCl3,300MHz<br>7.13(4H, s)<br>7.05(1H, d, J=8.4Hz),<br>6.75(1H, d, J=8.4Hz),<br>6.36(1H, bs)<br>4.03(1H, t, J=4.8Hz)<br>3.94(2H, t, J=6.9Hz)<br>3.87(2H, t, J=5.4Hz)<br>3.84(3H, s)<br>3.67(2H, q, J=6.6Hz)<br>2.94(2H, q, J=5.4Hz)<br>2.88(2H, t, J=5.4Hz)<br>2.33(3H, s)<br>1.7–1.8(2H, m)<br>1.3–1.5(4H, m)<br>0.92(3H, t, J=7.2Hz) | | FAB+<br>400[M+H+]<br>(100),<br>382(30). | |

TABLE 69-continued

| Ex. | Structural formula | m.p. | 1H NMR (δ) ppm | IR cm⁻¹ | MS | Elem. anal. |
|---|---|---|---|---|---|---|
| 2-72 | Colorless crystals | | CDCl3,300MHz<br>7.2–7.4(5H, m)<br>7.04(1H, d, J=8.4Hz),<br>6.75(1H, d, J=8.4Hz),<br>6.46(1H, bs)<br>3.98(1H, t, J=5.0Hz)<br>3.94(2H, t, J=6.6Hz)<br>3.86(2H, t, J=5.1Hz)<br>3.83(3H, s)<br>3.69(2H, q, J=6.6Hz)<br>2.9-3.0(4H, m)<br>1.75(2H, t, J=7.1Hz)<br>1.3–1.5(4H, m)<br>0.92(3H, t, J=6.9Hz) | | FAB+<br>386[M+H+]<br>(100) | |

TABLE 70

| Ex. | Structural formula | m.p. | 1H NMR (δ) ppm | IR cm⁻¹ | MS | Elem. anal. |
|---|---|---|---|---|---|---|
| 2-73 | Colorless crystals | | CDCl3,300MHz<br>7.16(1H, dd, J=4.7, 1.0Hz)<br>7.10(1H, d, J=8.5Hz),<br>6.95(1H, dd, J=4.7, 3.3Hz),<br>6.87(1H, dd, J=3.3, 1.0Hz)<br>6.73(1H, d, J=8.5Hz)<br>6.62(1H, bs)<br>3.94(2H, t, J=6.6Hz)<br>3.9–4.0(3H, m)<br>3.84(3H, s)<br>3.69(2H, q, J=6.3Hz)<br>3.14(2H, t, J=6.1Hz)<br>2.96(1H, t, J=5.5Hz)<br>1.75(2H, t, J=7.0Hz)<br>1.4–1.5(4H, m)<br>0.92(3H, t, J=7.0Hz) | | FAB+<br>293[M+H+]<br>(100),<br>374(25) | |
| 2-74 | Yellow crystals | | CDCl3,300MHz<br>8.18(2H, d, J=8.7Hz)<br>7.41(2H, d, J=8.7Hz)<br>7.16(1H, d, J=8.4Hz)<br>6.82(1H, d, J=8.4Hz)<br>6.40(1H, bs)<br>4.65(2H, t, J=6.6Hz),<br>3.97(2H, t, J=6.6Hz),<br>3.92(1H, t, J=6.6Hz),<br>3.86(3H, s)<br>3.74(2H, q, J=6.6Hz)<br>3.07(2H, t, J=6.6Hz)<br>1.7–1.9(2H, m)<br>1.3–1.5(4H, m)<br>0.93(3H, t, J=6.9Hz) | | FAB+<br>417<br>[M+H+](20),<br>399(100) | |
| 2-75 | | | | | | |

TABLE 71

| Ex. | Structural formula | m.p. | 1H NMR (δ) ppm | IR cm⁻¹ MS | Elem. anal. |
|---|---|---|---|---|---|
| 2-76 | | | CDCl3,300MHz<br>7.28(1H, s)<br>7.23(1H, t, J=8.0Hz)<br>7.15(1H, d, J=8.0Hz)<br>7.08(1H, s)<br>7.02(2H, d, J=8.4Hz)<br>6.98(1H, d, J=8.0Hz)<br>6.83(2H, d, J=8.4Hz)<br>6.32(1H, bt)<br>3.93(2H, t, J=7.6Hz)<br>3.64(2H, q, J=7.0Hz)<br>2.81(2H, t, J=7.0Hz)<br>1.7–1.8(2H, m)<br>1.3–1.4(4H, m)<br>0.91(3H, t, J=7.0Hz) | NaCl FAB+<br>3314 328<br>2932 [M+H+]<br>1638 (100)<br>1580 191(75)<br>1515 | |
| 2-77 | | 113.5~<br>114.2° C. | CDCl3,300MHz<br>7.43(1H, d, J=2.0Hz)<br>7.26(2H, dd, J=8.4,<br>2.0Hz)<br>6.85(1H, d, J=8.4Hz)<br>6.76(1H, bt)<br>4.06(2H, t, J=6.9Hz)<br>3.90(3H, s)<br>3.73(4H, t, J=4.6Hz)<br>3.55(2H, q, J=5.7Hz)<br>2.62(2H, t, J=5.7Hz)<br>2.53(4H, t, J=4.6Hz)<br>1.8–1.9(2H, m)<br>1.3–1.5(4H, m)<br>0.93(3H, t, J=7.0Hz) | KBr FAB+<br>3286 351<br>2945 [M+H+]<br>1654 (100)<br>1617 221(80)<br>1515 264(60) | $C_{19}H_{30}N_2O_4$<br>Calcd.<br>C; 65,12%<br>H; 8.63%<br>N; 7.99%<br>Found<br>C; 65.02%<br>H; 8.56%<br>N; 8.30% |
| 2-78 | | | | | |

TABLE 72

| Ex. | Structural formula | m.p. | 1H NMR (δ) ppm | IR cm⁻¹ MS | Elem. anal. |
|---|---|---|---|---|---|
| 2-79 | | | CDCl3,300MHz<br>7.4–7.7(5H, m)<br>7.2–7.4(1H, m)<br>6.6–6.9(7H, m)<br>3.92(2H, t, J=6.8Hz)<br>3.87(3H, s)<br>3.6–4.0(2H, m)<br>3.5–3.7(2H, m)<br>3.3–3.5(1H, m)<br>3.0–3.2(1H, m)<br>2.6–2.8(2H, m)<br>1.7–1.9(2H, m)<br>1.3–1.5(4H, m)<br>0.90(3H, t, J=7.0Hz) | Neat FAB+<br>3234 510<br>1609 [M+H+](65)<br>1516 384(45)<br>221(100) | |

TABLE 72-continued

| Ex. | Structural formula | m.p. | 1H NMR (δ) ppm | IR cm⁻¹ | MS | Elem. anal. |
|---|---|---|---|---|---|---|
| 2-80 | [Structure: 4-methoxy-3-pentyloxy-benzamide linked via NH to CH(CH₂OH)-CH₂-(4-hydroxyphenyl)] | 89.2~90.4° C. | CDCl3,300MHz<br>7.3(1H, d, J=3Hz)<br>7.2(1H, dd, J=9, 3Hz)<br>7.0(2H, d, J=9Hz)<br>6.8(1H, d, J=9Hz)<br>6.6(1H, bs)<br>6.4(1H, bt)<br>4.3–4.4(1H, m)<br>4.0(2H, t, J=7.5Hz)<br>3.9(3H, s)<br>3.4–3.8(2H, m)<br>3.2(1H, m)<br>2.8–2.9(2H, m)<br>1.7–1.9(2H, m)<br>1.2–1.5(4H, m)<br>0.91(3H, t, J=7.5Hz) | KBr<br>3324<br>2954<br>1616<br>1515<br>1264 | FAB+<br>388<br>[M+H+](45)<br>221(100) | $C_{22}H_{29}NO_5$<br>Calcd.<br>C; 68.20%<br>H; 7.54%<br>N; 3.61%<br>Found<br>C; 67.74%<br>H; 7.72%<br>N; 3.62% |
| 2-81 | [Structure: 4-methoxy-3-pentyloxy-benzamide linked via NH to CH(COOH)-CH₂-(4-hydroxyphenyl)] | | DMSO-d6,300MHz<br>12.50(1H, bs)<br>9.14(1H, s)<br>8.43(1H, d, J=8.2Hz)<br>7.42(2H, bd, J=8.5Hz)<br>7.35(1H, bs)<br>7.10(2H, d, J=8.3Hz)<br>7.00(1H, d, J=8.5Hz)<br>6.63(2H, d, J=8.3Hz)<br>4.4–4.6(1H, m)<br>3.97(2H, t, J=6.4Hz)<br>3.80(3H, s)<br>2.9–3.0(2H, m)<br>1.7–1.8(2H, m)<br>1.3–1.5(4H, m)<br>0.91(3H, t, J=6.9Hz) | KBr<br>3431<br>3303<br>1740<br>1641<br>1509 | FAB+<br>402<br>[M+H+](60)<br>221(100)<br>237(42) | $C_{22}H_{27}NO_6$<br>Calcd.<br>C; 65.82%<br>H; 6.78%<br>N; 3.49%<br>Found<br>C; 63.00%<br>H; 6.84%<br>N; 3.26% |

TABLE 73

| Ex. | Structural formula | m.p. | 1H NMR (δ) ppm | IR cm⁻¹ | MS | Elem. anal. |
|---|---|---|---|---|---|---|
| 2-82 | [Structure: 4-methoxy-3-pentyloxy-benzamide linked via NH-CH₂ to 4-methoxyphenyl] | | | | | |
| 2-83 | [Structure: 4-methoxy-3-pentyloxy-benzamide linked via NH-CH₂CH₂ to 3,4-dihydroxyphenyl]<br>Colorless crystals | | DMSO-d6,300MHz<br>8.55–8.80(2H, m)<br>8.35(1H, t)<br>7.38–7.47(2H, m)<br>7.00(1H, d, J=8.5Hz)<br>6.64(1H, d, J=8.5Hz)<br>6.62(1H, d, J=2.2Hz)<br>6.46(1H, dd, J=8.5, 2.2Hz)<br>3.98(2H, t, J=6.7Hz)<br>3.80(3H, s)<br>3.29–3.41(2H, m)<br>2.63(2H, t, J=8.3Hz)<br>1.68–1.80(2H, m)<br>1.28–1.47(4H, m)<br>0.90(3H, t, J=6.7Hz) | 3435<br>3253<br>1561<br>1508<br>1275 | FAB+<br>374<br>[M+H+](37)<br>307(19)<br>238(45)<br>169(57)<br>154(100) | $C_{21}H_{27}NO_5$<br>Calcd.<br>C; 67.54%<br>H; 7.29%<br>N; 3.75%<br>Found<br>C; 68.30%<br>H; 7.49%<br>N; 3.65% |

TABLE 73-continued

| Ex. | Structural formula | m.p. | 1H NMR (δ) ppm | IR cm⁻¹ | MS | Elem. anal. |
|---|---|---|---|---|---|---|
| 2-84 | 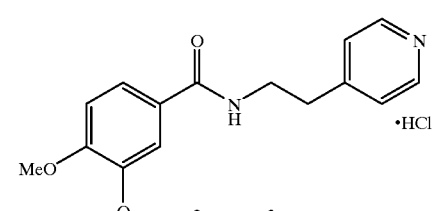<br>Pale-yellow amorphous | | DMSO-d6,300MHz<br>8.74(2H, d, J=6.0Hz)<br>8.50(1H, brs)<br>7.81(2H, d, J=6.0Hz)<br>7.38–7.42(2H, m)<br>6.99(1H, d, J=8.0Hz)<br>3.96(2H, t, J=6.8Hz)<br>3.80(3H, s)<br>3.60(2H, q, J=6.5Hz)<br>3.10(2H, t, J=6.5Hz)<br>1.66–1.78(2H, m)<br>1.27–1.46(4H, m)<br>0.90(3H, t, J=6.5Hz) | 2934<br>1638<br>1505<br>1268 | FAB+<br>343<br>[M+H+−HCl]<br>(100) | |

TABLE 74

| Ex. | Structural formula | m.p. | 1H NMR (δ) ppm | IR cm⁻¹ | MS | Elem. anal. |
|---|---|---|---|---|---|---|
| 2-85 | 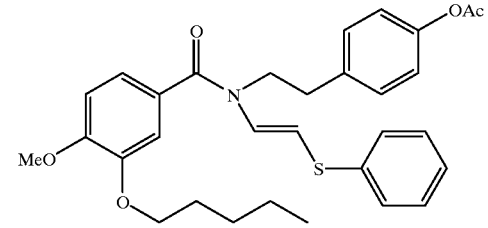 | | CDCl3,300MHz<br>7.1–7.3(5H, m)<br>7.27(1H, d, J=8.2Hz)<br>7.22(2H, d, J=8.5Hz)<br>7.04(2H, d, J=8.5Hz)<br>6.9–7.1(2H, m)<br>6.87(1H, d, J=8.2Hz)<br>5.68(1H, d, J=13.6Hz)<br>4.11(2H, t, J=7.8Hz)<br>3.98(2H, t, J=6.9Hz)<br>3.90(3H, s)<br>3.03(2H, t, J=7.8Hz)<br>2.29(3H, s)<br>1.7–1.9(2H, m)<br>1.3–1.5(4H, m)<br>0.92(3H, t, J=7.1Hz) | Neat<br>2932<br>1760<br>1659<br>1600 | | |
| 2-86 | 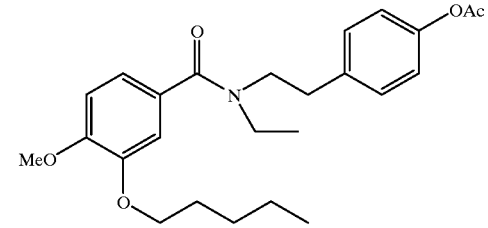 | | CDCl3,300MHz<br>6.8–7.3(7H, m)<br>3.99(2H, t, J=6.9Hz)<br>3.88(3H, s)<br>3.2–3.8 (4H, m)<br>2.8–3.0(2H, m)<br>2.28(3H, s)<br>1.8–1.9(2H, m)<br>1.3–1.5(4H, m)<br>1.0–1.2(3H, m)<br>0.92(3H, t, J=7.1Hz) | Neat<br>2933<br>1762<br>1628 | FAB+<br>482<br>[M+H+](25)<br>221(100) | |
| 2-87 | 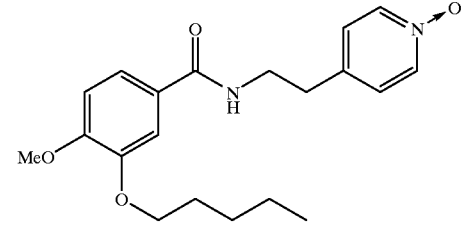<br>Colorless oil | | CDCl3,300MHz<br>8.07(2H, brd)<br>7.41(1H, d, J=1.7Hz)<br>7.20(1H, brd, J=8.3Hz)<br>7.13(2H, d, J=6.5Hz)<br>6.84(1H, d, J=8.3Hz)<br>6.44–6.65(1H, m)<br>4.05(2H, t, J=6.9Hz)<br>3.90(3H, s)<br>3.69(2H, q, J=6.7Hz)<br>2.96(2H, t, J=6.7Hz)<br>1.78–1.90(2H, m)<br>1.30–1.50(4H, m)<br>0.92(3H, t, J=7.0Hz) | | FAB+<br>359<br>[M+H+](95)<br>221(55)<br>151(53)<br>122(100) | |

TABLE 75

| Ex. | Structural formula | m.p. | 1H NMR (δ) ppm | IR cm$^{-1}$ | MS | Elem. anal. |
|---|---|---|---|---|---|---|
| 2-88 | Colorless crystals | 110~112° C. | CDCl3,300MHz<br>8.54–8.56(1H, m)<br>7.73(1H, td, J=7.7, 1.9Hz)<br>7.48(1H, d, J=7.9Hz)<br>7.36(1H, d, J=1.9Hz)<br>7.22–7.27(2H, m)<br>6.85(1H, d, J=8.4Hz)<br>6.59–6.69(1H, m)<br>5.00(2H, m)<br>3.99–4.09(3H, m)<br>3.90(3H, s)<br>3.60–3.69(1H, m)<br>1.81–1.91(2H, m)<br>1.36–1.50(4H, m)<br>0.93(3H, t, J=7.0Hz) | 3310<br>1637<br>1510<br>1269<br>1230 | FAB+<br>359<br>[M+H+](51)<br>307(27)<br>221(36)<br>154(100) | $C_{20}H_{26}N_2O_4$<br>Calcd.<br>C; 67.02%<br>H; 7.31%<br>N; 7.82%<br>Found<br>C; 67.11%<br>H; 7.43%<br>N; 7.78% |
| 2-89 | Colorless crystals | 117~118° C. | CDCl3,300MHz<br>8.18(1H, d, J=2.9Hz)<br>7.39(1H, d, J=1.8Hz)<br>7.05(1H, dd, J=8.3, 1.8Hz)<br>7.17–7.25(1H, m)<br>7.14(1H, dd, J=8.2, 2.9Hz)<br>7.08(1H, d, J=8.2Hz)<br>6.85(1H, d, J=8.3Hz)<br>4.04(2H, t, J=6.7Hz)<br>3.89(3H, s)<br>3.79(2H, q, J=6.4Hz)<br>1.77–1.90(2H, m)<br>1.32–1.49(4H, m)<br>0.92(3H, t, J=7.0Hz) | | FAB+<br>359<br>[M+H+](35)<br>221(29)<br>154(100) | |
| 2-90 | Colorless crystals | 93~94° C. | CDCl3,300MHz<br>8.46–8.52(2H, m)<br>7.54–7.60(1H, m)<br>7.36(1H, d, J=2.0Hz)<br>7.22–7.28(1H, m)<br>7.14(1H, dd, J=8.3, 2.0Hz)<br>6.82(1H, d, J=8.3Hz)<br>6.00–6.11(1H, m)<br>4.04(2H, t, J=6.9Hz)<br>3.88(3H, s)<br>3.69(2H, q, J=6.8Hz)<br>2.95(2H, t, J=6.8Hz)<br>1.77–1.89(2H, m)<br>1.28–1.48(4H, m)<br>0.92(3H, t, J=7.1Hz) | 3316<br>1521<br>1272<br>1231 | | $C_{20}H_{26}N_2O_3$<br>Calcd.<br>C; 70.15%<br>H; 7.65%<br>N; 8.18%<br>Found<br>C; 70.18%<br>H; 7.85%<br>N; 8.12% |

TABLE 76

| Ex. | Structural formula | m.p. | 1H NMR (δ) ppm | IR cm$^{-1}$ | MS | Elem. anal. |
|---|---|---|---|---|---|---|
| 2-91 | Colorless crystals | | DMSO-d6,300MHz,<br>8.83(2H, d, J=6.4Hz)<br>8.47(1H, bt)<br>7.98(2H, d, J=6.4Hz)<br>7.65(1H, d, J=8.5Hz)<br>7.59(1H, s)<br>6.98(1H, d, J=8.5Hz)<br>5.05(1H, bs)<br>3.82(3H, s)<br>3.62(2H, q, J=6.0Hz)<br>3.16(2H, t, J=6.5Hz)<br>1.70–1.80(2H, m)<br>1.29(6H, s)<br>1.03–1.25(6H, m)<br>0.75–0.92(5H, m) | | FAB-<br>418<br>[M-H+](20)<br>417(100)<br>381(90) | $C_{24}H_{35}N_2O_2Cl$ |

TABLE 76-continued

| Ex. | Structural formula | m.p. | 1H NMR (δ) ppm | IR cm-1 MS | Elem. anal. |
|---|---|---|---|---|---|
| 2-92 | (Colorless crystals) | | DMSO-d6,300MHz<br>9.85(1H, s)<br>8.77(2H, d, J=6.4Hz)<br>8.30(1H, bs)<br>7.87(2H, d, J=6.4Hz)<br>7.54(1H, s)<br>7.45(1H, d, J=8.3Hz)<br>6.76(1H, d, J=8.3Hz)<br>3.53–3.63(2H, m)<br>3.03–3.14(2H, m)<br>1.72–1.82(2H, m)<br>1.27(6H, s)<br>1.10–1.25(6H, m)<br>0.75–0.98(5H, m) | FAB-<br>403<br>[M-H+](10)<br>367(100) | $C_{23}H_{33}ClN_2O_2$ |
| 2-93 | | | | | |

TABLE 77

| Ex. | Structural formula | m.p. | 1H NMR (δ) ppm | IR cm$^{-1}$ MS | Elem. anal. |
|---|---|---|---|---|---|
| 2-94 | | | | | |
| 2-95 | (Pale-purple crystals) | 104~<br>106° C. | CDCl3, 300 MHz<br>8.03–8.11(2H, m)<br>7.40(1H, d, J=2.0 Hz)<br>7.16–7.26(3H, m)<br>6.82(1H, d, J=8.4 Hz)<br>6.58–6.70(1H, m)<br>4.04(2H, t, J=6.9 Hz)<br>3.89(3H, s)<br>3.67(2H, q, J=6.8 Hz)<br>2.92(2H, t, J=6.8 Hz)<br>1.71–1.90(2H, m)<br>1.30–1.50(4H, m)<br>0.92(3H, t, J=7.0 Hz) | 3318<br>1631<br>1512<br>1265 | FAB+<br>359[M+H+]<br>(100)<br>301(16)<br>221(21) |

TABLE 77-continued

| Ex. | Structural formula | m.p. | 1H NMR (δ) ppm | IR cm$^{-1}$ | MS | Elem. anal. |
|---|---|---|---|---|---|---|
| 2-96 | (structure) | | CDCl3, 300 MHz<br>7.37(1H, d, J=2.0 Hz)<br>7.22(1H, dd, J=8.4, 2.0 Hz)<br>7.07(2H, d, J=8.3 Hz)<br>7.01(1H, bs)<br>6.83(2H, d, J=8.4 Hz)<br>6.78(1H, d, J=8.3 Hz)<br>6.47(1H, bs)<br>4.3–4.5(1H, m)<br>4.02(2H, t, J=6.9 Hz)<br>3.88(3H, s)<br>3.41(2H, d, J=3.6 Hz)<br>3.37(3H, s)<br>2.7–3.0(2H, m)<br>1.8–1.9(2H, m)<br>1.3–1.5(4H, m)<br>0.91(3H, t, J=7.1 Hz) | Neat<br>3300<br>2933<br>1632<br>1504<br>1266 | FAB+<br>402<br>[M+H+](60)<br>221(80) | $C_{23}H_{32}NO_5$ |

TABLE 78

| Ex. | Structural formula | m.p. | 1H NMR (δ) ppm | IR cm$^{-1}$ | MS | Elem. anal. |
|---|---|---|---|---|---|---|
| 2-97 | (structure) | | CDCl3, 300 MHz<br>7.36(1H, d, J=2.0 Hz)<br>7.18(1H, dd, J=8.3, 2.0 Hz)<br>7.09(2H, d, 3=8.3 Hz)<br>6.84(1H, d, J=8.3 Hz)<br>6.77(2H, d, J=8.3 Hz)<br>6.23(1H, bd, J=6.9 Hz)<br>6.0(1H, bs)<br>4.4–4.6(1H, m)<br>4.00(2H, t, J=6.8 Hz)<br>3.89(3H, s)<br>2.94(2H, dd, J=6.9, 2.1 Hz)<br>2.71(2H, d, J=5.8 Hz)<br>2.15(3H, s)<br>1.8–1.9(2H, m)<br>1.3–1.5(4H, m)<br>0.92(3H, t, J=7.0 Hz). | Neat<br>3500<br>2926<br>1631<br>1512<br>1267 | FAB+<br>418<br>[M+H+](20)<br>221(40)<br>151(30) | |
| 2-98 | (structure) | 127.5~<br>128.5° C. | CDCl3, 300 MHz<br>7.05(1H, d, J=8.4 Hz)<br>7.02(2H, d, J=8.5 Hz)<br>6.75(2H, d, J=8.5 Hz)<br>6.74(1H, d, J=8.4 Hz)<br>6.46(1H, bs)<br>6.30(1H, bs)<br>4.50(1H, bs)<br>3.94(2H, t, J=6.7 Hz)<br>3.89(2H, q, J=5.6 Hz)<br>3.83(3H, s)<br>3.64(2H, q, J=6.9 Hz)<br>2.95(2H, t, J=5.6 Hz)<br>2.84(2H, t, J=6.9 Hz)<br>1.7–1.8(2H, m)<br>1.3–1.5(4H, m)<br>0.92(3H, t, J=7.0 Hz) | 3152<br>1943<br>1623<br>1543<br>1489<br>1279 | FB+<br>402[M+H+]<br>(100) | $C_{23}H_{31}NO_5$<br>Calcd.<br>C; 68.81%<br>H; 7.78%<br>N; 3.49%<br>Found<br>C; 68.34%<br>H; 7.70%<br>N; 3.53% |

TABLE 78-continued

| Ex. | Structural formula | m.p. | 1H NMR (δ) ppm | IR cm$^{-1}$ | MS | Elem. anal. |
|---|---|---|---|---|---|---|
| 2-99 | | | CDCl3, 300 MHz<br>7.17(2H, d, J=5.7 Hz)<br>7.11(2H, d, J=8.5 Hz)<br>6.92(1H, bs)<br>6.78(2H, d, J=8.5 Hz)<br>3.93(2H, t, J=6.7 Hz)<br>3.89(2H, q, J=5.7 Hz)<br>3.84(3H, s)<br>3.71(2H, q, J=6.7 Hz)<br>2.95(2H, t, J=6.7 Hz)<br>2.92(2H, t, J=5.7 Hz)<br>1.7–1.8(2H, m)<br>1.70(1H, bs)<br>1.3–1.5(4H, m)<br>0.92(3H, t, J=7.1 Hz) | Neat<br>3247<br>2935<br>1631<br>1596<br>1558<br>1488<br>1278<br>1086 | FAB+<br>387<br>[M+H+](90)<br>106(100) | C22H30N2O4<br>Calcd.<br>C; 68.37%<br>H; 7.82%<br>N; 7.25%<br>Found<br>C; 68.37%<br>H; 7.75%<br>N; 7.39% |

TABLE 79

| Ex. | Structural formula | m.p. | 1H NMR (δ) ppm | IR cm$^{-1}$ | MS | Elem. anal. |
|---|---|---|---|---|---|---|
| 2-100 | Colorless crystals | 96.6~<br>97.2° C. | CDCl$_3$, 300 MHz<br>8.19(1H, d, J=8.7 Hz)<br>8.02(1H, bt)<br>7.07(2H, d, J=8.4 Hz)<br>6.79(2H, d, J=8.4 Hz)<br>6.58(1H, dd, J=8.7, 2.1 Hz)<br>7.08(2H, d, J=8.0 Hz)<br>6.92(1H, d, J=8.0 Hz)<br>6.43(1H, d, J=2.1 Hz)<br>5.72(1H, s)<br>3.99(2H, t, J=6.6 Hz)<br>3.83(3H, s)<br>3.69(2H, q, J=6.7 Hz)<br>2.83(2H, t, J=6.9 Hz)<br>1.6–1.75(2H, m)<br>1.3–1.42(4H, m)<br>0.92(3H, t, J=7.1 Hz) | | FAB+<br>358<br>[M+H+]<br>(100)<br>221(20) | |
| 2-101 | | | CDCl$_3$, 300 MHz<br>7.39(1H, d, J=2.4 Hz)<br>7.22(1H, dd, J=8.4, 2.4 Hz)<br>7.05(2H, d, J=8.4 Hz)<br>6.81(2H, d, J=8.4 Hz)<br>6.79(1H, d, J=8.4 Hz)<br>6.17(1H, bt)<br>3.85(3H, s)<br>3.65(2H, q, J=6.6 Hz)<br>3.06(4H, t, J=7.8 Hz)<br>2.83(2H, t, J=7.1 Hz)<br>1.13–1.50(12H, m)<br>0.84(6H, t, J=6.8 Hz) | | FAB+<br>427<br>[M+H+]<br>(90)<br>369<br>(100) | |

TABLE 79-continued

| Ex. | Structural formula | m.p. | 1H NMR (δ) ppm | IR cm⁻¹ | MS | Elem. anal. |
|---|---|---|---|---|---|---|
| 2-102 | (structure: 4-MeO, 3-O-(4-methylpent-3-enyl)-benzamide linked to N-CH₂CH₂-(4-hydroxyphenyl)); Colorless crystals | 120.6~121.1° C. | CDCl$_3$, 300 MHz<br>7.35(1H, d, J=2.0 Hz)<br>7.16(1H, dd, J=8.1, 2.0 Hz)<br>7.07(2H, d, J=8.5 Hz)<br>6.83(2H, d, J=8.5 Hz)<br>6.80(1H, d, J=8.4 Hz)<br>6.08(1H, bt)<br>5.83(1H, bs)<br>5.1–5.2(1H, m)<br>4.00(2H, t, J=7.4 Hz)<br>3.89(3H, s)<br>3.66(2H, q, J=6.9 Hz)<br>2.84(2H, t, J=6.9 Hz)<br>2.54(2H, q, J=7.4 Hz)<br>1.73(3H, s)<br>1.65(3H, s) | Neat<br>3320<br>1510<br>1266 | FAB+<br>370<br>[M⁺H⁺]<br>(100) | C$_{22}$H$_{27}$NO$_4$<br>Calcd.<br>C; 71.52%<br>H; 7.37%<br>N; 3.79%<br>Found<br>C; 71.82%<br>H; 7.43%<br>N; 3.90% |

TABLE 80

| Ex. | Structural formula | m.p. | 1H NMR (δ) ppm | IR cm⁻¹ | MS | Elem. anal. |
|---|---|---|---|---|---|---|
| 2-103 | (structure: 4-MeO, 3-O-(4-methylpentyl)-benzamide linked to N-CH₂CH₂-(4-hydroxyphenyl)); Colorless crystals | 131.9~132.1° C. | CDCl$_3$, 300 MHz<br>7.35(1H, d, J=2.0 Hz)<br>7.13(1H, dd, J=8.4, 2.0 Hz)<br>7.06(2H, d, J=8.5 Hz)<br>6.81(1H, d, J=8.4 Hz)<br>6.79(1H, d, J=8.5 Hz)<br>6.00(1H, bs)<br>6.09(1H, bt)<br>3.99(2H, t, J=7.0 Hz)<br>3.87(3H, s)<br>3.64(2H, q, J=6.9 Hz)<br>2.83(2H, t, J=6.9 Hz)<br>1.7–1.9(2H, m)<br>1.5–1.7(1H, m)<br>1.2–1.4(2H, m)<br>0.91(3H, s)<br>0.89(3H, s) | KBr<br>3380<br>2954<br>1509<br>1267<br>1228 | FAB+<br>372[M⁺H⁺]<br>(100)<br>235(60) | C$_{22}$H$_{29}$NO$_4$<br>Calcd.<br>C; 71.13%<br>H; 7.87%<br>Np 3.77%<br>Found<br>C; 71.41%<br>H; 7.93%<br>N; 3.87% |
| 2-104 | (structure: 4-MeO, 3-N(Me)(pentyl)-benzamide linked to N-CH₂CH₂-(4-hydroxyphenyl)); Colorless crystals | 115.3~116.0° C. | CDCl$_3$, 300 MHz<br>7.36(1H, d, J=2.1 Hz)<br>7.21(1H, dd, J=8.4, 2.1 Hz)<br>7.10(2H, d, J=8.4 Hz)<br>6.8(2H, dd, J=8.4, 1.5 Hz)<br>6.05(1H, bt)<br>5.48(1H, s)<br>3.88(3H, s)<br>3.66(2H, q, J=6.6 Hz)<br>3.03(2H, t, J=7.7 Hz)<br>2.85(2H, t, J=7.1 Hz)<br>2.79(3H, s)<br>1.44–1.6(2H, m)<br>1.08–1.18(4H, m)<br>0.88(3H, t, J=6.9 Hz) | | FAB+<br>371<br>[M⁺H⁺](100)<br>313(70) | |

TABLE 80-continued

| Ex. | Structural formula | m.p. | 1H NMR (δ) ppm | IR cm⁻¹ | MS | Elem. anal. |
|---|---|---|---|---|---|---|
| 2-105 | Colorless crystals | 115.5~ 116.1° C. | CDCl₃, 300 MHz<br>7.09(2H, d, J=8.4 Hz)<br>6.98(1H, d, J=1.8 Hz)<br>6.89(1H, dd, J=8.1, 1.8 Hz)<br>6.79(2H, d, J=8.4 Hz)<br>6.68(1H, d, J=8.1 Hz)<br>6.06(1H, bt)<br>5.46(1H, bs)<br>4.25(1H, bs)<br>4.0(2H, t, J=6.5 Hz)<br>3.65(2H, q, J=6.6 Hz)<br>3.14(2H, t, J=7.1 Hz)<br>2.84(2H, t, J=6.9 Hz)<br>1.75–1.88(2H, m)<br>1.6–1.73(2H, m)<br>1.3–1.5(8H, m)<br>0.94(3H, t, J=6.8 Hz)<br>0.92(3H, t, J=7.1 Hz) | | FAB+<br>412<br>[M⁺H⁺](100)<br>276(40) | |

TABLE 81

| Ex. | Structural formula | m.p. | 1H NMR (δ) ppm | IR cm⁻¹ | MS | Elem. anal. |
|---|---|---|---|---|---|---|
| 2-106 | Pale-yellow crystals | 102.2~ 103.5° C. | CDCl₃, 300 MHz<br>7.25(1H, s)<br>7.07(2H, d, J=8.4 Hz)<br>7.07(1H, d, J=8.4 Hz)<br>6.78(2H, d, J=8.4 Hz)<br>6.46(1H, d, J=8.4 Hz)<br>5.98(1H, bt)<br>5.31(1H, bs)<br>4.01(2H, t, J=6.6 Hz)<br>3.63(2H, q, J=6.6 Hz)<br>3.14(2H, t, J=7.1 Hz)<br>2.82(2H, t, J=6.8 Hz)<br>1.75–1.85(2H, m)<br>1.58–1.7(2H, m)<br>1.3–1.5(8H, m)<br>0.85–0.97(6H, m) | | FAB+<br>413<br>[M⁺H⁺]<br>(70)<br>276<br>(100) | |
| 2-107 | Yellow oil | | CDCl3, 300 MHz<br>7.64(1H, d, J=2.2 Hz)<br>7.42(1H, d, J=1.5 Hz)<br>7.26(1H, d, J=1.5 Hz)<br>7.05–7.08(2H, m)<br>6.80–6.83(2H, m)<br>6.73–6.74(1H, d, J=2.2 Hz)<br>6.52(1H, brs)<br>6.29(1H, brt)<br>4.16(2H, t, J=6.8 Hz)<br>3.68(2H, q, J=6.8 Hz)<br>2.85(2H, t, J=6.8 Hz)<br>1.82–2.05(2H, m)<br>1.35–1.51(4H, m)<br>0.93(3H, t, J=7.2 Hz) | 2932<br>1595<br>1514<br>1341<br>1203 | FAB+<br>368<br>[M+H+]<br>(100)<br>231(90) | C₂₂H₂₅NO₄<br>Calcd.<br>C; 71.91%<br>H; 6.86%N;<br>3.81%<br>Found<br>C; 71.00%<br>H; 6.92%<br>N; 3.54% |

TABLE 81-continued

| Ex. | Structural formula | m.p. | 1H NMR (δ) ppm | IR cm⁻¹ | MS | Elem. anal. |
|---|---|---|---|---|---|---|
| 2-108 | 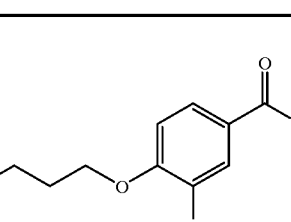 Colorless flakes | 187.0~ | DMSO-d6, 300 MHz<br>8.40(1H, bt)<br>7.74(2H, d, J=8.3 Hz)<br>7.42(2H, d, J=8.3 Hz)<br>7.3–7.5(2H, m)<br>7.26(2H, s)<br>6.70(1H, d, J=9.0 Hz)<br>3.99(2H, t, J=6.2 Hz)<br>3.97(2H, t, J=6.2 Hz)<br>3.45(2H, q, J=6.6 Hz)<br>2.91(2H, t, J=7.1 Hz)<br>1.6–1.8(4H, m)<br>1.3–1.5(8H, m)<br>0.91(3H, t, J=7.0 Hz)<br>0.90(3H, t, J=7.1 Hz). | KBr<br>3399<br>2939<br>1628<br>1505<br>1268<br>1161 | FAB+<br>477<br>[M⁺H⁺]<br>(100) | $C_{25}H_{36}N_2O_5S$<br>Calcd.<br>C; 63.00%<br>H; 7.61%<br>N; 5.88%<br>Found<br>C; 63.28%<br>H; 7.60%<br>N; 5.80% |

TABLE 82

| Ex. | Structural formula | m.p. | 1H NMR (δ) ppm | IR cm⁻¹ | MS | Elem. anal. |
|---|---|---|---|---|---|---|
| 2-109 | 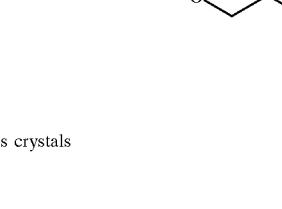 Colorless crystals | 163.5~<br>163.7° C. | CDCl₃, 300 MHz<br>7.58(1H, d, J=0.9 Hz)<br>7.43(1H, d, J=2.0 Hz)<br>7.29(1H, dd,<br>J=8.3, 2.0 Hz)<br>7.30(1H, bs)<br>6.85(1H, d, J=8.3 Hz)<br>6.85(1H, d, J=0.9 Hz)<br>4.0–4.1(4H, m)<br>3.71(2H, q, J=6.3 Hz)<br>2.90(2H, t, J=6.3 Hz)<br>1.7–1.9(4H, m)<br>1.3–1.5(8H, m)<br>0.93(3H, t, J=7.0 Hz)<br>0.92(3H, t, J=7.1 Hz) | KBr<br>3201<br>2933<br>1632<br>1514<br>1268<br>1222 | FAB+<br>388<br>[M⁺H⁺]<br>(100) | $C_{22}H_{33}N_3O_3$<br>Calcd.<br>C; 68.20%<br>H; 8.58%<br>N; 10.84%<br>Found<br>C; 68.23%<br>H; 8.61%<br>N; 10.66% |
| 2-110 | Colorless crystals | 118.3~<br>118.4° C. | CDCl₃, 300 MHz<br>8.17(2H, d, J=8.7 Hz)<br>7.40(2H, d, J=8.7 Hz)<br>7.35(1H, d, J=2.1 Hz)<br>7.13(1H, dd,<br>J=8.4, 2.1 Hz)<br>6.83(1H, d, J=8.4 Hz)<br>6.10(1H, bt)<br>4.03(2H, t, J=6.6 Hz)<br>4.02(2H, t, J=6.6 Hz)<br>3.72(2H, q, J=7.0 Hz)<br>3.05(2H, t, J=7.0 Hz)<br>1.8–1.9(4H, m)<br>1.3–1.5(8H, m)<br>0.93(3H, t, J=7.1 Hz)<br>0.92(3H, t, J=7.1 Hz) | KBr<br>3497<br>3286<br>1750<br>1627<br>1522 | FAB+<br>443<br>[M⁺H⁺]<br>(100) | $C_{25}H_{34}N_2O_5$<br>Calcd.<br>C; 67.85%<br>H; 7.74%<br>N; 6.33%<br>Found<br>C; 68.05%<br>H; 7.87%<br>N; 6.32% |

TABLE 82-continued

| Ex. | Structural formula | m.p. | 1H NMR (δ) ppm | IR cm⁻¹ | MS | Elem. anal. |
|---|---|---|---|---|---|---|
| 2-111 | (structure: 3,4-dipentyloxy-N-[2-(4-fluorophenyl)ethyl]benzamide) Colorless needles | 105.8~106.4° C. | CDCl₃, 300 MHz<br>7.34(1H, d, J=2.1 Hz)<br>7.20(1H, d, J=8.7 Hz)<br>7.18(1H, d, J=8.7 Hz)<br>7.13(1H, dd, J=8.3, 2.1 Hz)<br>7.02(1H, d, J=8.7 Hz)<br>6.99(2H, d, J=8.6 Hz)<br>6.82(1H, d, J=8.3 Hz)<br>6.00(1H, bt)<br>4.02(2H, t, J=6.7 Hz)<br>4.01(2H, t, J=6.6 Hz)<br>3.66(2H, q, J=6.8 Hz)<br>2.89(2H, t, J=6.9 Hz)<br>1.8–1.9(4H, m)<br>1.3–1.5(8H, m)<br>1.44–1.6(2H, m)<br>0.93(3H, t, J=7.1 Hz)<br>0.93(3H, t, J=7.1 Hz) | KBr<br>3279<br>2931<br>1628<br>1510<br>1227 | FAB+<br>416<br>[M⁺H⁺]<br>(100) | C₂₅H₃₄FNO₃·½H₂O<br>Calcd.<br>C; 70.73%<br>H; 8.31%N; 3.30%<br>Found<br>C; 70.70%<br>H; 8.26%<br>N; 3.26% |

TABLE 83

| Ex. | Structural formula | m.p. | 1H NMR (δ) ppm | IR cm⁻¹ | MS | Elem. anal. |
|---|---|---|---|---|---|---|
| 2-112 | (structure: 3-benzyloxy-4-methoxy-N-[2-(4-hydroxyphenyl)ethyl]benzamide) | 132~133° C. | CDCl3, 300 MHz<br>7.30–7.45(6H, m)<br>7.18(1H, dd, J=8.4, 2.2 Hz)<br>7.06–7.09(2H, m)<br>6.84(1H, d, J=8.4 Hz)<br>6.78–6.81(2H, m)<br>5.99(1H, brt)<br>5.32(1H, s)<br>5.15(2H, s)<br>3.90(3H, s)<br>3.63(2H, q, J=6.6 Hz)<br>2.83(2H, t, J=6.6 Hz) | | FAB+<br>378<br>[M+H+]<br>(27)<br>154(100) | |
| 2-113 | (structure: 4-methoxy-3-(pent-4-enyloxy)-N-[2-(4-hydroxyphenyl)ethyl]benzamide) | | | | | |
| 2-114 | (structure: 4-methoxy-3-(pent-4-ynyloxy)-N-[2-(4-hydroxyphenyl)ethyl]benzamide) | | | | | |

TABLE 84

| Ex. | Structural formula | m.p. | 1H NMR (δ) ppm | IR cm$^{-1}$ | MS | Elem. anal. |
|---|---|---|---|---|---|---|
| 2-115<br>Colorless crystals | (structure) | 114~116° C. | CDCl3, 300 MHz<br>7.36(1H, d, J=2.0 Hz)<br>7.06–7.12(3H, m)<br>6.78–6.84(3H, m)<br>6.00–6.10(2H, m)<br>5.60(1H, s)<br>5.26–5.44(2H, m)<br>4.60–4.63(3H, m)<br>4.02(2H, t, J=6.8 Hz)<br>3.65(2H, q, J=6.8 Hz)<br>2.84(2H, t, J=6.8 Hz)<br>1.79–1.88(2H, m)<br>1.30–1.50(4H, m)<br>0.92(3H, t, J=7.1 Hz) | | FAB+<br>384<br>[M+H+]<br>(100)<br>263(29)<br>247(62) | |
| 2-116<br>Colorless crystals | (structure) | 139~139° C. | CCl3, 300 MHz<br>7.34(1H, d, J=2.0 Hz)<br>7.16(1H, dd, J=8.4, 2.0 Hz)<br>7.05–7.08(2H, m)<br>6.79–6.84(3H, m)–5.97–6.09(3H, m)<br>5.24–5.43(2H, m)<br>4.57–4.60(2H, m)<br>4.02(2H, t, J=6.7 Hz)<br>2.83(2H, t, J=6.7 Hz)<br>1.78–1.87(2H, m)<br>1.37–1.45(4H, m)<br>0.92(3H, t, J=7.1 Hz) | | FAB+<br>384<br>[M+H+]<br>(100)<br>263(31)<br>247(48) | |
| 2-117 | (structure) | | | | | |

TABLE 85

| Ex. | Structural formula | m.p. | 1H NMR (δ) ppm | IR cm$^{-1}$ | MS | Elem. anal. |
|---|---|---|---|---|---|---|
| 2-118 | (structure) | | | | | |
| 2-119<br>Colorless flakes | (structure) | 121.2~121.6° C. | CDCl$_3$, 300 MHz<br>7.3–7.5(5H, m)<br>7.16(2H, d, J=8.5 Hz)<br>7.09(1H, d, J=8.5 Hz)<br>6.94(2H, d, J=8.5 Hz)<br>6.77(1H, d, J=8.5 Hz)<br>6.20(1H, bt)<br>5.05(2H, s)<br>4.66(2H, d, J=6.9 Hz)<br>4.17(1H, t, J=6.9 Hz)<br>3.98(4H, t, J=6.7 Hz)<br>3.70(2H, q, J=6.2 Hz)<br>2.88(2H, t, J=6.2 Hz)<br>1.7–1.9(4H, m)<br>1.3–1.6(8H, m)<br>0.94(3H, t, J=7.0 Hz)<br>0.94(3H, t, J=7.0 Hz) | KBr<br>3358<br>2953<br>1631<br>1511<br>1236 | FAB+<br>534<br>[M+H+](20)<br>516(100) | $C_{33}H_{43}NO_5$<br>Calcd.<br>C; 74.27%<br>H; 8.12%<br>N; 2.62%<br>Found<br>C; 74.54%<br>H; 8.15%<br>N 2.67% |

TABLE 85-continued

| Ex. | Structural formula | m.p. | 1H NMR (δ) ppm | IR cm⁻¹ | MS | Elem. anal. |
|---|---|---|---|---|---|---|
| 2-120 | | 117.7–118.7° C. | CDCl3, 300 MHz<br>8.17(2H, d, J=8.7 Hz)<br>7.41(2H, d, J=8.7 Hz),<br>7.14(1H, d, J=8.5 Hz),<br>6.80(1H, d, J=8.5 Hz)<br>6.53(1H, bt)<br>4.64(2H, s)<br>4.00(1H, bs)<br>3.98(2H, t, J=6.3 Hz),<br>3.98(2H, t, J=6.7 Hz)<br>3.73(2H, q, J=6.9 Hz)<br>3.06(2H, t, J=6.9 Hz)<br>1.7–1.9(4H, m)<br>1.3–1.5(8H, m)<br>0.94(3H, t, J=7.1 Hz)<br>093(3H, t, J=7.2 Hz) | KBr<br>3281<br>2958<br>1628<br>1522<br>1348 | FAB+<br>473<br>[M+H+](10),<br>455(100) | $C_{26}H_{36}N_2O_6$<br>Calcd.<br>C; 66.08%<br>H; 7.68%<br>N; 5.93%<br>Found<br>C; 66.38%<br>H; 7.73%<br>N; 5.88% |

TABLE 86

| Ex. | Structural formula | m.p. | 1H NMR (δ) ppm | IR cm⁻¹ | MS | Elem. anal. |
|---|---|---|---|---|---|---|
| 2-121 | Colorless crystals | 128.4~ | CDCl₃, 300 MHz<br>7.60(1H, s)<br>7.48(1H, bs)<br>7.33(1H, d, J=8.5 Hz)<br>7.33(1H, s)<br>690(1H, s)<br>6.88(1H, d, J=8.5 Hz)<br>4.77(2H, s)<br>4.70(1H, bs)<br>4.05(2H, t, J=6.6 Hz)<br>4.05(2H, t, J=6.6 Hz)<br>3.75(2H, q, J=6.0 Hz)<br>2.96(2H, t, J=6.0 Hz)<br>1.8–2.0(4H, m)<br>1.4–1.6(8H, m)<br>1.00(3H, t, J=7.1 Hz)<br>0.99(3H, t, J=7.0 Hz) | KBr<br>3205<br>2932<br>1618<br>1569<br>1276 | FAB+<br>418<br>[M⁺H⁺]<br>(30)400<br>(100) | $C_{23}H_{35}N_9O_4$<br>Calcd.<br>C; 66.16%<br>H; 8.45%<br>N; 10.06%<br>Found<br>C; 66.36%<br>H; 8.52%<br>N; 9.81% |
| 2-122 | Colorless crystals | 133~134° C. | CDCl3, 300 MHz<br>7.34(1H, d, J=1.8 Hz)<br>7.12(1H, dd, J=8.2, 1.8 Hz)<br>7.07–7.10(2H, m)<br>6.77–6.84(3H, m)<br>6.05(1H, m)<br>5.40(1H, s)<br>4.02(4H, t, J=6.6 Hz)<br>3.65(2H, q, J=6.7 Hz)<br>2.85(2H, t, J=6.7 Hz)<br>1.75–1.85(4H, m)<br>1.44–1.59(4H, m)<br>0.95–1.00(6H, m) | | FAB+<br>386<br>[M+H+]<br>(100) | |
| 2-123 | Colorless crystals | 124~125° C. | CDCl3, 300 MHz<br>7.34(1H, d, J=2.2 Hz)<br>7.07–7.26(3H, m)<br>6.78–6.83(3H, m)<br>6.06(1H, t, J=6.6 Hz)<br>5.53(1H, s)<br>4.01(4H, t, J=6.6 Hz)<br>3.65(2H, q, J=6.6 Hz)<br>2.84(2H, t, J=6.6 Hz)<br>1.74–1.88(4H, m)<br>1.22–1.52(16H, m)<br>0.89(6H, t, J=7.0 Hz) | | FAB+<br>470<br>[M+H+]<br>(100) | |

TABLE 87

| Ex. | Structural formula | m.p. | 1H NMR (δ) ppm | IR cm$^{-1}$ | MS | Elem. anal. |
|---|---|---|---|---|---|---|
| 2-124 | 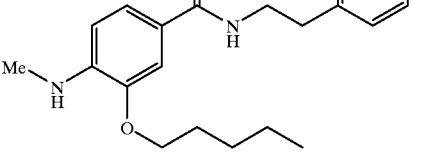 Colorless crystals | 215.1~ 215.7° C. | DMSO-d6, 300 MHz 9.12(1H, s) 8.09(1H, bt) 7.35(1H, d, J=8.4 Hz) 7.24(1H, d, J=1.5 Hz) 7.0(2H, d, J=8.1 Hz) 6.65(2H, d, J=8.1 Hz) 7.24(1H, d, J=1.5 Hz) 7.0(2H, d, J=8.1 Hz) 6.65(2H, d, J=8.1 Hz) 6.43(1H, d, J=8.4 Hz) 5.34(1H, q, J=2.7 Hz) 3.96(2H, t, J=6.6 Hz) 3.34(2H, q, J=7.8 Hz) 2.74(3H, d, J=2.7 Hz) 2.67(2H, t, J=7.5 Hz) 1.7–1.8(2H, m) 1.25–1.5(4H, m) 0.90(3H, t, J=7.1 Hz) | | FAB+ 357 [M$^+$H$^+$](70) 220(100) | |
| 2-125 | 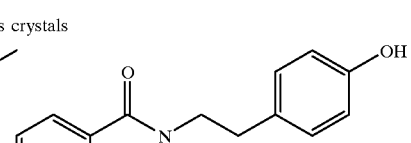 Colorless crystals | 85.3~ 86.3° C. | CDCl$_3$, 300 MHz 7.14(1H, d, J=1.8 Hz) 7.08(2H, d, J=8.4 Hz) 7.06(1H, dd, J=7.8, 1.8 Hz) 6.78(2H, d, J=8.4 Hz) 6.56(1H, d, J=7.8 Hz) 6.03(1H, bt) 3.65(2H, q, J=6.6 Hz) 3.11(2H, t, J=6.8 Hz) 3.10(2H, t, J=6.8 Hz) 1.6–1.8(4H, m) 1.3–1.5(8H, m) 0.93(6H, t, J=7.1 Hz) | | FAB+ 412 [M$^+$H$^+$](40) 185(100) | |
| 2-126 | 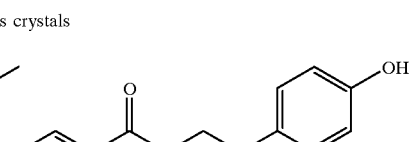 Colorless crystals | 109.4~ 110.4° C. | CDCl$_3$, 300 MHz 7.33(1H, d, J=2.4 Hz) 7.16(1H, dd, J=8.4 Hz) 7.09(2H, d, J=8.4 Hz) 6.75–6.82(3H, m) 6.04(1H, bt) 5.49(1H, bs) 4.00(2H, t, J=6.6 Hz) 3.65(2H, q, J=6.6 Hz) 3.04(2H, t, J=7.8 Hz) 2.84(2H, t, J=6.9 Hz) 2.80(3H, s) 1.8–1.95(2H, m) 1.2–1.65(8H, m) 0.93(3H, t, J=7.5 Hz) 0.88(3H, t, J=7.5 Hz) | | FAB+ 427 [M$^+$H$^+$](100) 369(50) | |

TABLE 88

| Ex. | Structural formula | m.p. | 1H NMR (δ) ppm | IR cm⁻¹ | MS | Elem. anal. |
|---|---|---|---|---|---|---|
| 2-127 | (structure: 4-amino-3-pentyloxy-N-[2-(4-hydroxyphenyl)ethyl]benzamide)<br>Colorless crystals | 138.5~<br>139.5° C. | CDCl₃, 300 MHz<br>7.29(1H, d, J=1.8 Hz)<br>7.08(2H, d, J=8.5 Hz)<br>7.0(1H, dd, J=8.1, 1.8 Hz)<br>6.9(2H, d, J=8.5 Hz)<br>6.61(1H, d, J=8.1 Hz)<br>6.0(1H, bt)<br>5.4(1H, bs)<br>4.09(2H, bs)<br>4.02(2H, t, J=6.6 Hz)<br>3.64(2H, q, J=6.6 Hz)<br>2.83(2H, t, J=6.9 Hz)<br>1.75–1.9(2H, m<br>1.3–1.5(4H, m)<br>0.93(3H, t, J=7.1 Hz) | | FAB+<br>343<br>[M⁺H⁺¹](50)<br>185(100) | |
| 2-128 | (structure: 4-methoxy-3-pentylthio-N-[2-(4-hydroxyphenyl)ethyl]benzamide)<br>Colorless crystals | 124.1~<br>124.9° C. | CDCl₃, 300 MHz<br>7.63(1H, d, J=2.1 Hz)<br>7.43(1H, dd, J=8.4, 2.1 Hz)<br>7.1(2H, d, J=8.4 Hz)<br>6.8(1H, d, J=8.4 Hz)<br>6.04(1H, bt)<br>5.25(1H, s)<br>3.92(3H, s)<br>3.66(2H, q, J=6.5Hz)<br>2.91(2H, t, J=7.4 Hz)<br>2.86(2H, t, J=6.9 Hz)<br>1.6–1.73(2H, m)<br>1.25–1.5(4H, m)<br>0.9(3H, t, J=7.2 Hz) | | FAB+<br>374<br>[M⁺H⁺](100)<br>237(60) | |
| 2-129 | (structure: 4-pentyloxy-3-pentylthio-N-[2-(4-hydroxyphenyl)ethyl]benzamide)<br>Colorless crystals | 116.3~<br>116.9° C. | CDCl₃, 300 MHz<br>7.62(1H, d, J=2.4 Hz)<br>7.41(1H, dd, J=8.7, 2.4 Hz)<br>7.09(2H, d, J=8.4 Hz)<br>6.8(2H, d, J=8.4 Hz)<br>6.78(1H, d, J=8.7 Hz)<br>6.02(1H, bt)<br>5.16(1H, s)<br>4.04(2H, t, J=6.6 Hz)<br>3.66(2H, q, J=6.5 Hz)<br>2.90(2H, t, J=7.4 Hz)<br>2.85(2H, t, J=7.4 Hz)<br>1.8–1.9(2H, m)<br>1.6–1.75(2H, m)<br>1.3–1.5(8H, m)<br>0.94(3H, t, J=69 Hz)<br>0.90(3H, t, J=7.2 Hz) | | FAB+<br>430<br>[M⁺H⁺](100)<br>309(50) | |

TABLE 89

| Ex. | Structural formula | m.p. | 1H NMR (δ) ppm | IR cm$^{-1}$ | MS | Elem. anal. |
|---|---|---|---|---|---|---|
| 2-130 | | | CDCl$_3$, 300 MHz<br>7.35(1H, d, J=2.2 Hz)<br>7.16(1H, dd, J=8.3, 2.2 Hz)<br>7.17(1H, dd, J=5.1, 1.0 Hz)<br>6.95(1H, dd, J=5.1, 3.5 Hz)<br>6.85(1H, dd, J=3.5, 1.0 Hz)<br>6.15(1H, bs)<br>4.02(2H, t, J=6.7 Hz)<br>4.01(2H, t, J=6.6 Hz)<br>3.71(2H, q, J=6.5 Hz)<br>3.14(2H, t, J=6.5 Hz)<br>1.8–1.9(4H, m)<br>1.3–1.5(8H, m)<br>0.92(3H, t, J=7.0 Hz)<br>0.92(3H, t, J=7.0 Hz) | | | |
| | Colorless crystals | | | | | |
| 2-131 | | | CDCl$_3$, 300 MHz<br>7.95(1H, s)<br>7.33(1H, d, J=2.1 Hz)<br>7.22(1H, d, J=8.7 Hz)<br>7.14(1H, dd, J=8.3, 2.1 Hz)<br>7.0–7.1(2H, m)<br>6.81(1H, dd, J=8.7, 2.5 Hz)<br>6.79(1H, d, J=6.8 Hz)<br>6.22(1H, bs)<br>5.50(1H, bs)<br>3.99(2H, t, J=6.6 Hz)<br>3.96(2H, t, J=6.3 Hz)<br>3.71(2H, q, J=6.5 Hz)<br>2.97(2H, t, J=6.5 Hz)<br>1.7–1.9(4H, m)<br>1.3–1.5(8H, m)<br>0.92(3H, t, J=6.9 Hz)<br>0.91(3H, t, J=7.0 Hz) | | FAB+<br>453<br>[M+H+]<br>(30)<br>159<br>(100)<br>277<br>(80) | |
| | Colorless amorphous | | | | | |
| 2-132 | | 130.7~<br>131.0° C. | CDCl3, 300 MHz<br>7.34(1H, d, J=2.1 Hz)<br>7.13(1H, dd, J=8.4, 2.1 Hz)<br>7.06(2H, d, J=8.5 Hz)<br>6.81(1H, d, J=8.4 Hz)<br>6.59(2H, d, J=8.5 Hz)<br>6.00(1H, bt)<br>4.02(2H, t, J=6.6 Hz)<br>4.00(1H, bs)<br>4.01(2H, t, J=6.6 Hz)<br>3.64(2H, q, J=6.7 Hz)<br>2.83(3H, s)<br>2.81(2H, t, J=6.7 Hz)<br>1.7–1.9(4H, m)<br>1.3–1.5(8H, m)<br>0.93(3H, t, J=7.1 Hz)<br>0.93(3H, t, J=7.1 Hz) | KBr<br>3370<br>2956<br>1624<br>1580<br>1523<br>1275<br>1225 | FAB+<br>427<br>[M+H+]<br>(50),<br>277<br>(100). | C26H38N2O3<br>Calcd.<br>C; 73.20%<br>H; 8.96%<br>N; 6.57%<br>Found C;<br>73.28%<br>H; 9.37%<br>N; 6.55% |
| | Colorless crystals | | | | | |

TABLE 90

| Ex. | Structural formula | m.p. | 1H NMR (δ) ppm | IR cm⁻¹ | MS | Elem. anal. |
|---|---|---|---|---|---|---|
| 2-133 | Colorless crystals | 118.5~ 118.7° C. | CDCl3, 300 MHz<br>7.34(1H, d, J=2.1 Hz)<br>7.14(1H, dd, J=8.4, 2.1 Hz)<br>7.11(2H, d, J=8.7 Hz)<br>6.82(1H, d, J=8.4 Hz)<br>6.71(2H, d, J=8.7 Hz)<br>6.00(1H, bt)<br>4.02(2H, t, J=6.6 Hz)<br>4.01(2H, t, J=6.6 Hz)<br>3.65(2H, q, J=6.7 Hz)<br>2.93(6H, s)<br>2.82(2H, t, J=6.7 Hz)<br>1.7–1.9(4H, m)<br>1.3–1.5(8H, m)<br>0.93(3H, t, J=7.1 Hz)<br>0.93(3H, t, J=7.1 Hz) | KBr<br>3302<br>2956<br>1630<br>1511<br>1269<br>1226 | FAB+441<br>[M+H+]<br>(50),<br>277<br>(100). | |
| 2-134 | Colorless crystals | 135.2~ 136.2° C. | CDCl₃, 300 MHz<br>8.40(1H, d, J=8.4 Hz)<br>7.90(1H, s)<br>7.44(1H, d, J=1.8 Hz)<br>.680(2H, d, J=8.1 Hz)<br>7.1(2H, d, J=8.1)<br>7.07(1H, d, J=8.4 Hz)<br>6.12(1H, bt)<br>5.15(1H, s)<br>4.10(2H, t,J=6.6 Hz)<br>3.66(2H, q, J=6.6 Hz)<br>2.85(2H, t, J=7.1 Hz)<br>2.42(2H, t, J=7.5 Hz)<br>1.64–1.9(4H, m)<br>1.35–1.5(6H, m)<br>0.96(3H, t, J=7.4 Hz)<br>0.95(3H, t, J=6.9 Hz) | | FAB+<br>427<br>[M⁺H⁺]<br>(100)<br>290<br>(65) | |
| 2-135 | Colorless crystals | 130.5~ 13.3° C. | CDCl₃, 300 MHz<br>7.38(1H, d, J=1.7 Hz)<br>7.34(1H, d, J=8.2 Hz)<br>7.09(2H, d, J=8.3 Hz)<br>7.02(1H, dd, J=2.1, 8.2 Hz)<br>6.78(2H, d, J=8.3 Hz)<br>6.05(1H, bt)<br>4.96(1H, s)<br>4.06(2H, t, J=6.6 Hz)<br>3.67(2H, q, J=60 Hz)<br>2.86(2H, t, J=6.9 Hz)<br>1.8–1.92(2H, m)<br>1.35–1.6(4H, m)<br>0.94(3H, t, J=7.1 Hz) | | FAB+<br>362<br>[M⁺H⁺]<br>(60)<br>225<br>(30) | |

TABLE 91

| Ex. | Structural formula | m.p. | 1H NMR (δ) ppm | IR cm⁻¹ | MS | Elem. anal. |
|---|---|---|---|---|---|---|
| 2-136 | (structure) Colorless crystals | 177.9~178.2° C. | CDCl₃, 300 MHz<br>9.62(1H, bs)<br>9.15(1H, s)<br>8.43(1H, bt)<br>8.37(1H, bs)<br>8.24(1H, d, J=8.4 Hz)<br>7.45(1H, bs)<br>7.40(1H, d, J=8.4 Hz)<br>7.01(2H, d, J=8.1 Hz)<br>6.67(2H, d, J=8.1 Hz)<br>4.07(2H, t, J=6.6 Hz)<br>3.38(2H, q, J=8.1 Hz)<br>2.70(2H, t, J=7.1 Hz)<br>1.7–1.9(2H, m)<br>1.3–1.5(4H, m)<br>0.91(3H, t, J=6.9 Hz) | | FAB+<br>371<br>[M⁺H⁺]<br>(30)<br>238<br>(20) | |
| 2-137 | (structure) Colorless crystals | 179.0~179.8° C. | DMSO-d6, 300 MHz<br>9.39(1H, bs)<br>9.33(1H, bs)<br>9.13(1H, bs)<br>8.45(1H, bt)<br>7.91(1H, bs)<br>7.67(1H, d, J=8.4 Hz)<br>7.59(1H, d, J=8.4 Hz)<br>7.0(2H, d, J=8.7 Hz)<br>6.67(2H, d, J=8.7 Hz)<br>3.38(2H, bq)<br>2.69(2H, t, J=7.4 Hz)<br>2.34(4H, t, J=7.4 Hz)<br>1.5–1.65(4H, m)<br>1.28–1.42(4H, m)<br>0.90(3H, t, J=7.4 Hz)<br>0.89(3H, t, J=7.4 Hz) | | FAB+<br>440<br>[M⁺H⁺]<br>(50)<br>356<br>(70) | |
| 2-138 | (structure) Colorless crystals | 126.9~127.6° C. | CDCl₃, 300 MHz<br>8.66(1H, s)<br>7.77(1H, bs)<br>7.69(1H, dd, J=2.2, 8.5 Hz)<br>7.08(2H, d, J=8.4 Hz)<br>6.92(1H, d, J=8.5 Hz)<br>7.68(2H, d, J=8.4 Hz)<br>6.37(1H, bt)<br>5.55(1H, s)<br>3.93(3H, s)<br>3.61(2H, q, J=6.7 Hz)<br>2.83(2H, t, J=7.1 Hz)<br>2.42(2H, t, J=7.5 Hz)<br>1.68–1.8(2H, m)<br>1.33–1.5(2H, m)<br>0.96(3H, t, J=7.3 Hz) | | FAB+<br>371<br>[M⁺H⁺]<br>(60)<br>234<br>(100) | |

TABLE 92

| Ex. | Structural formula | m.p. | 1H NMR (δ) ppm | IR cm⁻¹ | MS | Elem. anal. |
|---|---|---|---|---|---|---|
| 2-139 | [structure] Colorless crystals | 164.1~164.8° C. | CDCl$_3$, 300 MHz<br>8.64(1H, d, J=2.1 Hz)<br>7.80(1H, bs)<br>7.67(1H, dd, J=2.4, 9.0 Hz)<br>7.09(2H, d, J=8.4 Hz)<br>6.91(1H, d, J=9.0 Hz)<br>6.78(2H, d, J=8.4 Hz)<br>6.36(1H, bt)<br>5.59(1H, bs)<br>4.08(2H, t, J=6.6 Hz)<br>3.61(2H, q, J=6.7 Hz)<br>2.83(2H, t, J=6.9 Hz)<br>2.42(2H, t, J=7.5 Hz)<br>1.68–1.92(4H, m)<br>1.35–1.52(6H, m)<br>0.97(3H, t, J=7.1 Hz)<br>0.95(3H, t, J=6.9 Hz) | | FAB+<br>427<br>[M⁺H⁺](40)<br>195(100) | |
| 2-140 | [structure] Colorless crystals | 130.3~131.4° C. | CDCl$_3$, 300 MHz<br>7.26(1H, d, J=1.8 Hz)<br>7.05–7.15(4H, m)<br>6.80(2H, d, J=8.4 Hz)<br>6.05(1H br)<br>4.81(1H, s)<br>4.06(2H, t, J=6.6 Hz)<br>3.66(2H, q, 6.6 Hz)<br>2.89(2H, t, J=7.4 Hz)<br>2.86(2H, t, J=6.8 Hz)<br>1.63–1.8(4H, m)<br>1.3–1.55(8H, m)<br>0.94(3H, t, J=69 Hz)<br>0.90(3H, t, J=7.2 Hz) | | FAB+<br>430<br>[M⁺H⁺](100)<br>293(50) | |
| 2-141 | [structure] Pale-red crystals | 167.0~167.9° C. | DMSO-d6, 300 MHz<br>8.36(1H, t, J=5.4 Hz)<br>7.41(1H, dd, J=8.4, 2.1 Hz)<br>7.40(1H, d, J=2.1Hz)<br>7.00(2H, d, J=8.4Hz)<br>6.98(1H, d, J=8.4Hz)<br>6.66(2H, d, J=8.4 Hz)<br>4.02(2H, t, J=6.6 Hz)<br>3.78(3H, s)<br>3.37(2H, q, J=6.6 Hz)<br>2.69(2H, t, J=6.6 Hz)<br>2.58(2H, t, J=6.6 Hz)<br>2.26(3H, s)<br>1.84(2H, qui, J=6.6 Hz) | KBr<br>3325<br>1510 | FAB+<br>359[M+H+]<br>(100). | C20H25NO5<br>Calcd.<br>C; 66.83%<br>H; 7.01%<br>N; 3.89%<br>Found<br>C; 66.68%<br>H; 7.10%<br>N; 3.80% |

TABLE 93

| Ex. | Structural formula | m.p. | 1H NMR (δ) ppm | IR cm⁻¹ | MS | Elem. anal. |
|---|---|---|---|---|---|---|
| 2-142 | [structure] Colorless crystals | 169.0~170.0° C. | DMSO-d6, 300 MHz<br>8.36(1H, t, J=5.4 Hz)<br>7.41(1H, dd, J=8.4, 2.1 Hz)<br>7.40(1H, d, J=2.1 Hz)<br>7.00(2H, d, J=8.4 Hz)<br>6.98(1H, d, J=8.4 Hz)<br>6.66(2H, d, J=8.4 Hz)<br>4.02(2H, t, J=6.6 Hz)<br>3.78(3H, s)<br>3.37(2H, q, J=6.6 Hz)<br>2.69(2H, t, J=6.6 Hz)<br>2.58(2H, t, J=6.6 Hz)<br>2.26(3H, s)<br>1.84(2H, qui, J=6.6 Hz) | KBr<br>3500<br>1635<br>1516 | FAB+<br>359<br>[M+H+]<br>(100). | C22H26N2O4<br>Calcd.<br>C; 67.01%<br>H; 7.31%<br>N; 7.81%<br>Found<br>C; 62.45%<br>H; 6.99%<br>N; 7.23% |

TABLE 93-continued

| Ex. | Structural formula | m.p. | 1H NMR (δ) ppm | IR cm⁻¹ | MS | Elem. anal. |
|---|---|---|---|---|---|---|
| 2-143 | (structure with MeO, S-pentyl, benzamide, NH, CH2CH2, phenyl-NH2)<br>Colorless crystals | 139.1~<br>140.1° C. | CDCl₃, 300 MHz<br>7.62(1H, d, J=2.2 Hz)<br>7.42(1H, dd, J=2.3, 8.5 Hz)<br>7.01(2H, d, J=8.3 Hz)<br>6.79(1H, d, J=8.5 Hz)<br>6.64(2H, d, J=8.3 Hz)<br>5.98(1H, bt)<br>3.91(1H, s)<br>3.63(2H, q, J=6.4 Hz)<br>3.62(2H, bs)<br>2.90(2H, t, J=7.4 Hz)<br>2.80(2H, t, J=6.8 Hz)<br>1.55–1.7(2H, m)<br>1.25–1.48(4H, m)<br>0.89(3H, t, J=7.1 Hz) |  | FAB+<br>373<br>[M⁺H⁺]<br>(30)<br>237(50) |  |
| 2-144 | (structure with MeO, S-pentyl, benzamide, NH, CH2CH2, phenyl-NO2)<br>Colorless crystals | 106.9~<br>107.9° C. | CDCl₃, 300 MHz<br>8.19(2H, d, J=9.0 Hz)<br>8.65(1H, d, J=2.1 Hz)<br>7.44(1H, dd, J=2.1, 8.4 Hz)<br>7.41(2H, d, J=9.0 Hz)<br>6.82(1H, d, J=8.4 Hz)<br>6.05(1H, bt)<br>3.93(3H, t)<br>3.74(2H, q, J=6.6 Hz)<br>3.07(2H, t, J=6.9 Hz)<br>2.92(2H, t, J=7.5 Hz)<br>1.6–1.75(2H, m)<br>1.3–1.5(4H, m)<br>0.90(3H, t, J=7.1 Hz) |  | FAB+<br>403<br>[M⁺M⁺]<br>(30)<br>307(20) |  |

TABLE 94

| Ex. | Structural formula | m.p. | 1H NMR (δ) ppm | IR cm⁻¹ | MS | Elem. anal. |
|---|---|---|---|---|---|---|
| 2-145 | (structure with MeO, S-pentyl, benzamide, NH, CH2CH2, imidazole)<br>Colorless crystals | 132.2~<br>132.6° C. | CDCl₃, 300 MHz<br>7.75(1H, d, J=2.1 Hz)<br>7.60(1H, s)<br>7.59(1H, d, J=8.4 Hz)<br>7.38(1H, bs)<br>6.87(1H, s)<br>6.84(1H, d, J=8.4 Hz)<br>3.93(3H, s)<br>373(2H, q, J=6.0 Hz)<br>2.86–3.0(4H, m)<br>1.63–1.75(2H, m)<br>1.3–1.5(4H, m)<br>0.89(3H, t, J=7.2 Hz) |  | FAB+<br>348<br>[M⁺H⁺]<br>(80)<br>237(30) |  |
| 2-146 | (structure with pentyloxy, S-pentyl, benzamide, NH, CH2CH2, phenyl-NO2)<br>Colorless crystals | 106.4~<br>107.2° C. | CDCl₃, 300 MHz<br>8.19(2H, d, J=9.0 Hz)<br>7.64(1H, d, J=2.4 Hz)<br>7.42(1H, dd, J=2.7, 8.7 Hz)<br>7.41(2H, d, J=9.0 Hz)<br>6.80(1H, d, J=9.0 Hz)<br>6.04(1H, bt)<br>4.06(2H, t, J=6.5 Hz)<br>3.73(2H, q, J=6.6 Hz)<br>3.06(2H, t, J=6.9 Hz)<br>2.91(2H, t, J=7.4 Hz)<br>1.82–1.92(2H, m)<br>1.63–1.73(2H, m)<br>1.3–1.55(8H, m)<br>0.94(3H, t, J=6.9 Hz)<br>0.90(3H, t, J=7.2 Hz) |  | FAB+<br>459<br>[M⁺H⁺]<br>(90)<br>293(40) |  |

… TABLE 94-continued

| Ex. | Structural formula | m.p. | 1H NMR (δ) ppm | IR cm⁻¹ | MS | Elem. anal. |
|---|---|---|---|---|---|---|
| 2-147 | Colorless crystals | 133.2~ 134.1° C. | CDCl₃, 300 MHz<br>7.72(1H, d, J=2.2 Hz)<br>7.59(1H, s)<br>7.55(1H, dd, J=2.2, 8.5 Hz)<br>7.31(1H, bs)<br>6.85(1H, s)<br>6.80(1H, d, J=8.5 Hz<br>4.04(2H, t, J=6.6 Hz)<br>3.71(2H, q, J=5.9 Hz)<br>2.92(2H, t, J=7.3 Hz)<br>2.90(2H, t, J=6.5 Hz)<br>1.78–1.88(2H, m)<br>1.62–1.73(2H, m)<br>1.28–1.54(8H, m)<br>0.93(3H, t, J=6.7 Hz)<br>0.88(3H, t, J=7.1 Hz) | | FAB+<br>404<br>[M⁺H⁺]<br>(100)<br>293(40) | |

TABLE 95

| Ex. | Structural formula | m.p. | 1H NMR (δ) ppm | IR cm⁻¹ | MS | Elem. anal. |
|---|---|---|---|---|---|---|
| 2-148 | | | | | | |
| 2-149 | Amorphous | | CDCl3, 300 MHz<br>0.95(3H, t, J=7.00 Hz)<br>1.30–1.50(4H, m)<br>1.79(2H, q, J=7.12 Hz)<br>2.38(2H, t, J=7.61 Hz)<br>2.84(2H, t, J=7.67 Hz)<br>3.24(3H, s)<br>3.92(2H, t, J=6.59 Hz)<br>5.66(1H, s)<br>6.58–6.63(2H, m)<br>6.72(2H, d, J=8.34 Hz)<br>6.85(1H, dd, J=2.21, 8.41 Hz)<br>6.94(2H, d, J=8.25 Hz)<br>7.22–7.30(2H, m) | 3287<br>3014<br>2933<br>2871<br>1633<br>1588<br>1516 | FAB+<br>342[M+H+]<br>(100)<br>282(13) | |
| 2-150 | Colorless crystals | 83.9~ 84.2° C. | CDCl3, 300 MHz<br>0.92(3H, t, J=7.5 Hz)<br>1.32–1.45(4H, m)<br>1.76(2H, q, J=7.5 Hz)<br>2.60(2H, t, J=7.5 Hz)<br>2.96(2H, t, J=7.5 Hz)<br>3.92(2H, t, J=6.0 Hz)<br>5.42(1H, br)<br>6.65(1H, d, J=60 Hz)<br>6.75(2H, d, J=6.0 Hz)<br>6.85(1H, d, J=6.0 Hz)<br>7.07(2H, d, J=6.0 Hz)<br>7.13–7.26(1H, m) | 3092<br>2935<br>2867<br>1654<br>1620<br>1597 | FAB+<br>328[M+H+]<br>(100)<br>282(13)<br>258(12) | C₂₀H₂₅NO₃<br>Calcd.<br>C; 73.37%<br>H; 7.70%<br>N; 4.28%<br>Found<br>C; 73.22%<br>H; 7.94%<br>N; 4.30% |

TABLE 96

| Ex. | Structural formula | m.p. | 1H NMR (δ) ppm | IR cm⁻¹ | MS | Elem. anal. |
|---|---|---|---|---|---|---|
| 2-151 | (Colorless crystals) | 100.2~100.6° C. | CDCl3, 300 MHz<br>0.92(3H, t, J=7.08 Hz)<br>1.30–1.50(4H, m)<br>1.75–1.88(2H, m)<br>2.335(2H, t, J=7.61 Hz)<br>2.81(2H, t, J=7.67 Hz)<br>3.21(2H, s)<br>3.86(3H, s)<br>3.92(2H, t, J=.83 Hz)<br>6.33(1H, br)<br>6.52–6.56(2H, m)<br>6.72(2H, d, J=8.46 Hz)<br>6.80(1H, d, J=8.34 Hz) | 3272<br>2933<br>2870<br>1630<br>1593<br>1514 | | |
| 2-152 | (Colorless crystals) | | CDCl3, 300 MHz<br>0.93(3H, t, J=7.02 Hz)<br>1.27–1.48(4H, m)<br>1.78(2H, q, J=7.17 Hz)<br>3.97(2H, t, J=6.59 Hz)<br>5.43(1H, s)<br>6.39(1H, d, J=15.43 Hz)<br>6.68(1H, dd, J=1.90, 7.81 Hz)<br>6.85(2H, d, J=8.61 Hz)<br>6.96–7.04(1H, m)<br>7.18–7.26(2H, m)<br>7.41–7.45(3H, m)<br>7.69(1H, d, J=15.45 Hz) | 3302<br>2954<br>1661<br>1603<br>1544 | FAB+<br>326[M+H+]<br>(100)<br>248(47)<br>180(29) | C20H23NO3<br>Calcd.<br>C; 73.82%<br>H; 7.12%<br>N; 4.30%<br>Found<br>C; 73.16%<br>H; 7.28%<br>N; 4.53% |
| 2-153 | (Colorless crystals) | 121.6~121.9° C. | CDCl3, 500 MHz<br>0.91(3H, t, J=7.3 Hz)<br>1.34–1.47(4H, m)<br>1.79(2H, q, J=7.0 Hz)<br>3.39(3H, s)<br>3.96(2H, t, J=6.5 Hz)<br>6.26(1H, d, J=15.5 Hz)<br>6.36(1H, br)<br>6.76–6.80(4H, m)<br>6.89(1H, d, J=8.5 Hz)<br>7.21(2H, d, J=8.0 Hz)<br>7.31(1H, t, J=6.3 Hz)<br>7.61(1H, d, J=15.5 Hz) | 3168<br>2935<br>2871<br>1644<br>1581 | FAB+<br>340[M+H+]<br>(100)<br>233(34)<br>193(17) | C21H25NO3<br>C; 74.31%<br>H; 7.17%<br>N; 4.13%<br>Found<br>C; 74.54%<br>H; 7.54%<br>N; 6.82% |

TABLE 97

| Ex. | Structural formula | m.p. | 1H NMR (δ) ppm | IR cm⁻¹ | MS | Elem. anal. |
|---|---|---|---|---|---|---|
| 2-154 | (Colorless crystals) | 177.7~178.0° C. | DMSO-d6, 300 MHz<br>0.89(3H, t, J=7.5 Hz)<br>1.25–1.44(4H, m)<br>1.72(2H, q, J=6.0 Hz)<br>3.71(3H, s)<br>3.90(2H, t, J=7.5 Hz)<br>6.55(1H, d, J=18.0 Hz)<br>6.81(2H, d, J=6.0 Hz)<br>6.89(1H, d, J=6.0 Hz)<br>7.16(1H, d, J=6.0 Hz)<br>7.28–7.50(4H, m)<br>9.88(1H, s)<br>9.90(1H, s) | 3392<br>2956<br>1654<br>1605<br>1584<br>1510 | FAB+<br>356<br>[M+H+](58)<br>314(100)<br>209(69) | C21H25NO4<br>Calcd.<br>C; 70.96%<br>H; 7.09%<br>N; 3.94%<br>Found<br>C; 70.54%<br>H; 7.04%<br>N; 4.18% |

TABLE 97-continued

| Ex. | Structural formula | m.p. | 1H NMR (δ) ppm | IR cm⁻¹ | MS | Elem. anal. |
|---|---|---|---|---|---|---|
| 2-155 | (structure) Colorless crystals | 169.1~169.4° C. | CDCl3, 300 MHz<br>0.89(3H, t, J=7.5 Hz)<br>1.28–1.46(4H, m)<br>1.81(2H, q, J=5.3 Hz)<br>3.37(3H, s)<br>3.91(3H, s)<br>3.97(2H, t, J=7.5 Hz)<br>6.23(1H, d, J=15.0 Hz)<br>6.73–6.90(5H, m)<br>7.19(2H, d, J=9.0 Hz)<br>7.60(1H, d, J=15.0 Hz)<br>7.74(1H, s) | 3074<br>2933<br>1642<br>1578<br>1509 | FAB+<br>370<br>[M+H+](74)<br>223(46)<br>147(100) | $C_{22}H_{27}NO_4$<br>Calcd.<br>C; 71.52%<br>H; 7.37%<br>N; 3.79%<br>Found<br>C; 71.32%<br>H; 7.38%<br>N; 3.70% |
| 2-156 | (structure) Colorless crystals | 152.7~152.9° C. | CDCl3, 300 MHz<br>0.92(3H, t, J=7.07 Hz)<br>1.31–1.42(4H, m)<br>1.71(2H, q, J=6.89 Hz)<br>3.46, (3H, s)<br>3.82(2H, t, J=6.60 Hz)<br>6.53–6.75(5H, m)<br>7.11–7.17(3H, m)<br>7.45(1H, s) | 3127<br>2937<br>1575<br>1518 | FAB+<br>314<br>[M+H+]<br>(100)<br>230(10)<br>193(27) | Calcd.<br>C; 72.82%<br>H; 7.40%<br>N; 4.34%<br>Found<br>C; 72.15%<br>H; 7.40%<br>N; 4.44% |

TABLE 98

| Ex. | Structural formula | m.p. | 1H NMR (δ) ppm | IR cm⁻¹ | MS | Elem. anal. |
|---|---|---|---|---|---|---|
| 2-157 | (structure) Colorless crystals | 125.8~126.1° C. | CDCl3, 300 MHz<br>0.91(3H, t, J=7.5 Hz)<br>1.27–1.44(4H, m)<br>1.82(2H, q, J=7.5 Hz)<br>2.59(2H, d, J=7.5 Hz)<br>2.97(2H, d, J=7.5 Hz)<br>3.82(3H, s)<br>3.98(2H, t, J=7.5 Hz)<br>5.28(1H, s)<br>6.73–6.78(4H, m)<br>6.97(1H, br)<br>7.08(2H, d, J=7.5 Hz)<br>7.23(1H, br) | 3406<br>3240<br>3145<br>3085<br>2930<br>2865<br>1649<br>1613<br>1553<br>1512 | FAB+<br>358<br>[M+H+]<br>(83)<br>357(100)<br>288(13)<br>209(23) | $C_{21}H_{27}NO_4$<br>Calcd.<br>C; 70.56%<br>H; 7.61%<br>N; 3.92%<br>Found<br>C; 70.57%<br>H; 7.88%<br>N; 3.96% |
| 2-158 | (structure) Colorless crystals | 137.7~138.0° C. | CDCl3, 500 MHz<br>0.90(3H, t, J=7.0 Hz)<br>1.30–1.43(4H, m)<br>1.73(2H, q, J=6.9 Hz)<br>3.73(3H, s)<br>3.91(2H, t, J=6.5 Hz)<br>6.84(2H, d, J=7.5 Hz)<br>6.89(1H, d, J=9.0 Hz)<br>7.29(1H, d, J=9.0 Hz)<br>7.44(1H, br)<br>7.83(2H, d, J=7.5 Hz)<br>9.80(1H, br)<br>10.05(1H, br) | 3406<br>3240<br>3145<br>3085<br>2930<br>2865<br>1649<br>1613<br>1553<br>1512 | FAB+<br>358<br>[M+H+]<br>(83)<br>357(100)<br>288(13)<br>209(23) | $C_{19}H_{23}NO_4$<br>Calcd.<br>C; 69.28%<br>H; 7.04%<br>N; 4.25%<br>Found<br>C; 69.03%<br>H; 7.14%<br>N; 5.56% |

TABLE 98-continued

| Ex. | Structural formula | m.p. | 1H NMR (δ) ppm | IR cm$^{-1}$ | MS | Elem. anal. |
|---|---|---|---|---|---|---|
| 2-159 | 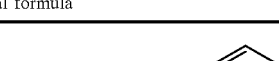<br>Colorless crystals | 138.7~138.9° C. | CDCl3, 500 MHz<br>0.91(3H, t, J=7.0 Hz)<br>1.34–1.40(4H, m)<br>1.67–1.74(2H, m)<br>3.44(3H, s)<br>3.78–3.95(5H, m)<br>6.52–6.72(5H, m)<br>7.13–7.16(3H, m) | 3154<br>2933<br>1615<br>1589<br>1571<br>1507 | FAB+<br>344<br>[M+H+]<br>(100)<br>343(99)<br>223(35) | C$_{20}$H$_{25}$NO$_4$<br>Calcd.<br>C; 69.95%<br>H; 7.34%<br>N; 4.08%<br>Found<br>C; 69.09%<br>H; 7.42%<br>N; 5.73% |

TABLE 99

| Ex. | Structural formula | m.p. | 1H NMR (δ) ppm | IR cm$^{-1}$ | MS | Elem. anal. |
|---|---|---|---|---|---|---|
| 2-160 | | 257.1~258.2° C. | CDCl3, 300 MHz<br>6.7–6.9(7H, m)<br>4.70(1H, bs)<br>3.94(2H, t, J=6.8 Hz)<br>3.9–4.0(2H, m)<br>3.80(3H, s)<br>3.6–3.7(2H, m)<br>3.4–3.5(1H, m)<br>3.0–3.1(2H, bs)<br>2.6–2.9(2H, m)<br>1.7–1.8(2H, m)<br>1.2–1.5(4H, m)<br>0.88(3H, t, J=7.0 Hz) | Neat<br>3288<br>2936<br>1515<br>1264 | FAB+<br>374<br>[M+H+]<br>(30)<br>330(100) | |
| 2-161 | Colorless crystals | 101.6~101.8° C. | CDCl3, 300 MHz<br>0.98(3H, t, J=6.98 Hz)<br>1.38–1.52(4H, m)<br>1.83(2H, q, J=6.68 Hz)<br>4.01(2H, t, J=6.51 Hz)<br>6.75(1H, dd, J=2.21, 8.09 Hz)<br>6.93(2H, d, J=8.61 Hz)<br>7.12(1H, d, J=7.70 Hz)<br>7.28(1H, t, J=8.04 Hz)<br>7.41–7.73(2H, m)<br>7.76(1H, d, J=8.54 Hz)<br>7.97(1H, br) | 3299<br>2938<br>2868<br>1640<br>1542<br>1508 | | C$_{18}$H$_{21}$NO$_3$<br>Calcd.<br>C; 72.22%<br>H; 7.07%<br>N; 4.68%<br>Found<br>C; 72.17%<br>H; 7.15%<br>N; 4.67% |

TABLE 100

| Ex. | Structural formula | m.p. | 1H NMR (δ) ppm | IR cm⁻¹ | MS | Elem. anal. |
|---|---|---|---|---|---|---|
| 3-1 | (structure: MeO, pentyloxy-substituted phenyl cinnamate ester of 4-hydroxyphenethyl alcohol) | 102.1~102.3° C. | CDCl$_3$, 300 MHz 7.61(1H, d, J=15.9 Hz) 7.11(2H, d, J=8.5 Hz) 7.08(1H, dd, J=8.2, 1.9 Hz) 7.04(1H, d, J=1.9 Hz) 6.85(1H, d, J=8.2 Hz) 6.79(2H, d, J=8.5 Hz) 6.28(1H, d, J=15.9 Hz) 5.20(1H, bs) 4.37(2H, t, J=7.1 Hz) 4.02(2H, t, J=6.9 Hz) 3.89(3H, s) 2.94(2H, t, J=7.1 Hz) 1.8–1.9(2H, m) 1.4–1.5(4H, m) 0.93(3H, t, J=7.0 Hz) | KBr 3449 1514 1260 | FAB+ 385[M⁺H⁺] (80) 384 (100) | C$_{23}$H$_{28}$O$_5$ Calcd. C; 71.85% H; 7.34% Found C; 72.22% H; 7.49% |
| 3-2 | (structure: MeO, pentyloxy-substituted benzoate ester of 4-hydroxyphenethyl alcohol) | 104.1~104.3° C. | CDCl$_3$, 300 MHz 7.63(1H, dd, J=8.4, 2.0 Hz) 7.51(1H, d, J=2.0 Hz) 7.14(2H, d, J=8.5 Hz) 6.87(1H, d, J=8.4 Hz) 6.78(2H, d, J=8.5 Hz) 6.50(1H, bs) 4.45(2H, t, J=7.0 Hz) 4.04(2H, t, J=6.9 Hz) 3.91(3H, s) 2.99(2H, t, J=6.9 Hz) 1.8–1.9(2H, m) 1.3–1.5(4H, m) 0.93(3H, t, J=7.0 Hz) | KBr 3377 2941 1687 1273 | FAB+ 359 [M⁺H⁺] (30) 238(90) 221(95) | C$_{21}$H$_{26}$O$_5$ Calcd. C; 70.37% H; 7.31% Found C; 70.55% H; 7.44% |
| 3-3 | (structure: MeO, pentyloxy-substituted cinnamate ester of 1-hydroxybenzotriazole) | 170.1~171.2° C. | CDCl3, 300 MHz 8.1(1H, d, J=9 Hz) 8.0(1H, d, J=15 Hz) 7.4–8.0 3H, m) 7.2(1H, d, J=9 Hz) 7.2(1H, s) 6.9(1H, d, J=9 Hz) 6.6(1H, d, J=15 Hz) 4.1(2H, t, J=4 Hz) 4.0(3H, s) 1.8–2.0(2H, m) 1.4–1.6(4H, m) 1.0(3H, t, J=7.5 Hz) | KBr 3448 2929 1777 1621 1595 1508 1260 1083 | FAB+ 382 [M+H+] (20) 247 (100) | C$_{29}$H$_{23}$N$_3$O$_4$ Calcd. C; 66.13% H; 6.08% N; 11.02% Found C; 66.21% H; 6.09% N; 11.00% |

TABLE 101

| Ex. | Structural formula | m.p. | 1H NMR (δ) ppm | IR cm$^{-1}$ | MS | Elem. anal. |
|---|---|---|---|---|---|---|
| 4-1 |  | 205.4~ 206.0° C. | DMSO-d6, 300 MHz<br>9.15(1H, s)<br>8.17–8.30(3H, m)<br>7.98(1H, d, J=15.6 Hz)<br>7.72(1H, t, J=6.98 Hz)<br>7.64(1H, t, J=6.98 Hz)<br>7.15(1H, s)<br>7.14(2H, d, J=8.94 Hz)<br>6.80(1H, d, J=15.6 Hz)<br>6.69(2H, d, J=8.94 Hz)<br>4.23(2H, t, J=6.39 Hz)<br>3.39(2H, q, J=6.56 Hz)<br>2.69(2H, t, J=7.35 Hz)<br>1.85–1.98(2H, m)<br>1.35–1.60(4H, m)<br>0.94(3H, t, J=7.13 Hz) | | FAB+<br>483<br>[M$^+$H$^+$]<br>(55)<br>485(30)<br>482(100) | |
| 4-2 |  | 148.2~ 148.8° C. | DMSO-d6, 300 MHz<br>8.49(2H, d, J=5.97 Hz)<br>8.20*8.34(3H, m)<br>8.00(1H, d, J=15.6 Hz)<br>7.74(1H, t, J=7.70 Hz<br>7.65(1H, t, J=7.70 Hz)<br>7.29(2H, d, J=5.97 Hz)<br>7.15(1H, s)<br>6.79(1H, d, J=15.6 Hz)<br>4.23(2H, t, J=6.42 Hz)<br>3.50 (2H, q, J=6.34 Hz)<br>2.85(2H, t, J=7.0 Hz)<br>1.85–1.98(2H, m)<br>1.35–1.60(4H, m)<br>0.94(3H, t, J=7.16 Hz) | | FAB+<br>468<br>[M$^+$H$^+$]<br>(20)<br>469(40)<br>467(45) | |
| 4-3 |  | 148.3~ 149.5° C. | CDCl$_3$, 300MHz<br>8.76–8.82(1H, m)<br>8.55(2H, dd, J=4.2, 1.2 Hz)<br>8.22–8.37(1H, m)<br>7.74(1H, d, J=15.3 Hz)<br>7.45–7.54(3H, m)<br>7.26(1H, s)<br>7.18(2H, d, J=6.0 Hz)<br>6.89(1H, s)<br>6.39(1H, d, J=15.3 Hz)<br>5.67–5.75(1H, m)<br>4.15(2H, t, J=6.5 Hz)<br>3.71(2H, q, J=6.6 Hz)<br>2.93(2H, t, J=6.9 Hz)<br>1.90–2.00 (2H, m)<br>1.39–1.70(4H, m)<br>0.97(3H, t, J=7.4 Hz) | | FAB+<br>389<br>[M$^+$H$^+$]<br>(60)<br>307(30)<br>197(30) | |

TABLE 102

| Ex. | Structural formula | m.p. | 1H NMR (δ) ppm | IR cm$^{-1}$ | MS | Elem. anal. |
|---|---|---|---|---|---|---|
| 4-4 | | 175.5~ 176.1° C. | DMSO-d6, 300 MHz<br>9.15(1H, s)<br>8.06–8.14(2H, m)<br>7.84–7.90(1H, m)<br>7.61(1H, s)<br>7.47–7.56(4H, m)<br>7.09(1H, s)<br>7.02(2H, d, J=8.4 Hz)<br>6.74(1H, d, J=15.6 Hz)<br>6.67(2H, d, J=8.4 Hz)<br>4.2(2H, t, J=6.45 Hz)<br>3.38(2H, q, J=6.8 Hz)<br>2.66(2H, t, J=7.35 Hz)<br>1.83–1.95(2H, m)<br>1.35–1.58(4H, m)<br>0.93(3H, t, J=7.2 Hz) | | FAB+<br>404<br>[M$^+$H$^+$]<br>(60)<br>197(45) | |

TABLE 103

| Ex. | Structural formula | m.p. | 1H NMR (δ)ppm | IR cm$^{-1}$ | MS | Elem. anal. |
|---|---|---|---|---|---|---|
| 5-1 | | | CDCl$_3$, 300 MHz<br>9.15(1H, s)<br>8.51(1H, s)<br>8.50(2H, d, J=4.66 Hz)<br>7.61(1H, d, J=9.02 Hz)<br>7.40(1H, d, J=9.02 Hz)<br>7.17(2H, d, J=4.66 Hz)<br>6.64–6.75(1H, m)<br>4.26(2H, t, J=7.01 Hz)<br>4.03(3H, s)<br>3.80(2H, q, J=6.51 Hz)<br>2.99(2H, t, J=6.85 Hz)<br>1.80–195(2H, m)<br>1.26–1.53(4H, m) | | FAB+<br>394<br>[M$^+$H$^+$](100)<br>336(25) | |
| 5-2 | | | CDCl$_3$, 300 MHz<br>8.25–8.30(1H, m)<br>7.76–7.83(1H, m)<br>7.61(1H, s)<br>7.47–7.58(2H, m)<br>7.19(1H, s)<br>7.13(2H, d, J=8.3 Hz)<br>6.81(2H, d, J=8.3 Hz)<br>6.20–6.35(1H, m)<br>5.23(1H, s)<br>4.18(2H, t, J=6.44 Hz)<br>3.72(2H, q, J=6.56 Hz)<br>2.90(2H, t, J=6.92 Hz)<br>1.85–2.00(2H, m)<br>1.35–1.62(4H, m)<br>0.96(3H, t, J=7.14 Hz) | | FAB+<br>378<br>[M$^+$H$^+$](80)<br>257(35)<br>241(50) | |
| 5-3 | | 103.6~ 105.4° C. | CDCl$_3$, 300 MHz<br>8.55(1H, d, J=6.0 Hz)<br>8.25–8.31(1H, m)<br>7.77–7.83(1H, m)<br>7.63(1H, s)<br>7.50–7.57(2H, m)<br>7.21(1H, s)<br>7.20(2H, d, J=6.0 Hz)<br>6.30–6.45(1H, m)<br>4.19(2H, t, J=6.44 Hz)<br>3.78(2H, q, J=6.66 Hz)<br>3.00(2H, t, J=6.98 Hz)<br>1.89–2.00(2H, m)<br>1.37–1.60(4H, m)<br>0.96(3H, t, J=7.17 Hz) | | FAB+<br>363<br>[M$^+$H$^+$](100)<br>305(15)<br>241(20) | |

TABLE 104

| Ex. | Structural formula | m.p. | 1H NMR (δ) ppm | IR cm⁻¹ | MS | Elem. anal. |
|---|---|---|---|---|---|---|
| 5-4 | (1-bromo-4-pentyloxy-naphthalene-2-carboxamide with N-[2-(4-hydroxyphenyl)ethyl]) | 135.2~135.8° C. | CDCl₃, 300 MHz<br>8.28(1H, t, J=8.13 Hz)<br>8.25(1H, t, J=8.13 Hz)<br>7.64(1H, t, J=8.13 Hz)<br>7.55(1H, t, J=8.13 Hz)<br>7.15(2H, d, J=8.51 Hz)<br>6.80(1H, s)<br>6.78(2H, d, J=8.51 Hz)<br>5.92–6.03(1H, m)<br>4.89(1H, s)<br>4.11(2H, t, J=6.43 Hz)<br>3.76(2H, q, J=6.61 Hz)<br>2.93(2H, t, J=6.95 Hz) | | FAB+<br>457<br>[M⁺H⁺](50)<br>458(90)<br>456(100) | |
| 5-5 | (1-bromo-4-pentyloxy-naphthalene-2-carboxamide with N-[2-(pyridin-4-yl)ethyl]) | 131.9~132.6° C. | CDCl₃, 300 MHz<br>8.54(2H, d, J=5.96 Hz)<br>8.28(1H, d, J=6.98 Hz)<br>8.25(1H, d, J=6.98 Hz)<br>7.65(1H, d, J=6.98 Hz)<br>7.55(1H, d, J=6.98 Hz)<br>7.23(2H, d, J=5.96 Hz)<br>6.80(1H, s)<br>6.02–6.16(1H, m)<br>4.11(2H, t, J=6.42 Hz)<br>3.82(2H, q, J=6.71 Hz)<br>3.03(2H, t, J=7.03 Hz)<br>1.87–2.00(2H, m)<br>1.36–1.62(4H, m)<br>0.94(3H, t, J=7.16 Hz) | | FAB+<br>442<br>[M⁺H⁺](40)<br>443(80)<br>441(100 | |
| 5-6 | (7-methoxy-8-pentyloxy-quinoline-3-carboxamide with N-[2-(4-hydroxyphenyl)ethyl])<br>Colorless crystals | 141.2~142.6° C. | DMSO-d6, 300 MHz<br>9.13(1H, d, J=2.4 Hz)<br>8.62(1H, d, J=2.4 Hz)<br>7.78(1H, d, J=9.9 Hz)<br>7.60(1H, d, J=9.9 Hz)<br>7.1(2H, d, J=8.7 Hz)<br>6.73(2H, d, J=8.7 Hz)<br>4.18(2H, t, J=6.8 Hz)<br>4.04(3H, s)<br>3.60(2H, t, J=7.4 Hz)<br>2.86(2H, t, J=7.4 Hz)<br>1.77–1.9(2H, m)<br>1.3–1.5(4H, m)<br>0.94(3H, t, J=7.2 Hz) | | FAB+<br>409<br>[M⁺H⁺](100)<br>339(50) | |

TABLE 105

| Ex. | Structural formula | m.p. | 1H NMR (δ) ppm | IR cm⁻¹ | MS | Elem. anal. |
|---|---|---|---|---|---|---|
| 5-7 | (7-methoxy-8-pentyloxy-quinoline-3-carboxamide with N-[2-(4-nitrophenyl)ethyl])<br>Pale-yellow crystals | 109.8~110.6° C. | CDCl₃, 300 MHz<br>9.12(1H, d, J=2.1 Hz)<br>8.50(1H, d, J=2.1 Hz)<br>8.20(2H, d, J=9.0 Hz)<br>7.64(1H, d, J=9.0 Hz)<br>7.43(2H, d, J=9.0 Hz)<br>7.42(1H, d, J=9.0 Hz)<br>6.29(1H, bt)<br>4.27(2H, t, J=6.9 Hz)<br>4.04(3H, s)<br>3.83(2H, q, J=6.7 Hz)<br>3.12(2H, t, J=7.1 Hz)<br>1.83–1.95(2H, m)<br>1.3–1.6(4H, m)<br>0.92(3H, t, J=7.2 Hz) | | FAB+<br>438<br>[M⁺H⁺](30)<br>307(20) | |

TABLE 105-continued

| Ex. | Structural formula | m.p. | 1H NMR (δ) ppm | IR cm$^{-1}$ | MS | Elem. anal. |
|---|---|---|---|---|---|---|
| 5-8 | (structure: 7-MeO, 8-pentyloxy quinoline-3-carboxamide with N-CH₂CH₂-C₆H₄-NH₂) <br> Colorless crystals | 106.2~ 107.7° C. | CDCl₃, 300 MHz <br> 9.11(1H, d, J=2.2 Hz) <br> 8.51(1H, d, J=2.2 Hz) <br> 7.65(1H, d, J=9.1 Hz) <br> 7.42(1H, d, J=9.1 Hz) <br> 7.07(2H, d, J=9.1 Hz) <br> 6.70(2H, d, J=9.1 Hz) <br> 6.22(1H, bt) <br> 4.29(2H, t, J=7.1 Hz) <br> 4.05(3H, s) <br> 3.75(2H, q, J=6.2 Hz) <br> 3.65(2H, bs) <br> 2.88(2H, t, J=6.6 Hz) <br> 1.8–1.95(2H, m) <br> 1.3–1.6(4H, m) <br> 0.94(3H, t, J=7.1 Hz) | | FAB+ <br> 408 <br> [M⁺H⁺](70) <br> 307(20) | |
| 5-9 | (structure: 7-MeO, 8-pentyloxy quinoline-3-carboxamide with N-CH₂CH₂-imidazole) <br> Colorless crystals | 73.2~ 74.7° C. | CDCl₃, 300 MHz <br> 9.34(1H, d, J=2.2 Hz) <br> 8.67(1H, d, J=2.1 Hz) <br> 8.30(1H, bs) <br> 7.75(1H, s) <br> 7.68(1H, d, J=9.1 Hz) <br> 7.41(1H, d, J=9.1 Hz) <br> 6.92(1H, s) <br> 4.29(2H, t, J=7.1 Hz) <br> 4.05(3H, s) <br> 3.75–3.86(2H, m) <br> 2.85–2.95(2H, m) <br> 1.8–1.95(2H, m) | | FAB+ <br> 383 <br> [M⁺H⁺](70) <br> 307(20) | |

TABLE 106

| Ex. | Structural formula | m.p. | 1H NMR (δ) ppm | IR cm$^{-1}$ | MS | Elem. anal. |
|---|---|---|---|---|---|---|
| 6-1 | (structure: 4-MeO, 3-pentyloxy phenyl 4,4-dimethyloxazoline) | 62.0~ 63.2° C. | CDCl₃, 300 MHz <br> 7.51(1H, dd, J=8.4, 1.8 Hz) <br> 7.46(1H, d, J=1.8 Hz) <br> 6.86(1H, d, J=8.4 Hz) <br> 4.07(2H, s) <br> 4.05(2H, t, J=6.9 Hz) <br> 3.89(3H, s) <br> 1.8–2.0(2H, m) <br> 1.3–1.5(4H, m) <br> 1.37(6H, s) <br> 0.93(3H, t, J=7.0 Hz) | Neat <br> 2959 <br> 1648 <br> 1513 | FAB+ <br> 292 <br> [M⁺H⁺](100) <br> 291(80) <br> 276(75) | C₁₇H₂₅NO₃ <br> Calcd. <br> C; 70.07% <br> H; 8.65% <br> N; 4.81% <br> Found <br> C; 69.86% <br> H; 8.70% <br> N; 5.01% |
| 6-2 | (structure: 4-MeO, 3-pentyloxy phenyl with 4,4-dimethyloxazoline and CH₂CH₂OH) | | CDCl₃, 300MHz <br> 7.5(1H, d, J=9.0 Hz) <br> 6.89(1H, d, J=9.0 Hz) <br> 6.2(1H, bs) <br> 4.1(2H, s) <br> 4.0(2H, t, J=7.5 Hz) <br> 4.0(2H, t, J=4.5 Hz) <br> 3.9(3H, s) <br> 3.3(2H, t, J=4.5 Hz) <br> 1.6–1.8(2H, m) <br> 1.3–1.5(4H, m) <br> 1.4(6H, s) <br> 0.93(3H, t, J=7.5 Hz) | Neat <br> 3264 <br> 2960 <br> 1640 | FAB+ <br> 336 <br> [M⁺H⁺](100) <br> HRFAB(m/z) <br> 336.2189 <br> Calcd. <br> C₁₉H₃₀NO₄ <br> 336.4558 <br> Found <br> 336.2189 | C₁₉H₂₉NO₄ <br> Calcd. <br> C; 68.03% <br> H; 8.71% <br> Np; 4.18% <br> Found <br> C; 67.66% <br> H; 9.01% <br> N; 4.28% |

TABLE 106-continued

| Ex. | Structural formula | m.p. | 1H NMR (δ) ppm | IR cm⁻¹ | MS | Elem. anal. |
|---|---|---|---|---|---|---|
| 6-3 | (structure: benzene with 4,4-dimethyl oxazoline, MeO, OCOEt, O-pentyl) | | CDCl$_3$, 300 MHz<br>7.63(1H, dd, J=8.7 Hz)<br>6.90(1H, d, J=8.7 Hz)<br>4.36(2H, q, J=7.2 Hz)<br>4.02(2H, s)<br>4.00(2H, t, J=6.7 Hz)<br>3.88(3H, s)<br>1.6–1.8(2H, m)<br>1.37(2H, t, J=7.2 Hz)<br>1.32(6H, s)<br>1.3–1.5(4H, m)<br>0.92(3H, t, J=7.0 Hz) | Neat<br>2961<br>173712 | FAB+<br>364<br>[M⁺H⁺](100)<br>318(70)<br>176(50) | |

TABLE 107

| Ex. | Structural formula | m.p. | 1H NMR (δ) ppm | IR cm⁻¹ | MS | Elem. anal. |
|---|---|---|---|---|---|---|
| 6-4 | (structure with OH, MeO, O-pentyl, oxazoline) | | CDCl$_3$, 300 MHz<br>7.59(1H, d, J=8.7 Hz)<br>6.84(1H, d, J=8.7 Hz)<br>6.66(1H, bs)<br>4.80(2H, s)<br>4.09(2H, s)<br>3.95(2H, t, J=6.7 Hz)<br>3.88(3H, s)<br>1.7–1.9(2H, m)<br>1.39(6H, s)<br>1.3–1.6(4H, m)<br>0.94(3H, t, J=7.1 Hz) | Neat<br>3300<br>2960<br>1635<br>1273 | FAB+<br>322<br>[M⁺H⁺](100)<br>304(80)<br>HRFAB<br>(m/z)<br>Calcd.<br>C$_{25}$H$_{32}$NO$_5$<br>322.4286<br>Found<br>322.2027 | |
| 6-5-1 | (structure with MeO, O-pentyl, oxazoline-pyridine) | | CDCl$_3$ 300 MHz<br>8.06–8.13(1H, m)<br>7.70(1H, td, J=7.8, 1.7 Hz)<br>7.61(1H, dd, J=8.4, 1.9 Hz)<br>7.56(1H, d, J=1.9 Hz)<br>7.42(1H, d, J=7.8 Hz)<br>7.21–7.25(1H, m)<br>6.90(1H, d, J=8.4 Hz)<br>5.75(1H, dd, J=10.2, 7.2 Hz)<br>4.13(1H, dd, J=14.8, 7.2 Hz)<br>4.07(2H, t, J=6.9 Hz)<br>3.92(3H, s)<br>1.82–1.92(2H, m)<br>1.37–1.47(4H, m)<br>0.92(3H, t, J=7.1 Hz) | | FAB+<br>341<br>[M⁺H⁺](100)<br>221(60) | |
| 6-6 | (structure with MeO, S-pentyl, oxazoline) | | 7.80(1H, d, J=2.0 Hz),<br>7.60(1H, dd, J=8.5, 2.0 Hz),<br>6.83(1H, d, J=8.5 Hz),<br>4.08(2H, s),<br>3.93(3H, s),<br>2.93(2H, t, J=7.3 Hz),<br>1.3–1.5(10H, m,<br>involving a singlet at 1.37),<br>0.90(3H, t, J=7.2 Hz). | | FAB+<br>308[M+H+]<br>(100),<br>292(20). | |

TABLE 108

| Ex. | Structural formula | m.p. | 1H NMR (δ) ppm | IR cm⁻¹ | MS | Elem. anal. |
|---|---|---|---|---|---|---|
| 6-7 | Colorless oil | | CDCl3, 300 MHz<br>7.55(1H, d, J=8.1 Hz)<br>7.44(1H, s)<br>7.37(1H, d, J=8.1 Hz)<br>4.13(2H, s)<br>4.08(2H, t, J=6.6 Hz)<br>1.80–1.93(2H, m)<br>1.33–1.60(4H, m)<br>1.38(6H, s)<br>0.94(3H, t, J=7.1 Hz) | | FAB+<br>341[M+H+]<br>(100)<br>340(100) | |
| 6-8 | Colorless oil | | CDCl3, 300 MHz<br>7.48(1H, dd, J=8.4, 2.2 Hz),<br>7.45(2H, d, J=2.2 Hz)<br>6.85(1H, d, J=8.4 Hz)<br>4.07(2H, s)<br>4.0–4.1(4H, m)<br>1.7–1.9(4H, m)<br>1.37(6H, m)<br>1.3–1.6(8H, m)<br>0.93(3H, t, J=7.1 Hz)<br>0.93(3H, t, J=7.1 Hz) | Neat<br>2958<br>1648<br>1512 | FAB+<br>348[M+H+]<br>(100) | |
| 6-9 | Colorless oil | | CDCl3, 300 MHz<br>7.60(1H, d, J=8.7 Hz)<br>6.88(1H, d, J=8.7 Hz)<br>4.36(2H, q, J=7.2 Hz)<br>4.01(2H, s)<br>3.9–4.1(4H, m)<br>1.6–2.0(4H, m)<br>1.38(3H, t, J=7.2 Hz)<br>1.32(6H, s)<br>1.3–1.5(8H, m)<br>0.8–1.0(6H, m) | Neat<br>2958<br>1739<br>1652<br>1276 | FAB+<br>420[M+H+]<br>(100) | |

TABLE 109

| Ex. | Structural formula | m.p. | 1H NMR (δ) ppm | IR cm⁻¹ | MS | Elem. anal. |
|---|---|---|---|---|---|---|
| 6-10 | Colorless oil | | CDCl₃, 300 MHz<br>7.56(1H, d, J=8.7 Hz)<br>6.81(1H, d, J=8.7 Hz)<br>6.64(1H, bs)<br>4.80(2H, s)<br>4.07(2H, s)<br>4.00(2H, t, J=6.5 Hz)<br>3.95(2H, t, J=6.7 Hz)<br>1.7–1.9(4H, m)<br>1.3–1.5(8H, m)<br>1.38(6H, s)<br>0.93(3H, t, J=7.1 Hz)<br>0.93(3H, t, J=7.1 Hz) | Neat<br>3317<br>2957<br>1635<br>1301<br>1273<br>1010 | FAB+<br>378<br>[M+H+](100)<br>360(80) | |

TABLE 109-continued

| Ex. | Structural formula | m.p. | 1H NMR (δ) ppm | IR cm⁻¹ | MS | Elem. anal. |
|---|---|---|---|---|---|---|
| 6-11 | (MeS, pentyloxy substituted phenyl oxazoline) Pale-yellow oil | | CDCl3, 300 MHz<br>7.50(1H, d, J=8.1 Hz)<br>7.36(1H, s)<br>7.08(1H, d, J=8.1 Hz)<br>4.08(2H, t, J=6.5 Hz)<br>4.08(2H, s)<br>2.43(3H, s)<br>1.80–1.90(2H, m)<br>1.35–1.50(4H, m)<br>1.37(6H, s)<br>0.93(3H, t, J=7.2 Hz) | | FAB+<br>308[M+H+]<br>(100) | |
| 6-12 | (pentylthio, pentyloxy substituted phenyl oxazoline) Pale-yellow oil | | CDCl3, 300 MHz<br>7.47(1H, d, J=8.1 Hz),<br>7.36(1H, s),<br>7.16(1H, d, J=8.1 Hz),<br>4.08(2H, s),<br>4.07(2H, t, J=6.5 Hz),<br>2.90(2H, t, J=7.4 Hz),<br>1.80–1.90(2H, m),<br>1.60–1.75(2H, m),<br>1.33–1.55(8H, m)<br>1.37(6H, s)<br>0.93(3H, t, J=6.9 Hz),<br>0.90(3H, t, J=6.9 Hz) | | FAB+<br>364[M+H+]<br>(100) | |

TABLE 110

| Ex. | Structural formula | m.p. | 1H NMR (δ) ppm | IR cm⁻¹ | MS | Elem. anal. |
|---|---|---|---|---|---|---|
| 6-13 | (PenO, pentylthio substituted phenyl oxazoline) Colorless oil | | CDCl3, 300 MHz<br>7.78(1H, d, J=2.4 Hz),<br>7.73(1H, dd, J=8.4, 1.8 Hz),<br>6.81(1H, d, J=8.4 Hz),<br>4.07(2H, s),<br>4.06(2H, t, J=6.5 Hz),<br>2.92(2H, t, J=7.4 Hz),<br>1.80–1.90(2H, m),<br>1.60–1.75(2H, m),<br>1.33–1.55(14H, m,<br>involving a singlet at 1.37),<br>094(3H, t, J=6.9 Hz),<br>0.90(3H, t, J=6.9 Hz). | | FAB+<br>364[M+H+]<br>(100),<br>294(20). | |

TABLE 111

| Ex. | Structural formula | m.p. | 1H NMR (δ) ppm | IR cm⁻¹ | MS | Elem. anal. |
|---|---|---|---|---|---|---|
| 7-1 | (nitro-phthalimide with hydroxyphenethyl) | 108.2~<br>109.2° C. | DMSO-d6, 300 MHz<br>9.19(1H, s)<br>8.26(1H, d, J=7.7 Hz)<br>8.13(1H, d, J=7.7 Hz)<br>8.03(1H, d, J=7.7 Hz)<br>6.99(1H, d, J=8.4 Hz)<br>6.68(2H, d, J=8.4 Hz)<br>3.72(2H, t, J=7.5 Hz)<br>2.78(2H, t, J=7.5 Hz) | KBr<br>3366<br>1777<br>1710 | FAB+<br>313<br>[M+H+]<br>(20) | |

TABLE 111-continued

| Ex. | Structural formula | m.p. | 1H NMR (δ) ppm | IR cm$^{-1}$ | MS | Elem. anal. |
|---|---|---|---|---|---|---|
| 7-2 | | 2100~211.0° C. | DMSO-d6, 300 MHz<br>9.16(1H, s)<br>7.39(1H, dd, J=7.0 Hz)<br>6.39(2H, d, J=8.4 Hz)<br>6.94(1H, d, J=8.3 Hz)<br>6.91(1H, d, J=8.3 Hz)<br>6.63(2H, d, J=8.4 Hz)<br>6.40(2H, bs)<br>3.65(2H, t, J=7.3 Hz)<br>2.75(2H, t, J=7.3 Hz) | KBr<br>3382<br>3254<br>2942<br>1744<br>1673 | FAB+<br>283<br>[M$^+$H$^+$]<br>(40) | |
| 7-3 | | 119.0~120.2° C. | CDCl$_3$, 300 MHz<br>9.5(1H, s)<br>8.8(1H, d, J=6 Hz)<br>7.6(1H, t, J=6 Hz)<br>7.5(2H, d, J=6 Hz)<br>7.2(2H, d, J=9 Hz)<br>7.0(2H, d, J=9 Hz)<br>3.9(2H, t, J=7.5 Hz)<br>3.0(2H, t, J=7.5 Hz)<br>2.5(2H, t, J=7.5 Hz)<br>2.5(2H, t, J=7.5 Hz)<br>1.6–1.8(4H, m)<br>1.4–1.6(4H, m)<br>0.9–1.0(6H, m) | KBr<br>3479<br>3372<br>1739<br>1692<br>1633 | FAB+<br>451<br>[M$^+$H$^+$]<br>(30)<br>367<br>(20) | |

TABLE 112

| Ex. | Structural formula | m.p. | 1H NMR (δ) ppm | IR cm$^{-1}$ | MS | Elem. anal. |
|---|---|---|---|---|---|---|
| 7-4 | | | DMSO-d6, 300 MHz<br>7.50(1H, d, J=8.0 Hz)<br>7.09(2H, d, J=8.3 Hz)<br>7.07(1H, d, J=8.0 Hz)<br>6.74(2H, d, J=8.3 Hz)<br>5.40(1H, bs)<br>4.26(2H, t, J=6.8 Hz)<br>3.92(3H, s)<br>3.83(2H, t, J=7.7 Hz)<br>2.89(2H, t, J=7.7 Hz)<br>1.7–19(2H, m)<br>1.3–1.5(4H, m)<br>0.92(3H, t, J=7.2 Hz) | | | |
| 7-5 | | 146.3~146.9° C. | CDCl$_3$, 300 MHz<br>7.52(1H, d, J=8.3 Hz)<br>7.06(2H, d, J=8.4 Hz)<br>6.97(1H, d, J=8.3 Hz)<br>6.75(2H, d, J=8.4 Hz)<br>6.40(1H, bs)<br>4.24(2H, s)<br>4.03(2H, t, J=6.7 Hz)<br>3.89(3H, s)<br>3.82(2H, t, J=7.2 Hz)<br>2.91(2H, t, J=7.2 Hz)<br>1.6–1.8(2H, m)<br>1.3–1.5(4H, m)<br>0.94(3H, t, J=7.1 Hz) | KBr<br>3129<br>2956<br>1659<br>1273 | FAB+<br>370<br>[M$^+$H$^+$](100)<br>262(40) | C$_{22}$H$_{27}$NO$_4$<br>Calcd.<br>C; 71.52%<br>H; 7.37%<br>N; 3.79%<br>Found<br>C; 71.50%<br>H; 7.39%<br>N; 3.87% |

TABLE 112-continued

| Ex. | Structural formula | m.p. | 1H NMR (δ) ppm | IR cm⁻¹ | MS | Elem. anal. |
|---|---|---|---|---|---|---|
| 7-6 | | | CDCl₃, 300 MHz<br>7.61(1H, t, J=7.83 Hz)<br>7.38(1H, d, J=7.22 Hz)<br>7.16(1H, d, J=8.43 Hz)<br>7.11(2H, d, J=8.30 Hz)<br>6.75(2H, d, J=8.33 Hz)<br>4.5–4.8(1H, br)<br>4.16(2H, t, J=6.64 Hz)<br>3.84(2H, t, J=7.69 Hz)<br>2.90(2H, t, J=7.68 Hz)<br>1.84–1.92(2H, m)<br>1.35–1.52(4H, m)<br>0.94(3H, t, J=7.04 Hz) | Neat<br>3422<br>3021<br>2955<br>2871<br>1766<br>1704<br>1614<br>1516 | | |

TABLE 113

| Ex. | Structural formula | m.p. | 1H NMR (δ) ppm | IR cm⁻¹ | MS | Elem. anal. |
|---|---|---|---|---|---|---|
| 7-7 | | 161.3~<br>161.6° C. | CDCl₃, 300 MHz<br>7.39(1H, t, J=7.90 Hz)<br>7.04(2H, d, J=7.50 Hz)<br>6.89(1H, d, J=7.40 Hz)<br>6.85(1H, d, J=8.10 Hz)<br>6.80(2H, d, J=8.50 Hz)<br>4.14(2H, s)<br>4.07(2H, t, J=6.75 Hz)<br>3.76(2H, t, J=7.15 Hz)<br>2.87(2H, t, J=7.15 Hz)<br>1.88(2H, quint, J=7.15 Hz)<br>1.30–1.51(4H, m)<br>0.90(3H, t, J=7.15 Hz) | Neat<br>3163<br>2950<br>2868<br>1662<br>1612<br>1596 | FAB+<br>340<br>[M⁺H⁺](100)<br>326(60)<br>270(18) | |
| 7-8 | | 107.8~<br>108.1° C. | CDCl₃, 300 MHz<br>7.26(1H, t, J=7.76 Hz)<br>7.07(2H, d, J=8.47 Hz)<br>6.79(1H, d, J=7.44 Hz)<br>6.69(1H, d, J=8.07 Hz)<br>6.67(2H, d, J=8.45 Hz)<br>4.02(4H, s)<br>3.97(2H, t, J=6.54 Hz)<br>2.80–3.00(4H, m)<br>1.70–1.85(2H, m)<br>1.30–1.45(4H, m)<br>0.93(3H, t, J=7.01 Hz) | Neat<br>3400<br>2943<br>2870<br>2806<br>1613<br>1594 | FAB+<br>326<br>[M⁺H⁺](100)<br>218(62)<br>121(20) | |
| 7-9 | | 114.7~<br>115.1° C. | CDCl₃, 300 MHz<br>7.69(1H, d, J=8.25 Hz)<br>7.26(1H, d, J=2.19 Hz)<br>7.05–1.12(3H, m)<br>6.73(2H, d, J=8.46 Hz)<br>5.83(1H, s)<br>4.03(2H, t, J=6.54 Hz)<br>3.85(2H, t, J=7.52 Hz)<br>2.89(2H, t, J=7.49 Hz)<br>1.75–1.84(2H, m<br>1.32–1.47(4H, m)<br>0.93(3H, t, J=7.01 Hz) | Neat<br>3435<br>2934<br>1765<br>1696<br>1613<br>1515 | FAB+<br>354<br>[M⁺H⁺](100)<br>289(16)<br>246(20) | C₂₁H₂₃NO₄<br>Calcd.<br>C; 71.37%<br>H; 6.56%<br>N; 3.96%<br>Found<br>C; 71.39%<br>H; 6.62%<br>N; 3.99% |

TABLE 114

| Ex. | Structural formula | m.p. | 1H NMR (δ) ppm | IR cm⁻¹ | MS | Elem. anal. |
|---|---|---|---|---|---|---|
| 7-10-1 | 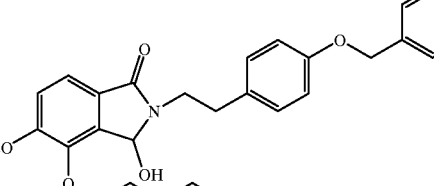 | 138.5~138.8° C. | CDCl3, 300 MHz<br>7.72(1H, d, J=8.42 Hz)<br>7.04(2H, d, J=8.50 Hz)<br>6.93(1H, dd, J=8.44, 2.17 Hz)<br>6.85(1H, d, J=1.73 Hz)<br>6.76(2H, d, J=6.48 Hz)<br>3.92(2H, t, J=6.53 Hz)<br>3.83(2H, t, J=7.09 Hz)<br>2.90(2H, t, J=7.07 Hz)<br>1.77–1.82(2H, m)<br>1.37–1.45(4H, m)<br>0.93(3H, t, J=7.06 Hz) | Neat<br>3132<br>3012<br>2953<br>2867<br>1738<br>1662<br>1617<br>1594 | FAB+<br>340<br>[M⁺H⁺](100)<br>324(28)<br>232(33) | |
| 7-10-2 | | 137.5~137.8° C. | CDCl₃, 300 MHz<br>7.31(1H, d, J=2.33 Hz)<br>7.24(1H, d, J=7.89 Hz)<br>7.03–7.08(3H, m)<br>6.76(2H, d, J=8.48 Hz)<br>6.24(1H, br)<br>3.97(2H, t, J=6.59 Hz)<br>3.84(2H, t, J=7.19 Hz)<br>2.91(2H, t, J=7.16 Hz)<br>1.75–1.81(2H, m)<br>1.38–1.42(4H, m)<br>0.93(3H, t, J=7.03 Hz) | Neat<br>3103<br>2934<br>1654<br>1618<br>1594 | FAB+<br>340<br>[M⁺H⁺](100)<br>324(25)<br>232(32) | |
| 7-11 | | 120.5~120.7° C. | CDCl₃, 300 MHz<br>7.04–7.09(3H, m)<br>6.64–6.75(4H, m)<br>3.90–3.96(6H, m)<br>2.80–2.97(4H, m)<br>1.74–1.79(2H, m)<br>1.36–1.44(4H, m)<br>0.93(3H, t, J=7.04 Hz) | Neat<br>2941<br>2873<br>2807<br>1612<br>1590 | FAB+<br>326<br>[M⁺H⁺](97)<br>218(100)<br>191(26)<br>121(8) | $C_{21}H_{27}NO_2$<br>Calcd.<br>C; 77.50%<br>H; 8.36%<br>N; 4.30%<br>Found<br>C; 77.29%<br>H; 8.56%<br>N; 4.29% |

TABLE 115

| Ex. | Structural formula | m.p. | 1H NMR (δ) ppm | IR cm⁻¹ | MS | Elem. anal. |
|---|---|---|---|---|---|---|
| 7-13 | 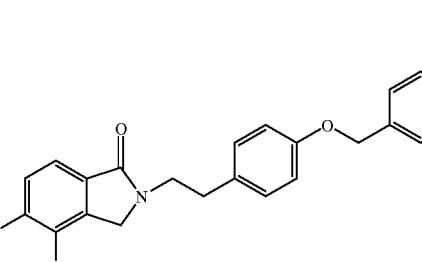 | | CDCl₃, 300 MHz<br>7.38(1H, d, J=8.4 Hz)<br>7.3–7.5(5H, m)<br>7.13(2H, d, J=8.6 Hz)<br>6.91(1H, d, J=8.4 Hz)<br>6.88(2H, d, J=8.6 Hz)<br>5.64(1H, d, J=9.8 Hz)<br>5.01(2H, s)<br>4.0–4.2(2H, m)<br>3.86(3H, s)<br>3.7–3.8(1H, m)<br>3.5–3.6(1H, m)<br>2.97(2H, d, J=9.8 Hz)<br>2.8–3.0(2H, m)<br>1.7–1.8(2H, m)<br>1.3–1.5(4H, m)<br>0.92(3H, t, J=7.1 Hz) | Neat<br>3300<br>2933<br>1670<br>1268 | FAB+<br>476<br>[M⁺H⁺](50)<br>458(60) | $C_{29}H_{33}NO_5$<br>Calcd.<br>C; 73.24%<br>H; 6.99%<br>N; 2.95%<br>Found<br>C; 73.06%<br>H; 7.06%<br>N; 2.81% |
| 7-14 | | | CDCl₃, 300 MHz<br>7.53(1H, d, J=8.2 Hz)<br>7.3–7.5(5H, m)<br>7.15(2H, d, J=8.6 Hz)<br>6.99(1H, d, J=8.2 Hz)<br>6.90(2H, d, J=8.6 Hz)<br>5.02(2H, s)<br>4.20(2H, s)<br>4.03(2H, d, J=6.7 Hz)<br>3.90(3H, s)<br>3.80(2H, t, J=7.4 Hz)<br>3.80(2H, t, J=7.4 Hz)<br>2.92(2H, t, J=7.4 Hz)<br>1.6–1.8(2H, m)<br>1.3–1.5(4H, m)<br>0.93(3H, t, J=6.8 Hz) | | FAB+<br>460<br>[M⁺H⁺](100)<br>262(50) | |

TABLE 115-continued

| Ex. | Structural formula | m.p. | 1H NMR (δ) ppm | IR cm$^{-1}$ | MS | Elem. anal. |
|---|---|---|---|---|---|---|
| 7-17 | | 106.3~107.2° C. | CDCl$_3$, 300 MHz<br>8.20(1H, d, J=9.1 Hz)<br>7.3–7.5(5H, m)<br>7.13(1H, d, J=9.1 Hz)<br>7.12(2H, d, J=8.6 Hz)<br>6.90(2H, d, J=8.6 Hz)<br>6.77(1H, d, J=7.7 Hz)<br>6.65(1H, d, J=7.7 Hz)<br>5.04(2H, s)5.04(2H, s)<br>4.13(2H, t, J=7.4 Hz)<br>4.01(2H, t, J=6.7 Hz)<br>3.92(3H, s)<br>3.01(2H, t, J=7.3 Hz)<br>1.7–1.9(2H, m)<br>1.3–1.6(4H, m)<br>0.94(3H, t, J=7.1 Hz) | KBr<br>3438<br>2950<br>1652<br>1623<br>1597<br>1510<br>1283<br>1085 | FAB+<br>472<br>[M$^+$H$^+$](100) | C$_{30}$H$_{33}$NO$_4$<br>Calcd.<br>C; 76.41%<br>H; 7.05%<br>N; 2.97%<br>Found<br>C; 76.55%<br>H; 7.06%<br>N; 2.96% |

TABLE 116

| Ex. | Structural formula | m.p. | 1H NMR (δ) ppm | IR cm$^{-1}$ | MS | Elem. anal. |
|---|---|---|---|---|---|---|
| 7-18 | | | CDCl$_3$, 300 MHz<br>7.83(1H, d, J=8.5 Hz)<br>6.88(1H, d, J=8.5 Hz)<br>3.93(2H, t, J=6.6 Hz)<br>3.89(3H, s)<br>3.63(2H, t, J=7.4 Hz)<br>3.54(2H, t, =6.6 Hz)<br>3.02(2H, t, J=6.6 Hz)<br>2.3–2.4(4H, m<br>2.1–2.2(2H, m)<br>1.5–1.9(5H, m)<br>1.3–1.5(6H, m)<br>0.94(3H, t, J=7.2 Hz) | Neat<br>2954<br>1714<br>1644<br>1279 | FAB+<br>388[M+H+]<br>(100) | |
| 7-19-1 | | 130.3~131.1° C. | CDCl$_3$, 300 MHz<br>8.20(1H, d, J=8.9 Hz)<br>7.13(1H, d, J=8.9 Hz)<br>7.08(1H, bs)<br>7.02(2H, d, J=8.2 Hz)<br>6.85(1H, d, J=7.5 Hz)<br>6.82(2H, d, J=8.2 Hz)<br>6.72(1H, d, J=7.5 Hz)<br>4.15(2H, t, J=7.5 Hz)<br>4.01(2H, t, J=6.7 Hz)<br>3.95(3H, s)<br>2.98(2H, t, J=7.5 Hz)<br>1.7–1.9(2H, m)<br>1.3–1.5(4H, m)<br>0.93(3H, t, J=7.0 Hz) | Neat<br>3250<br>2959<br>1642<br>1586<br>1514<br>1283 | FAB+<br>381<br>[M$^+$H$^+$](100)<br>261(40)<br>191(40) | C$_{23}$H$_{27}$NO$_4$<br>Calcd.<br>C; 72.42%<br>H; 7.13%<br>N; 3.66%<br>Found<br>C; 72.30%<br>H; 7.21%<br>N; 3.58% |
| 7-19-2 | | | | | | |

TABLE 117

| Ex. | Structural formula | m.p. | 1H NMR (δ) ppm | IR cm⁻¹ | MS | Elem. anal. |
|---|---|---|---|---|---|---|
| 7-20 | (isoquinolinone with MeO, O-pentyl, N-CH2CH2-4-pyridyl) | 90.2~90.3° C. | CDCl$_3$, 300 MHz<br>8.51(2H, d, J=5.9 Hz)<br>8.19(1H, d, J=8.9 Hz)<br>7.14(1H, d, J=8.9 Hz)<br>7.14(2H, d, J=5.9 Hz)<br>6.76(1H, d, J=7.6 Hz)<br>6.67(1H, d, J=7.6 Hz)<br>4.19(2H, t, J=7.3 Hz)<br>4.01(2H, t, J=6.7 Hz)<br>3.97(3H, s)<br>3.09(2H, t, J=7.3 Hz)<br>1.7–1.9(2H, m)<br>1.3–1.5(4H, m)<br>0.94(3H, t, J=7.1 Hz) | Neat<br>3478<br>2936<br>1650<br>1625<br>1596<br>1484<br>1284 | FAB+<br>367<br>[M⁺H⁺](50) | C$_{22}$H$_{26}$N$_2$O$_3$<br>Calcd.<br>C; 72.11%<br>H; 7.15%<br>N; 7.64%<br>Found<br>C; 72.03%<br>H; 7.25%<br>N; 7.54% |
| 7-22 | (isoquinolinone with MeO, O-pentyl, N-CH2CH2-4-C6H4-OAc) | | CDCl$_3$, 300 MHz<br>8.20(1H, d, J=8.9 Hz)<br>7.22(2H, d, J=8.5 Hz)nl<br>7.14(1H, d, J=8.9 Hz)<br>7.01(2H, d, J=8.5 Hz)<br>6.80(1H, d, J=7.6 Hz)<br>6.67(1H, d, J=7.6 Hz)<br>4.15(2H, t, J=7.5 Hz)<br>4.01(2H, t, J=6.7 Hz)<br>3.96(3H, s)<br>3.07(2H, t, J=7.5 Hz)<br>2.29(3H, s)<br>1.7–1.9(2H, m)<br>1.3–1.5(4H, m)<br>0.94(3H, t, J=7.1 Hz) | KBr<br>3438<br>2957<br>1762<br>1654<br>1627<br>1283 | FAB+<br>424<br>[M⁺H⁺](50) | C$_{25}$H$_{29}$NO$_5$<br>Calcd.<br>C; 70.90%<br>H; 6.90%<br>N; 3.31%<br>Found<br>C; 71.10%<br>H; 6.99%<br>N; 3.22% |
| 7-23 | (3,4-dihydroisoquinolinone with MeO, O-pentyl, N-CH2CH2-4-C6H4-OAc) | | CDCl$_3$, 300 MHz<br>7.84(1H, d, J=8.6 Hz)<br>7.27(2H, d, J=8.4 Hz)<br>7.01(2H, d, J=8.4 Hz)<br>6.87(1H, d, J=8.6 Hz)<br>3.90(2H, t, J=6.7 Hz)<br>3.88(3H, s)<br>3.75(2H, t, J=7.5 Hz)<br>3.38(2H, t, J=6.6 Hz)<br>2.95(2H, t, J=7.5 Hz)<br>2.89(2H, t, J=6.6 Hz)<br>2.28(3H, s)<br>1.7–1.8(2H, m)<br>1.3–1.5(4H, m)<br>0.93(3H, t, J=7.0 Hz) | KBr<br>2936<br>1756<br>1646<br>1219 | FAB+<br>426<br>[M⁺H⁺](100)<br>276(50) | |

TABLE 118

| Ex. | Structural formula | m.p. | 1H NMR (δ) ppm | IR cm⁻¹ | MS | Elem. anal. |
|---|---|---|---|---|---|---|
| 7-24 | (3,4-dihydroisoquinolinone with MeO, O-pentyl, N-CH2CH2-4-C6H4-OH) | 143.6~144.4° C. | CDCl$_3$, 300 MHz<br>7.82(1H, d, J=8.6 Hz)<br>7.08(2H, d, J=8.4 Hz)<br>6.85(1H, d, J=8.6 Hz)<br>6.9(2H, d, J=8.4 Hz)<br>6.35(1H, s)<br>3.90(2H, t, J=8.4 Hz)<br>6.35(1H, s)<br>3.90(2H, t, J=6.7 Hz)<br>3.87(3H, s)<br>3.73(2H, t, J=7.1 Hz)<br>3.39(2H, t, J=6.6 Hz)<br>2.90(2H, t, J=6.6 Hz)<br>2.86(2H, t, J=7.1 Hz)<br>1.6–1.8(2H,m)<br>1.3–1.5(4H, m)<br>0.92(3H, t, J=7.1 Hz) | | FAB+<br>384<br>[M⁺H⁺](100)<br>276(60)<br>264(40) | C$_{23}$H$_{29}$NO$_4$<br>Calcd.<br>C; 72.04%<br>H; 7.62%<br>N; 3.65%<br>Found<br>C; 72.04%<br>H; 7.79%<br>N; 3.55% |

TABLE 118-continued

| Ex. | Structural formula | m.p. | 1H NMR (δ) ppm | IR cm⁻¹ | MS | Elem. anal. |
|---|---|---|---|---|---|---|
| 7-25 | | 170.6~171.4° C. | CDCl$_3$, 300 MHz<br>7.59(1H, s)<br>7.10(2H, d, J=8.5 Hz)<br>7.00(1H, bs)<br>6.77(2H, d, J=8.5 Hz)<br>6.58(1H, s)<br>4.02(2H, t, J=6.9 Hz)<br>3.88(3H, s)<br>3.73(2H, t, J=7.3 Hz)<br>3.39(2H, t, J=6.7 Hz)<br>2.87(2H, t, J=7.3 Hz)<br>2.77(2H, t, J=6.7 Hz)<br>1.8–1.9(2H, m)<br>1.3–1.5(4H, m)<br>0.93(3H, t, J=7.1 Hz) | Neat<br>3227<br>2934<br>2361<br>1600<br>1516<br>1280 | FAB+<br>384<br>[M⁺H⁺](40) | C$_{23}$H$_{29}$NO$_4$<br>Calcd.<br>C; 72.04%<br>H; 7.62%<br>N; 3.65%<br>Found<br>C; 71.93%<br>H; 7.65%<br>N; 1113.62 |
| 7-26 | | | CDCl$_3$, 300 MHz<br>7.82(1H, s)<br>7.21(2H, d, J=8.5 Hz)<br>7.00(2H, d, J=8.5 Hz)<br>6.83(1H, s)<br>6.74(1H, d, J=7.3 Hz)<br>6.31(1H, d, J=7.3 Hz)<br>4.19 2H, t, J=7.3 Hz)<br>4.10(2H, t, J=6.9 Hz)<br>4.00(3H, s)<br>3.08(2H, t, J=7.3 Hz)<br>2.29(3H, s)<br>1.8–2.0(2H, m)<br>1.3–1.5(4H, m)<br>0.95(3H, t, J=7.1 Hz) | | FB+<br>424<br>[M⁺H⁺](100)<br>261(70) | |

TABLE 119

| Ex. | Structural formula | m.p. | 1H NMR (δ) ppm | IR cm⁻¹ | MS | Elem. anal. |
|---|---|---|---|---|---|---|
| 7-27 | | 209.4~210.7° C. | DMSO-d6, 300 MHz<br>9.2(1H, bs)<br>7.6(1H, s)<br>7.2(1H, d, J=6 Hz)<br>7.1(1H, s)<br>7.0(2H, d, J=9 Hz)<br>6.6(2H, d, J=9 Hz)<br>6.4(1H, d, J=6 Hz)<br>4.0–4.1(2H, m)<br>4.0(2H, t, J=6 Hz)<br>3.9(3H, s)<br>2.8(2H, t, J=8 Hz)<br>1.7–1.8(2H, m)<br>1.3–1.5(4H, m)<br>0.90(3H, t, J=8 Hz) | KBr<br>3441<br>2953<br>1565<br>1516 | FAB+<br>382<br>[M⁺H⁺](100)<br>261(50) | |
| 7-28 | | 147.2~148.3° C. | DMSO-d6, 300 MHz<br>9.2(1H, bs)<br>7.6(1H, s)<br>7.2(1H, d, J=6 Hz)<br>7.1(1H, s)<br>7.0(2H, d, J=9 Hz)<br>6.6(2H, d, J=9 Hz)<br>6.4(1H, d, J=6 Hz)<br>4.0–4.1(2H, m)<br>4.0(2H, t, J=6 Hz)<br>3.9(3H, s)<br>2.8(2H, t, J=8 Hz)<br>17–1.8(2H, m)<br>1.3–1.5(4H, m)<br>0.90(3H, t, J=8 Hz) | KBr<br>3441<br>2953<br>1565<br>1516 | FAB+<br>382<br>[M⁺H⁺](100)<br>261(50) | |

TABLE 119-continued

| Ex. | Structural formula | m.p. | 1H NMR (δ) ppm | IR cm⁻¹ | MS | Elem. anal. |
|---|---|---|---|---|---|---|
| 7-29 | 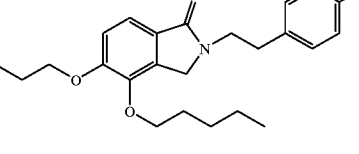 | 93.2~ 94.1° C. | CDCl₃, 300 MHz 7.60(1H, s) 7.27(2H, d, J=8.5 Hz) 7.01(2H, d, J=8.5 Hz) 6.59(1H, s) 4.02(2H, t, J=6.9 Hz) 3.90(3H, s) 3.75(2H, t, J=7.3 Hz) 3.38(2H, t, J=6.7 Hz) 2.95(2H, t, J=7.3 Hz) 2.77(2H, t, J=6.7 Hz) 2.28(3H, s) 1.8–1.9(2H, m) 1.3–1.5(4H, m) 0.93(3H, t, J=7.0 Hz) | Neat | FAB+ 426 [M+H+](60) 276(55) HRFAB (m/z) Calcd. $C_{25}H_{32}NO_5$ 426.5380 Found 426.2277 | $C_{25}H_{31}NO_5$ Calcd. C; 70.57% H; 7.34% N; 3.29% Found C; 70.19% H; 7.36% N; 3.24% |

TABLE 120

| Ex. | Structural formula | m.p. | 1H NMR (δ) ppm | IR cm⁻¹ | MS | Elem. anal. |
|---|---|---|---|---|---|---|
| 7-30 | 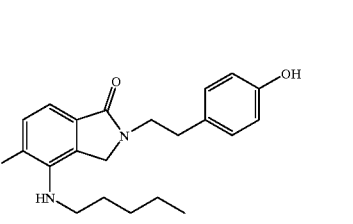 | 96.2– 96.7° C. | CDCl3, 300 MHz 8.15(2H, d, J=8.7 Hz) 7.49(1H, d, J=8.3 Hz) 7.42(2H, d, J=8.7 Hz), 6.99(1H, d, J=8.3 Hz) 4.22(2H, s), 4.06(2H, t, J=6.7Hz) 4.04(2H, t, J=6.5 Hz) 3.88(2H, t, J=7.2 Hz) 3.11(2H, t, J=7.2 Hz) 1.8–1.9(2H, m) 1.7–1.8(2H, m) 1.3–1.5(8H, m) 0.94(3H, t, J=7.1 Hz) 0.93(3H, t, J=7.1 Hz) | KBr 2933 1687 1516 1344 | FAB+ 455[M+H+](100), 318(100) | C26H34N2O5 Calcd. C; 68.70% H; 76.54% N; 6.16% Found C; 68.92% H; 7.54% N; 6.05% |
| 7-31 | 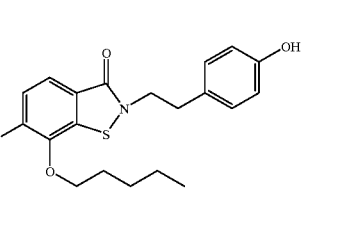 | 115.0~ 116.5° C. | CDCl₃, 300 MHz 7.27(1H, d, J=8.2 Hz) 7.10(2H, d, J=8.4 Hz) 6.84(1H, d, J=8.2 Hz) 6.69(2H, d, J=8.4 Hz) 5.38(2H, s) 3.88(3H, s) 3.70(2H, t, J=7.7 Hz) 3.14(2H, t, J=7.1 Hz) 2.89(2H, t, J=7.7 Hz) 1.5–1.63(2H, m) 1.3–1.4(4H, m) 0.91(3H, t, J=8.0 Hz) | KBr 2932 1676 1515 1261 | FAB+ 369[M⁺H⁺](100) 261(50) | |
| 7-32 | | 11.0– 111.0° C. | CDCl3, 300 MHz 7.71(1H, d, J=8.4 Hz) 7.39(1H, bs) 7.05(2H, d, J=8.1 Hz) 7.00(1H, d, J=8.4 Hz) 6.76(2H, d, J=8.1 Hz) 4.13(2H, t, J=6.6 Hz) 4.07(2H, t, J=7.4 Hz) 3.93(3H, s) 2.97(2H, t, J=7.4 Hz) 1.65–1.8(2H, m) 1.3–1.5(4H, m) 0.94(3H, t, J=7.1 Hz) | | FAB+ 388[M+H+](100) 267(50) | C21H25NO4S |

TABLE 121

| Ex. | Structural formula | m.p. | 1H NMR (δ) ppm | IR cm⁻¹ | MS | Elem. anal. |
|---|---|---|---|---|---|---|
| 7-33 | | | CDCl3, 300 MHz<br>8.12(2H, d, J=8.6 Hz)<br>7.90(1H, d, J=8.6 Hz)<br>7.31(1H, d, J=8.2 Hz)<br>6.89(1H, d, J=8.2 Hz)<br>5.69(2H, d, J=9.6 Hz)<br>4.0–4.2(2H, m)<br>3.98(2H, t, J=6.5 Hz)<br>3.7–3.9(1H, m)<br>3.6–3.8(1H, m)<br>3.2–3.3(1H, m)<br>3.08(2H, , J=7.0 Hz)<br>1.7–1.9(4H, m)<br>1.3–1.5(8H, m)<br>0.9–1.0(6H, m) | Neat<br>3300<br>2960<br>1673<br>1520<br>1345<br>1269 | FAB+<br>471<br>[M+H+](20),<br>453(60),<br>165(100). | |
| 7-34 | | 67.2–<br>67.8° C. | CDCl3, 300 MHz<br>7.46(1H, d, J=8.2 Hz)<br>7.02(2H, d, J=8.3 Hz)<br>6.97(1H, d, J=8.2 Hz)<br>6.61(2H, d, J=8.3 Hz)<br>4.20(2H, s)<br>4.05(2H, t, J=6.6 Hz)<br>4.03(2H, t, J=6.5 Hz),<br>3.76(2H, t, J=7.4 Hz)<br>3.58(2H, bs),<br>2.86(2H, t, J=7.4 Hz)<br>1.8–1.9(2H, m)<br>1.7–1.8(2H, m)<br>1.3–1.6(8H, m)<br>0.94(3H, t, J=7.0 Hz)<br>0.94(3H, t, J=7.0 Hz) | Neat<br>3346<br>2931<br>1681<br>1620<br>1272 | FAB+<br>425[M+H+](65),<br>120(100) | C26H36N2O3<br>Calcd.<br>C; 73.55%<br>H; 8.55%<br>N; 6.60%<br>Found<br>C; 73.39%<br>H; 8.74%<br>N; 6.47% |
| 7-35 | | 213.6–<br>214.6° C. | DMSO-d6, 300 MHz<br>10.19(3H, bs)<br>7.34(1H, d J=8.4 Hz)<br>7.28(2H, d, J=8.4 Hz)<br>7.26(2H, d, J=8.4 Hz)<br>7.06(1H, d, J=8.4 Hz)<br>4.40(2H, s)<br>4.03(4H, t, J=6.6 Hz)<br>3.70(2H, t, J=7.2 Hz)<br>2.93(2H, t, J=7.2 Hz)<br>1.6–1.8(4H, m)<br>1.2–1.5(8H, m)<br>0.89(6H, t, J=7.2 Hz) | KBr | FAB+<br>425[M+H+](100) | C26H36N2O3.HCl<br>Calcd.<br>C; 50.00%<br>H; 10.00%<br>N; 5.00% |

TABLE 122

| Ex. | Structural formula | m.p. | 1H NMR (δ) ppm | IRcm⁻¹ | MS | Elem. anal. |
|---|---|---|---|---|---|---|
| 7-36 | | | CDCl3, 300 MHz<br>8.15(2H, d, J=8.4 Hz)<br>7.52(1H, d, J=8.4 Hz)<br>7.41(2H, d, J=8.4 Hz),<br>7.00(1H, d, J=8.4 Hz)<br>4.23(2H, s),<br>4.04(2H, t, J=6.6 Hz)<br>3.90(3H, s)<br>3.88(2H, t, J=7.5 Hz)<br>3.11(2H, t, J=7.5 Hz)<br>1.7–1.8(2H, m)<br>1.3–1.5(8H, m)<br>0.92(3H, t, J=6.9 Hz) | | FAB+<br>399[M+H+]<br>(100),<br>262(80) | |

TABLE 122-continued

| Ex. | Structural formula | m.p. | 1H NMR (δ) ppm | IRcm⁻¹ | MS | Elem. anal. |
|---|---|---|---|---|---|---|
| 7-37 | | 64–67° C. | CDCl3, 300 MHz<br>7.52(1H, d, J=8.4 Hz)<br>7.02(2H, d, J=8.4 Hz)<br>6.98(1H, d, J=8.4 Hz)<br>4.20(2H, s)<br>6.61(2H, d, J=8.4 Hz)<br>4.02(2H, t, J=6.6 Hz)<br>3.90(3H, s)<br>3.76(2H, t, J=6.9 Hz)<br>3.30(2H, bs)<br>2.86(1H, d, J=6.9 Hz)<br>1.7–1.9(2H, m)<br>1.3–4.5(4H, m)<br>0.94(3H, t, J=7.2 Hz) | KBr<br>3348<br>2931<br>1682<br>1621<br>1518<br>1272 | FAB+<br>369[M+H+]<br>(100) | |
| 7-38 | | 212~215° C.(dec) | CDCl3, 300 MHz<br>10.46(3H, bs)<br>7.71(1H, d, J=8.4 Hz)<br>7.49(2H, d, J=8.4 Hz)<br>7.26(2H, d, J=8.4 Hz)<br>6.82(1H, d, J=6.0 Hz)<br>3.89(2H, d, J=6.6 Hz)<br>3.85(3H, s)<br>3.71(2H, t, J=7.5 Hz)<br>3.44(2H, t, J=6.0 Hz)<br>2.92(4H, qu, J=6.6 Hz)<br>1.7–1.8(2H, m)<br>1.3–1.5(4H, m)<br>0.91(3H, t, J=6.9 Hz) | | FAB+<br>383<br>[M+H+](50),<br>120(100). | |

TABLE 123

| Ex. | Structural formula | m.p. | 1H NMR (δ) ppm | IRcm⁻¹ | MS | Elem. anal. |
|---|---|---|---|---|---|---|
| 7-39 | | | DMSO-d6, 300 MHz<br>10.7(1H, s)<br>8.14(2H, d, J=8.4 Hz)<br>7.66(1H, d, J=8.7 Hz)<br>7.50(2H, d, J=8.4 Hz)<br>6.97(1H, d, J=8.7 Hz)<br>4.15(2H, t, J=7.4 Hz)<br>3.91 (2H, t, J=6.9 Hz)<br>3.88(3H, s)<br>3.03(2H, t, J=7.1 Hz)<br>1.70–1.80(2H, m)<br>1.30–1.45(4H, m)<br>0.88(3H, t, J=7.1 Hz) | | | |
| 7-40 | | 154.9~155.7° C. | CDCl3, 300 MHz<br>8.05(1H, s)<br>7.83(1H, d, J=9.0 Hz)<br>7.12(2H, d, J=7.8 Hz)<br>6.80(1H, d, J=9.0 Hz)<br>6.64(2H, d, J=7.8 Hz)<br>4.18(2H, t, J=8.0 Hz)<br>4.08(2H, t, J=7.1 Hz)<br>3.95(3H, s,)<br>3.58(2H, bs)<br>2.86(2H, t, J=8.1 Hz)<br>1.73–1.85(2H, m)<br>1.30–1.50(4H, m)<br>0.95(3H, t, J=7.1 Hz) | 77KBr<br>2954<br>1708<br>1654<br>1618 | FAB+<br>398<br>[M+H+]<br>(30) | |

TABLE 123-continued

| Ex. | Structural formula | m.p. | 1H NMR (δ) ppm | IRcm$^{-1}$ | MS | Elem. anal. |
|---|---|---|---|---|---|---|
| 7-41 | (structure: quinazoline-2,4-dione with MeO, pentyloxy, N-CH2CH2-C6H4-NH2·HCl) | 244–249 °C. (decomp) | DMSO-d6, 300 MHz 10.73(1H, s) 10.17(2H, bs) 7.66(1H, d, J=8.7 Hz) 7.32(2H, d, J=8.7 Hz) 7.28(2H, d, J=8.7 Hz) 6.96(1H, d, J=8.7 Hz) 4.08(2H, t, J=7.5 Hz) 3.91(2H, t, J=7.4 Hz) 3.88(3H, s) 3.44(2H, bs) 2.88(2H, t, J=7.5 Hz) 1.66–1.80(2H, m) 1.25–1.45(4H, m) 0.881(3H, t, J=7.2 Hz) | KBr 2953 2542 1705 1665 1621 1412 | FAB− 396(20) 326(20) | C22H28-ClN3O4 Calcd. C; 60.89% H; 6.50% N; 9.68% Found C; 60.95% H; 6.56% N; 9.63% |

TABLE 124

| Ex. | Structural formula | m.p. | 1H NMR (δ) ppm | IRcm$^{-1}$ | MS | Elem. anal. |
|---|---|---|---|---|---|---|
| 7-42 | (structure: benzodiazepine-dione with MeO, pentyloxy, N-CH2CH2-C6H4-NH2) | 161.0~ 164.0° C. | DMSO-d6, 300 MHz 9.43(1 H, s) 7.46(1H, d, J=9.0 Hz) 6.97(2H, d, J=9.0 Hz) 6.88(2H, d, J=8.1 Hz) 6.47(2H, d, J=8.1 Hz) 4.87(2H, s) 3.90(2H, t, J=6.6 Hz) 3.84(3H, s) 3.78(2H, bs) 3.62(2H, t, J=7.7 Hz) 2.64(2H, t, J=7.7 Hz) 1.60–1.75(2H, m) 1.25–1.45(4H, m) 0.88(3H, t, J=6.9 Hz) | KBr 3455 3360 2935 1694 1634 1465 1290 | FAB+412 [M+H+] (50) | C23H29N3O4 |
| 7-43 | (structure: 2,2-dimethyl dihydroquinazolinone with MeO, pentyloxy, N-CH2CH2-C6H4-NO2) | | | | | |
| 7-44 | (structure: 2-methyl quinazolinone with MeO, pentyloxy, N-CH2CH2-C6H4-NO2) | | | | | |

TABLE 125

| Ex. | Structural formula | m.p. | 1H NMR (δ) ppm | IRcm⁻¹ | MS | Elem. anal. |
|---|---|---|---|---|---|---|
| 7-45 | | 210.1~ 212.3° C. | DMSO-d6, 300 MHz 10.81(1H, s) 8.78(2H, d, J=6.5 Hz) 7.89(2H, d, J=6.5 Hz) 7.65(1H, d, J=8.9 Hz) 6.98(1H, d, J=8.9 Hz) 4.24(2H, t, J=6.9 Hz) 3.91(2H, t, J=6.2 Hz) 3.89(3H, s) 3.18(2H, t, J=6.9 Hz) 1.70–1.80(2H, m) 1.23–1.40(4H, m) 0.89(3H, t, J=7.04 Hz) | KBr 2933 1714 1672 1616 1370 1296 | FAB+ 384[M+H+] (100) 238(20) | C21H25N3O4 |
| 7-46 | | 107.5~ 108.5° C. | CDCl3, 300 MHz 9.51(1H, s) 8.54(2H, d, J=6.0 Hz) 7.82(1H, d, J=9.0 Hz) 7.32(2H, d, J=6.0 Hz) 6.91(1H, d, J=9.0 Hz) 4.71(2H, t, J=8.3 Hz) 4.14(2H, t, J=7.1 Hz) 3.97(3H, s) 3.10(2H, t, J=8.1 Hz) 1.75–1.90(2H, m) 1.30–1.50(4H, m) 0.96(3H, t, J=7.1 Hz) | KBr 3415 2952 2363 1687 1620 1488 1144 1094 | FAB+ 400 [M+H+] (20) | C21H25N3O3S |
| 7-47 | | | CDCl3, 300 MHz 8.54(2H, d, J=5.9 Hz) 8.08(1H, d, J=9.0 Hz) 7.75(1H, s) 7.18(1H, d, J=9.0 Hz) 7.14(2H, d, J=5.9 Hz) 4.21(2H, t, J=7.2 Hz) 4.14(2H, t, J=7.0 Hz) 3.99(3H, s) 3.12(2H, t, J=7.3 Hz) 1.75–1.90(2H, m) 1.30–1.50(4H, m) 0.92(3H, t, J=7.1 Hz) | | | |

TABLE 126

| Ex. | Structural formula | m.p. | 1H NMR (δ) ppm | IRcm⁻¹ | MS | Elem. anal. |
|---|---|---|---|---|---|---|
| 7-48 | | | DMSO-d6, 300 MHz 8.79(2H, d, J=6.0 Hz) 7.95(2H, d, J=6.0 Hz) 7.76(1H, d, J=8.7 Hz) 7.18(1H, d, J=8.7 Hz) 4.18(2H, t, J=6.9 Hz) 3.91(2H, t, J=7.7 Hz) 3.91(2H, s) 3.88(3H, s) 3.14(2H, t, J=6.8 Hz) 1.60–1.78(2H, m) 1.25–1.50(4H, m) 0.90(3H, t, J=7.1 Hz) | | | |

TABLE 126-continued

| Ex. | Structural formula | m.p. | 1H NMR (δ) ppm | IRcm⁻¹ | MS | Elem. anal. |
|---|---|---|---|---|---|---|
| 7-49 | 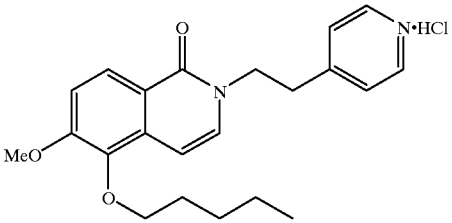 | 152.8~ 153.3° C. | DMSO-d6, 300 MHz<br>8.81(2H, d, J=6.6 Hz)<br>7.95(1H, d, J=9.0 Hz)<br>7.92(2H, d, J=6.6 Hz)<br>7.38(1H, d, J=7.5 Hz)<br>7.30(1H, d, J=9.0 Hz)<br>6.61(1H, d, J=7.5 Hz)<br>4.30(2H, t, J=6.9 Hz)<br>3.95(2H, t, J=6.6 Hz)<br>3.91(3H, s)<br>3.31(2H, t, J=7.2 Hz)<br>1.65–1.77(2H, m)<br>1.28–1.49(4H, m)<br>0.90(3H, t, J=6.9 Hz) | KBr<br>3436<br>2389<br>1655<br>1630<br>1285<br>1087 | | C22H27ClN2O3<br>Calcd.<br>C; 65.58%<br>H; 6.75%<br>N: 6.95%<br>Found<br>C; 65.34%<br>H; 6.89%<br>N: 6.98% |
| 7-50 | 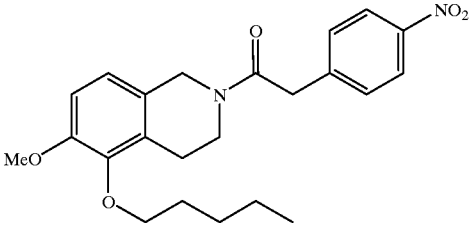 | | | | | |

TABLE 127

| Ex. | Structural formula | m.p. | 1H NMR (δ) ppm | IRcm⁻¹ | MS | Elem. anal. |
|---|---|---|---|---|---|---|
| 7-51 | 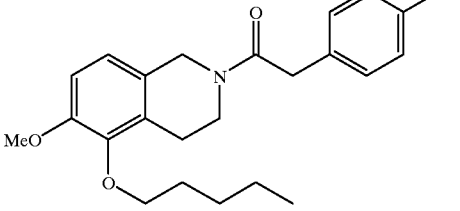<br>Colorless oil | | DMSO-d6, 300 MHz<br>6.77–6.93(4H, m)<br>6.51(2H, d, J=8.4 Hz)<br>4.52(2H, s)<br>4.51 (2H, bs)<br>3.88(2H, t, J=6.5 Hz)<br>3.75(3H, s)<br>3.63(2H, t, J=6.0 Hz)<br>3.56(2H, s)<br>2.68(2H, t, J=5.9 Hz)<br>1.60–1.73(2H, m)<br>1.30–1.50(4H, m)<br>0.89(3H, t, J=7.2 Hz) | | FAB+<br>383<br>[M+H+] (80)<br>289(50) | C23H30N2O3 |
| 7-52 | 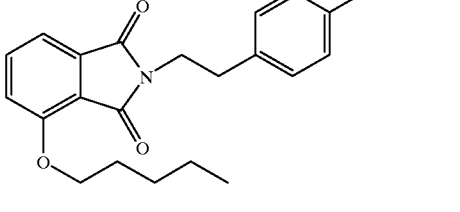<br>Colorless crystals | | CDCl3, 300 MHz<br>7.61(1H, t, J=7.83 Hz)<br>7.38(1H, d, J=7.22 Hz)<br>7.16(1H, d, J=8.43 Hz)<br>7.11(2H, d, J=8.30 Hz)<br>6.75(2H, d, J=8.33 Hz)<br>4.5–4.8(1H, br)<br>4.16(2H, t, J=6.64 Hz)<br>3.84(2H, t, J=7.69 Hz)<br>2.90(2H, t, J=7.68 Hz)<br>1.84–1.92(2H, m)<br>1.35–1.52(4H, m)<br>0.94(3H, t, J=7.04 Hz) | Neat<br>3422<br>3021<br>2955<br>2871<br>1766<br>1704<br>1614<br>1516 | | |

TABLE 128

| Ex. | Structural formula | m.p. | 1H NMR (δ) ppm | IRcm⁻¹ | MS | Elem. anal. |
|---|---|---|---|---|---|---|
| 7-54 | 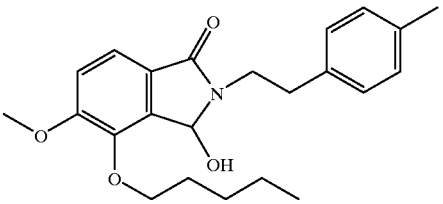<br>Pale-yellow crystals | | CDCl3, 300 MHz<br>8.12(2H, d, J=8.7 Hz)<br>7.39(2H, d, J=8.7 Hz)<br>7.33(1H, d, J=8.1 Hz)<br>6.90(1H, d, J=8.1 Hz)<br>5.69(2H, d, J=9.4 Hz)<br>4.0–4.2(2H, m)<br>3.85(3H, s)<br>3.7–3.9(1H, m)<br>3.6–3.7(1H, m)<br>3.15(1H, d, J=9.4 Hz)<br>3.08(2H, q, J=6.6 Hz)<br>1.7–1.8(2H, m)<br>1.2–1.5(4H, m)<br>0.92(3H, t, J=6.9 Hz) | | FAB+<br>415<br>[M+H+1(60),<br>397(80),<br>179(100). | |
| 7-55 | 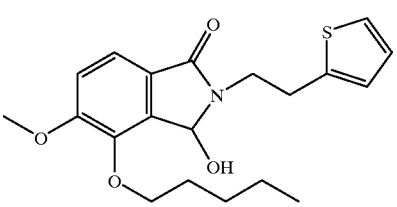<br>Colorless crystals | | CDCl3, 300 MHz<br>7.37(1H, d, J=8.4 Hz)<br>7.11(1H, dd, J=5.1, 1.2 Hz)<br>6.92(1H, d, J=8.4 Hz)<br>6.89(1H, dd, J=5.1, 3.3 Hz)<br>6.83(1H, dd, J=3.3, 1.2 Hz)<br>5.65(1H, d, J=9.9 Hz)<br>4.0–4.1(2H, m)<br>3.87(3H, s)<br>3.80(1H, q, J=6.9 Hz)<br>3.61(1H, qui, J=6.9 Hz)<br>3.47(1H, d, J=4.5 Hz)<br>3.17(2H, t, J=7.2 Hz)<br>1.7–1.8(2H, m)<br>1.3–1.5(4H, m)<br>0.93(3H, t, J=7.2 Hz) | KBr<br>3312<br>1672<br>1267 | FAB+376<br>(M+H+](50),<br>358(100). | |
| 7-56 | 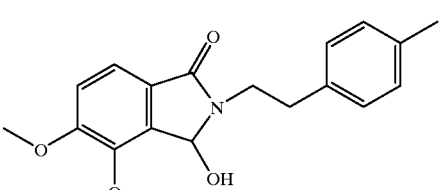<br>Colorless crystals | | CDCl3, 300 MHz<br>7.40(1H, d, J=8.1 Hz)<br>7.12(1H, d, J=8.1 Hz)<br>7.07(2H, d, J=8.1 Hz)<br>6.94(1H, d, J=8.1 Hz)<br>5.61(1H, d, J=9.5 Hz)<br>4.0–4.2(2H, m)<br>3.87(3H, s)<br>3.80(1H, q, J=6.9 Hz)<br>3.60(2H, q, J=6.9 Hz)<br>2.93(2H, t, J=7.2 Hz)<br>2.68(1H, d, J=9.8 Hz)<br>2.30(3H, s)<br>1.7–1.8(2H, m)<br>1.2–1.5(4H, m)<br>0.93(3H, t, J=7.1 Hz) | | FAB+<br>384[M+H+]<br>(100),<br>366(100). | |

TABLE 129

| Ex. | Structural formula | m.p. | 1H NMR (δ) ppm | IRcm⁻¹ | MS | Elem. anal. |
|---|---|---|---|---|---|---|
| 7-57 | 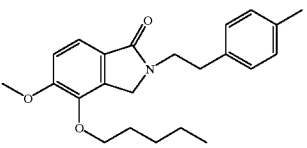<br>Colorless crystals | 57.4–<br>58.5° C. | CDCl3, 300 MHz<br>7.52(1H, d, J=8.1 Hz)<br>7.13(2H, d, J=8.1 Hz)<br>7.08(2H, d, J=8.1 Hz)<br>6.98(1H, d, J=8.1 Hz)<br>4.17(2H, s)<br>4.01(2H, t, J=6.9 Hz)<br>3.90(3H, s)<br>3.80(2H, t, J=7.2 Hz)<br>2.99(2H, t, J=7.2 Hz)<br>1.7–1.8(2H, m)<br>1.3–1.5(4H, m)<br>0.93(3H, t, J=7.2 Hz) | | FAB+<br>368[M+H+]<br>(100) | |

TABLE 129-continued

| Ex. | Structural formula | m.p. | 1H NMR (δ) ppm | IRcm$^{-1}$ | MS | Elem. anal. |
|---|---|---|---|---|---|---|
| 7-58 | | | | Neat 3500 2956 1769 1274 | FAB+416 [M+H+] (10) 398(100) | |
| 7-59 | | 108.2~ 108.4° C. | CDCl$_3$, 300 MHz 7.3–7.5(5H, m) 7.39(1H, d, J=8.6 Hz) 7.14(2H, d, J=8.6 Hz) 6.91(1H, d, J=8.6 Hz) 6.88(2H, d, J=8.6 Hz) 5.65(1H, d, J=9.8 Hz) 5.02(2H, s) 4.0–4.2(2H, m) 3.99(2H, t, J=6.5 Hz) 3.7–3.9(1H, m) 3.5–3.6(1H, m) 2.91(2H, t, J=6.8 Hz) 2.7–2.8(1H, m) 1.7–1.9(4H, m) 1.3–1.5(8H, m) 0.9–1.0(6H, m) | KBr 3252 2951 1659 1271 | FAB+ 531 [M+H+] (20) 514(80) 165(100) | C$_{33}$H$_{41}$NO$_5$ Calcd. C; 74.55% H; 7.77% N; 2.63% Found C; 74.82% H; 7.77% N; 2.67% |
| | Colorless crystals | | | | | |

TABLE 130

| Ex. | Structural formula | m.p. | 1H NMR (δ) ppm | IRcm$^{-1}$ | MS | Elem. anal. |
|---|---|---|---|---|---|---|
| 7-60 | | 114.2~ 114.6° C. | CDCl$_3$, 300 MHz 7.61(1H, s) 7.45(1H, d, J=8.3 Hz) 6.97(1H, d, J=8.3 Hz) 6.86(1H, s) 4.60(1H, bs) 4.31(2H, s) 4.07(2H, t, J=6.6 Hz) 4.04(2H, t, J=6.5 Hz) 3.91(2H, t, J=6.8 Hz) 3.04(2H, t, J=6.8 Hz) 1.8–1.9(2H, m) 1.7–1.8(2H, m) 1.3–1.5(8H, m) 0.93(3H, 1, J=7.0 Hz) 0.93(3H, 1, J=7.0 Hz) | Neat 3238 2926 1660 1464 1268 | FAB+ 400 [M+H+] (100) | |
| | Colorless crystals | | | | | |
| 7-61 | | | CDCl$_3$, 300 MHz 7.50(1H, d, J=8.2 Hz) 7.3–7.5(5H, m) 7.16(2H, d, J=8.6 Hz) 6.97(1H, d, J=8.2 Hz) 6.90(2H, d, J=8.6 Hz) 5.03(2H, s) 4.19(2H, s) 4.05(2H, t, J=6.6 Hz) 4.04(2H, t, J=6.5 Hz) 3.80(2H, t, J=7.6 Hz) 2.93(2H, t, J=7.6 Hz) 1.8–1.9(2H, m) 1.7–1.8(2H, m) 1.3–1.5(8H, m) 0.94(3H, t, J=7.1 Hz) 0.93(3H, t, J=7.1 Hz) | Neat 2931 1687 1618 1511 1271 | FAB+516 [M+H+] (100) 318(50). | C$_{33}$H$_{41}$NO$_4$ Calcd. C; 76.86% H; 8.01% N; 2.72% Found C; 76.26% H; 8.17% N; 2.43% |
| | Colorless oil | | | | | |

TABLE 130-continued

| Ex. | Structural formula | m.p. | 1H NMR (δ) ppm | IRcm$^{-1}$ | MS | Elem. anal. |
|---|---|---|---|---|---|---|
| 7-62 | | 122.2~ 122.6° C. | CDCl$_3$, 300 MHz<br>7.49(1H, d, J=8.3 Hz)<br>7.06(2H, d, J=8.5 Hz)<br>6.95(1H, d, J=8.3 Hz)<br>6.75(2H, d, J=8.5 Hz)<br>6.72(1H, bs)<br>4.24(2H, s)<br>4.06(2H, t, J=6.7 Hz)<br>4.02(2H, t, J=6.5 Hz)<br>3.83(2H, t, J=7.2 Hz)<br>2.91(2H, t, J=7.2 Hz)<br>1.8–1.9(2H, m)<br>1.7–1.8(2H, m)<br>1.3–1.5(8H, m)<br>0.94(3H, t, J=7.0 Hz)<br>0.94(3H, t, J=7.0 Hz) | KBr<br>3156<br>2932<br>1657<br>1464<br>1273 | FAB+<br>426<br>[M$^+$H$^+$]<br>(100) | C$_{26}$H$_{35}$NO$_4$<br>Calcd.<br>C; 73.38%<br>H; 8.29%<br>N; 3.29%<br>Found<br>C; 73.60%<br>H; 8.30%<br>N; 3.29% |
| | Colorless needles | | | | | |

TABLE 131

| Ex. | Structural formula | m.p. | 1H NMR (δ) ppm | IR cm$^{-1}$ | MS | Elem. anal. |
|---|---|---|---|---|---|---|
| 7-63 | | 78.3~ 78.6° C. | CDCl3, 300 MHz<br>7.08(2H, d, J=8.5 Hz)<br>6.82(1H, d, J=8.1 Hz)<br>6.75(1H, d, J=8.1 Hz)<br>6.68(2H, d, J=8.5 Hz)<br>3.9–4.1(8H, m)<br>2.9–3.0(2H, m)<br>2.9–2.9(2H, m)<br>1.7–1.9(4H, m)<br>1.3–1.5(8H, m)<br>0.93(3H, t, J=7.0 Hz)<br>0.92(3H, t, J=7.0 Hz) | KBr<br>3500<br>2932<br>1613<br>1515<br>1490<br>1263 | FAB+<br>412[M+H+]<br>(100). | |
| | Colorless crystals | | | | | |
| 7-64 | | 91.7~ 92.0° C. | CDCl3, 300 MHz<br>7.50(1H, d, J=8.2 Hz)<br>7.06(2H, d, J=8.4 Hz)<br>6.97(1H, d, H=8.2 Hz)<br>6.54(2H, d, J=8.4 Hz)<br>4.19(2H, s)<br>4.05(2H, t, J=6.6 Hz)<br>4.04(2H, t, J=6.6 Hz)<br>3.76(2H, t, J=7.1 Hz)<br>3.60(1H, bs)<br>2.86(2H, t, J=7.1 Hz)<br>2.81(3H, s)<br>1.8–1.9(2H, m)<br>1.6–1.8(2H, m)<br>1.3–1.5(8H, m)<br>0.94 (3H, t, J=7.1 Hz)<br>0.93 (3H, t, J=7.1 Hz) | | FAB+<br>439[M+H+]<br>(100) | C27H38N2O3<br>Calcd.<br>C; 73.94%<br>H; 8.73%<br>N; 6.39%<br>Found<br>C; 73.89%<br>H; 9.10%<br>N; 6.41% |
| | Colorless crystals | | | | | |

TABLE 131-continued

| Ex. | Structural formula | m.p. | 1H NMR (δ) ppm | IR cm⁻¹ | MS | Elem. anal. |
|---|---|---|---|---|---|---|
| 7-65 | (structure) Colorless oil | | CDCl3, 300 MHz<br>7.50(1H, d, J=8.2 Hz)<br>7.10(2H, d, J=8.7 Hz)<br>6.98(1H, d, J=8.2 Hz)<br>6.68(2H, d, J=8.7 Hz)<br>4.20(2H, s)<br>4.03(4H, t, J=6.6 Hz)<br>3.78(2H, t, J=7.1 Hz)<br>2.90(6H, s)<br>2.88(2H, t, J=7.1 Hz)<br>1.8–1.9(2H, m)<br>1.6–1.8(2H, m)<br>1.3–1.5(8H, m)<br>0.94 (3H, t, J=7.0 Hz)<br>0.93 (3H, t, J=7.0 Hz) | Neat<br>3280<br>2931<br>2870<br>1666<br>1617<br>1523<br>1273 | FAB+<br>453[M+H+]<br>(100) | |

TABLE 132

| Ex. | Structural formula | m.p. | 1H NMR (δ) ppm | IRcm⁻¹ | MS | Elem. anal. |
|---|---|---|---|---|---|---|
| 7-66 | (structure) Amorphous | | CDCl3, 300 MHz<br>8.51(2H, d, J=6.0 Hz)<br>7.53(1H, d, J=8.4 Hz)<br>7.19(2H, d, J=6.0 Hz)<br>7.00(1H, d, J=8.4 Hz)<br>4.23(2H, s)<br>4.04(2H, t, J=6.6 Hz)<br>3.91(3H, s)<br>3.87(2H, t, J=7.2 Hz)<br>3.00(2H, t, J=7.2 Hz)<br>1.7–1.8(2H, m)<br>1.3–1.5(4H, m)<br>0.94(3H, t, J=7.2 Hz)<br>0.94(3H, t, J=7.1 Hz) | | FAB+<br>355[M+H+]<br>(100). | |
| 7-67 | (structure) Amorphous | | CDCl3, 300 MHz<br>7.53(1H, d, J=8.1 Hz)<br>7.11(2H, d, J=8.4 Hz)<br>6.99(1H, d, J=8.1 Hz)<br>6.68(2H, d, J=8.4 Hz)<br>4.20(2H, s)<br>4.01(2H, t, J=6.9 Hz)<br>3.90(3H, s)<br>3.78(2H, t, J=7.2 Hz)<br>2.91(6H, s)<br>2.88(1H, d, J=6.9 Hz)<br>1.5–1.8(2H, m)<br>1.3–1.5(4H, m)<br>0.93(3H, t, J=6.9 Hz) | Neat<br>2926<br>1682<br>1615<br>1522<br>1494<br>1270<br>1076 | FAB+<br>397<br>[M+H+)(30),<br>147(100). | |

TABLE 132-continued

| Ex. | Structural formula | m.p. | 1H NMR (δ) ppm | IRcm$^{-1}$ | MS | Elem. anal. |
|---|---|---|---|---|---|---|
| 7-68 | (structure) Amorphous | | CDCl3, 300 MHz<br>7.52(1H, d, J=8.1 Hz)<br>7.05(2H, d, J=8.4 Hz)<br>6.99(1H, d, J=8.1 Hz)<br>6.54(2H, d, J=8.4 Hz)<br>4.36(1H, s)<br>4.21(2H, s)<br>4.02(2H, t, J=6.6 Hz)<br>3.90(3H, s)<br>3.77(2H, t, J=7.2 Hz)<br>2.87(1H, t, J=7.2 Hz)<br>2.81(3H, s)<br>1.6–1.8(2H, m)<br>1.3–1.5(4H, m)<br>0.94(3H, t, J=7.2 Hz) | Neat<br>2931<br>1650<br>1622<br>1595<br>1524<br>1484<br>1282 | FAB+<br>383[M+H+]<br>(100). | |

TABLE 133

| Ex. | Structural formula | m.p. | 1H NMR (δ) ppm | IRcm$^{-1}$ | MS | Elem. anal. |
|---|---|---|---|---|---|---|
| 7-69 | (structure) Pale-green solid | | CDCl3, 300 MHz<br>8.17(1H, d, J=8.8 Hz)<br>8.14(1H, d, J=8.8 Hz)<br>7.36(2H, d, J=8.8 Hz)<br>7.14(1H, d, J=8.8 Hz)<br>6.75(1H, d, J=7.5 Hz)<br>6.67(1H, d, J=7.5 Hz)<br>4.20(2H, t, J=7.2 Hz)<br>4.01(2H, d, J=6.8 Hz)<br>3.96(3H, s)<br>3.20(2H, t, J=7.2 Hz)<br>1.7–1.9(2H, m)<br>1.4–1.6(4H, m)<br>0.93(3H, t, J=7.1 Hz) | | FAB+<br>380[M+H+]<br>(100),<br>119(50). | |
| 7-70 | (structure) Colorless solid | | CDCl3, 300 MHz<br>8.19(1H, d, J=8.8 Hz)<br>7.12(1H, d, J=8.8 Hz)<br>7.09(4H, s)<br>6.78(1H, d, J=7.5 Hz)<br>6.65(1H, d, J=7.5 Hz)<br>4.14(2H, t, J=7.2 Hz)<br>4.01(2H, t, J=6.6 Hz)<br>3.96(3H, s)<br>3.02(2H, t, J=7.2 Hz)<br>2.31(3H, s)<br>1.7–1.9(2H, m)<br>1.3–1.5(4H, m)<br>0.93(3H, t, J=7.1 Hz | | FAB+<br>380[M+H+]<br>(100),<br>119(50). | |
| 7-71 | (structure) Colorless oil | | CDCl3, 300 MHz<br>8.20(1H, d, J=9.0 Hz)<br>7.2–7.4(5H, m)<br>7.13(1H, d, J=9.0 Hz)<br>6.76(1H, d, J=7.5 Hz)<br>6.64(1H, d, J=7.5 Hz)<br>4.17(2H, t, J=7.5 Hz)<br>4.00(2H, t, J=6.6 Hz)<br>3.96(3H, s)<br>3.07(2H, t, J=7.5 Hz)<br>1.7–1.9(2H, m)<br>1.3–1.5(4H, m)<br>0.93(3H, t, J=7.5 Hz) | | FAB+<br>366[M+H+]<br>(100),<br>261(50). | |

TABLE 134

| Ex. | Structural formula | m.p. | 1H NMR (δ) ppm | IRcm$^{-1}$ | MS | Elem. anal. |
|---|---|---|---|---|---|---|
| 7-72 | Colorless oil | | CDCl3, 300 MHz<br>7.84(1H, d, J=9.0 Hz)<br>7.2–7.4(5H, m)<br>6.56(1H, d, J=9.0 Hz)<br>3.89(2H, t, J=6.6 Hz)<br>3.87(3H, s)<br>3.76(2H, t, J=7.5 Hz)<br>3.34(2H, t, J=6.6 Hz)<br>2.95(2H, t, J=7.5 Hz)<br>2.56(2H, t, J=6.6 Hz)<br>1.7–1.8(2H, m)<br>1.3–1.5(4H, m)<br>0.92(3H, t, J=7.5 Hz) | | FAB+<br>368[M+H+]<br>(100),<br>276(50). | |
| 7-73 | Colorless crystals | | CDCl3, 300 MHz<br>8.19(1H, d, J=9.0 Hz)<br>7.41(2H, d, J=5.4 Hz)<br>7.15(2H, d, J=8.4 Hz)<br>7.12(2H, d, J=8.4 Hz)<br>6.76(1H, d, J=7.5 Hz)<br>6.64(1H, d, J=7.5 Hz)<br>4.41(2H, t, J=7.5 Hz)<br>4.00(2H, t, J=6.6 Hz)<br>3.96(3H, s)<br>3.07(2H, t, J=7.5 Hz)<br>2.16(3H, s)<br>1.7–1.8(2H, m)<br>1.3–1.5(4H, m)<br>0.93(3H, t, J=7.5 Hz) | | FAB+<br>423[M+H+]<br>(100) | |
| 7-74 | Pale-yellow crystals | | CDCl3, 300 MHz<br>7.82(1H, d, J=8.7 Hz)<br>7.42(2H, d, J=8.4 Hz)<br>7.19(2H, d, J=8.4 Hz)<br>6.86(1H, d, J=8.7 Hz)<br>3.90(2H, t, J=6.9 Hz)<br>3.88(3H, s)<br>3.73(2H, t, J=7.2 Hz)<br>3.36(2H, t, J=6.6 Hz)<br>2.89(4H, q, J=6.6 Hz)<br>2.16(3H, s)<br>1.7–1.8(2H, m)<br>1.3–1.5(4H, m)<br>0.92(3H, t, J=6.9 Hz) | | FAB+<br>425[M+H+]<br>(109),<br>276(40). | |

TABLE 135

| Ex. | Structural formula | m.p. | 1H NMR (δ) ppm | IRcm$^{-1}$ | MS | Elem. anal. |
|---|---|---|---|---|---|---|
| 7-75 | | 184.5~<br>154.8° C. | CDCl3, 300 MHz<br>7.74(1H, d, J=8.5 Hz)<br>7.03(2H, d, J=8.0 Hz)<br>6.5–7.0(2H, bs)<br>6.86(1H, d, J=8.5 Hz)<br>6.75(2H, d, J=8.0 Hz)<br>3.83(2H, t, J=6.8 Hz)<br>3.72(2H, t, J=7.4 Hz)<br>3.39(2H, t, J=6.6 Hz)<br>2.86(2H, t, J=6.6 Hz)<br>2.84(2H, t, J=7.4 Hz)<br>1.7–1.8(2H, m)<br>1.2–1.5(4H, m)<br>0.91(3H, t, J=7.0 Hz) | 3295<br>2957<br>1595<br>1306<br>1244 | FAB+<br>370[M+H+]<br>(100) | |

TABLE 135-continued

| Ex. | Structural formula | m.p. | 1H NMR (δ) ppm | IRcm⁻¹ | MS | Elem. anal. |
|---|---|---|---|---|---|---|
| 7-76 | Colorless crystals | 68.3~ 68.8° C. | CDCl3, 300 MHz<br>7.84(1H, d, J=9.0 Hz)<br>7.15(2H, d, J=8.1 Hz)<br>7.09(2H, d, J=8.1 Hz)<br>6.86(1H, d, J=9.0 Hz)<br>3.90(2H, t, J=6.6 Hz)<br>3.88(3H, s)<br>3.73(2H, t, J=7.5 Hz)<br>3.61(2H, t, J=6.6 Hz)<br>2.89(4H, qu, J=7.2 Hz)<br>2.31(3H, s)<br>1.7–1.8(2H, m)<br>1.3–1.5(4H, m)<br>0.92(3H, t, J=7.2 Hz) | | FAB+<br>382[M+H+]<br>(100),<br>276(80). | |
| 7-77 | Pale-yellow solid | 75.5~ 75.9° C. | CDCl3, 300 MHz<br>7.83(2H, d, J=8.4 Hz)<br>7.04(2H, d, J=8.4 Hz)<br>6.86(1H, d, J=8.4 Hz)<br>6.63(2H, d, J=8.4 Hz)<br>3.89(2H, t, J=6.9 Hz)<br>3.88(3H, s)<br>3.70(2H, t, J=6.9 Hz)<br>3.57(2H, s)<br>3.35(2H, t, J=6.6 Hz)<br>2.8–3.0(4H, m)<br>1.7–1.8(2H, m)<br>1.3–1.5(4H, m)<br>0.93(3H, t, J=6.9 Hz) | | FAB+<br>383[M+H+]<br>(50),<br>153(100),<br>118.9(100). | |

TABLE 136

| Ex. | Structural formula | m.p. | 1H NMR (δ) ppm | IR cm⁻¹ | MS | Elem. anal. |
|---|---|---|---|---|---|---|
| 7-78 | Colorless needles | 111.2~ 111.7° C. | DMSO-d6, 300 MHz<br>9.17(1H, s)<br>7.95(1H, d, J=6.6 Hz)<br>7.26(1H, d, J=6.6 Hz)<br>7.25(1H, d, J=5.6 Hz)<br>7.00(2H, d, J=6.2 Hz)<br>6.66(2H, d, J=6.2 Hz)<br>6.55(1H, d, J=5.6 Hz)<br>4.11(2H, t, J=4.7 Hz)<br>4.05(2H, t, J=5.5 Hz)<br>3.96(2H, t, J=4.9 Hz)<br>2.83(2H, t, J=5.5 Hz)<br>1.7–1.9(4H, m)<br>1.3–1.5(8H, m)<br>0.91(3H, t, J=5.3 Hz)<br>0.83(3H, t, J=5.4 Hz) | KBr<br>3336<br>2360<br>1505 | FAB+<br>438<br>[M+]<br>(100). | |
| 7-79 | | | CDCl3, 300 MHz<br>8.53(2H, d, J=5.3 Hz)<br>7.83(1H, d, J=8.6 Hz)<br>7.21(2H, d, J=5.3 Hz)<br>6.87(1H, d, J=8.6 Hz)<br>3.89(3H, s)<br>4.04(2H, t, J=6.6 Hz)<br>3.79(2H, t, J=7.4 Hz)<br>3.38(2H, t, J=6.6 Hz)<br>2.97(2H, t, J=7.4 Hz)<br>2.90(2H, t, J=6.6 Hz)<br>1.7–1.9(2H, m)<br>1.3–1.5(4H, m)<br>0.93(3H, t, J=7.0 Hz) | Neat<br>1931<br>2360<br>1727<br>1649<br>1599<br>1475<br>1279 | FAB+<br>369[M+H+]<br>(100). | |

TABLE 136-continued

| Ex. | Structural formula | m.p. | 1H NMR (δ) ppm | IR cm⁻¹ | MS | Elem. anal. |
|---|---|---|---|---|---|---|
| | Colorless oil | | | | | |
| 7-80 | | 78.6~ 79.2° C. | CDCl3, 300 MHz<br>8.20(1H, d, J=8.7 Hz)<br>7.13(1H, d, J=8.7 Hz)<br>6.98(2H, d, J=8.4 Hz)<br>6.77(1H, d, J=7.2 Hz)<br>6.65(1H, d, J=7.2 Hz)<br>6.62(2H, d, J=8.4 Hz)<br>4.11(2H, t, J=7.2 Hz)<br>4.01(2H, t, J=6.6 Hz)<br>3.96(3H, s)<br>3.56(2H, bs)<br>2.95(2H, t, J=7.2 Hz)<br>1.7–1.9(2H, m)<br>0.1.3–1.5(4H, m)<br>0.94(3H, t, J=7.2 Hz) | Neat<br>3347<br>2934<br>2358<br>1650<br>1622<br>1594<br>1518<br>1281 | FAB+<br>381[M+H+]<br>(100). | |
| | Colorless crystals | | | | | |

TABLE 137

| Ex. | Structural formula | m.p. | 1H NMR (δ) ppm | IR cm⁻¹ | MS | Elem. anal. |
|---|---|---|---|---|---|---|
| 7-81 | | 199.3~ 199.6° C. | DMSO-d6, 300 MHz<br>9.89(3H, bs)<br>7.90(1H, d, J=6.7 Hz)<br>7.25(1H, d, J=5.7 Hz)<br>7.22(1H, d, J=6.7 Hz)<br>7.20(2H, d, J=6.2 Hz)<br>7.18(2H, d, J=6.2 Hz)<br>4.07(2H, t, J=6.0 Hz)<br>3.88(2H, t, J=5.0 Hz)<br>3.84(3H, s)<br>2.92(2H, t, J=6.0 Hz)<br>1.6–1.7(2H, m)<br>1.2–1.4(4H, m)<br>0.83(3H, t, J=5.4 Hz) | Neat<br>3448<br>2936<br>1644<br>1582<br>1287 | FAB+<br>381<br>[M+](100). | |
| | Colorless crystals | | | | | |
| 7-82 | | | CDCl3, 300 MHz<br>8.20(1H, d, J=8.9 Hz)<br>7.13(1H, d, J=8.9 Hz)<br>7.01(2H, d, J=8.4 Hz)<br>6.81(1H, d, J=7.5 Hz)<br>6.72(2H, d, J=8.4 Hz)<br>6.66(1H, d, J=7.5 Hz)<br>4.13(2H, t, J=7.2 Hz)<br>4.01(2H, t, J=6.7 Hz)<br>3.96(3H, s)<br>2.98(2H, d, J=7.2 Hz)<br>2.93(6H, s)<br>1.7–1.9(2H, m)<br>1.3–1.5(4H, m)<br>0.94(3H, t, J=7.1 Hz) | Neat<br>2925<br>2360<br>1652<br>1282 | FAB+<br>409[M+H+]<br>(100). | |
| | Amorphous | | | | | |

TABLE 137-continued

| Ex. | Structural formula | m.p. | 1H NMR (δ) ppm | IR cm⁻¹ | MS | Elem. anal. |
|---|---|---|---|---|---|---|
| 7-83 | Amorphous | | CDCl3, 300 MHz<br>8.20(1H, d, J=9.0 Hz)<br>7.13(1H, d, J=9.0 Hz)<br>7.03(2H, d, J=8.4 Hz)<br>6.80(1H, d, J=7.5 Hz)<br>6.65(1H, d, J=7.5 Hz)<br>6.50(2H, d, J=8.4 Hz)<br>4.11(2H, t, J=7.2 Hz)<br>4.01(2H, t, J=6.7 Hz)<br>3.96(3H, s)<br>2.96(2H, t, J=7.2 Hz)<br>2.94(1H, s)<br>2.82(3H, s)<br>1.7–1.9(2H, m)<br>1.2–1.5(4H, m)<br>0.94(3H, t, J=7.1 Hz) | Neat<br>2931<br>2359<br>1681<br>1671<br>1524<br>1270 | FAB+395<br>[M+H+](20),<br>133(100). | |

TABLE 138

| Ex. | Structural formula | m.p. | 1H NMR (δ) ppm | IR cm⁻¹ | MS | Elem. anal. |
|---|---|---|---|---|---|---|
| 7-84 | Amorphous | | CDCl3, 300 MHz<br>8.20(1H, d, J=8.7 Hz)<br>7.13(1H, d, J=8.7 Hz)<br>7.08(2H, d, J=8.4 Hz)<br>6.87(2H, d, J=8.4 Hz)<br>6.77(1H, d, J=7.5 Hz)<br>6.64(1H, d, J=7.5 Hz)<br>4.13(2H, t, J=7.5 Hz)<br>4.01(2H, t, J=6.6 Hz)<br>3.96(3H, s)3.1–3.2(4H, m)<br>2.98(2H, d, J=7.5 Hz)<br>1.3–2.0(12H, m)<br>0.94(3H, t, J=7.2 Hz) | Neat<br>2934<br>2359<br>1650<br>1624<br>1595<br>1281 | FAB+<br>449[M+H+](60),<br>187(100). | C28H36N2O3 |
| 7-85 | Colorless needles | 175.7~<br>176° C. | CDCl3, 300 MHz<br>7.93(1H, d, J=8.44 Hz)<br>7.17(2H, d, J=8.4 Hz)<br>6.98(1H, d, J=8.4 Hz)<br>6.76(2H, d, J=8.4 Hz)<br>4.75(1H, s)4.0–4.2(6H, m)<br>3.94(2H, s)2.8–2.9(2H, m)<br>1.7–1.9(4H, m)<br>1.3–1.6(8H, m)<br>0.95(6H, t, J=6.9 Hz) | KBr<br>3426<br>2935<br>1654 | FAB+<br>454[M+H+](100). | |
| 7-86 | Pale-yellow crystals | 196.9~<br>198.1° C. | DMSO-d6, 300 MHz<br>11.21(1H, s)8.49(2H, bs)<br>7.32(2H, d, J=5.4 Hz)<br>7.26(1H, s)6.66(1H, s)<br>4.14(2H, t, J=7.5 Hz)<br>3.95(2H, t, J=6.6 Hz)<br>3.82(3H, s)<br>2.93(2H, t, J=7.4 Hz)<br>1.60–1.80(2H, m)<br>1.30–1.50(4H, m)<br>0.89(3H, t, J=6.9 Hz) | KBr<br>2936<br>2362<br>1718<br>1654<br>1623<br>1459<br>1245 | FAB+<br>384[M+H+](60) | C21H25N3O4 |

TABLE 139

| Ex. | Structural formula | m.p. | 1H NMR (δ) ppm | IR cm$^{-1}$ | MS | Elem. anal. |
|---|---|---|---|---|---|---|
| 7-87 | Colorless crystals | 187.0~187.8° C. | DMSO-d6, 300 MHz<br>10.7(1H, s)<br>9.17(1H, s)<br>7.67(1H, d, J=8.7 Hz)<br>7.00(2H, d, J=7.5 Hz)<br>6.97(1H, d, J=8.7 Hz)<br>6.66(2H, d, J=7.5 Hz)<br>4.01(2H, t, J=7.7 Hz)<br>3.91(2H, t, J=7.7 Hz)<br>3.88(3H, s)<br>2.72(2H, t, J=7.7 Hz)<br>1.70–1.80(2H, m)<br>1.25–1.45(4H, m)<br>0.89(3H, t, J=6.9 Hz) | KBr<br>3399<br>1707<br>1637<br>1432<br>1298 | FAB+<br>399<br>[M+H+]<br>(50)<br>279(40) | C22H26N2O5 |
| 7-88 | Colorless needles | 144.2~144.5° C. | CDCl3, 300 MHz<br>7.97(1H, d, J=9.0 Hz)<br>7.10(2H, d, J=8.1 Hz)<br>7.00(1H, d, J=9.0 Hz)<br>6.63(2H, d, J=8.1 Hz)<br>4.1–4.2(2H, m)<br>4.00(2H, t, J=6.6 Hz)<br>3.94(2H, s)<br>3.93(3H, s)<br>3.59(2H, s)<br>2.7–2.9(2H, m)<br>1.7–1.9(2H, m)<br>1.3–1.6(4H, m)<br>0.95(3H, t, J=6.9 Hz) | KBR<br>2925<br>1666<br>1518<br>1350<br>1285 | FAB+<br>383<br>[M+H+]<br>(100). | |
| 7-89 | Colorless needles | 113.2~113.6° C. | CDCl3, 300 MHz<br>8.53(2H, d, J=5.7 Hz)<br>7.95(1H, d, J=9.0 Hz)<br>7.23(2H, d, J=57 Hz)<br>7.00(1H, d, J=9.0 Hz)<br>4.1–4.3(2H, m)<br>4.00(2H, t, J=6.9 Hz)<br>3.96(2H, s)<br>3.94(3H, s)<br>2.93(2H, m)<br>1.7–1.9(2H,m)<br>1.3–1.7(4H, m)<br>0.95(3H, t, J=7.2 Hz) | KBr<br>1708<br>1662<br>1598<br>1353<br>1081 | FAB+<br>383<br>[M+H+]<br>(100). | |

TABLE 140

| Ex. | Structural formula | m.p. | 1H NMR (δ) ppm | IR cm$^{-1}$ | MS | Elem. anal. |
|---|---|---|---|---|---|---|
| 7-90 | Colorless crystals | 172.0~173.0° C. | CDCl3, 300 MHz<br>8.00(1H, s)<br>7.83(1H, d, J=8.4 Hz)<br>7.16(2H, d, J=8.4 Hz)<br>6.81(1H, d, J=8.4 Hz)<br>6.57(2H, d, J=8.4 Hz)<br>4.18(2H, t, J=8.3 Hz)<br>4.08(2H, t, J=6.9 Hz)<br>3.95(3H, s)<br>2.86(2H, t, J=8.1 Hz)<br>2.82(3H, s)<br>1.70–1.85(2H, m)<br>1.35–1.50(4H, m)<br>0.95(3H, t, J=7.2 Hz) | KBr<br>3397<br>1707<br>1647<br>1615 | FAB+<br>412<br>[M+H+]<br>(30) | C23H29N3O4 |

TABLE 140-continued

| Ex. | Structural formula | m.p. | 1H NMR (δ) ppm | IR cm⁻¹ | MS | Elem. anal. |
|---|---|---|---|---|---|---|
| 7-91 | (structure: quinazolinedione with MeO, O-pentyl, N-CH2CH2-C6H4-NMe2) Colorless crystals | 127.0~128.5° C. | CDCl3, 300 MHz<br>8.00(1H, s)<br>7.84(1H, s, J=8.7 Hz)<br>7.22(2H, dJ =8.7 Hz)<br>6.81(1H, d, J=8.7 Hz)<br>6.71(2H, d, J=8.7 Hz)<br>4.19(2H, t, J=8.3 Hz)<br>4.08(2H, t, J=7.1 Hz)<br>3.95(3H, s)<br>2.92(6H, s)<br>2.88(2H, t, J=8.3 Hz)<br>1.70–1.85(2H, m)<br>1.30–1.50(4H, m)<br>0.95(3H, t, J=7.1 Hz) | KBR<br>2956<br>1709<br>1651<br>1619<br>1094 | FAB+<br>426<br>[M+H+]<br>(20) | C24H31N3O4 |
| 7-92 | (structure: dihydroquinazolinone with MeO, O-pentyl, gem-dimethyl, N-CH2CH2-4-pyridyl) Colorless crystals | 83.2~83.8° C. | CDCl3, 300 MHz<br>8.53(2H, d, J=6.0 Hz)<br>7.64(1H, d, J=8.8 Hz)<br>7.22(2H, d, J=6.0 Hz)<br>6.44(1H, d, J=8.8 Hz)<br>4.52(1H, s)<br>3.96(2H, t, J=6.8 Hz)<br>3.88(3H, s)<br>3.63(2H, t, J=8.0 Hz)<br>2.96(2H, t, J=8.0 Hz)<br>1.68–1.82(2H, m)<br>1.53(6H, s)<br>1.30–1.50(4H, m)<br>0.94(3H, t, J=7.1 Hz) | KBR<br>3448<br>3285<br>2954<br>1630<br>1303 | FAB+<br>398<br>[M+H+]<br>(80)<br>382<br>(60)<br>276<br>(40) | C23H31N3O3 |

TABLE 141

| Ex. | Structural formula | m.p. | 1H NMR (δ) ppm | IR cm⁻¹ | MS | Elem. anal. |
|---|---|---|---|---|---|---|
| 7-93 | (structure: dihydroquinazolinone with MeO, O-pentyl, gem-dimethyl, N-CH2CH2-C6H4-NH2) Pale-orange oil | | CDCl3, 300 MHz<br>7.65(1H, d, J=8.7 Hz)<br>7.10(2H, d, J=8.3 Hz)<br>6.66(2H, d, J=8.3 Hz)<br>6.43(1H, d, J=8.7 Hz)<br>4.51(1H, s)<br>3.97(2H, t, J=6.8 Hz)<br>3.88(3H, s)<br>3.60(2H, bs)<br>3.57(2H, t, J=8.2 Hz)<br>2.85(2H, t, J=8.2 Hz)<br>1.70–1.85(2H, m)<br>1.54(6H, s)<br>1.35–1.50(4H, m)<br>0.95(3H, t, J=7.1 Hz) | Neat<br>3345<br>2956<br>1632<br>1301 | FAB+<br>412<br>[M+H+]<br>(60)<br>276<br>(100) | C24H33N3O3 |
| 7-94 | (structure: quinazolinone with MeO, O-pentyl, 2-methyl, N-CH2CH2-C6H4-NH2) Pale-yellow crystals | 80.3~82.5° C. | CDCl3, 300 MHz<br>8.02(1H, d, J=8.9 Hz)<br>7.09(1H, d, J=8.9 Hz)<br>7.01(2H, d, J=8.3 Hz)<br>6.63(2H, d, J=8.3 Hz)<br>4.15–4.25(4H, m)<br>3.96(3H, s)<br>3.60(2H, bs)<br>2.92(2H, t, J=7.6 Hz)<br>2.48(3H, s)<br>1.72–190(2H, m)<br>1.30–1.55(4H, m)<br>0.92(3H, t, J=7.2 Hz) | KBr<br>3356<br>2932<br>1658<br>1598<br>1101 | FAB+<br>396<br>[M+H+]<br>(20)<br>307<br>(10) | C23H29N3O2 |

TABLE 141-continued

| Ex. | Structural formula | m.p. | 1H NMR (δ) ppm | IR cm$^{-1}$ | MS | Elem. anal. |
|---|---|---|---|---|---|---|
| 7-95 | Pale-yellow crystals | 145.5~ 148.3° C. | DMSO-d6, 300 MHz 8.83(2H, d, J=5.4 Hz) 8.28(1H, s) 7.97(2H, d, J=5.4 Hz) 7.86(1H, d, J=8.7 Hz) 7.32(1H, d, J=8.7 Hz) 4.32(2H, t, J=6.9 Hz) 4.03(2H, t, J=6.5 Hz) 3.90(3H, s) 3.34(2H, t, J=6.8 Hz) 1.60–1.75(2H, m) 1.25–1.50(4H, m) 0.88(3H, t, J=6.9 Hz) | KBr 3426 2958 1724 1655 1603 1498 1295 | FAB+ 368 [M+H+] (30) 263 (30) | C21H26ClN3O3 |

TABLE 142

| Ex. | Structural formula | m.p. | 1H NMR (δ) ppm | IR cm$^{-1}$ | MS | Elem. anal. |
|---|---|---|---|---|---|---|
| 7-96 | Colorless crystals | | | | | |
| 7-97 | Colorless crystals | 157.0~ 158.0° C. | CDCl3, 300 MHz 11.5(1H, s)7.89(1H, d, J=8.4 Hz)7.34 (2H, d, J=8.7 Hz) 6.93(1H, s, J= 8.4 Hz)6.68(2H, d, J=8.7 Hz)4.19(2H, t, J=6.5 Hz) 3.95(2H, t, J= 6.5 Hz)3.93(3H, s)3.03(2H, t, J= 6.5 Hz)1.70–1.83 (2H, m)1.33–1.52 (4H, m) 0.94(3H, t, J= 7.2 Hz) | KBr 3228 2948 1703 1593 1543 1395 1286 | FAB+ 398 [M+H+] (30) 264 (30) | C22H27N3O4 |
| 7-98 | Colorless crystals | | DMSO-d6, 300 MHz 9.74(2H, t, J= 5.9Hz)7.75(1H, d, J=8.7 Hz)7.40(2H, d, J=8.4 Hz)7.25 (2H, d, J=8.4 Hz) 7.11(1H, d, J= 8.7 Hz)4.44(2H, d, J=5.9 Hz)3.99(2H, t, J=6.2 Hz)3.88 (2H, t, J=6.3 Hz) 3.87(3H, s)2.94 (2H, t, J=6.3 Hz) 1.60–1.72(2H, m) 1.25–1.45(4H, m 0.90(3H, t, J= 7.2 Hz) | | FAB+ 412(30) | C23H30ClN3O4 |

TABLE 143

| Ex. | Structural formula | m.p. | 1H NMR (δ) ppm | IR cm⁻¹ | MS | Elem. anal. |
|---|---|---|---|---|---|---|
| 7-99 | Colorless oil | | CDCl3, 300 MHz<br>7.03(2H, d, J=8.3 Hz)<br>6.73(2H, s)<br>6.64(2H, d, J=8.3 Hz)<br>3.91(2H, t, J=6.7 Hz)<br>3.81(3H, s)<br>3.63(2H, s)<br>3.56(2H, bs)<br>2.65–2.95(8H, m)<br>1.70–1.83(2H, m)<br>1.30–1.50(4H, m)<br>0.93(3H, t, J=7.1 Hz) | | FAB+<br>369<br>[M+H+](50)<br>262(100) | C23H32N2O2 |
| 7-100 | Colorless amorphous | | CDCl3, 300 MHz<br>7.14(2H, d, J=9.0 Hz)<br>6.85(1H, d, J=8.4 Hz)<br>6.79(1H, d, J=8.4 Hz)<br>6.64(2H, d, J=9.0 Hz)<br>6.17(1H, bs)<br>4.57(2H, s)<br>3.93(2H, t, J=6.6 Hz)<br>3.84(3H, s)<br>3.65(2H, t, J=5.9 Hz)<br>2.94(2H, t, J=5.9 Hz)<br>1.70–1.82(2H, m)<br>1.32–1.55(4H, m)<br>0.94(3H, t, J=7.1 Hz) | | FAB+<br>384<br>[M+H+](80)<br>248(100) | C22H29N3O3 |
| 7-101 | Colorless oil | | DMSO-d6, 300 MHz<br>9.95(1H, bs)<br>7.33(2H, d, J=8.7 Hz)<br>7.21(2H, d, J=8.7 Hz)<br>7.19(1H, bt)<br>6.88(1H, d, J=8.4 Hz)<br>6.82(1H, d, J=8.4 Hz)<br>4.43(2H, s)<br>4.25(2H, d, J=4.8 Hz)<br>3.85(2H, t, J=6.6 Hz)<br>3.75(3H, s)<br>3.54(2H, bs)<br>3.54(2H, t J=5.9 Hz)<br>2.71(2H, t, J=5.7 Hz)<br>1.60–1.72(2H, m)<br>1.25–1.50(4H, m)<br>0.90(3H, t, J=6.9 Hz) | | FAB-<br>432<br>[M-H+](5)<br>396(10)<br>265(40) | C23H32ClN3O3 |

TABLE 144

| Ex. | Structural formula | m.p. | 1H NMR (δ) ppm | IR cm⁻¹ | MS | Elem. anal. |
|---|---|---|---|---|---|---|
| 7-102 | Colorless crystals | 98.0~<br>99.0° C. | CDCl3, 300 MHz<br>9.74(1H, bt)<br>9.13(1H, bs)<br>8.49(1H, s)<br>8.53(2H, d, J=6.0 Hz)<br>7.46(1H, d, J=8.9 Hz)<br>7.22(2H, d, J=6.0 Hz)<br>6.94(1H, d, J=8.9 Hz)<br>4.14(2H, t, J=6.9 Hz)<br>3.98(3H, s)<br>3.76(2H, q, J=6.7 Hz)<br>2.97(2H, t, J=7.2 Hz)<br>1.74–1.88(2H, m)<br>1.35–1.53(4H, m)<br>0.95(3H, t, J=7.1 Hz) | KBr<br>3257<br>2938<br>1672<br>1622<br>1530<br>1261<br>1112<br>805 | FAB+<br>410<br>[M+H+](60)<br>288(60) | C23H27N3O4 |

TABLE 145

| Ex. | Structural formula | m.p. | 1H NMR (δ) ppm | IR cm⁻¹ | MS | Elem. anal. |
|---|---|---|---|---|---|---|
| 8-1 | (structure) | 185.5~186.5° C. | DMSO-d6, 300 MHz<br>7.73(1H, d, J=15.4 Hz)<br>7.58(1H, d, J=8.5 Hz)<br>7.00(1H, d, J=15.4 Hz)<br>6.98(1H, bs)<br>6.44(1H, s)<br>6.42(1H, d, J=8.5 Hz)<br>3.73(3H, s)<br>3.5–3.7(4H, m)<br>3.2–3.5(4H, m) | KBr<br>3424<br>1629<br>1560 | FAB+<br>264<br>[M⁺H⁺](85) | |
| 8-2 | (structure) | | CDCl₃, 300 MHz<br>7.82(1H, d, J=15.5 Hz)<br>7.38(1H, d, J=8.4 Hz)<br>6.97(1H, d, J=15.5 Hz)6.48(1H, dd, J=8.4, 2.4 Hz)<br>6.45(1H, d, J=2.4 Hz)<br>4.11(2H, t, J=6.4 Hz)<br>3.82(3H, s)<br>3.70(8H, s)<br>3.70(8H, bs)<br>1.8–1.9(2H, m)<br>1.3–1.5(4H, m)<br>0.94(3H, t, J=7.1 Hz) | Neat<br>2956<br>1643<br>1600 | FAB+<br>334<br>[M⁺H⁺](70)<br>246(30)<br>177(100) | C₁₉H₂₇NO₄<br>Calcd.<br>C; 68.44%<br>H; 8.16%<br>N; 4.20%<br>Found<br>C; 68.55%<br>H; 8.43%<br>N; 4.25% |
| 8-3 | (structure) | | DMSO-d6, 300 MHz<br>9.00(1H, s)<br>7.36(1H, d, J=15.4 Hz)<br>7.14(1H, d, J=2.2 Hz)<br>7.09(1H, dd, J=8.4, 2.2 Hz)<br>6.97(1H, d, J=15.4 Hz)<br>6.92(1H, d, J=8.4 Hz)<br>3.79(3H, s)<br>3.58(8H, bs) | KBr<br>3426<br>3200<br>1640<br>1574 | FAB+<br>264<br>[M⁺H⁺](100)<br>177(70) | C₁₄H₁₇NO₄<br>Calcd.<br>C; 63.87%<br>H; 6.51%<br>N; 5.32%<br>Found<br>C; 63.67%<br>H; 6.63%<br>N; 5.35% |

TABLE 146

| Ex. | Structural formula | m.p. | 1H NMR (δ) ppm | IR cm⁻¹ | MS | Elem. anal. |
|---|---|---|---|---|---|---|
| 8-4 | (structure) | | CDCl₃, 300 MHz<br>6.99(1H, d, J=1.7 Hz)<br>6.96(1H, dd, J=8.1, 1.7 Hz)<br>6.86(1H, d, J=8.1 Hz)<br>4.02(2H, t, J=6.9 Hz)<br>3.89(3H, s)<br>3.69(8H, bs)<br>1.8–1.9(2H, m)<br>1.3–1.5(4H, m)<br>0.93(3H, t, J=7.0 Hz) | Neat | | |
| 8-5 | (structure) | | DMSO-d6, 300 MHz<br>9.00(1H, s)<br>7.36(1H, d J=15.4 Hz)<br>7.14(1H, d, J=2.2 Hz)<br>7.09(1H, dd, J=8.4, 2.2 Hz)<br>6.97(1H, d, J=15.4 Hz)<br>6.92(1H, d, J=8.4 Hz)<br>3.79(3H, s)<br>3.58(8H, bs) | KBr,<br>3426<br>3200<br>1640<br>1574 | FAB+<br>264[M+H+]<br>(100)<br>177(70) | C₁₄H₁₇NO₄<br>Calcd.<br>C; 63.87%<br>H; 6.51%<br>N; 5.32%<br>Found<br>C; 63.67%<br>H; 6.63%<br>N; 5.35% |

TABLE 146-continued

| Ex. | Structural formula | m.p. | 1H NMR (δ) ppm | IR cm$^{-1}$ | MS | Elem. anal. |
|---|---|---|---|---|---|---|
| 8-6 | (structure: MeO, pentyloxy-phenyl acrylyl imidazole) | | CDCl3, 300 MHz<br>8.33(1H, s)<br>8.01(1H, d, J=11.5 Hz)<br>7.63(1H, s)<br>7.26(1H, s)<br>7.25(1H, dd, J=6.3, 1.5 Hz)<br>7.15(1H, d, J=6.3 Hz)<br>6.93(1H, d, J=1.5 Hz)<br>6.89(1H, d, J=11.5 Hz)<br>4.07(2H, t, J=5.1 Hz)<br>3.93(3H, s)<br>1.8–1.9(2H, m)<br>1.4–1.5(4H, m)<br>0.95(3H, t, J=5.4 Hz) | 2934<br>1702<br>1616<br>1514 | FAB+<br>315<br>[M+H+](20)<br>247(100) | $C_{18}H_{22}N_2O_3$<br>Calcd.<br>C; 68.77%<br>H; 7.05%<br>N; 8.91%<br>Found<br>C; 68.01%<br>H; 7.04%<br>N; 8.41% |

TABLE 147

| Ex. | Structural formula | m.p. | 1H NMR (δ) ppm | IR cm$^{-1}$ | MS | Elem. anal. |
|---|---|---|---|---|---|---|
| 8-7 | (structure: MeO, pentyloxy-phenyl carbonyl imidazole) | 110.9~111.1° C. | CDCl3, 300 MHz<br>8.11(1H, s)<br>7.54(1H, s)<br>7.40(1H, dd, J=6.3, 1.5 Hz)<br>7.16(1H, s)<br>6.95(1H, d, J=6.3 Hz)<br>4.06(2H, t, J=5.1 Hz)<br>3.96(3H, s)<br>1.8–1.9(2H, m)<br>1.3–1.5(4H, m)<br>0.93(3H, t, J=5.3 Hz) | KBr<br>3500<br>2957<br>1698 | FAB+<br>298[M+H+]<br>(40)<br>221(100) | $C_{16}H_{20}N_2O_3$<br>Calcd.<br>C; 66.65%<br>H; 6.99%<br>N; 9.72%<br>Found<br>C; 66.69%<br>H; 7.08%<br>N; 9.23% |

PHARMACOLOGICAL EXPERIMENT

[I] Binding Assay (in vitro)

As the sample rich in cannabinoid central type (CB1) and peripheral type (CB2) receptors, rat cerebellar membrane fraction and spleen cells were respectively used (male SD rats, 7–9 weeks old). A sample (cerebellar membrane fraction: 50 μg/ml or spleen cells: 1×10$^7$ cells/ml), labeled ligand ([$^3$H]Win55212-2, 2 nM) and unlabeled Win55212-2 or a test compound were plated in round bottom 24 well plates, and incubated at 30° C. for 90 min in the case of cerebellar membrane fraction, and at 4° C. for 360 min in the case of spleen cells. As the assay buffer, 50 mM Tris solution containing 0.2% BSA was used for cerebellar membrane fraction, and 50 mM Tris-HBSS containing 0.2% BSA was used for spleen cells. After incubation, the samples were filtrated through a filter (Packard, Unifilter 24 GF/B) and dried. A scintillation solution (Packard, Microsint-20) was added, and the radioactivity of the samples was determined (Packard, Top count A9912V). The non-specific binding was determined by adding an excess Win55212-2 (1 μM), and specific binding was calculated by subtracting non-specific binding from the total binding obtained by adding the labeled ligand alone. The test compounds were dissolved in DMSO to the final concentration of DMSO of 0.1%. IC$_{50}$ was determined from the proportion of the specifically-bound test compounds, and the Ki value of the test compounds was calculated from IC$_{50}$ and Kd value of [$^3$H]Win55212-2.

[II] Carageenan-induced paw edema model (in vivo)

Female ddy mice (6–8 weeks old) were used. The volume of the right paw was measured (Unicom, Prethysumometer TK-101) before administration, and two hours later, the test compounds dissolved in olive oil were orally administered at 10 ml/kg. One hour after the administration, 50 μL of 1% carageenan dissolved in physiological saline was intradermally injected into the right foot pad. Three hours later, the volume of the right paw was measured and compared with that measured before the carageenan injection.

[III] Sheep red blood cell (SRBC)-induced delayed type hypersensitivity (DTH) model (in vivo)

Female ddy mice (6–8 weeks old) were used. On day 1, SRBC 10$^7$ cells were intradermally injected into the left foot pad of the mice (40 μl/foot) to immunize the mice. Five days later, the test compounds dissolved in olive oil were orally administered at 10 ml/kg. One hour later, SRBC 10$^8$ cells were intradermally injected into the right foot pad to induce the response. Twenty-four hours after the induction, the volume of the both paws was measured, and edema ratio was calculated by subtracting the volume of the right paw from that of the left paw.

In both [II] and [III], the test compounds were dissolved in DMSO and used upon dilution with olive oil (final concentration of DMSO 1%).

The results of the above [I], [II] and [III] are shown in Table 148 and Table 149.

TABLE 148

| Example | Ki value (nM) Central receptor (C) | Ki value (nM) Peripheral receptor (S) | C/S | ED50 (mg/kg:po) Carageenan-induced paw edema model | ED50 (mg/kg:po) Sheep red blood cell-induced delayed type hyper-sensitivity model |
|---|---|---|---|---|---|
| 1-1 | 230 | 4.8 | 48 | 1.00 | 1.52 |
| 1-2 | 400 | 1.8 | 222 | >1.00 | 0.48 |
| 1-4 | 960 | 7.7 | 125 | 0.55 | 0.71 |
| 1-5 | 450 | 4.4 | 102 | 1.20 | 2.45 |
| 1-13 | 3700 | 44.0 | 84 | 0.25 | 9.20 |
| 1-22 | 480 | 1.4 | 343 | 0.14 | 0.77 |
| 1-34 | 930 | 1.1 | 845 | 0.59 | 1.95 |
| 1-35 | 160 | 10 | 16 | 0.12 | 0.063 |
| 2-1 | 1400 | 2.5 | 560 | 0.040 | 0.14 |
| 2-2 | 1100 | 1.1 | 1000 | 0.51 | 0.90 |
| 2-3 | >3300 | 0.44 | >8250 | 0.17 | 0.053 |
| 2-5 | 330 | 3.6 | 92 | 0.40 | 3.25 |
| 2-6 | 500 | 1.1 | 455 | 0.30 | 0.72 |
| 2-7 | >2500 | 9.5 | 263 | 2.28 | 2.35 |
| 2-8 | 1000 | 3.7 | 270 | 0.73 | 1.45 |
| 2-13 | 5600 | 6.6 | 849 | 3.20 | 5.60 |
| 2-16 | >4300 | 73 | >59 | 1.10 | 1.95 |

TABLE 149

| Example | Ki value (nM) Central receptor (C) | Ki value (nM) Peripheral receptor (S) | C/S | ED50 (mg/kg:po) Carageenan-induced paw edema model | ED50 (mg/kg:po) Sheep red blood cell-induced delayed type hyper-sensitivity model |
|---|---|---|---|---|---|
| 2-26 | >2500 | 18.0 | >139 | >10.0 | 3.75 |
| 2-52 | >4300 | 1.9 | >2300 | 1.85 | 0.58 |
| 6-4 | 650 | 11.0 | 59 | 0.25 | 10.0 |
| 7-4 | 1000 | 7.3 | 137 | 1.60 | 1.60 |
| 7-5 | >2500 | 11.0 | >227 | 0.014 | 0.038 |
| 7-19-1 | 200 | 3.7 | 54 | 0.092 | 0.033 |
| 7-20 | 400 | 8.4 | 48 | 0.195 | 0.084 |
| 7-24 | >2500 | 1.8 | >1389 | 0.028 | 0.027 |
| 7-30 | 2600 | 1.8 | 1440 | <0.01 | 0.021 |
| 7-31 | 11 | 0.088 | 125 | 0.012 | 0.08 |
| 7-34 | 330 | 0.11 | 3000 | 0.29 | 0.012 |
| 7-37 | 1300 | 14 | 93 | 0.49 | 0.058 |
| 7-38 | 220 | 9.9 | 22 | 0.11 | 0.011 |
| 7-40 | 109 | <3.7 | >30 | 0.016 | — |
| 8-2 | 560 | 8.4 | 67 | 0.50 | >10.0 |

[IV] Anti-thy-1 antibody-induced nephritis model (in vivo)

The test compound (prednisolone, compound of Example 7-35) was orally administered to male Wistar rats (6 weeks old), and one hour later, an anti-thy-1 antibody (ox-7, 0.938 mg/ml) was administered at 0.1 ml/rat from the tail vein. The test compound was administered once a day thereafter until day 6. At day 6, the rats were forcibly loaded with 8 ml of tap water and then deprived of water for consecutive 16 hours, during which period urine samples were taken from the rats. At day 7, the rats were killed by exsanguination. The kidney was removed, weighed and fixed with formalin, and tissue samples (PAS stained) were prepared therefrom. Evaluation was done by measuring urinary protein and nuclear cell count in nephritic glomerulus section. The test compound was prepared into a suspension with 0.5% HPMC and administered at 10 ml/kg per dose. The results are shown in Table 150.

TABLE 150

| Test group | Urinary protein (mg/16 hr) | Nuclear cell count in nephritic glomerulus (nuclei/glomerulus) |
|---|---|---|
| Sham | 2.6 ± 0.3 | 67.6 ± 0.9 |
| Control | 31.9 ± 4.0 | 90.1 ± 1.4 |
| Prednisolone (3 mg/kg) | 20.9 ± 2.7 | 76.9 ± 0.9 |
| Compound of Ex. 7-35 (0.1 mg/kg) | 15.2 ± 2.4 | 84.8 ± 1.2 |

| | |
|---|---|
| Sham | no administration of anti-thy-1 antibody, loaded with water and orally administered with solvent (HPMC) |
| Control | administration of anti-thy-1 antibody, loaded with water and orally administered with solvent (HPMC) |
| Prednisolone Compound of Ex. 7-35 | administration of anti-thy-1 antibody, loaded with water and orally administered with said test compound |

The compound of Ex. 7-35 of the present invention showed a significant suppressive effect by the administration of 0.1 mg/kg thereof on the increase in both urinary protein and nuclear cell count in nephritic glomerulus, the increase being induced by the administration of the anti-thy-1 antibody.

The formulation example is given below, to which the present invention is not limited.

FORMULATION EXAMPLE

| | |
|---|---|
| (1) Compound of Example 1-1 | 10 g |
| (2) Lactose | 50 g |
| (3) Corn starch | 15 g |
| (4) Sodium carboxymethylcellulose | 44 g |
| (5) Magnesium stearate | 1 g |

The entire amounts of (1), (2) and (3), and 30 g of (4) are kneaded with water, dried in vacuo and granulated. The granules are admixed with 14 g of (4) and 1 g of (5), and tableted with a tableting machine to give 1,000 tablets containing 10 mg of (1) per tablet.

The Compound (I) of the present invention and pharmaceutically acceptable salts thereof selectively act on a cannabinoid receptor, particularly peripheral type receptor, cause less central side effects, and have superior immuno-regulating action, antiinflammatory action, antiallergic action and nephritis therapy effect. Therefore, they are useful as cannabinoid receptor (particularly peripheral cannabinoid receptor) activators or antagonists, immunoregulators, therapeutic agents for autoimmune diseases, antiinflammatory agents, antiallergic agents or therapeutic agents of nephritis.

What is claimed is:
1. A compound of the formula (Ic)

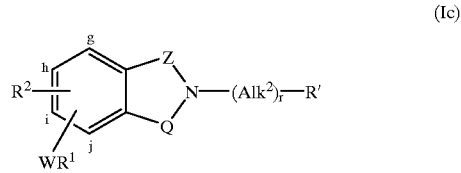

(Ic)

wherein

W is —O—, —S(O)$_t$—, —CR$^5$R$^6$—, —NR$^7$—, —NR$^7$CO—, —CONR$^7$—, —COO— or —OCO— wherein

R$^5$ and R$^6$ are the same or different and each is hydrogen atom or alkyl, R$^7$ is hydrogen atom or alkyl, and t is 0, 1 or 2;

R$^1$ is an alkyl, an alkenyl, an alkynyl, an aryl, an arylalkyl, a heteroaryl, a heteroarylalkyl, a cycloalkyl or a cycloalkylalkyl wherein each group at R$^1$ is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;

R$^2$ is a hydrogen atom, an alkyl, —OR$^{15}$ wherein R$^{15}$ is hydrogen atom, alkyl, alkenyl, alkynyl, aryl, arylalkyl, heteroaryl, heteroarylalkyl, cycloalkyl or cycloalkylalkyl, —NR$^8$R$^9$ wherein R$^8$ and R$^9$ are the same or different and each is hydrogen atom, alkyl, alkenyl, alkynyl, acyl, aryl, arylalkyl, heteroaryl, heteroarylalkyl, cycloalkyl or cycloalkylalkyl, or R$^8$ and R$^9$ optionally form heteroaryl together with the adjacent nitrogen atom, or —(CH$_2$)$_u$, S(O)$_u$R$^{12}$ wherein R$^{12}$ is hydrogen atom, alkyl, alkenyl or alkynyl, u is 0, 1 or 2 and u' is 0, 1 or 2 wherein each group at said R$^2$ except hydrogen atom is optionally substituted by alkyl, alkylamino, amino, hydroxy, alkoxy, alkoxycarbonyl, acyl, acyloxy, acylthio, mercapto, alkylthio, alkylsulfinyl or alkylsulfonyl;

Z is —CH$_2$— or —CO—;

Q is —NHCR$^{28}$(CH$_2$)$_{v'}$—, wherein

R$^{28}$ is oxygen atom or sulfur atom, and v' is 0;

Alk$^2$ is an alkylene, —COCH$_2$— or —CONH(H$_2$)$_v$ wherein v is 0, 1 or 2 wherein alkylene and alkenylene at said Alk$^2$ are each optionally substituted by hydroxy, carboxyl, alkoxycarbonyl, alkyl optionally substituted by hydroxy, alkoxy or alkylthio, or —CONR$^{13}$R$^{14}$ wherein R$^{13}$ and R$^{14}$ are the same or different and each is hydrogen atom or alkyl, or R$^{13}$ and R$^{14}$ optionally form heteroaryl together with the adjacent nitrogen atom;

R' is an aryl, a heteroaryl, a cycloalkyl or a benzene-condensed cycloalkyl wherein said aryl and heteroaryl are each optionally substituted by alkyl optionally substituted by hydroxy, hydroxyalkoxy, alkenyloxy, acyl, acyloxy, halogen atom, nitro, amino, sulfonamide, alkylamino, aralkyloxy, acylamino, piperidino or pyridyl, said cycloalkyl is optionally substituted by hydroxy, alkoxy or =O, and said benzene-condensed cycloalkyl is optionally substituted by hydroxy or alkoxy; and r is 0 or 1;

provided that when Z is —CO— and Q is —NHCR$^{28}$(CH$_2$)$_{v'}$— wherein R$^{28}$ is oxygen atom and v' is 0, R$^2$ is substituted at the i-position on the benzene ring, and —WR$^1$ is substituted at the j-position on the benzene ring;

or a pharmaceutically acceptable salt thereof.

2. The compound of claim 1, which is represented by the compound of the formula (Ic)

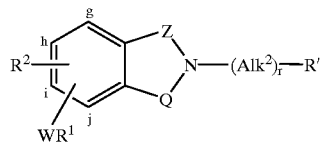

wherein

W is —O—, —S(O)$_t$—, —CR$^5$R$^6$—, —NR$^7$—, or —NR$^7$CO—, wherein

R$^5$ and R$^6$ are the same or different and each is hydrogen atom or alkyl, R$^7$ is hydrogen atom or alkyl, and t is 0, 1 or 2;

R$^1$ is an alkyl;

R$^2$ is a hydrogen atom, an alkyl, or —OR$^{15}$ wherein R$^{15}$ is hydrogen atom or alkyl;

Z is —CH$_2$— or —CO—;

Q is —NHCR$^{28}$(CH$_2$)$_{v'}$—, wherein

R$^{28}$ is oxygen atom or sulfur atom, and v' is 0 or 1;

Alk$_2$ is an alkylene, —COCH$_2$— or —CONH(CH$_2$)$_v$ wherein v is 0, 2;

R' is an aryl, a heteroaryl, or a cycloalkyl wherein said aryl and heteroaryl are each optionally substituted by alkyl, hydroxy, acyloxy, nitro, amino, alkylamino, aralkyloxy, acylamino, or piperidino, and said cycloalkyl is optionally substituted by =O;

r is 0 or 1;

provided that when Z is —CO— and Q is —NHCR$^{28}$(CH$_2$)$_{v'}$— wherein R$^{28}$ is oxygen atom and v' is 0, R$^2$ is substituted at the i-position on the benzene ring, and —WR$^1$ is substituted at the j-position on the benzene ring;

or a pharmaceutically acceptable salt thereof.

3. The compound of claim 2, wherein Z is —CO—, Q is —NHCR$^{28}$(CH$_2$)$_{v'}$—, wherein R$^{28}$ is oxygen atom and v' is 0, R$^2$ is —OR$^{15}$, W is —O—, —NR$^7$— or —NR$^7$CO—, R$^2$ is substituted at the i-position on the benzene ring, and —WR$^1$ is substituted at the j-position on the benzene ring, or a pharmaceutically acceptable salt thereof.

4. The compound of claim 3, wherein R$^1$ is alkyl having 4 to 6 carbon atoms, or a pharmaceutically acceptable salt thereof.

5. The compound of claim 4, which is selected from the group consisting of 7-methoxy-3-[2-(4-nitrophenyl)ethyl]-8-pentyloxy-(1H,3H)-quinazoline-2,4-dione, 7-methoxy-3-[2-(4-pyridyl)ethyl]-8-pentyloxy-(1H,3H)-quinazoline-2,4-dione, 3-[2-(4-aminophenyl)ethyl]-7-methoxy-8-pentyloxy-(1H,3H)-quinazoline-2,4-dione, 3-[2-(4-hydroxyphenyl)ethyl]-7-methoxy-8-pentyloxy-(1H,3H)-quinazoline-2,4-dione, 3-[2-(4-methylaminophenyl)ethyl]-7-methoxy-8-pentyloxy-(1H,3H)-quinazoline-2,4-dione and 3-[2-(4-dimethylaminophenyl)ethyl]-7-methoxy-8-pentyloxy-(1H,3H)-quinazoline-2,4-dione, or a pharmaceutically acceptable salt thereof.

6. A pharmaceutical composition comprising, as an active ingredient, a compound of claim 1, or a pharmaceutically acceptable salt thereof.

7. A pharmaceutical composition comprising, as an active ingredient, a compound of claim 2, or a pharmaceutically acceptable salt thereof.

8. A pharmaceutical composition comprising, as an active ingredient, a compound of claim 3, or a pharmaceutically acceptable salt thereof.

9. A pharmaceutical composition comprising, as an active ingredient, a compound of claim 4, or a pharmaceutically acceptable salt thereof.

10. A pharmaceutical composition comprising, as an active ingredient, a compound of claim 5, or a pharmaceutically acceptable salt thereof.

* * * * *